US007807389B2

(12) United States Patent
Ritchlin et al.

(10) Patent No.: US 7,807,389 B2
(45) Date of Patent: Oct. 5, 2010

(54) METHODS AND COMPOSITIONS RELATED TO JOINT INFLAMMATION DISEASES

(75) Inventors: Christopher T. Ritchlin, Canadagua, NY (US); Sally A. Haas-Smith, Ridgefield, CT (US); Edward M. Schwarz, Rochester, NY (US)

(73) Assignee: University of Rochester, Rochester, NY (US)

( * ) Notice: Subject to any disclaimer, the term of this patent is extended or adjusted under 35 U.S.C. 154(b) by 1382 days.

(21) Appl. No.: 10/799,345

(22) Filed: Mar. 12, 2004

(65) Prior Publication Data
US 2004/0209316 A1 Oct. 21, 2004

Related U.S. Application Data

(60) Provisional application No. 60/454,573, filed on Mar. 14, 2003.

(51) Int. Cl.
*G01N 33/567* (2006.01)
*G01N 31/00* (2006.01)

(52) U.S. Cl. .................. 435/7.21; 435/2; 435/7.92; 435/372; 435/373; 435/287.2; 435/973; 436/501; 436/540; 436/10; 436/56; 436/63; 436/811

(58) Field of Classification Search .............. 435/2, 435/7.21, 7.92, 372, 373, 377, 286.5, 287.2, 435/287.3, 973; 436/501, 516, 517, 548, 436/18, 56, 63, 811, 540, 10
See application file for complete search history.

(56) References Cited

U.S. PATENT DOCUMENTS

2004/0209316 A1* 10/2004 Ritchlin et al. ............... 435/7.2

OTHER PUBLICATIONS

Hirayama et al., Osteoclast formation and activity in the pathogenesis of osteoporosis in Rheumatoid Arthritis, Rheumatology 41: 1232-1239 (2002).*
Jevon et al., Osteoclast formation from circulating precursors in Osteoporosis, Scand J Rheumatol 32: 95-100 (Jan. 1, 2003).*
Li et al., Systemic TNFa Promotes Erosive Bone Resorption by Increasing the Number of CD11b+ Osteoclast Progenitors in the Periphery which are Dependent on RANK Signaling of Osteoclastogenesis, Journal of Bone and Mineral Research: JBMR Program and Abstracts (2002).*
Gregoretti et al., Osteoclast precursors circulate n the peripheral blood of patients with aggressive multiple myeloma, Leukemia 9: 1392-1397 (1995).*
Massey et al., Human Osteoclasts derive from CD14 positive monocytes, British Journal of Hematology 106: 167-170 (1999).*
Aaronson and Horvath, 2002. A road map for those who don't know JAK-STAT. *Science* 296:1653-55.
Abu-Amer et al.2000. Tumor necrosis factor receptors types 1 and 2 differentially regulate osteoclastogenesis [In Process Citation]. *J Biol Chem* 275(35):27307-10.

(Continued)

*Primary Examiner*—Gailene R Gabel
(74) *Attorney, Agent, or Firm*—Ballard Spahr LLP

(57) ABSTRACT

Disclosed are compositions and methods related to joint inflammation diseases. Disclosed is the relationship between osteoclasts and inflammatory joint diseases and osteoclast precursor cells.

22 Claims, 34 Drawing Sheets

OTHER PUBLICATIONS

Figure 1:
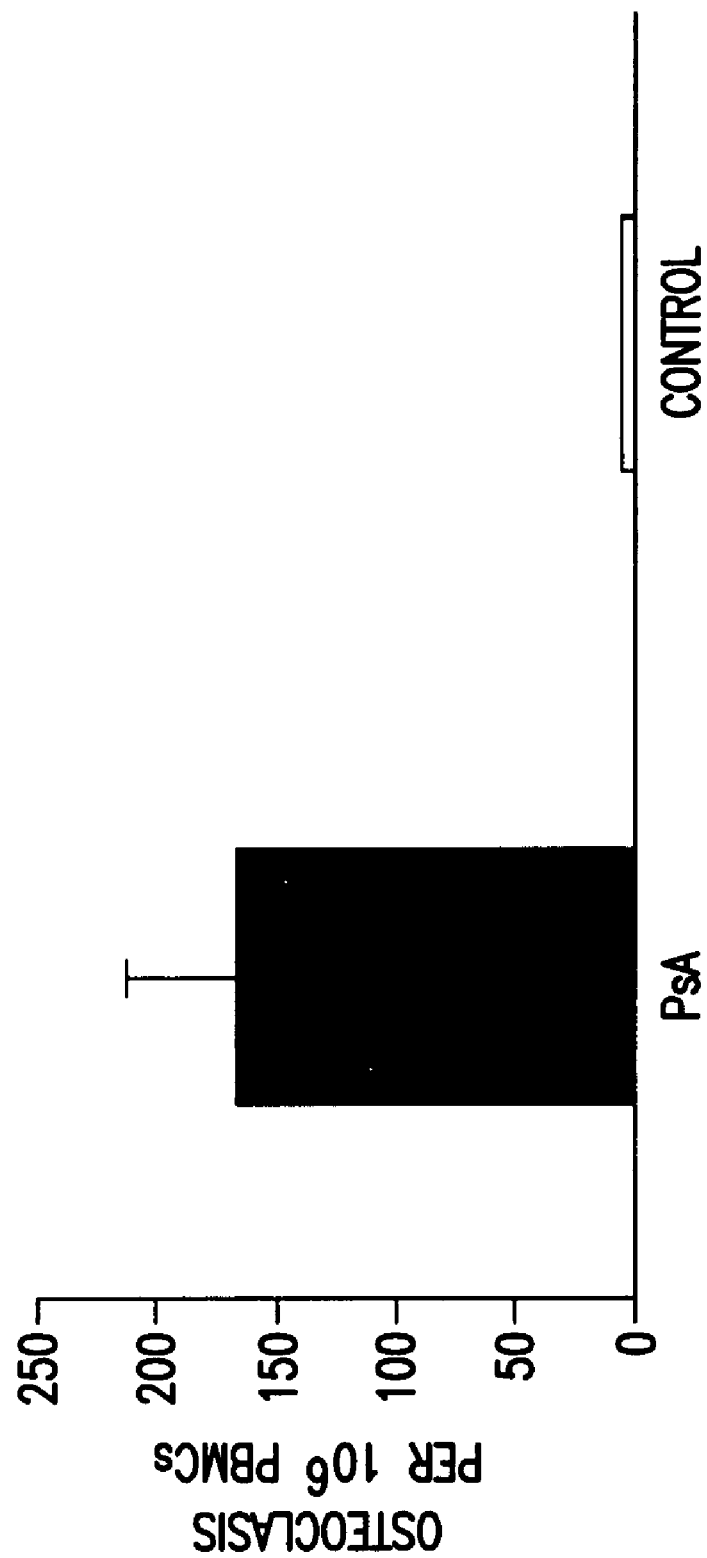

Anderson et al.A homologue of the TNF receptor and its ligand enhance T-cell growth and dendritic-cell function. *Nature* 1997; 390(6656):175-9.

Anolik et al. 2002. B lymphocyte depletion in the treatment of systemic lupus: phase I/II trial of rituximab in SLE. *Arthritis Rheum* 47:S289.

Anolik et al.2003. The relationship of FcgammaRIIIa genotype to degree of B cell depletion by rituximab in the treatment of systemic lupus erythematosus. *Arthritis Rheum* 48:455-459.

Antoni, 2003. The one year results of the infliximab multinational psoriatic arthritis controlled trial (IMPACT). *Arthritis & Rheumatism*. 48: (9S):S265.

Arai et al.Commitment and differentiation of osteoclast precursor cells by the sequential expression of c-Fms and receptor activator of nuclear factor kappaB (RANK) receptors. *J Exp Med* 1999; 190(12):1741-54.

Arend and Dayer, 1990. Cytokines and cytokine inhibitors or antagonists in rheumatoid arthritis. *Arthritis Rheum* 33:305-315.

Arend, 2001. The innate immune system in rheumatoid arthritis. *Arthritis Rheum* 44:2224-34.

Arnett et al.1988. The American Rheumatism Association 1987 revised criteria for the classification of rheumatoid arthritis. *Arthritis Rheum.* 31:315-324.

Azuma et al.2000. Tumor necrosis factor-α induces differentiation of and bone resorption by osteoclasts. *J Biol Chem* 275:4858-64.

Baechler et al.2003. Interferon-inducible gene expression signature in peripheral blood cells of patients with severe lupus. *Proc Natl Acad Sci U S A* 100:2610.

Bathon et al.2000. A comparison of etanercept and methotrexate in patients with early rheumatoid arthritis. *N Engl J Med* 343(22):1586-93.

Behar and Porcelli, 1995. Mechanisms of autoimmune disease induction. The role of the immune response to microbial pathogens. *Arthritis Rheum* 38:458-476.

Bennett et al.2003. Interferon and granulopoiesis signatures in systemic lupus erythematosus blood. *J Exp Med* 197:711-723.

Bertolini et al.1986. Stimulation of bone resorption and inhibition of bone formation in vitro by human tumour necrosis factors. *Nature* 319:516-518.

Blanco et al. 2001. Induction of dendritic cell differentiation by IFN-α in systemic lupus erythematosus. *Science* 294:1540-1543.

Boyce et al.Requirement of pp60c-src expression for osteoclasts to form ruffled borders and resorb bone in mice. *J Clin Invest* 1992; 90(4):1622-7.

Boyle et al.2003. Osteoclast differentiation and activation. *Nature* 423:337-342.

Braun et al.2002. Treatment of active ankylosing spondylitis with infliximab: a randomised controlled multicentre trial. *Lancet* 359:1187-1193.

Bromley and Woolley, 1984. Chondroclasts and osteoclasts at subchondral sites of erosion in the rheumatoid joint. *Arthritis Rheum.* 27:968-975.

Bromley et al.1985. Bidirectional erosion of cartilage in the rheumatoid knee joint. *Ann Rheum Dis* 44:676.

Bywaters and Dixon, 1965. Paravertebral ossification in psoriatic arthritis. *Annals of the Rheum. Dis.* 24:313-331.

Campbell et al.2001. Severe inflammatory arthritis and lymphadenopathy in the absence of TNF. *J Clin Invest* 107(12):1519-1527.

Cenci et al.2000. Estrogen deficiency induces bone loss by enhancing T-cell production of TNF-alpha. *J Clin Invest* 106(10):1229-37.

Chen and Goeddel, 2002. TNF-R1 signaling: a beautiful pathway. *Science* 296:1634.

Childs et al.. 2001. Efficacy of Etanercept for Wear Debris-Induced Osteolysis. *J. Bon. Min. Res.* 16:338-47.

Childs et al.2002. In vivo RANK signaling blockade using the receptor activator of NF-kappaB:Fc effectively prevents and ameliorates wear debris-induced osteolysis via osteoclast depletion without inhibiting osteogenesis. *J Bone Miner Res* 17:192-199.

Chomarat et al.2000. IL-6 switches the differentiation of monocytes from dendritic cells to macrophages. *Nat Immunol* 1:510-514.

Collin-Osdoby et al. 2001. Receptor activator of NF-κB and osteoprotegerin expression by human microvascular endothelial cells, regulation by inflammatory cytokines, and role in human osteoclastogenesis. *J Biol Chem* 276(23):20659-72.

Danning et al. 2000. Macrophage-derived cytokine and nuclear factor kappa B p65 expression in synovial membrane and skin of patients with psoriatic arthritis. Arthritis Rheum. 43:1244-1256.

Daro et al. Polyethylene glycol-modified GM-CSF expands CD11b(high)CD11c(high) but notCD11b(low)CD11c(high) murine dendritic cells in vivo: a comparative analysis with Flt3 ligand. *J Immunol* 2000; 165(1):49-58.

De et al. 2003. Failure of monocytes of trauma patients to convert to immature dendritic cells is related to preferential macrophage-colony-stimulating factor-driven macrophage differentiation. *J Immunol* 170:63556362.

Delneste et al. 2003. Interferon gamma switches monocyte differentiation from dendritic cells to macrophages. *Blood* 101:143-150.

Demulder et al. 1993. Abnormalities in osteoclast precursors and marrow accessory cells in Paget's disease. *Endocrinology* 133:1978-1982.

den Broeder et al. 2002. A single dose, placebo controlled study of the fully human anti-tumor necrosis factor-alpha antibody adalimumab (D2E7) in patients with rheumatoid arthritis. *J Rheumatol* 29:2288-2298.

Dougall et al. 1999. RANK is essential for osteoclast and lymph node development. *Genes Dev* 13(18):2412-24.

Douni et al. 1996. Transgenic and knockout analyses of the role of TNF in immune regulation and disease pathogenesis. *J. Inflam.* 47:27-38.

Drake et al. 1995. Analysis of the New Zealand Black contribution to lupus-like renal disease. Multiple genes that operate in a threshold manner. *J Immunol* 154:2441-2447.

Esdaile et al. 1981. Deforming arthritis in systemic lupus erythematosus. *Ann Rheum Dis* 40:124-126.

Faust et al. 1999. Osteoclast markers accumulate on cells developing from human peripheral blood mononuclear precursors. Journal of Cellular Biochemistry 72:67-80.

Fearon et al. 2003. Angiopoietins, growth factors, and vascular morphology in early arthritis. *J Rheumatol* 30:260-268.

Feldmann et al. 1996. Rheumatoid arthritis. *Cell* 85:307-310.

Flick et al. 2003. Effects of receptor activator of NFkappaB (RANK) signaling blockade on fracture healing. *J Orthop Res* 21:676-683.

Franzoso et al. 1998. Mice deficient in nuclear factor (NF)-kappa B/p52 present with defects in humoral responses, germinal center reactions, and splenic microarchitecture. *J of Exp. Med.* 187(2):147-59.

Franzoso et al.1997. Requirement for NF-kappaB in osteoclast and B-cell development. *Genes & Dev.* 11(24):3482-96.

Fujikawa et al.1996. Human osteoclast formation and bone resorption by monocytes and synovial macrophages in rheumatoid arthritis. *Ann.of Rheum.Dis.* 55:816-822.

Gladman et al.1995. Clinical indicators of progression in psoriatic arthritis: multivariate relative risk model. *J Rheumatol* 22:675-679.

Gladman, 1998. Psoriatic arthritis. Rheumatic Diseases Clinics of North America 24:829-844.

Goldenberg and Cohen, 1978. Synovial membrane histopathology in the differential diagnosis of rheumatoid arthritis, gout, pseudogout, systemic lupus erythematosus, infectious arthritis and degenerative joint disease. *Medicine (Baltimore)* 57:239-253.

Goldring and Gravallese, 2000. Mechanisms of bone loss in inflammatory arthritis: diagnosis and therapeutic implications. *Arthritis Res* 2(1):33-7.

Gori et al. 2000. The expression of osteoprotegerin and RANK ligand and the support of osteoclast formation by stromal-osteoblast lineage cells is developmentally regulated. Endocrinology 141:4768-4776.

Gravallese et al. 1998. Identification of cell types responsible for bone resorption in rheumatoid arthritis and juvenile rheumatoid arthritis. *Am J Path* 152:943-951.

Gravallese et al. 2000. Synovial tissue in rheumatoid arthritis is a source of osteoclast differentiation factor. *Arthritis Rheum.* 43:250-258.

Gregoretti et al. 1995. Osteoclast precursors circulate in the peripheral blood of patients with aggressive multiple myeloma. *Leukemia* 9:1392-1397.

Grigor et al. 1978. Systemic lupus erythematosus. A prospective analysis. *Ann Rheum Dis* 37:121-128.

Hahn, 1998. Antibodies to DNA. *N Engl J Med* 338:1359-1368.

Hanekom, et al. 2003. *Mycobacterium tuberculosis* inhibits maturation of human monocyte-derived dendritic cells in vitro. *J Infect Dis* 188:257-266.

Harley et al. 1998. The genetics of human systemic lupus erythematosus. *Curr Opin Immunol* 10:690-696.

Helliwell et al. 1991. A re-evaluation of the osteoarticular manifestations of psoriasis British Journal of Rheumatology 30:339-345.

Hofbauer and Heufelder, 2000. The role of receptor activator of nuclear factor-kappa B ligand and osteoprotegerin in the pathogenesis and treatment of metabolic bone diseases. *J Clin Endocrin & Metabolism* 85:2355-2363.

Hofbauer and Heufelder, 2001. The role of osteoprotegerin and receptor activator of nuclear factor kappaB ligand in the pathogenesis and treatment of rheumatoid arthritis. *Arthritis Rheum.* 44:253-259.

Hofbauer et al. 1999. Interleukin-1β and tumor necrosis factor-α, but not interleukin-6, stimulate osteoprotegerin ligand gene expression in human osteoblastic cells. *Bone* 25:255-9.

Hofbauer et al. 2000. The roles of osteoprotegerin and osteoprotegerin ligand in the paracrine regulation of bone resorption. *J Bone Miner Res* 15:2-12.

Hsu et al. 1999 Tumor necrosis factor receptor family member RANK mediates osteoclast differentiation and activation induced by osteoprotegerin ligand. Proc Natl Acad Sci U S A; 96(7):3540-5.

Huang et al. 2000. Gene expression of osteoprotegerin ligand, osteoprotegerin, and receptor activator of NF-kappaB in giant cell tumor of bone: possible involvement in tumor cell-induced osteoclast-like cell formation. *Am J Path* 156:761-767.

Huang et al. 2003. Exposure to receptor-activator of NFκB ligand renders pre-osteoclasts resistant to IFN_y by inducing terminal differentiation. *Arthritis Res Ther* 5:R49-R59.

Huang et al. 2003. A Rapid Multiparameter Approach to Study Factors that Regulate Osteoclastogenesis: Demonstration of the Combinatorial Dominant Effects of TNF-alpha and TGF-ss in RANKL-Mediated Osteoclastogenesis. *Calcif Tissue Int.* 73:584-593.

Iotsova et al. Osteopetrosis in mice lacking NF-kappaB1 and NF-kappaB2 Medicine 1997; 3(11):1285-9.

Johnson et al. Pleiotropic effects of a null mutation in the c-fos proto-oncogene. Cell 1992; 71(4):577-86.

Kaarela and Sarna, 1993. Correlations between clinical facets of outcome in rheumatoid arthritis. *Clin Exp Rheumatol* 11:643-644.

Kaarela et al. 1993. How often is seropositive rheumatoid arthritis an erosive disease? A 17-year followup study. *J Rheumatol* 20:1670-1693.

Kanematsu et al. . 2000. Prostaglandin E2 induces expression of receptor activator of nuclear factor-kappa B ligand/osteoprotegrin ligand on pre-B cells: implications for accelerated osteoclastogenesis in estrogen deficiency. *J Bone Miner Res* 15:1321-9.

Karsenty, 1999 The genetic transformation of bone biology. Genes Dev; 13(23):3037-51.

Keffer et al. 1991. Transgenic mice expressing human tumour necrosis factor: a predictive genetic model of arthritis. *Embo J* 10:4025-31.

Keystone, 2001 Tumor necrosis factor-α blockade in the treatment of rheumatoid arthritis. Rheum Dis Clin North Am; 27(2):427-43.

Knight et al. 1993. Construction and initial characterization of a mouse-human chimeric anti-TNF antibody. *Mol Immunol* 30:1443-1453.

Kobayashi et al. 2000. Tumor necrosis factor alpha stimulates osteoclast differentiation by a mechanism independent of the ODF/RANKL-RANK interaction. *J Exp Med* 191:275-86.

Kobayashi et al. Segregation of TRAF6-mediated signaling pathways clarifies its role in osteoclastogenesis. Embo J 2001; 20(6):1271-1280.

Kodama et al. 1991. Congenital osteoclast deficiency in osteopetrotic (op/op) mice is cured by injections of macrophage colony-stimulating factor. *J Exp Med* 173:269-72.

Koller et al. 1996 Immunophenotyping of human bone marrow-derived macrophages. Scand J Immunol; 43(6):626-32.

Kong et al. 1999. Activated T cells regulate bone loss and joint destruction in adjuvant arthritis through osteoprotegerin ligand. *Neurosurgery* 402:304-309.

Kong et al. 1999. OPGL is a key regulator of osteoclastogenesis, lymphocyte development and lymph-node organogenesis. *Nature* 397:315-323.

Kono et al. 1994. Lupus susceptibility loci in New Zealand mice. *Proc Natl Acad Sci U S A* 91:10168-10172.

Kotake et al. 2001. Activated human T cells directly induce osteoclastogenesis from human monocytes: possible role of T cells in bone destruction in rheumatoid arthritis patients. Arthritis Rheum. 44:1003-1012.

Kotzin, 1996. Systemic lupus erythematosus. *Cell* 85:303-306.

Kunisada et al.. 1990. The murine mutation osteopetrosis is in the coding region of the macrophage colony stimulating factor gene. *Nature* 345:442.

Labowitz and Schumacher, Jr., 1971. Articular manifestations of systemic lupus erythematosus. *Ann Intern Med* 74:911-921.

Lacey et al. 1998. Osteoprotegerin ligand is a cytokine that regulates osteoclast differentiation and activation. *Cell* 93:165-176.

Lam et al. 2000. TNF-alpha induces osteoclastogenesis by direct stimulation of macrophages exposed to permissive levels of RANK ligand. *J of Clin. Inv.* 106:1481-1488.

Landewé et al. 2003. Serum RANK-ligand Modifies the effect of Disease Activity on Radiographic Progression. *Arthritis & Rheumatism* 48:S268.

Larsen and Thoen, 1987. Hand radiography of 200 patients with rheumatoid arthritis repeated after an interval of one year. *Scand J Rheumatol* 16:395.

Li et al. 2000. NF-kappaB Regulates VCAM-1 Expression on Fibroblast-Like Synoviocytes. *J Immunol.* 164(11):5990-5997.

Li et al. 2002. Systemic TNFa promotes erosive bone resorption by increasing the number of CD11b+ osteoclast progenitors in the periphery which are dependent on RANK signaling for osteoclastogenesis . *J Bone & Mineral Res.* 17:s130.

Li et al. 2003. The TNF-alpha transgenic mouse model of inflammatory arthritis. *Springer Semin Immunopathol* 25:19.

Li et al. 2004. Systemic TNFa mediates an increase in peripheral CD11bhi osteoclast precursors in TNFa transgenic mice. *Arthritis Rheum* 50:265-276.

Lipsky et al. 2000. Infliximab and methotrexate in the treatment of rheumatoid arthritis. Anti-Tumor Necrosis Factor Trial in Rheumatoid Arthritis with Concomitant Therapy Study Group. *N Engl J Med* 343:1594-1602.

Locksley et al. 2001. The TNF and TNF receptor superfamilies: integrating mammalian biology. *Cell* 104:487-501.

Logan et al. 1996 Tumor necrosis factor administration is associated with increased endogenous production of M-CSF and G-CSF but not GM-CSF in human cancer patients. *Exp Hematol*; 24(1):49-53.

Lomaga et al. 1999 TRAF6 deficiency results in osteopetrosis and defective interleukin-1, CD40, and LPS signaling. *Genes Dev*; 13(8):1015-24.

Looney et al. 2002. Volumetric computerized tomography as a measurement of periprosthetic acetabular osteolysis and its correlation with wear. *Arthritis Res* 4:59-63.

Maini et al. 1995 Monoclonal anti-TNF alpha antibody as a probe of pathogenesis and therapy of rheumatoid disease. *Immunol Rev*; 144:195-223.

Maini et al. 1995. Monoclonal anti-TNF alpha antibody as a probe of pathogenesis and therapy of rheumatoid disease. *Immunol Rev* 144:195-215.

Martel et al. 1965. The pattern of bone erosion in the hand and wrist in rheumatoid arthrits. *Radiology* 84:204.

Marzo-Ortega et al. 2001. Efficacy of etanercept in the treatment of the entheseal pathology in resistant spondylarthropathy: a clinical and magnetic resonance imaging study. *Arthritis Rheum.* 44:2112-2117.

Massey and Flanagan, 1999. Human osteoclasts derive from CD14-positive monocytes. British Journal of Haematology 106:167-170.

McGowan et al. 2001. Cytokine-activated endothelium recruits osteoclast precursors. *Endocrinology* 142:1678-1681.

McQueen et al. 2003. Bone edema scored on magnetic resonance imaging scans of the dominant carpus at presentation predicts radiographic joint damage of the hands and feet six years later in patients with rheumatoid arthritis. *Arthritis Rheum* 48:1814-1827.

Mease et al. 1999. Embrel (Etanercept) in patients with Psoriatic Arthritis and Psoriasis. *Arthritis Rheum*. 42:377 (Abstr.).

Mease et al. 2000. Etanercept in the treatment of psoriatic arthritis and psoriasis: a randomised trial. *Lancet* 356:385-390.

Mease, 2002. Tumour necrosis factor (TNF) in psoriatic arthritis: pathophysiology and treatment with TNF inhibitors. *Ann Rheum Dis* 61:298-304.

Mills, 1994. Systemic lupus erythematosus. *N Engl J Med* 330:1871-1879.

Molina et al. 1995. Coexistence of human immunodeficiency virus infection and systemic lupus erythematosus. *J Rheumatol* 22:347-250.

Moll and Wright, 1973. Familial occurrence of psoriatic arthritis. *Ann Rheum Dis* 32:181-201.

Moll and Wright, 1973. Psoriatic arthritis. Seminars in Arthritis & Rheumatism 3:55-78.

Morel et al. 1994. Polygenic control of susceptibility to murine systemic lupus erythematosus. *Immunity* 1:219-229.

Moreland et al. 1997. Treatment of rheumatoid arthritis with a recombinant human tumor necrosis factor receptor (p75)-Fc fusion protein. *N Engl J Med* 337:141-147.

Moreland et al. 2001. Long-term safety and efficacy of etanercept in patients with rheumatoid arthritis. *J Rheumatol* 28(6):1238-44.

Myers et al. 1999. Expression of functional RANK on mature rat and human osteoclasts. *FEBS Letters* 463:295-300.

Nakagawa et al. 1998. *Biochemical & Biophysical Research Communications* 253:395-400.

Nakagawa et al. 1998. RANK is the essential signaling receptor for osteoclast differentiation factor in osteoclastogenesis. Biochemical & Biophysical Research Communications 253:395-400.

Natour et al. 1991. A study of synovial membrane of patients with systemic lupus erythematosus (SLE). *Clin Exp Rheumatol* 9:221-225.

Nicholson et al. 2000. Induction of osteoclasts from CD14-positive human peripheral blood mononuclear cells by receptor activator of nuclear factor kappaB ligand (RANKL). Clinical Science 99:133-140.

Partsch et al. 1998. T cell derived cytokines in psoriatic arthritis synovial fluids. Ann.of Rheum.Dis. 57:691-693.

Pascual et al. 2003. The central role of dendritic cells and interferon-alpha in SLE. *Curr Opin Rheumatol* 15:548-556.

Penit and Vasseur, Phenotype analysis of cycling and postcycling thymocytes: evaluation of detection methods for BrdUrd and surface proteins. Cytometry 1993; 14(7):757-63.

Pettit et al. 2001. TRANCE/RANKL knockout mice are protected from bone erosion in a serum transfer model of arthritis. *Am. J. Pathol.* 159:1689-1699.

Quinn et al. 1998. A combination of osteoclast differentiation factor and macrophage-colony stimulating factor is sufficient for both human and mouse osteoclast formation in vitro. Endocrinology 139:4424-4427.

Redlich et al. 2002. Tumor necrosis factor alpha-mediated joint destruction is inhibited by targeting osteoclasts with osteoprotegerin. Arthritis Rheum. 46:785-792.

Reece et al. 1999. Distinct vascular patterns of early synovitis in psoriatic, reactive, and rheumatoid arthritis. Arthritis Rheum. 42:1481-1484.

Resnick and Niwayama, 1977. On the nature and significance of bony proliferation in "rheumatoid variant" disorders. AJR *Am J Roentgen*. 129:275-278.

Resnick and Niwayama, 1981. Psoriatic Arthritis. *In Diagnosis of Bone and Joint Disorders*. D.Resnick and Niwayama,G., editors. W.B.Saunders, Philadelphia. 1103-1129.

Resnick and Niwayama, 1989. Psoriatic Arthritis. *In Bone and Joint Imaging*. D.Resnick, editor. W. B. Saunders, Philadelphia,PA. 320-328.

Ritchlin and Haas-Smith, 2001. Expression of interleukin 10 mRNA and protein by synovial fibroblastoid cells. *Journal of Rheumatology* 28:698-705.

Ritchlin and Schwarz, Grant Application, "mechanisms of inflammatory osteolysis in psoriatic arthritis" Howard Hughes Biomedical Research Support Program, Jul. 1, 2001 to Jun. 30, 2002.

Ritchlin et al. 1998. Patterns of Cytokine Production in Psoriatic Synovium. Journal of Rheumatology 25:1544-1552.

Ritchlin et al. 2003. Etanercept Lowers the Frequency of Circulating Osteoclast Precursors (OCP) and Improves Bone Marrow Edema in Patients with Erosive Psoriatic Arthritis. *Late-Breaking Abstract ACR*.

Ritchlin et al. Mechanisms of TNF-alpha- and RANKL-mediated osteoclastogenesis and bone resorption in psoriatic arthritis. *J Clin Invest* 2003; 111(6):821-31.

Ritchlin, Grant Application, Department of Health and Human Services, Public Health Service, "Osteoclastic Bone Resorption in Psoriatic Arthritis" Sep. 1, 2001 to Aug. 31, 2004.

Rozzo et al. 1996. Effect of genetic background on the contribution of New Zealand black loci to autoimmune lupus nephritis. *Proc Natl Acad Sci U S A* 93:15164.

Rozzo et al. 2000. Enhanced susceptibility to lupus contributed from the nonautoimmune C57BL/10, but not C57BL/6, genome. *J Immunol* 164:5515-5521.

Rozzo et al. 2001. Evidence for an interferon-inducible gene, Ifi202, in the susceptibility to systemic lupus. *Immunity* 15:435-443.

Santiago-Raber et al. 2003. Type-I interferon receptor deficiency reduces lupus-like disease in NZB mice. *J Exp Med* 197:777-788.

Santiago-Schwarz et al. Distinct alterations in lineage committed progenitor cells exist in the peripheral blood of patients with rheumatoid arthritis and primary Sjogren's syndrome. J Rheumatol 1996; 23(3):439-46.

Schwarz et al. 2000. Anti-TNFα therapy as a clinical intervention for periprosthetic osteolysis. Arthritis Res. 2:165-168.

Schwarz et al. 1998. NFκB mediated inhibition of apoptosis is required for encephalomyocarditis virus virulence: A mechanism of resistance in p50 knockout mice. *J. Virol.* 72:5654-5660.

Schwarz et al. 2003. Use of volumetric computerized tomography as a primary outcome measure to evaluate drug efficacy in the prevention of peri-prosthetic osteolysis: a 1-year clinical pilot of etanercept vs. placebo. *J Orthop Res* 21:1049-1055.

Schwarz, et al. 1997. Immunological defects in mice with a targeted disruption in Bcl-3. *Genes Dev* 11:187-197.

Shalhoub et al. 2000. Characterization of osteoclast precursors in human blood. British Journal of Haematology 111:501-512.

Sharp et al. 1971. Methods of scoring the progression of radiologic changes in rheumatoid arthritis. Correlation of radiologic, clinical and laboratory abnormalities. *Arthritis Rheum* 14:706-720.

Sharp et al. 1985. How many joints in the hands and wrists should be included in a score of radiologic abnormalities used to assess rheumatoid arthritis? *Arthritis Rheum* 28:1326-1335.

Shealy et al. 2002. Anti-TNFα antibody allows healing of joint damage in polyarthritic transgenic mice. *Arthritis Res* 4:R7.

Shigeyama et al.. 2000. Expression of osteoclast differentiation factor in rheumatoid arthritis. *Arthritis Rheum* 43:2523-2530.

Shlomchik et al. 2001. From T to B and back again: positive feedback in systemic autoimmune disease. *Nat Rev Immunol* 1:147-153.

Simonet et al. 1997. Osteoprotegerin: a novel secreted protein involved in the regulation of bone density [see comments]. *Cell* 89:309-319.

Srivastava et al. Estrogen decreases osteoclast formation by down-regulating receptor activator of NF-κB ligand (RANKL)-induced JNK activation. J Biol Chem 2001; 276(12):8836-40.

Steinman and Nussenzweig, 2002. Avoiding horror autotoxicus: the importance of dendritic cells in peripheral T cell tolerance. *Proc Natl Acad Sci U S A* 99:351-358.

Steinman et al. 2000. The induction of tolerance by dendritic cells that have captured apoptotic cells. *J Exp Med* 191:411-416.

Steinman, 1991. The dendritic cell system and its role in immunogenicity. *Annu Rev Immunol* 9:271-296.

Stevens, 1983. The clinical management of systemic lupus erythematosus. *In: Shur PH, ed New York: Grune & Stratton*:63-83.

Suda et al. 1999. Modulation of osteoclast differentiation and function by the new members of the tumor necrosis factor receptor and ligand families. Endocrine Reviews 20:345-357.

Suda et al. Regulation of osteoclast function. *J Bone Miner Res* 1997; 12(6):869-79.

Takahashi et al. 1998. Impaired yield, phenotype, and function of monocyte-derived dendritic cells in humans at risk for insulin-dependent diabetes. *J Immunol* 161:2629-2635.

Takayanagi et al. 2000. T-cell-mediated regulation of osteoclastogenesis by signalling cross-talk between RANKL and IFNγ. *Nature* 408:600-605.

Takayanagi et al. 1997. A new mechanism of bone destruction in rheumatoid arthritis: synovial fibroblasts induce osteoclastogenesis. *Biochem. Biophys. Res. Comm.* 240:279-286.

Takayanagi et al. 2000. Involvement of receptor activator of nuclear factor kappaB ligand/osteoclast differentiation factor in osteoclastogenesis from synoviocytes in rheumatoid arthritis. *Arthritis Rheum* 43:259-269.

Takayanagi et al. 2002. RANKL maintains bone homeostasis through c-Fos-dependent induction of *interferonβ*. *Nature* 416:744-749.

Tan et al. 1982. The 1982 revised criteria for the classification of systemic lupus erythematosus. *Arthritis Rheum* 25:12711277.

Teitelbaum, 2000. Bone Resorption by Osteoclasts. *Science* 289:1504-1508.

Theofilopoulos and Kono, 1999. The genes of systemic autoimmunity. *Proc Assoc Am Physicians* 111:228240.

Thiele et al. 1998. Detection of the bcr/abl gene in bone marrow macrophages in CML and alterations during interferon therapy—a fluorescence in situ hybridization study on trephine biopsies. *Journal of Pathology*. 186:331-335.

Toritsuka et al. 1997. Osteoclastogenesis in iliac bone marrow of patients with rheumatoid arthritis. Journal of Rheumatology 24:1690-1696.

van der Heijde, D. M. 1996. Plain X-rays in rheumatoid arthritis: overview of scoring methods, their reliability and applicability. *Baillieres Clin Rheumatol* 10:435-453.

Vyse and Kotzin, 1998. Genetic susceptibility to systemic lupus erythematosus. *Annu Rev Immunol* 16:261-292.

Vyse et al. 1997. Control of multiple autoantibodies linked with a lupus nephritis susceptibility locus in New Zealand black mice. *J Immunol* 158:5566-5574.

Vyse et al. 1998. Contributions of $Ea^z$ and $Eb^z$ MHC genes to lupus susceptibility in New Zealand mice. *J Immunol* 160:2757-2766.

Wakeland et al. 1999. Genetic dissection of systemic lupus erythematosus. *Curr Opin Immunol* 11:701-707.

Wang et al. Bone and haematopoietic defects in mice lacking c-fos. Nature 1992; 360(6406):741-5.

Weinblatt et al. 2003. Adalimumab, a fully human anti-tumor necrosis factor alpha monoclonal antibody, for the treatment of rheumatoid arthritis in patients taking concomitant methotrexate: the ARMADA trial. *Arthritis Rheum* 48:35-45.

Winchester, 1993. *Psoriatic Arthritis. In Dermatology in General Medicine*. T.B.Fitzpatrick, Eisen,A.Z., Wolff,K., Freeberg,F.M., and Austin,K.F., editors. McGraw-Hill, New York. 515-527.

Wong et al. TRANCE is a novel ligand of the tumor necrosis factor receptor family that activates c-Jun N-terminal kinase in T cells. J Biol Chem 1997; 272(40):25190-4.

Xing et al. NF-kappaB p50 and p52 expression is not required for RANK-expressing osteoclast progenitor formation but is essential for RANK- and cytokine- mediated osteoclastogenesis. J Bone Miner Res 2002; 17(7):1200-10.

Yasuda et al. 1998. Osteoclast differentiation factor is a ligand for osteoprotegerin/osteoclastogenesis-inhibitory factor and is identical to TRANCE/RANKL. *Proc Natl Acad Sci U S A* 95:3597-3602.

Yin et al. 2002. Endostatin gene transfer inhibits joint angiogenesis and pannus formation in inflammatory arthritis. *Mol Ther* 5:547-554.

Yoshida, 1990 "The murine mutation osteopetrosis is in the coding region of the marcrophage colony stimulating factor gene." Letters to Nature:345:442-444.

Zhang et al. 2002. Cyclooxygenase-2 regulates mesenchymal cell differentiation into the osteoblast lineage and is critically involved in bone repair. *J Clin Invest* 109:1405.

Lubberts, E., "Increase in Expression of Receptor Activator of Nuclear Factor kB at Sites of Bone Erosion Correlates With Expression of Inflammation in Evolving Collagen-Induced Arthritis," *Arthritis and Rheumatism*, 46(11):3055-3064 (2002).

EPO Form 1507.3, Aug. 24, 2007, European Supplemental Search Report.

Fujikawa, Y. et al., "Pathological Bone Resorption in Rheumatic Diseases," *Japanese Journal of Rheumatology*, vol. 8, No. 4, pp. 335-367 (1998).

Gravallese, E. et al., "Differentiation of Osteoclast Precursor Cells in Bone Erosions in Rheumatoid Arthritis" *Arthritis and Rheumatism* (1999) 42:5246.

Hamzei, M. et al., "Osteoclast Stimulating and Differentiating Factors in Human Cholesteatoma," 2003 *Laryngoscope*, 113:436-442.

Hirayama, T. et al., "Osteoclast Formation and Activity in the Pathogenesis of Osteoporosis in Rheumatoid Arthritis," *Rheumatology* 2002;41:1232-1239.

Jevon, M. et al., "Osteoclast Formation from Circulating Precursors in Osteoporosis," *Scand J Rheumatol* 2003:32:95-100.

Li, P. et al., "Systemic Tumor Necrosis Factor α Mediates an Increase in Peripheral $CD11b^{high}$ Osteoclast Precursors in Tumor Necrosis Factor α-Transgenic Mice," *Arthritis & Rheumatism*, 2004 50:265-276.

\* cited by examiner

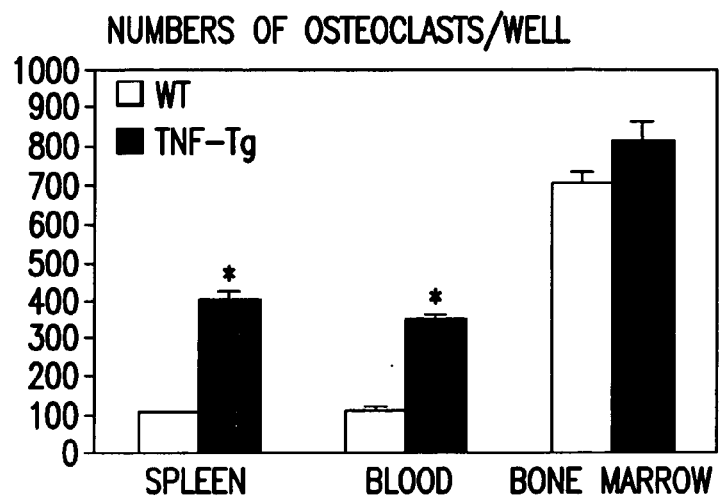
FIG.8A
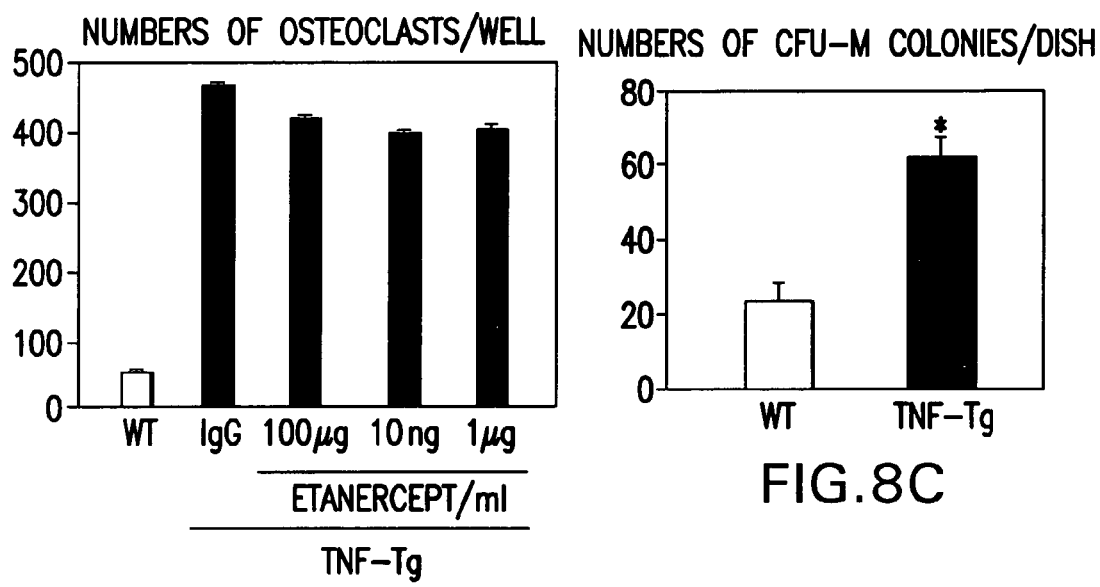
FIG.8B
FIG.8C

| P | Gene | patient 30 pre | patient 30 post | patient 25 pre | patient 25 post | patient 5 pre | patient 5 post | patient 30 pre | patient 30 post | patient 25 pre | patient 25 post | patient 5 pre | patient 5 post |
|---|---|---|---|---|---|---|---|---|---|---|---|---|---|
| * | TRIP 14 | | | | | | | 30.0 | 1.0 | 4.2 | 1.0 | 5.7 | 0.6 |
| * | IFN-ind 17kD-like | | | | | | | 40.0 | 0.7 | 4.7 | 0.7 | 3.9 | 0.7 |
| ** | GS3686 | | | | | | | 25.2 | 0.6 | 16.6 | 1.2 | 14.4 | 1.1 |
| * | XIAPAF-1 | | | | | | | 8.9 | 0.2 | 2.9 | 0.6 | 4.4 | 0.6 |
| ** | CD59 | | | | | | | 7.7 | 0.5 | 3.1 | 1.2 | 5.0 | 1.2 |
| ** | MX2 | | | | | | | 4.7 | 0.7 | 2.7 | 1.0 | 2.5 | 0.6 |
| ** | P69 OIAS | | | | | | | 3.6 | 0.6 | 2.9 | 1.0 | 2.5 | 0.5 |
| ** | EST hute1 | | | | | | | 2.9 | 0.4 | 2.4 | 0.2 | 3.0 | 0.5 |
| ** | IRF-7 | | | | | | | 3.0 | 0.4 | 3.2 | 0.8 | 3.1 | 0.8 |
|  | 9-27 | | | | | | | 2.8 | 0.4 | 2.3 | 0.3 | 1.9 | 0.8 |
|  | ISG 15 | | | | | | | 20.2 | 0.7 | 9.2 | 0.6 | 6.0 | 0.7 |
| ** | hep C-ass | | | | | | | 14.5 | 0.7 | 5.2 | 1.3 | 4.2 | 1.1 |
| ** | MX1 | | | | | | | 10.0 | 0.3 | 9.2 | 0.9 | 6.9 | 0.6 |
| * | IFI 56 | | | | | | | 70.0 | 0.9 | 10.2 | 1.2 | 6.7 | 0.8 |
| * | cig 49 | | | | | | | 70.7 | 0.7 | 13.6 | 1.1 | 12.2 | 1.3 |
|  | MCP-1 | | | | | | | 70.5 | 2.5 | 6.3 | 3.0 | 8.8 | 1.4 | p=0.002    p=0.0002    p<0.0001

| P | Gene | | | | | 30 pre | 30 post | 25 pre | 25 post |
|---|---|---|---|---|---|---|---|---|---|
| ** | DEF3 | | | | | 4.6 | 10.8 | 15.4 | 6.7 |
| * | RNS2 | | | | | 2.9 | 3.6 | 7.4 | 3.8 |
| * | DEFA1 | | | | | 6.8 | 43.5 | 35.8 | 3.0 |
| * | FALL39 | | | | | 4.5 | 38.0 | 9.7 | 1.0 |
| * | sim to calgranulin | | | | | 2.4 | 3.0 | 3.3 | 3.0 |
| * | F2RPA | | | | | 4.1 | 1.6 | 2.9 | 5.0 | p=0.14    p=0.15

FIG. 21C

METHODS AND COMPOSITIONS RELATED TO JOINT INFLAMMATION DISEASES

This application claims benefit of U.S. Provisional Application No. 60/454,573, filed Mar. 14, 2003, which is incorporated herein in its entirety.

This work was funded by NIAMS #AR 47186-01 and a Howard Hughes Pilot Grant. This work was also funded by National Institutes of Health grants PHS AR45791, AR43510, AR44220, and AR48697. The United States Government may have certain rights in the inventions disclosed herein.

I. BACKGROUND

Inflammatory joint diseases, such as psoriatic and rheumatoid arthritis, involve a number of debilitating symptoms for those who suffer from them. The underlying reasons for these symptoms include bone and cartilage degradation. This degradation occurs through bone resorption, which is a process wherein osteoclast cells degrade existing bone. The present application discloses that the increase in osteoclast cells is preceded by an increase of osteoclast precursor cells (OPCs) in the peripheral blood of a subject with an inflammatory joint disease. Disclosed are methods of diagnosing inflammatory joint disease, as well as treatments for inflammatory disease, among other methods and compositions related to osteoclasts and osteoclast precursor cells and inflammatory joint diseases.

II. SUMMARY

Disclosed are methods and compositions related to inflammatory joint disease.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows large numbers of osteoclasts arise from unstimulated PsA PBMC. PBMC were obtained from 24 PsA patients and 12 healthy controls, cultured in the absence of M-CSF and RANKL for 14 days, fixed and stained for TRAP. The number of TRAP+ multinucleated cells (osteoclasts) were counted and are presented as osteoclasts per million PBMC plated.

Figure 2:
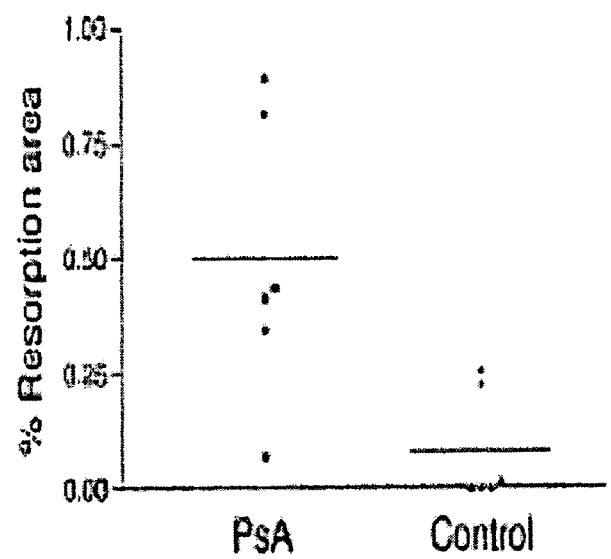

FIG. 2 shows culture PsA PBMC erode bone in a wafer assay. PBMC were cultured with or without M-CSF and RANKL on cortical bovine bone wafers. After 21 days the wafers were stained with toludine blue to identify resorption lacunae. The percentages of eroded surface area on the wafers from unstimulated cultures from PsA (n=6) and healthy controls (n=6) were quantified as described in Methods.

Figure 3:
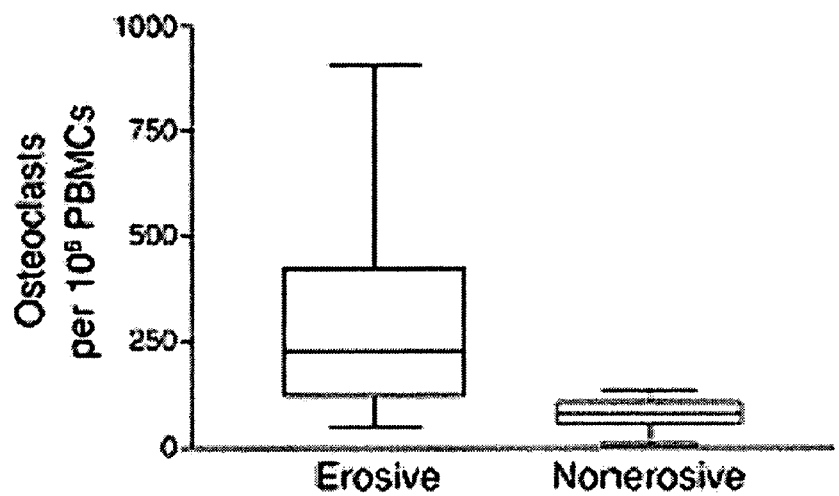

FIG. 3 shows OCP frequency in peripheral blood is greater in PsA patients with erosive arthritis. PBMC were obtained from 10 PsA patients with and 10 PsA patients without erosions on plain radiographs. The cells were cultured, fixed, stained for TRAP, and osteoclast numbers were determined as described in Methods. Data expressed as median OCP per $10^6$ PBMC.

Figure 4:
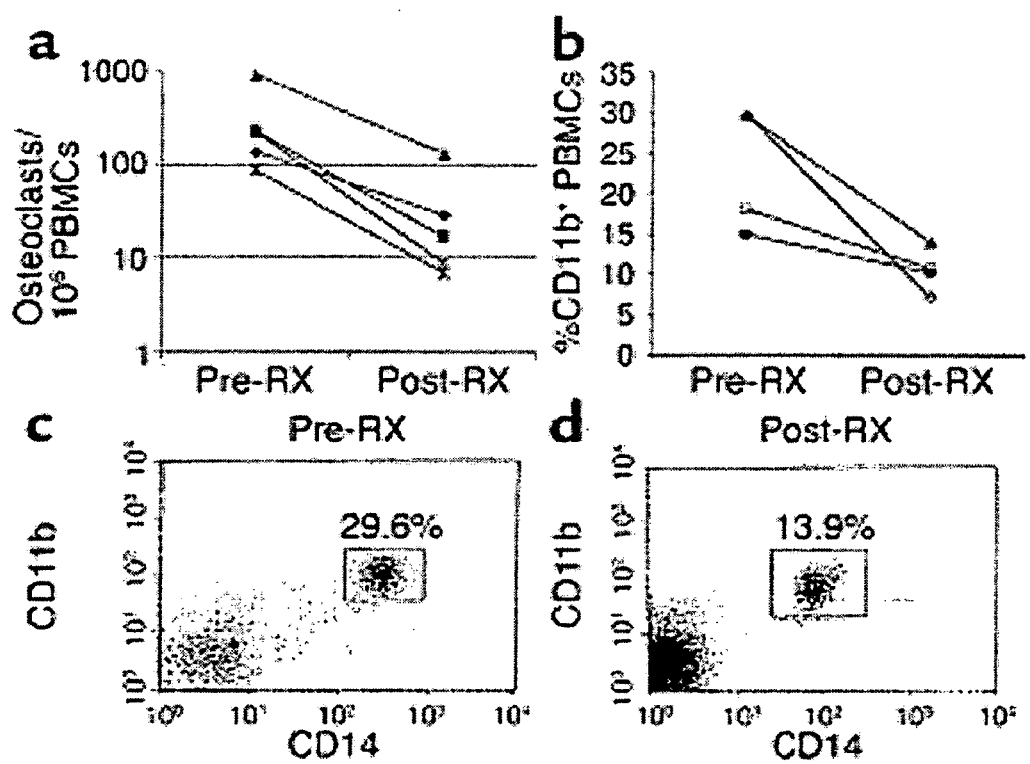

FIG. 4 shows Anti-TNF-α therapy reduces OCP frequency in patients with PsA. (A) PBMC from five PsA patients were cultured to determine the OCP frequency before and following 12 weeks of anti-TNF-α therapy (4 with Enbrel® (etanercept) and one with infliximab). The data are expressed as OCP per $10^6$ PBMC. The number of OCP in peripheral blood was significantly reduced in all of the patients (p<0.001). (B). The percentage of CD11b+PBMC significantly declined in 4 patients with erosive PsA, following 2 weeks of Enbrel® (etanercept) therapy as determined by FACS (p<0.026). Representative histograms of CD14/CD11b staining from a PsA patient before (C) and after Enbrel® (etanercept) therapy (D) are shown.

Figure 5:
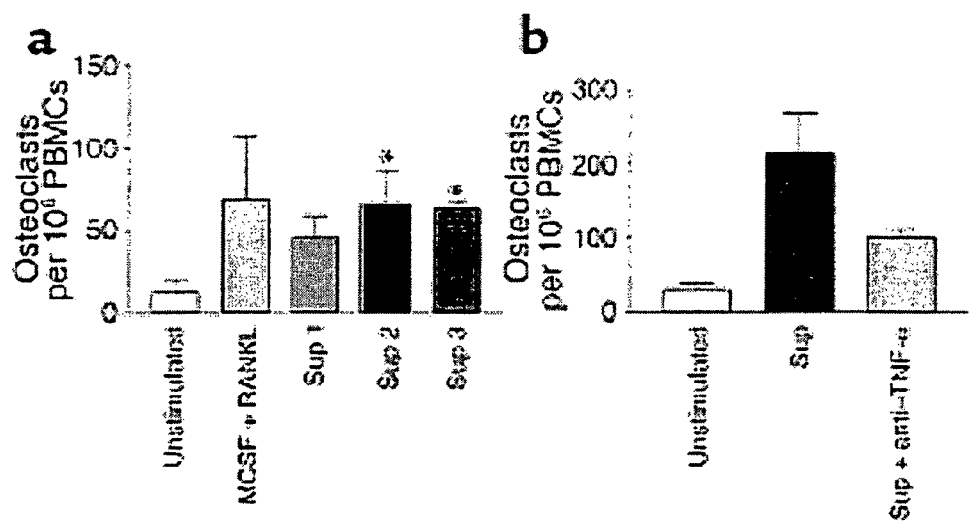

FIG. 5 shows TNF-α produced by PsA PBMC enhances osteoclastogenesis. (A) Supernatants from cultured PsA PBMC were added to PBMC from healthy donors to stimulate osteoclastogenesis as described in the Examples. The mean number of osteoclasts that arose from 3 unstimulated healthy control PBMC cultures (open bar), incubated with MCSF and RANKL (gray bar), and co-cultured with PsA PBMC supernatants (black and striped bars) are presented as the mean±S.D. (*p<0.02). (B) To determine the effect of TNF-α in the co-cultures, PsA PBMC supernatant #2 from (A) was added to 2 different healthy control PBMC cultures and osteoclasts were counted with or without anti-TNF antibodies.

Figure 6:
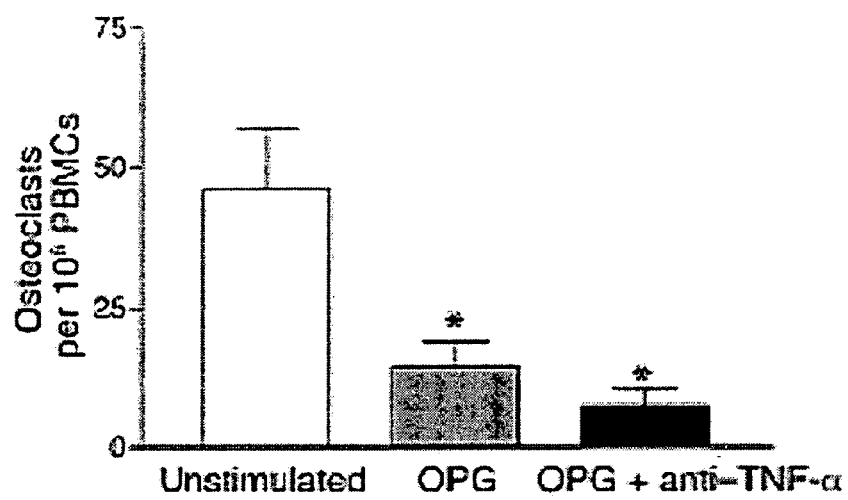

FIG. 6 shows OPG inhibits osteoclast formation in unstimulated PsA PBMC. TRAP osteoclastogenesis assays were performed on PsA PBMC cultured without RANKL or M-CSF in the continuous presence of OPG-Fc (1 u g/ml). Enbrel® (etanercept) (1 u g/ml) was added as indicated. One representative experiment out of 3 is shown. Data are expressed as the mean±SEM of four independent wells (*p<0.05).

Figure 7:
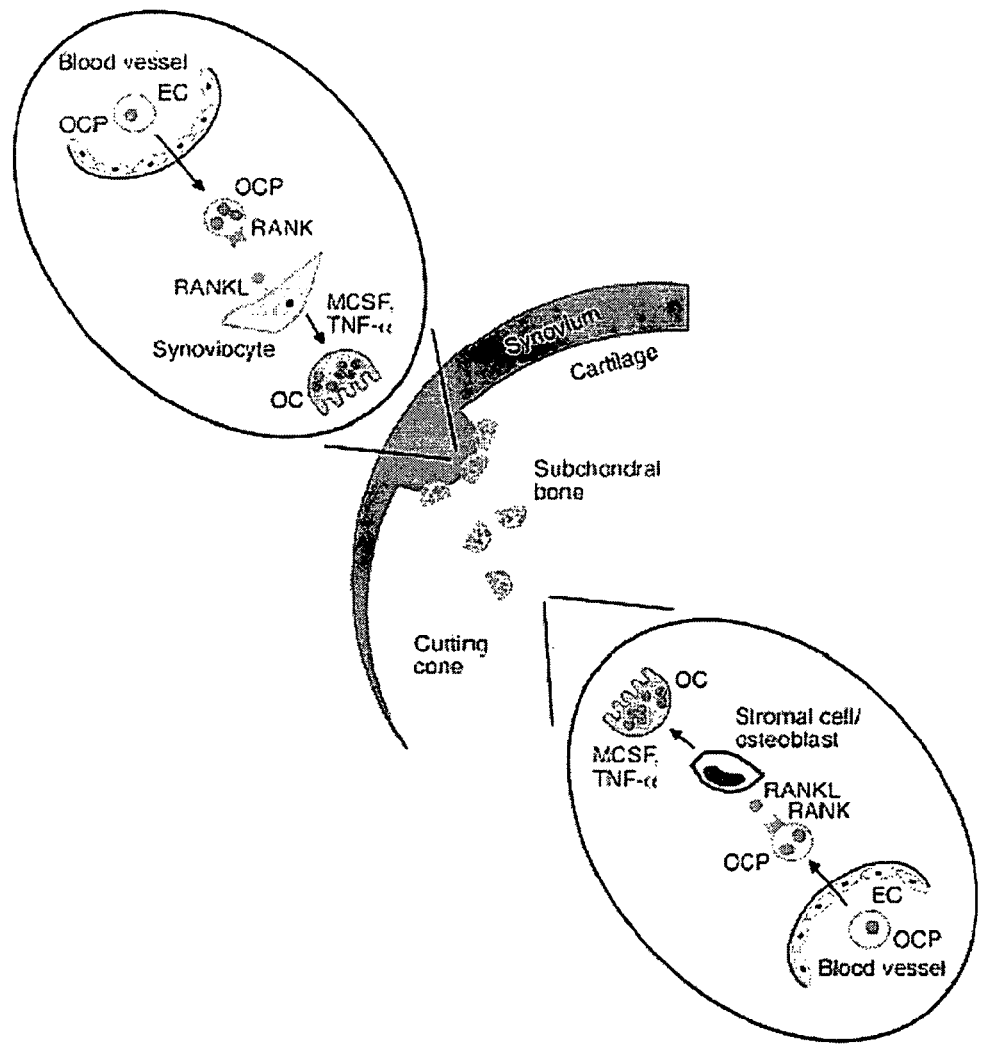

FIG. 7 shows a schematic model of osteolysis in the psoriatic joint. Extensive erosions observed in the PsA joint are mediated by a bi-directional attack on bone. OCP can enter the synovium and are induced to become osteoclasts by RANKL expressed by synoviocytes (outside-in). In parallel, OCP traverse endothelial cells in the subchondral bone and undergo osteoclastogenesis following RANKL stimulation from osteoblasts/stromal cells (inside-out).

FIG. 8 shows chronic systemic TNFα increases the osteoclast precursor frequency in spleen and blood. Splenocytes, blood cells, and adherent bone marrow cells from wild type (WT) or TNF-Tg mice were cultured with M-CSF and RANKL to determine their osteoclastogenic potential by TRAP assay (A, B); or with M-CSF in methylcellulose to determine their CFU-M colony-forming potential (C), as described in the Examples. The data are presented as the mean±SEM of 4 replicate samples (*p<0.005) from a representative mouse. Similar results were obtained with 2 additional pairs of wt and TNF-Tg mice.

Figure 9:
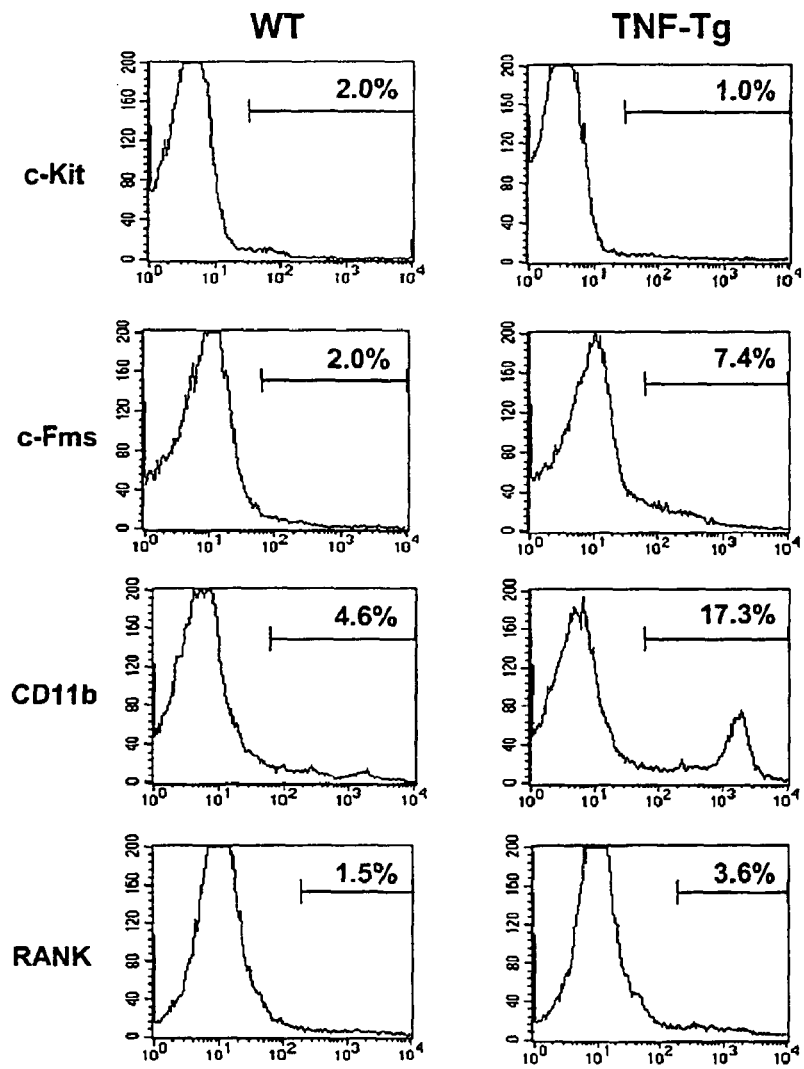

FIG. 9 shows that the CD11b+ population is markedly increased in the spleen of TNF-Tg mice. Splenocytes from WT or TNF-Tg mice were stained with fluorescent probes specific for c-Kit, c-Fms, CD11b, or RANK and analyzed by FACS, as described in the Examples. The data are presented as the percentage of cells that were positive for the indicated surface protein from representative animals. A total of 5 pairs of WT and TNF-Tg mice were examined with similar results.

FIG. 10 shows that all of the splenocytes with osteoclastogenic potential are in the $CD11b^{hi}$ population. Splenocytes from WT and TNF-Tg mice were stained with fluorescent antibodies specific for CD11b (A). The $CD11b^{hi}$ [R1], $CD11b^{lo}$ [R2], and $CD11b^{-}$ [R3] populations were sorted and cultured with M-CSF and RANKL, and their osteoclastogenic potential was determined by TRAP assay (B). The photographs show TRAP+ osteoclasts only formed from $CD11b^{hi}$ [R1] cells. The data are representative of three independent experiments. Statistical analysis of the distribution of CD11b$^{hi}$ splenocytes from 16 pairs of mice shows the significant increase in the TNF-Tg vs. control (C).

Figure 11:
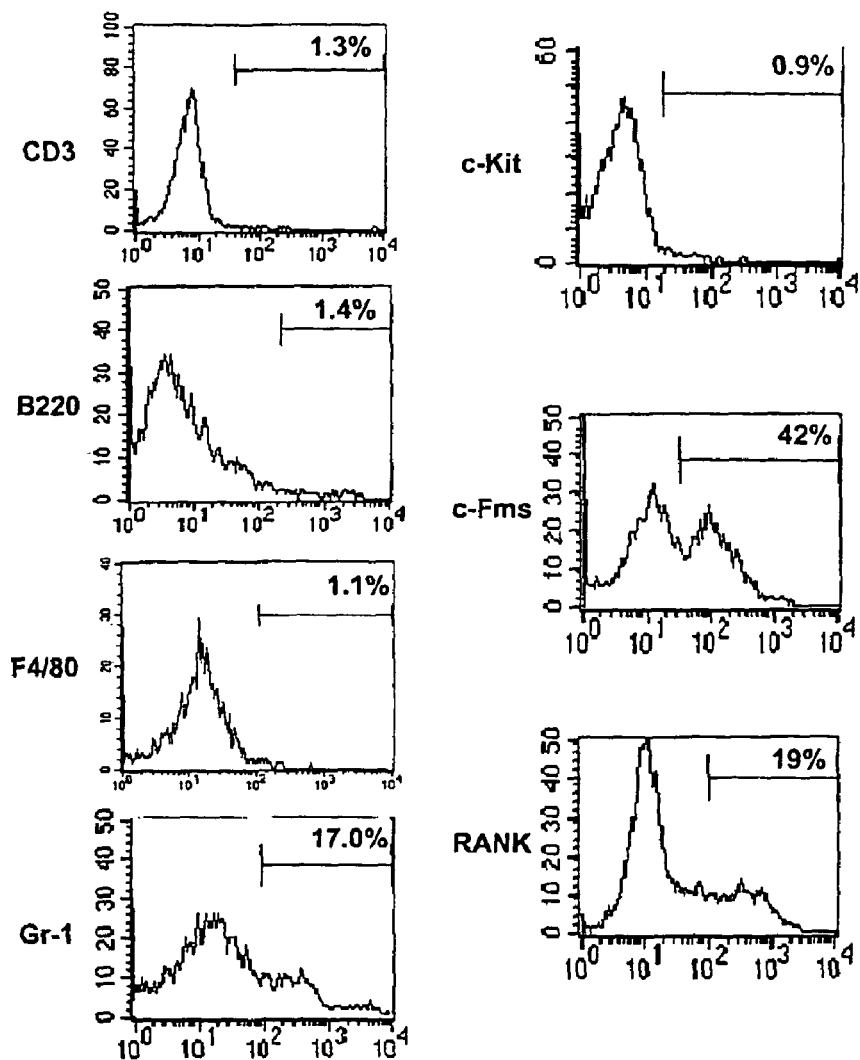

FIG. 11 shows the phenotypic characterization of the CD11b$^{hi}$ splenocyte population. Splenocytes from TNF-Tg mice were double-stained with anti-CD11b antibody in combination with probes for CD3, B220, F4/80, Gr-1, c-Kit, c-Fms, and RANK. Live CD11b$^{hi}$ cells were gated, and the histograms show the expression of the indicated markers in this population. The histograms are representative of three independent experiments.

Figure 12:
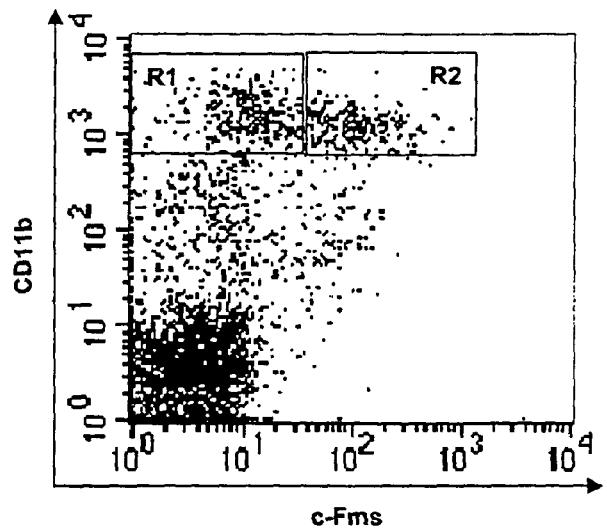
Figure 12:
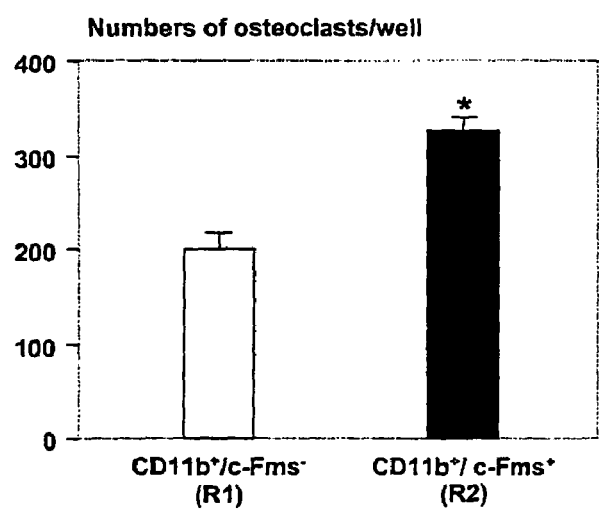

FIG. 12 shows that both CD11b$^{hi}$/c-Fms$^-$ and CD11b$^{hi}$/c-Fms$^+$ splenocytes form osteoclasts. Splenocytes from TNF-Tg mice were double-stained with antibodies for CD11b and c-Fms. CD11b$^{hi}$/c-Fms$^-$ and CD11b$^{hi}$/c-Fms$^+$ populations were sorted (A) and cultured as in FIG. 10, and the number of TRAP$^+$ osteoclasts was counted (B). The data are representative of two independent experiments.

Figure 13:
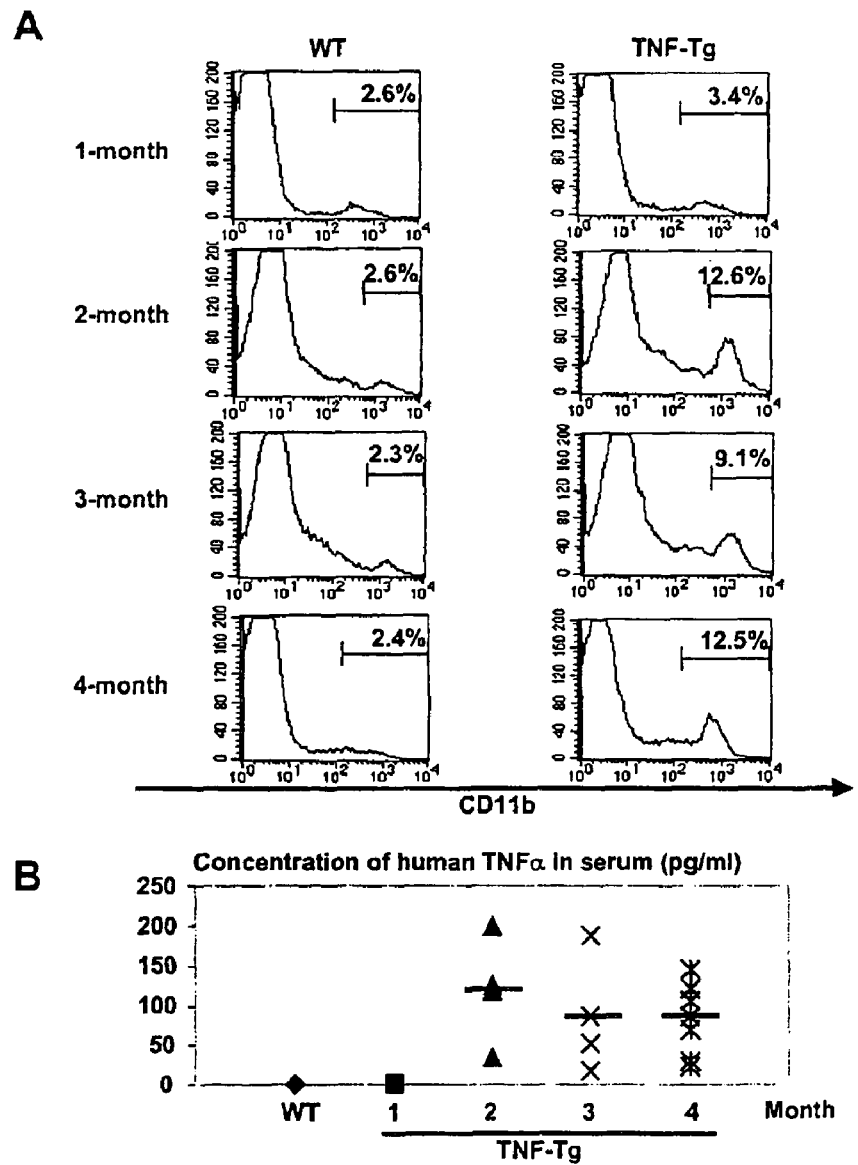

FIG. 13 shows the CD11b$^{hi}$ OCP frequency and serum human TNFα concentrations increase in TNF-Tg mice at 2-3 months of age. Splenocytes and blood were collected from TNF-Tg mice and their wt littermates at 1, 2, 3, and 4 months of age. The frequency of CD11b$^{hi}$ OCP in the spleen was determined by FACS (A). The concentration of human TNFα in the serum was analyzed by ELISA (B). The data from FACS are shown as representative animals (n>3 per group). No statistical differences were found in the frequency of CD11b$^{hi}$ OCP and the serum levels of human TNFα between 2, 3, and 4 months old TNF-Tg mice.

Figure 14:
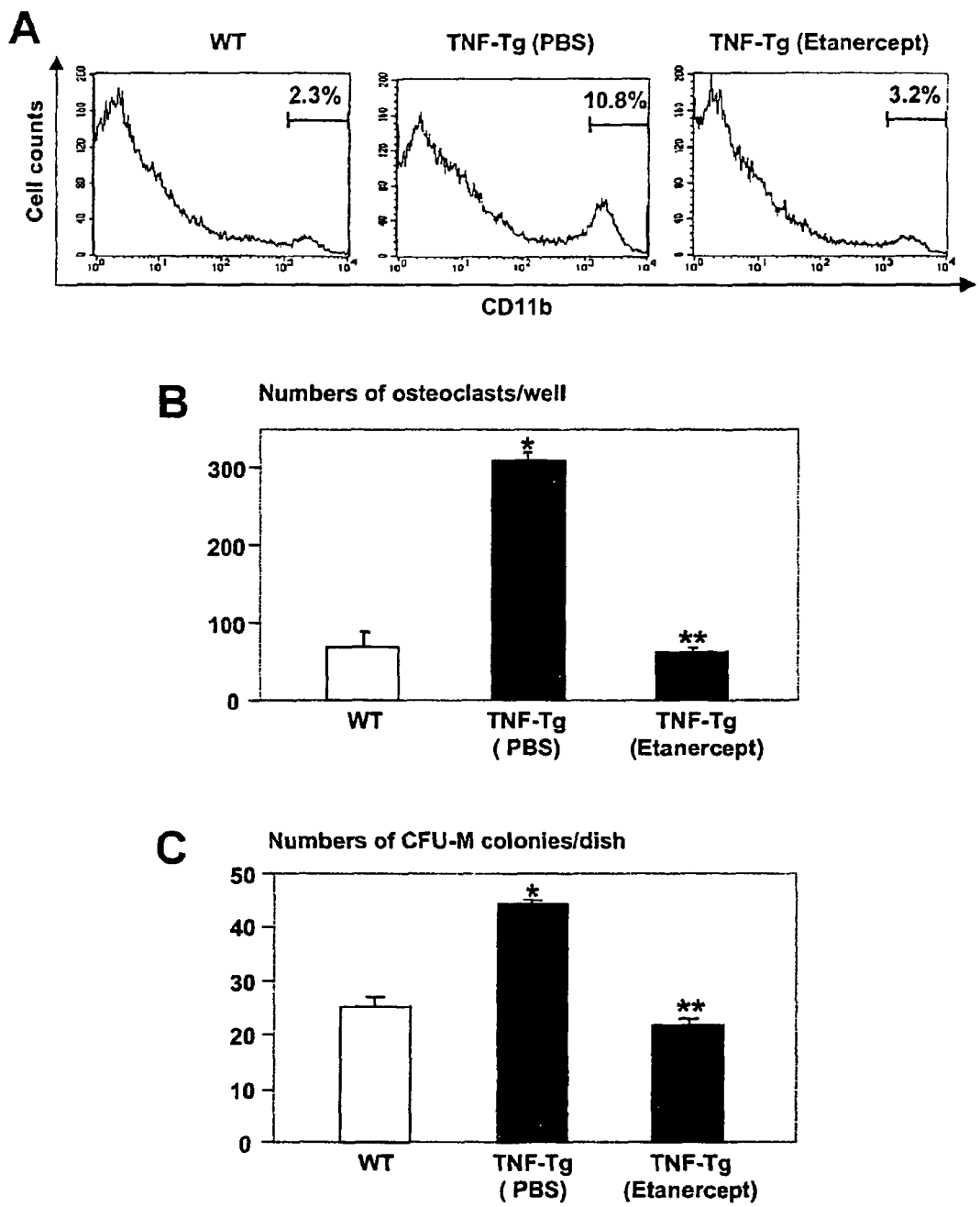

FIG. 14 shows that the increased CD11b$^{hi}$ osteoclast precursor frequency in TNF-Tg mice is reversible with anti-TNF therapy. TNF-Tg mice were treated with peritoneal injections of Enbrel® (etanercept) (10 mg/kg) or placebo twice a week for 2 weeks. Splenocytes were isolated from these mice and analyzed for CD11b expression by FACS (A), osteoclastogenic potential by TRAP (B), and CFU-M forming potential by colony assay (C). The data are shown as representative animals (A) or the mean±SEM of 4 replicate samples (*p<0.005 vs. WT, **p<0.01 vs. PBS) from a representative mouse (B and C)(n=3 per group). Similar results were obtained with 2 additional pairs of wt and TNF-Tg mice.

Figure 15:
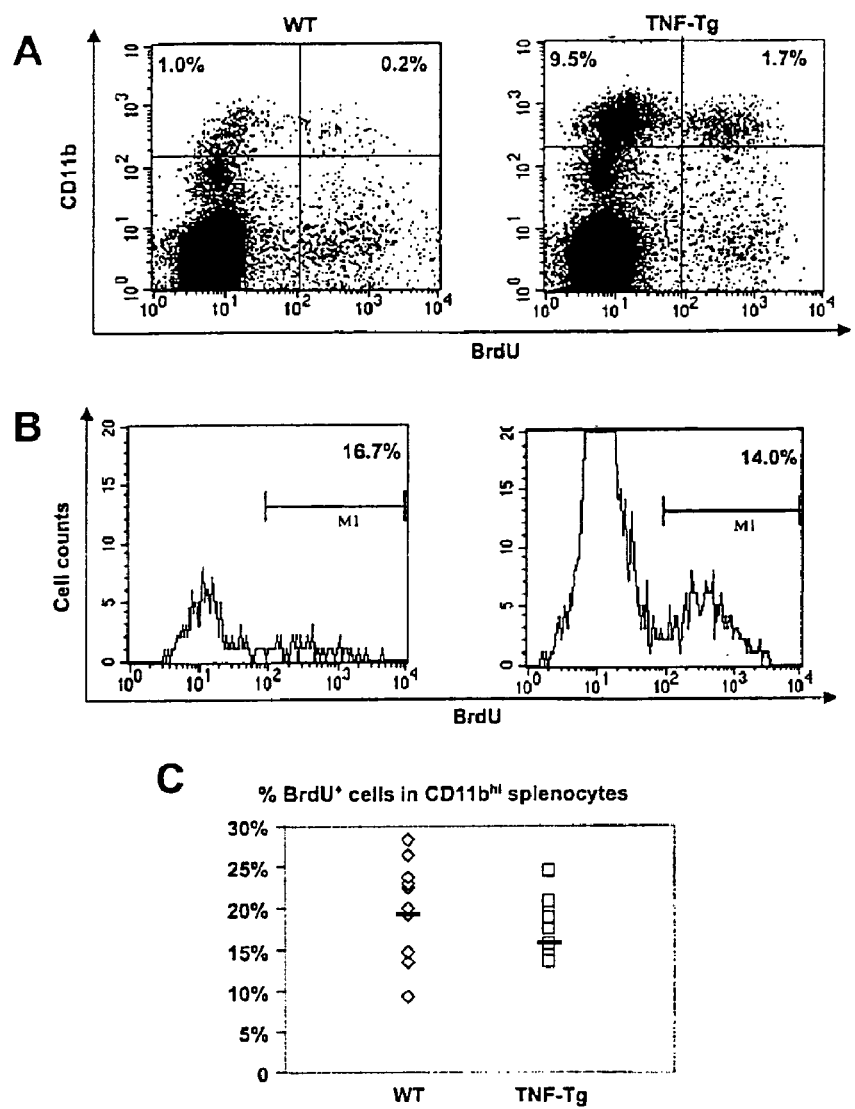

FIG. 15 shows Systemic TNFα does not effect proliferation of CD11bhi in vivo. TNF-Tg and wt mice were labeled with BrdU for 24 hr as described in Methods. Splenocytes were isolated, double stained with antibodies for CD11b and BrdU, and analyzed by FACS. The percentage of CD11bhi/BrdU+ cells is shown in dot plot (A). Live CD11bhi cells were gated and the histograms showed the percentage of BrdU+ cells in this population (B). Statistical analysis of 10 pairs of mice demonstrates no significant difference in the percentage of BrdU+ cells in the CD11bhi population of TNF-Tg and wt mice (C).

Figure 16:
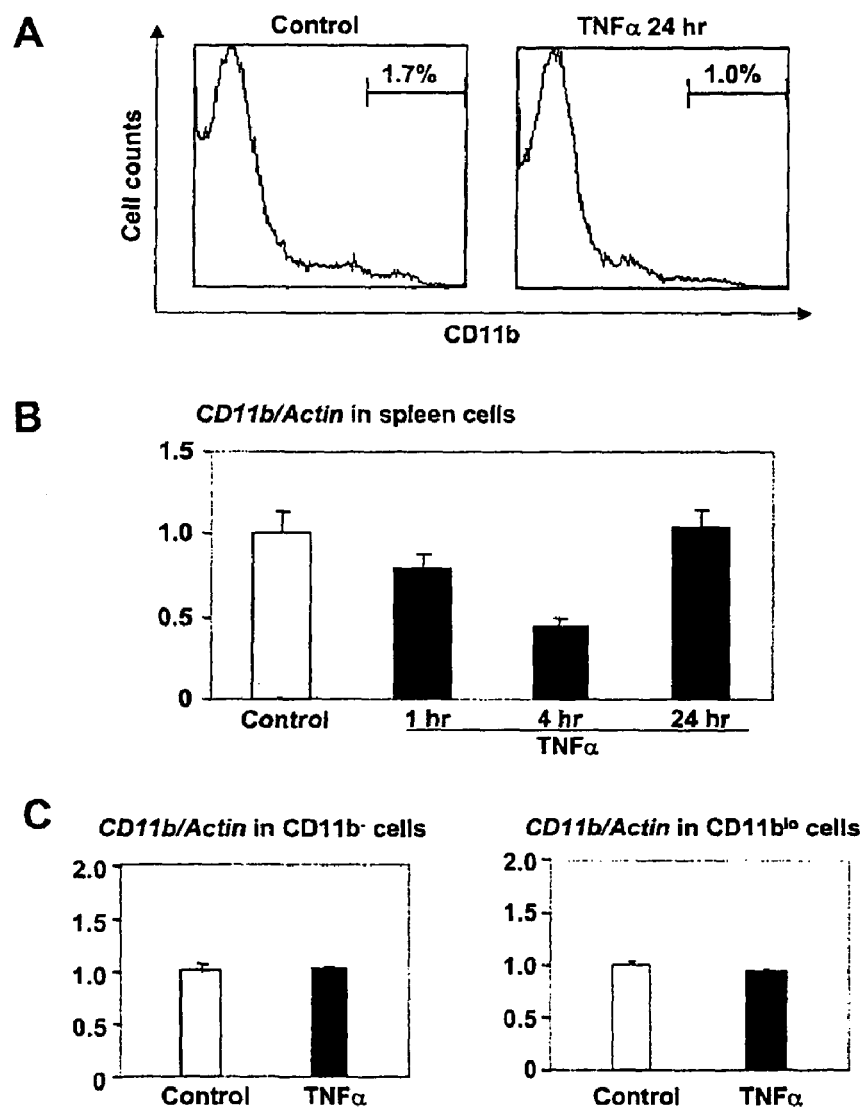

FIG. 16 shows that TNFα does not induce the differentiation of CD11b$^{-/lo}$ to CD11b$^{hi}$ splenocytes in vitro. Wild type spleen cells were treated with TNFα (10 ng/ml) for 24 hr and subjected to FACS analysis using anti-CD11b antibody, and the percentage of CD11b$^{hi}$ cells is shown (A). Wild type total (B), sorted CD11b- and CD11b$^{lo}$ (C) splenocytes were treated with TNFα (10 ng/ml), and total RNA was extracted at various time points and analyzed by real-time PCR using CD11b specific primers. The data are representative of two independent experiments.

Figure 17:
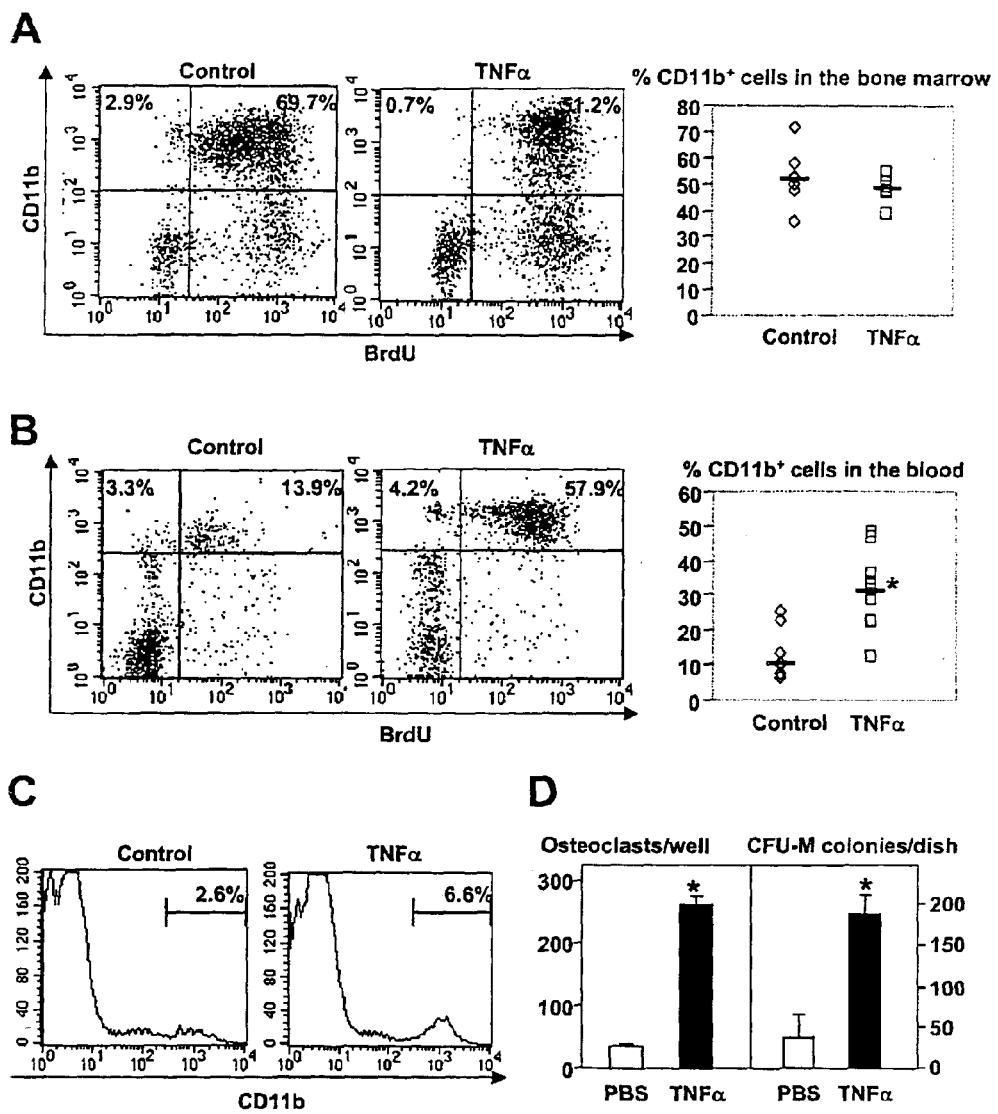

FIG. 17 shows that TNFα stimulates the release of CD11b$^+$ osteoclast precursors from the bone marrow to the periphery. (A-B) Eight-week-old wt mice were labeled with BrdU in vivo for 3 days and then challenged with TNFα (1 μg/mouse, i.p) for 4 hr. Bone marrow cells (A) and blood cells (B) were collected, stained with antibodies for BrdU and CD11b, and analyzed by FACS. The percentage of CD11b$^+$/BrdU$^+$ cells is shown on the upper-right corners, and that of CD11b$^+$/BrdU$^-$ cells is in the upper-left corners. (C-D) Wild type mice were given intraperitoneal injections of PBS or TNFα (1 μg/mouse), 4× daily for 3 days. Splenocytes were analyzed for CD11b expression by FACS(C), assessed for their osteoclastogenic potential by TRAP assay and CFU-M forming potential by colony assay (D). The data are presented as the mean±SEM of 4 replicate samples (*p<0.005) from a representative mouse. Similar data were obtained from 2 additional mice.

Figure 18:
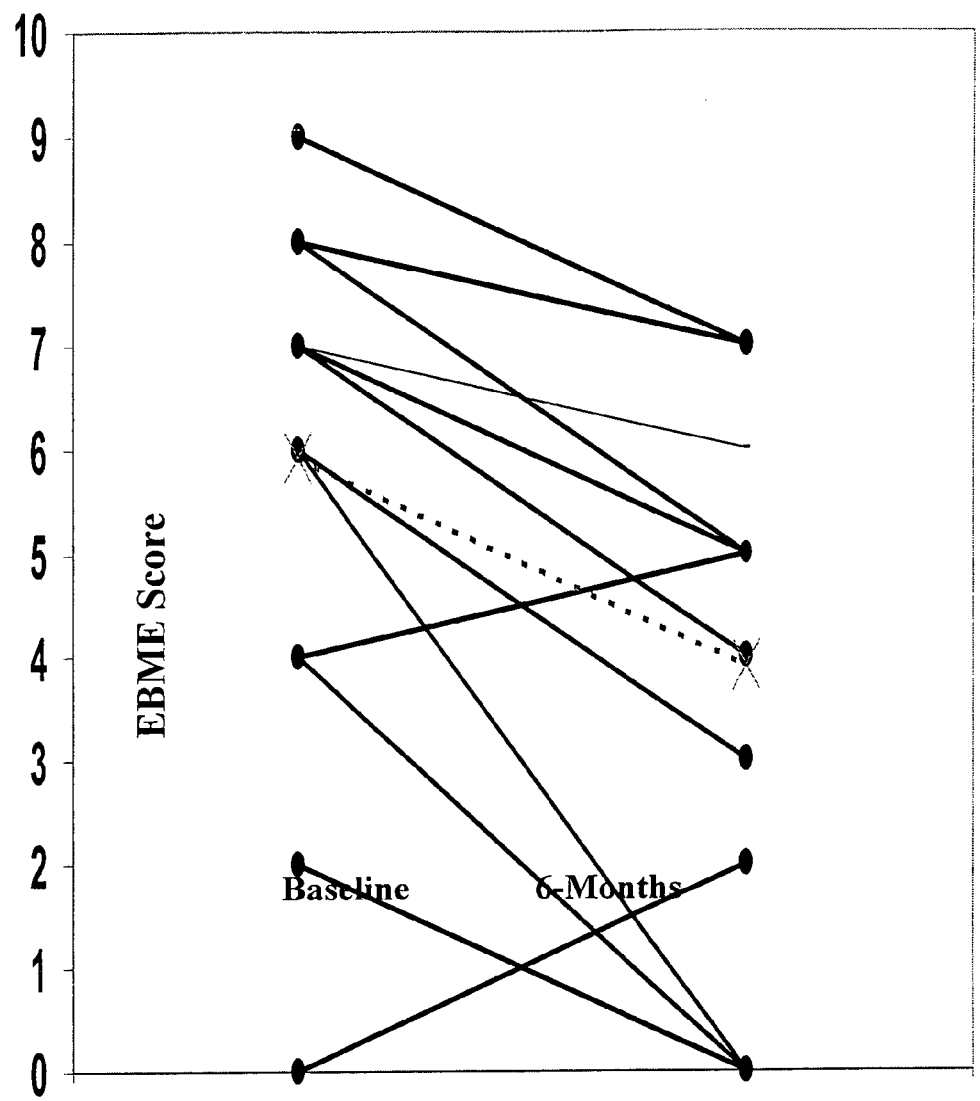

FIG. 18 shows that Enbrel® (etanercept) reduces bone marrow edema in PsA. Enhanced bone marrow edema (EBME) was determined by Gd-enhanced fat suppressed MRI in 13 of 20 patients, scored by 2 independent radiologists on a 0-9 point scale. EMBE was assessed at screening (Baseline) and again following 6 months of Enbrel® etanercept therapy. The means are illustrated by the X. Improvement was significant (p≦0.002). The change in EBME correlated with the decrease in OCP; R2=0.26.

Figure 19:
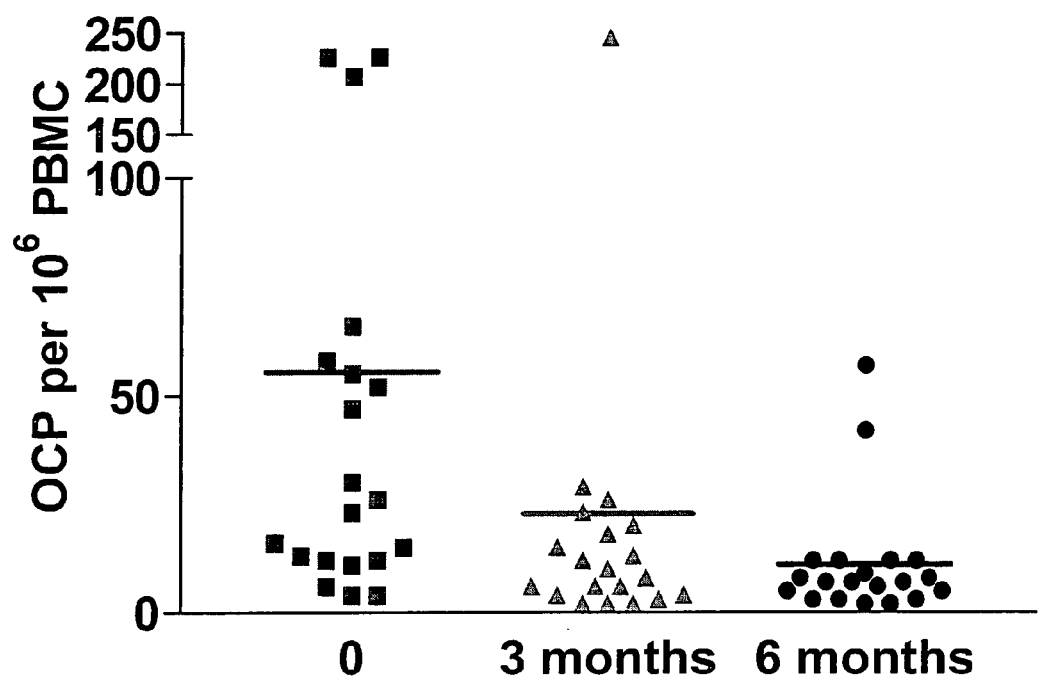

FIG. 19 shows EBME as determined by Gd-enhanced fat suppressed MRI in 13 of 20 patients, scored by 2 independent radiologists on a 0-9 point scale. EMBE was assessed at screening and again following 6 months of etanercept therapy. The means are illustrated by the X. Improvement was significant (p≦0.002). The change in EBME correlated with the decrease in OCP; R2=0.26.

Figure 20:
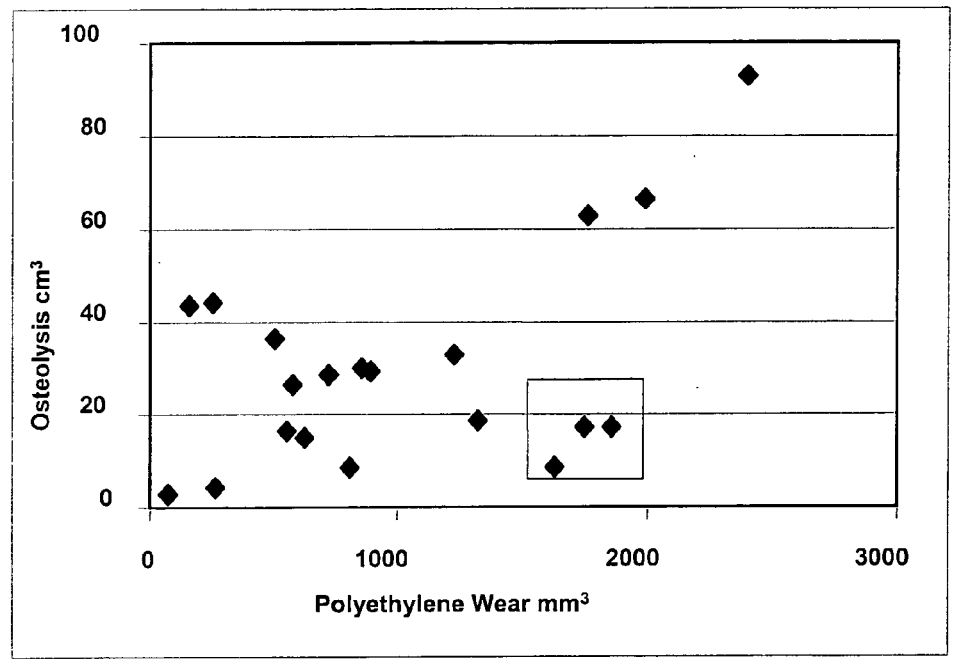

FIG. 20 shows that polyethylene wear correlates with peri-acetabular osteolysis. The osteolytic volume (in cm3) is plotted as a function of the volume of polyethylene wear (in mm3) for 20 patients with peri-acetabular osteolysis of an uncemented cup (C). Of note are 3 patients that are resistant to osteolysis (box).

Figure 21A:
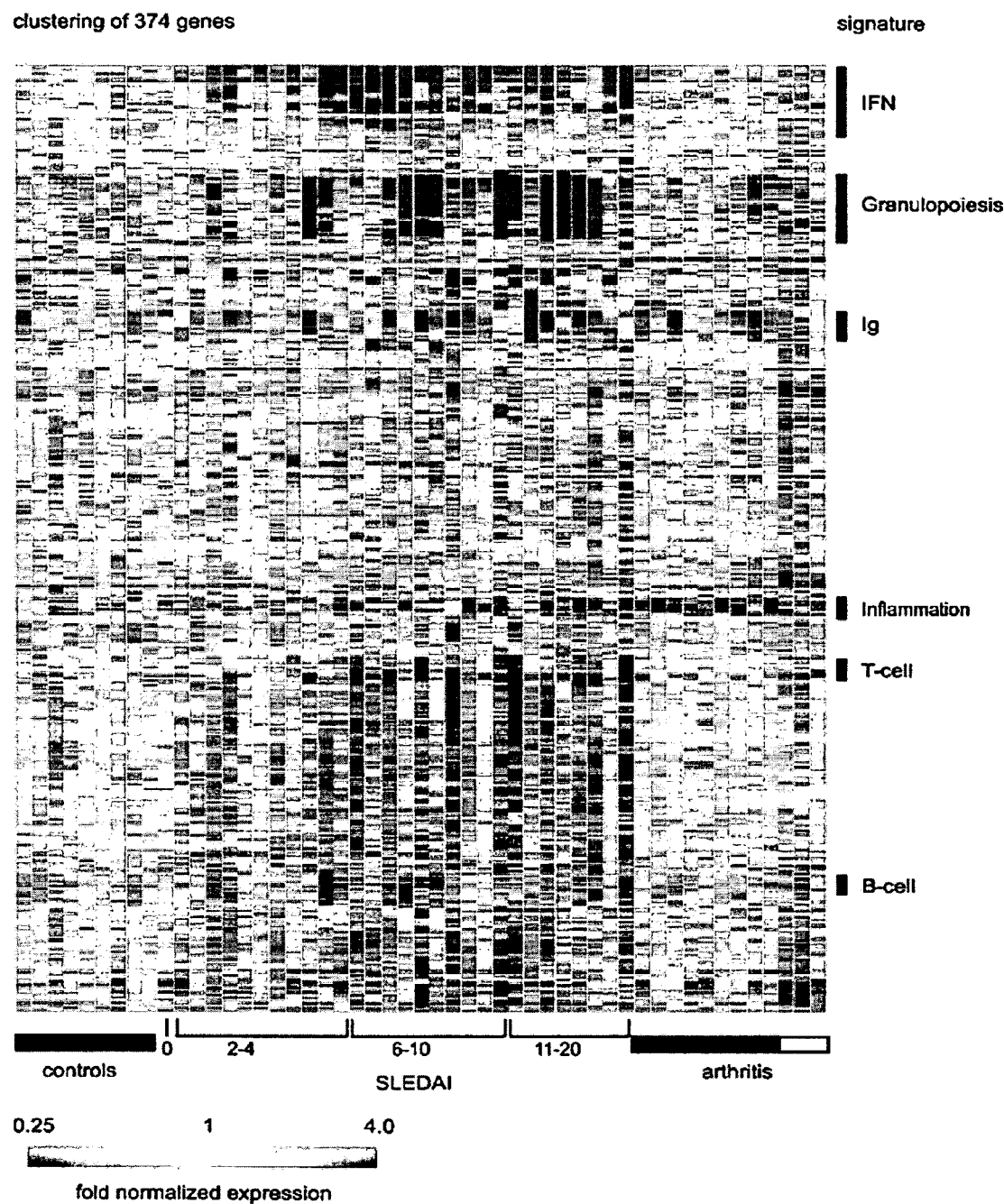
Figure 21B:
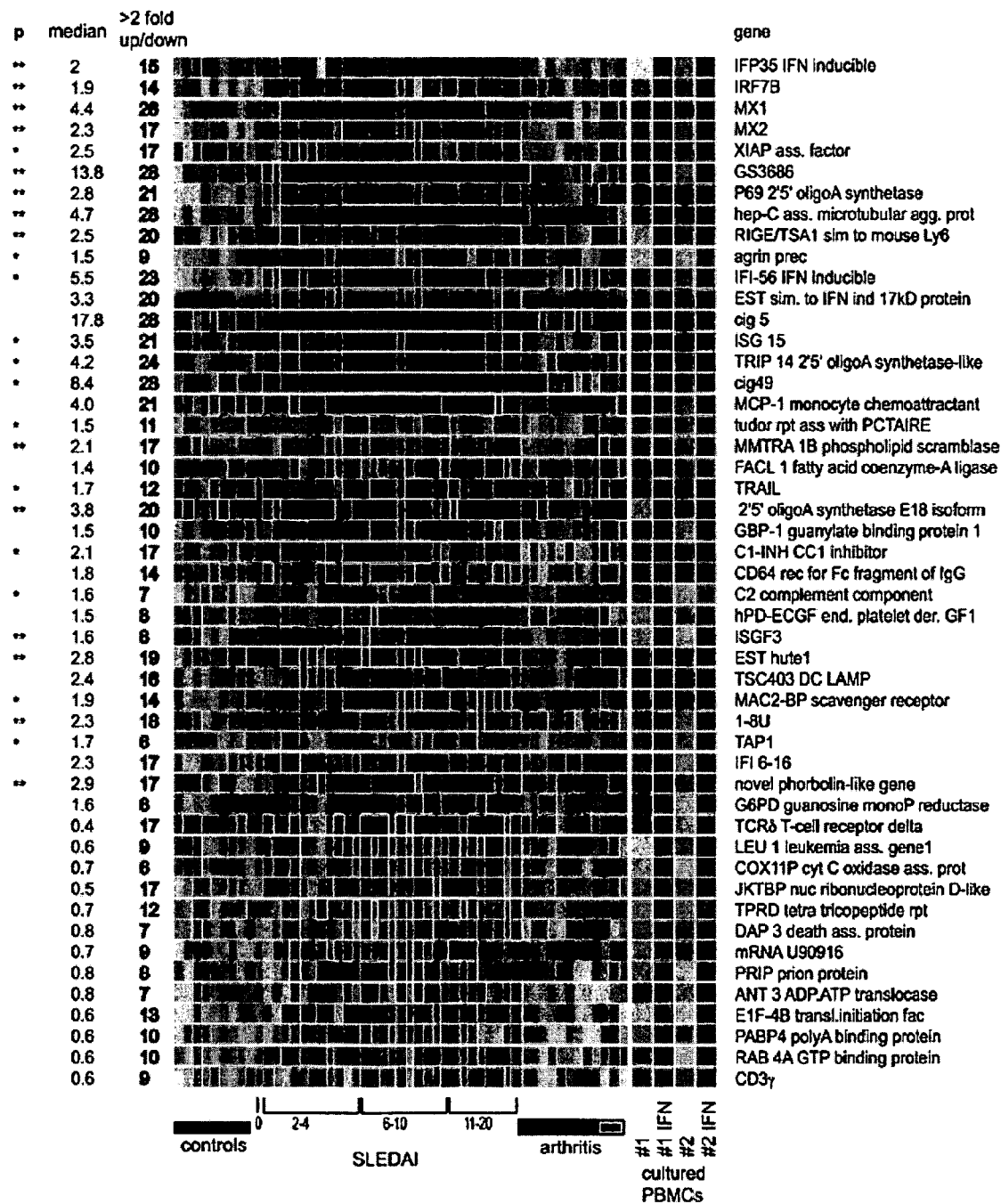

FIG. 21 shows a SLE-TNF transcriptome. (A) Hierarchical clustering of gene expression data by blood leukocytes of 9 healthy children, 30 with SLE, and 12 with juvenile chronic arthritis including 3 systemic arthritis. The SLE patients have been ranked according to their SLEDAI at time of blood draw. Each row represents a separate gene and each column a separate patient. 374 transcript sequences have been selected which were differentially expressed in SLE by comparison to healthy patients. The normalized expression index for each transcript sequence (rows) in each sample (columns) is indicated by a color code. Gray, light gray, and dark gray squares indicate that expression of the gene is greater than, equal to or less than the mean level of expression across 9 healthy controls. The scale extends from fluorescence ratios of 0.25 to 4.0. (B) Active SLE patients leukocytes display 36 IFN-up-regulated and 13 down-regulated transcript sequences. The same genes are altered in healthy PBMCs cultured in vitro with IFN. Median expression and the number of patients who display more than twofold increase in gene expression. ** Significant after Bonferroni correction, * significant after Benjamini and Hochberg correction. (C) Extinction of IFN signature after steroid infusion. Analysis of PBMCs from 3 patients (#30, 25, and 5, see online Table S1) before and after (1-4 d) treatment with high dose intravenous GC (1 g/day for 3 d). All patients show down-regulation of IFN-regulated genes. P values on the right indicate significance of the gene expression level before and after GC (paired t test).

Figure 22:
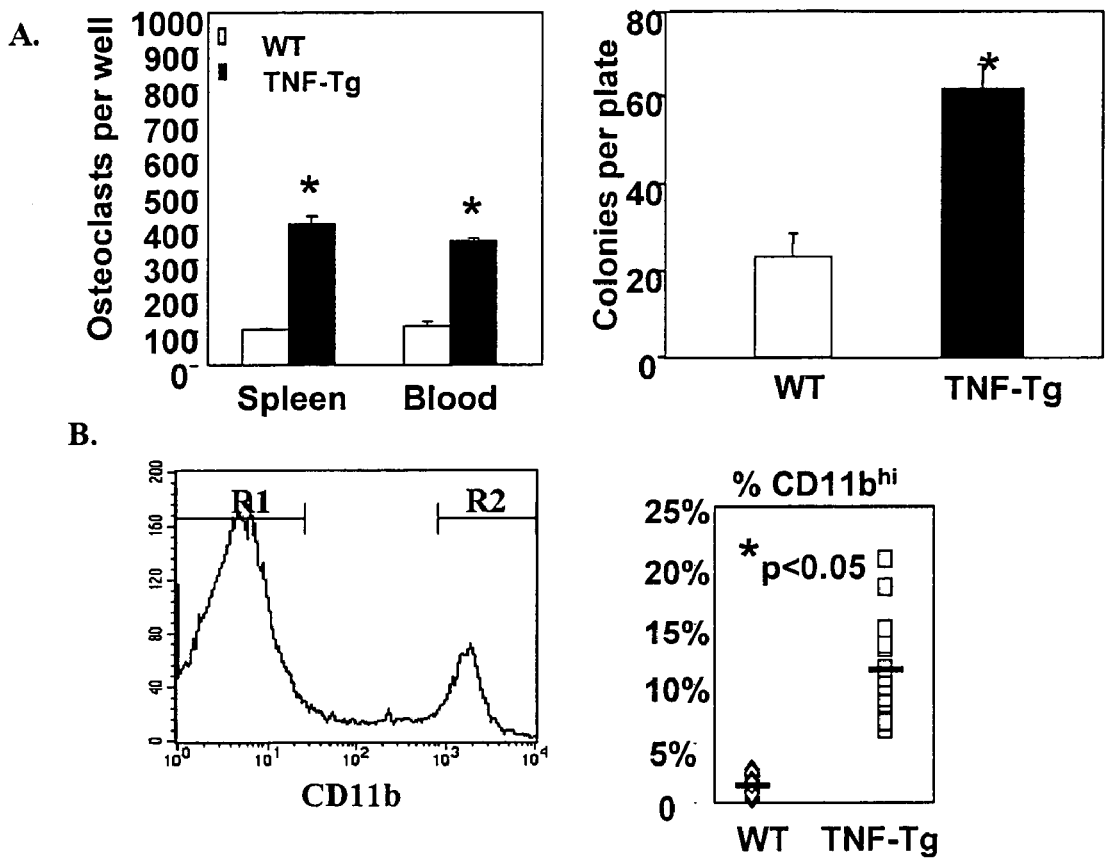

FIG. 22 shows systemic TNFα increases CD11b+ osteoclast progenitors in spleen and blood. (A) Splenocytes and PBMC from five hTNF-Tg mice and their wild-type littermate controls were cultured for 5 days in 10 ng/ml M-CSF and 100 ng/ml RANKL, then fixed and stained for TRAP. The number of TRAP+ multinucleated cells per well was determined and the means±SEM are presented (*p<0.005). (B) To phenotype these OCP FACS analysis was performed with a variety of surface markers. The most reliable proved to be CD11b as all of the OCP are in the CD11bhi population, as determined by cell sorting followed by TRAP osteoclastogenesis assay, and TNF-Tg splenocytes have a significant increase in this population.

Figure 23:
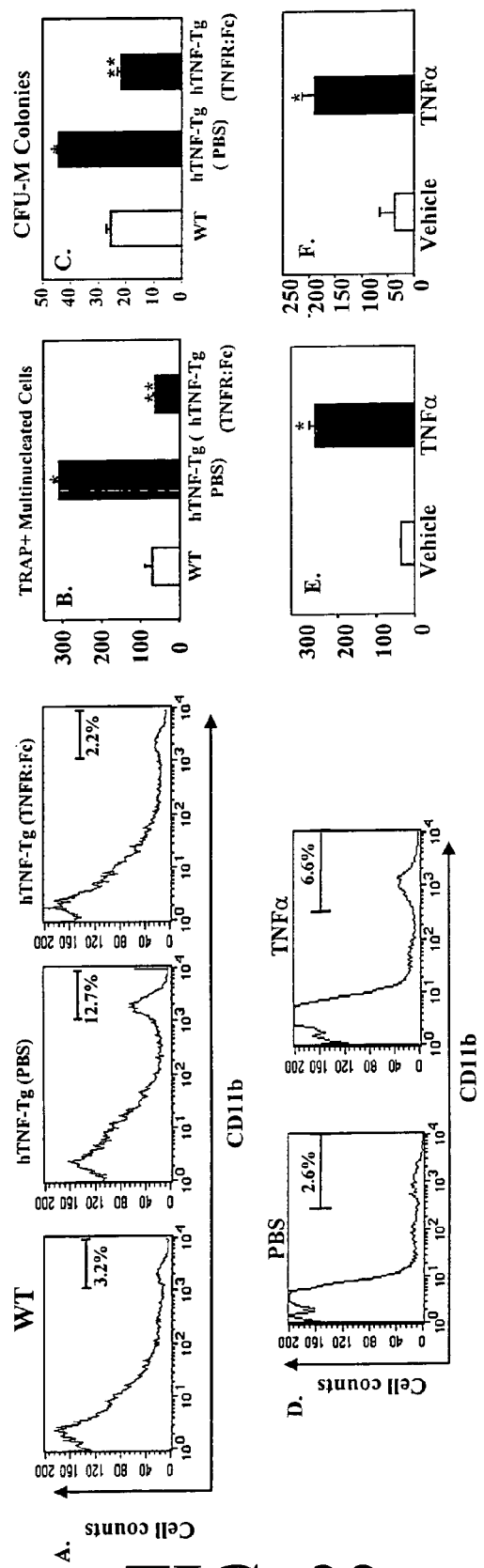

FIG. 23 shows that TNFα disregulation leads to an increase in CD11b+ osteoclast progenitors that is reversible with anti-TNF therapy. (A-C) hTNF-Tg mice were treated with 10 mg/kg of Enbrel® (etanercept) or placebo i.p. twice a week for 2-week. Afterwards, splenocytes were isolated from these mice, together with untreated WT controls, and analyzed for (A) CD11b expression by FACS, (B) osteoclastogenic potential by TRAP assay, and (C)CFU-γM colony forming potential by methocellulose plating. (A) Data from a representative mouse (n=3). (B and C) The data are presented as the mean±SEM of 4 replicate samples (*$p<0.005$ vs. WT, **$p<0.01$ vs. PBS) from a representative mouse. Similar findings were also obtained from wild-type mice injected with 10 ug of TNF for three days (D-F).

Figure 24:
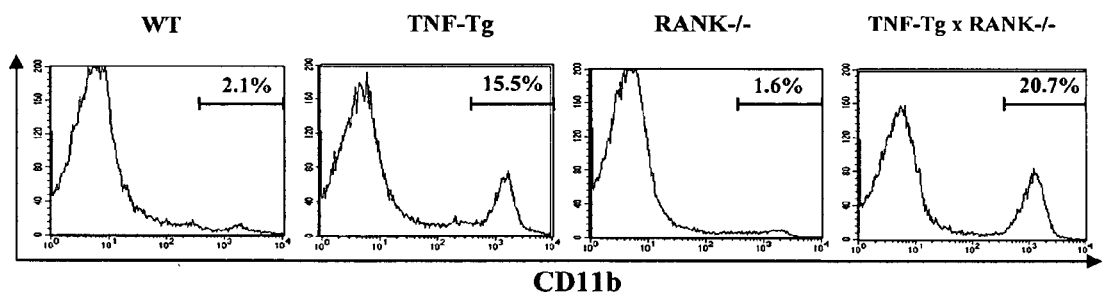

FIG. 24 shows that TNF-Tg mice in a RANK null background have osteopetrosis due to the absence of mature osteoclasts but still have an increase in OCP. Four-month-old TNF-Tg×RANK−/− mice were obtained by crossing TNF-Tg and RANK knockout mice. Splenocytes from these mice were stained for CD11b and analyzed by FACS. The data are presented as representative animals (n=3 per group).

Figure 25:
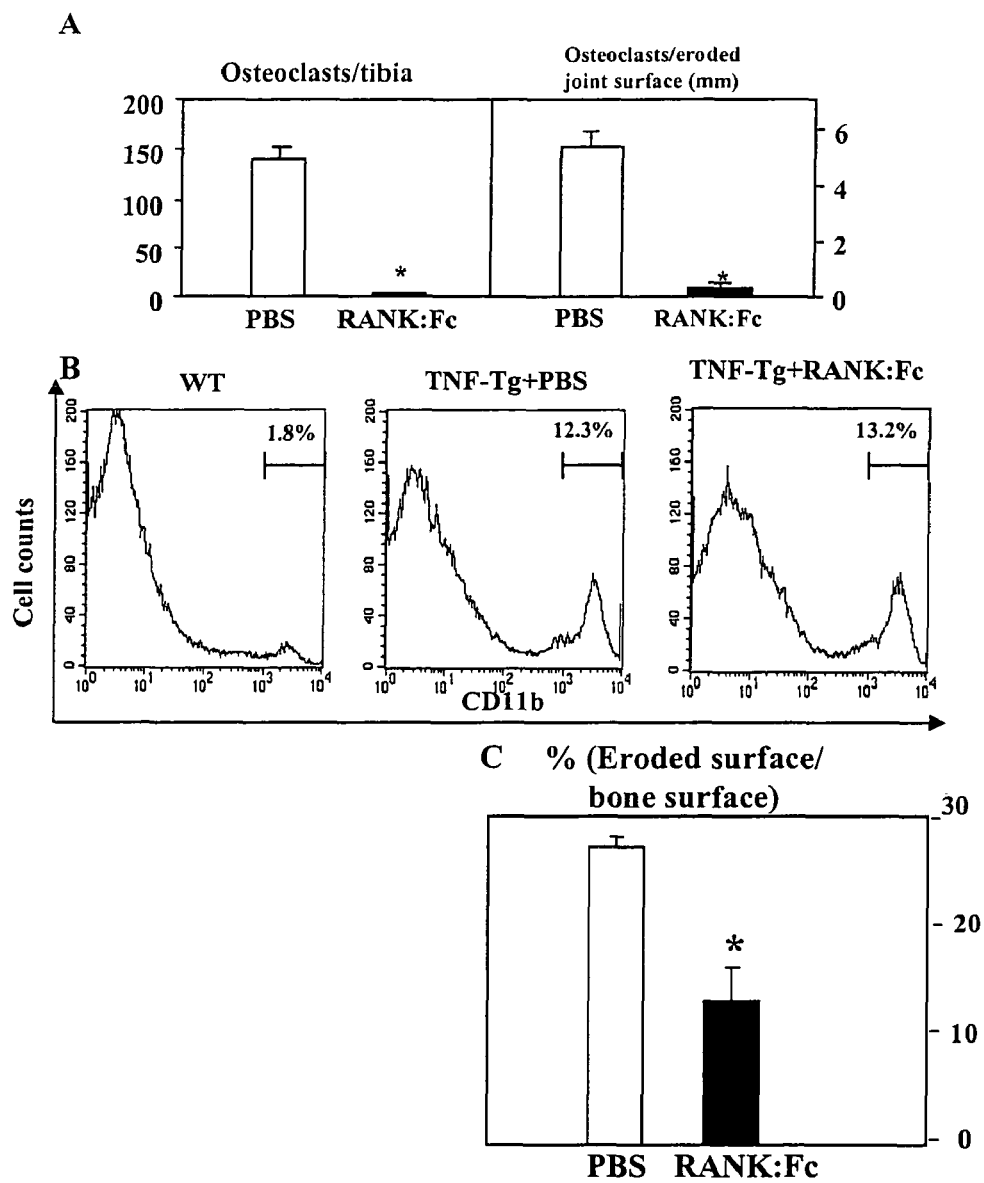

FIG. 25 shows that a high dose RANK blockade effectively reduces osteoclast numbers and prevents erosive arthritis in hTNF-Tg mice, but does not affect OCP frequency. 4-month-old hTNF-Tg mice with established arthritis were treated with 10 mg/kg of RANK:Fc or placebo i.p. daily for 2-week. After sacrifice the knee joints were prepared for histology, stained for TRAP activity and counter stained with hematoxylin/fast-green. Osteoclast numbers in the tibia (remodeling) and at the pannus-bone junction (erosion) of the hTNF-Tg mice were quantified by histomorphometry (A). A similar analysis was performed with H&E and TRAP stained sections to evaluate bone erosion, which was done by dividing the eroded surface in mm by the total surface of the proximal tibia and distal femur (C). The spleens of these mice were also taken at the time of sacrifice and CD11b expression was determined by FACS (B). The data are presented as a representative animal or the mean±SEM (*$p<0.01$) of the group (n=5).

Figure 26:
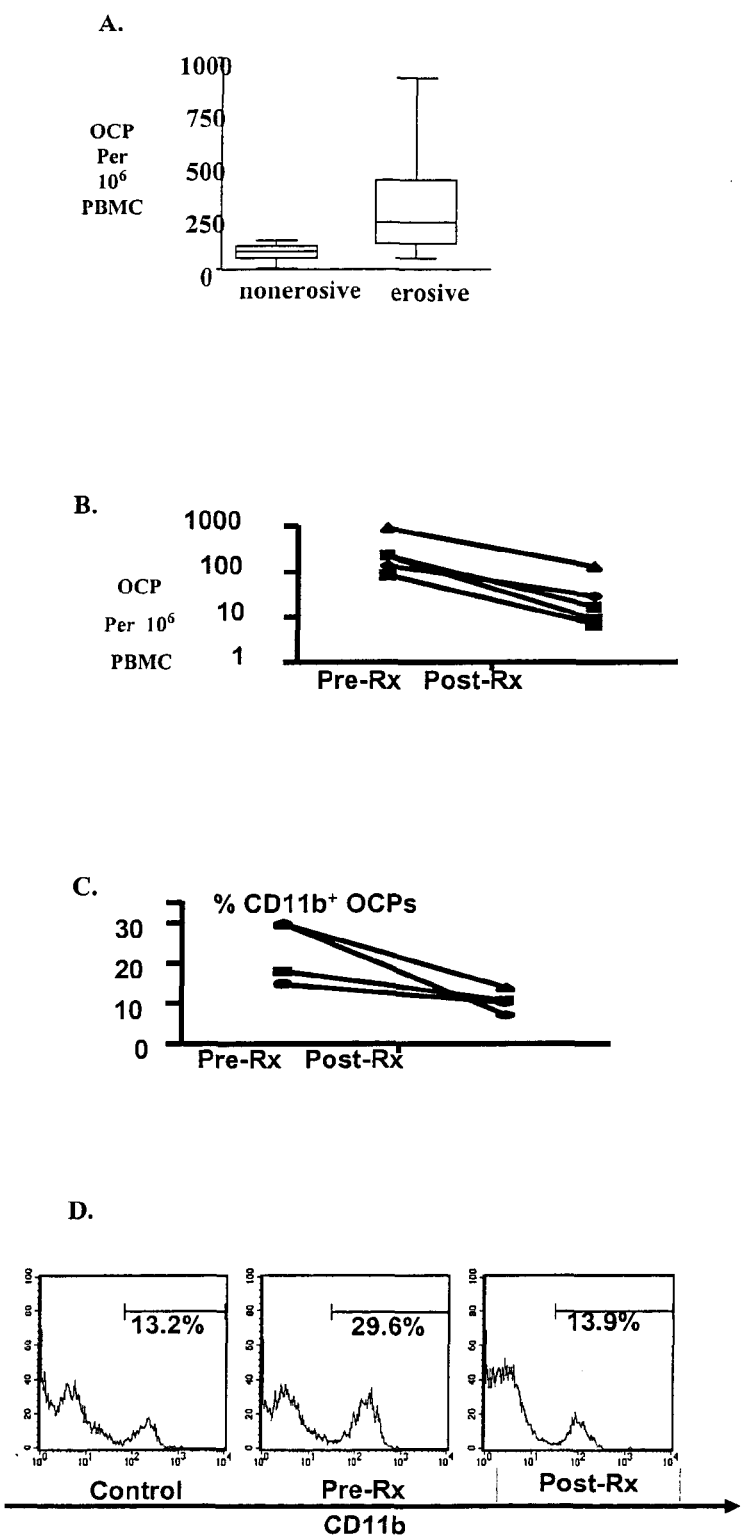

FIG. 26 shows TNF-induced OCP in PsA. PBMC from a healthy donor or PsA patient were culture with and without M-CSF and RANKL on glass slides or on cortical bone wafers. After the culture period the slides were stained for TRAP to visualize multinucleated osteoclasts, and the bone wafers were stained with toludine blue to visualize resorption lacunae. (B-D) PBMC from PsA patients before and 12 weeks after etancercept therapy were assayed for OCP frequency via TRAP osteoclastogenesis assay (A) or CD11b expression by FACS(C & D).

Figure 27:
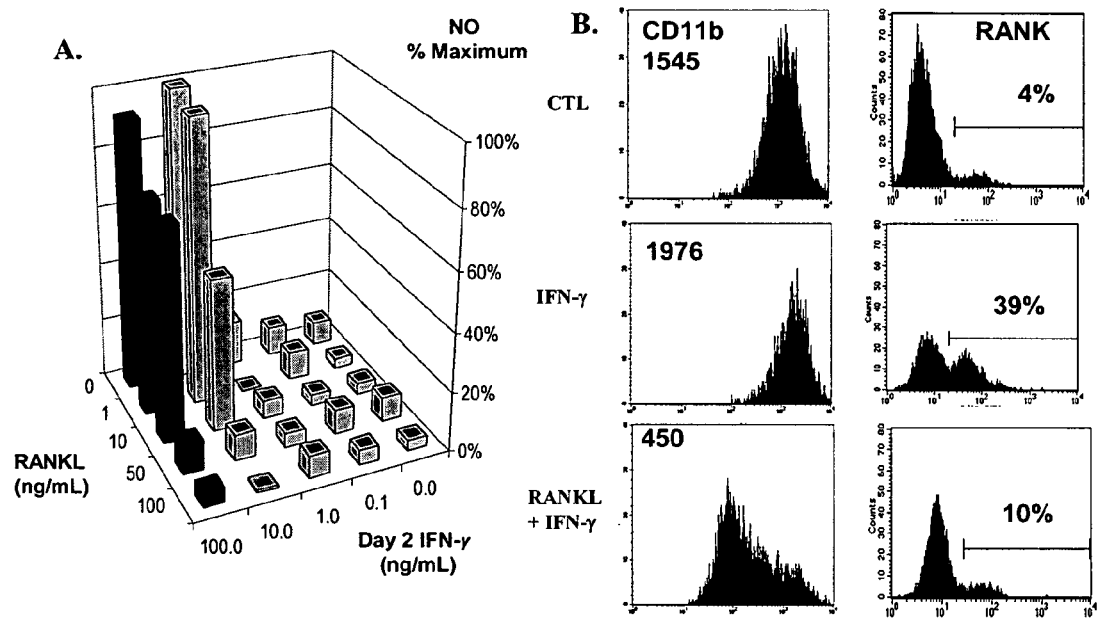

FIG. 27 shows that RANKL priming inhibits macrophage activation. (A) RAW cells were grown for 2 days in the indicated dose of RANKL and then stimulated with the indicated does of IFN-γ for 24 hr. The culture supernatants were then analyzed for NO via Greiss reaction. (B) RAW cells were grown in media for 3 days (CTL), media for 2 days and stimulated with IFN-γ for 24 hr (IFN-γ), or RANKL for 2 days and stimulated with IFN-γ for 24 hr (RANKL+IFN-γ) and analyzed for CD11b (mean fluorescence intensity and RANK (% pos.) expression by FACS.

Figure 28:
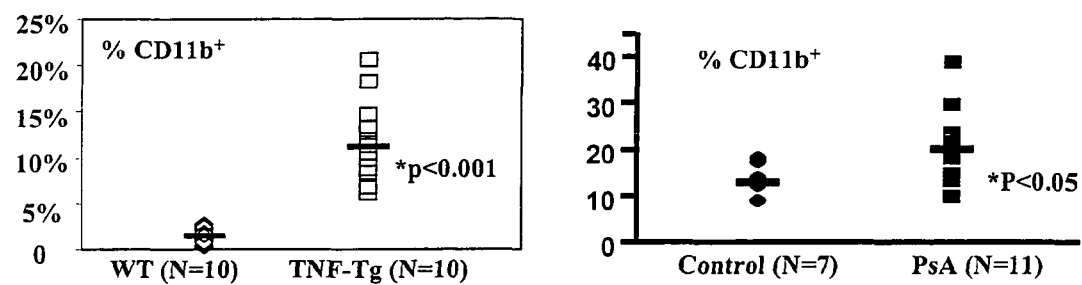

FIG. 28 shows TNF-induced OCP in mice and man. Splenocytes from TNF-Tg and non-Tg littermate controls (WT) mice (left) and PBMC from healthy donors and PsA patients (right) were analyzed for CD11b expression by FACS.

Figure 29:
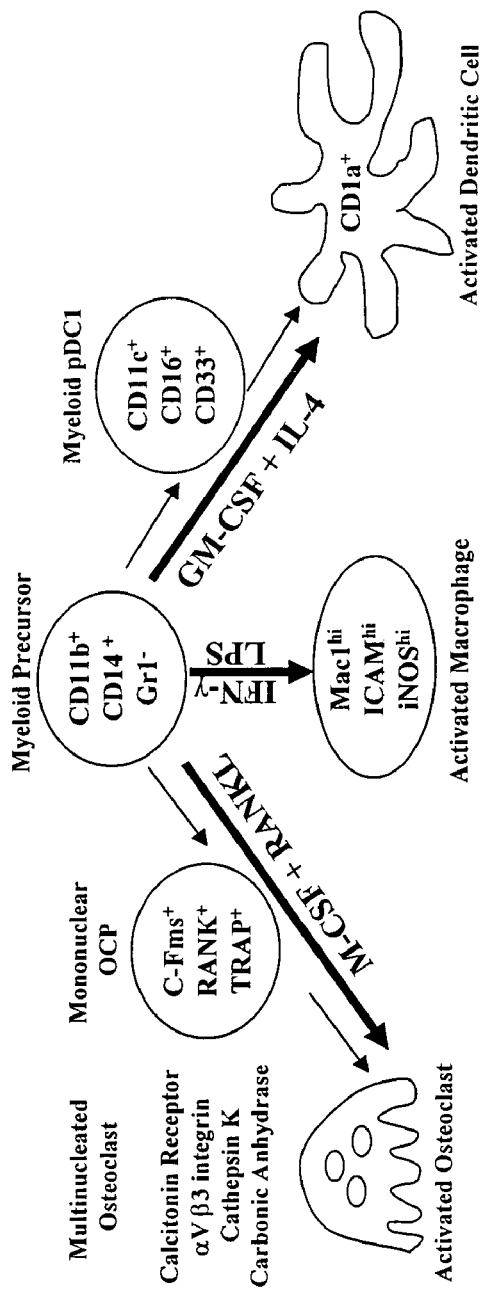

FIG. 29 shows a schematic model of mutually-exclusive osteoclast, macrophage and dendritic cell differentiation. The central hypothesis of this program is that a chronic-systemic innate immune response drive by the TNF/IFN axis dominantly regulates the erosive phenotype of inflammatory arthritis by altering myelopoiesis towards osteoclast and dendritic cell differentiation in a mutually exclusive fashion. This process starts following the release of an early Myeloid Precursor that has left the granulocyte lineage (Grl−), and is released from the bone marrow into the blood. Following entry into the end-organ this cell will receive a signal to terminally differentiate into an osteoclast, activated macrophage, or a dendritic cell in a mutually exclusive fashion.

Figure 30A:
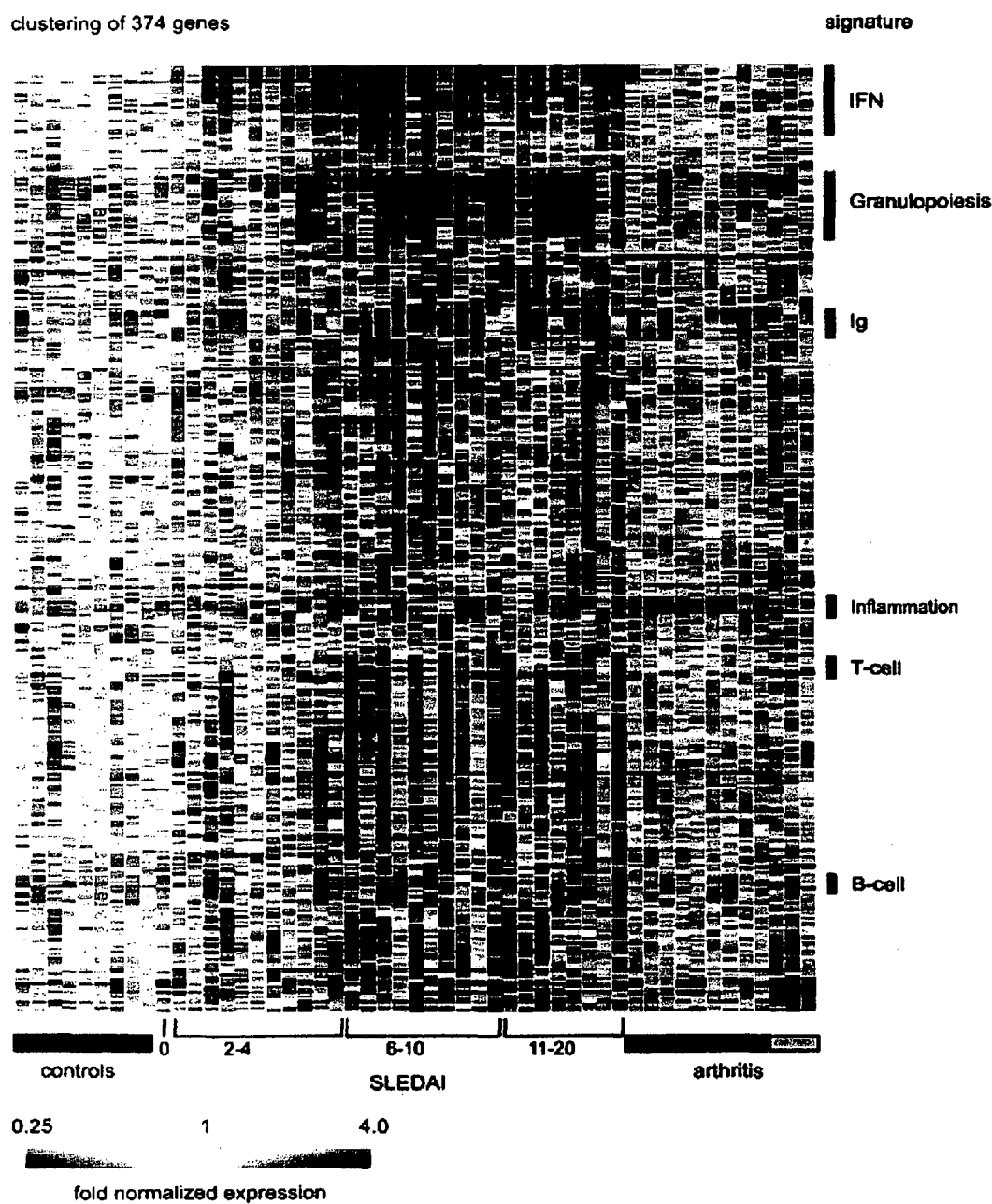
Figure 30B:
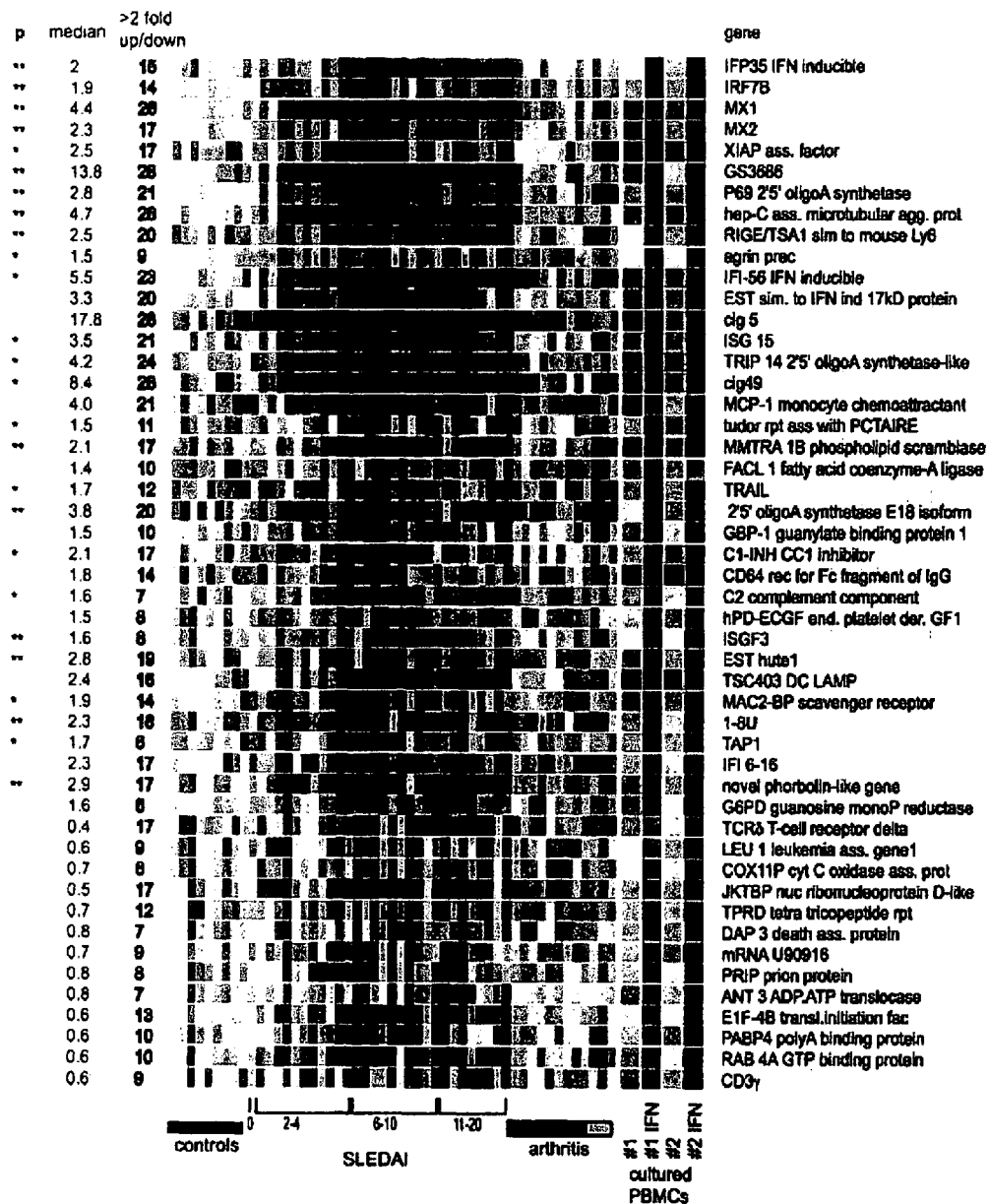
Figure 30C:
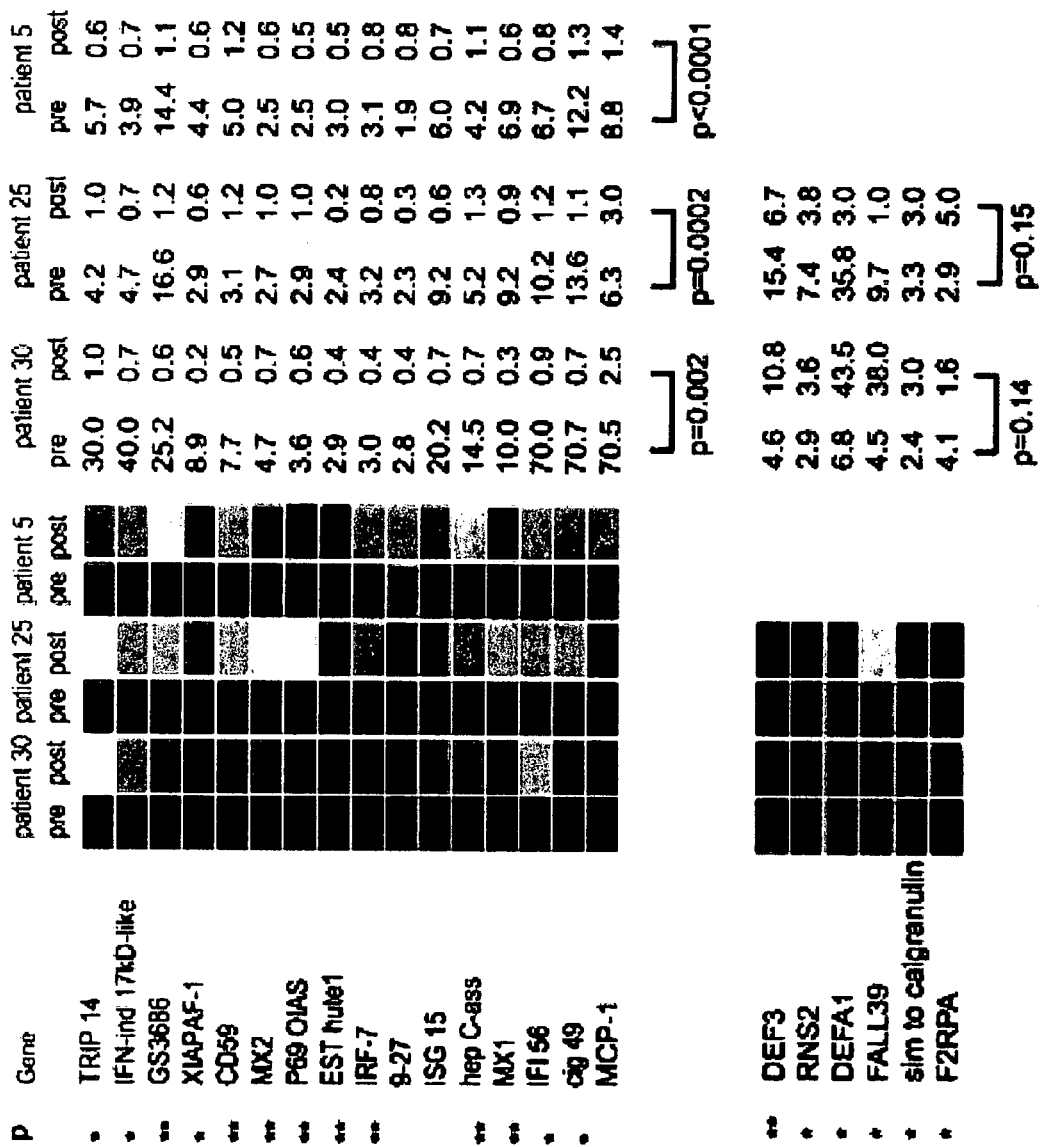

FIG. 30 shows a SLE-TNF transcriptome. (A) Hierarchical clustering of gene expression data by blood leukocytes of 9 healthy children, 30 with SLE, and 12 with juvenile chronic arthritis including 3 systemic arthritis. The SLE patients have been ranked according to their SLEDAI at time of blood draw. Each row represents a separate gene and each column a separate patient. 374 transcript sequences have been selected which were differentially expressed in SLE by comparison to healthy patients. The normalized expression index for each transcript sequence (rows) in each sample (columns) is indicated by a color code. Red, yellow, and blue squares indicate that expression of the gene is greater than, equal to or less than the mean level of expression across 9 healthy controls. The scale extends from fluorescence ratios of 0.25 to 4.0. (B) Active SLE patients leukocytes display 36 IFN-up-regulated and 13 down-regulated transcript sequences. The same genes are altered in healthy PBMCs cultured in vitro with IFN. Median expression and the number of patients who display more than twofold increase in gene expression. ** Significant after Bonferroni correction, * significant after Benjamini and Hochberg correction. (C) Extinction of IFN signature after steroid infusion. Analysis of PBMCs from 3 patients (#30, 25, and 5, see online Table S1) before and after (1-4 d) treatment with high dose intravenous GC (1 g/day for 3 d). All patients show down-regulation of IFN-regulated genes. P values on the right indicate significance of the gene expression level before and after GC (paired t test).

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Primers are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

Probes are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular inflammatory joint disease is disclosed and discussed and a number of modifications that can be made to a number of molecules including the inflammatory joint disease are discussed, specifically contemplated is each and every combination and permutation of inflammatory joint disease and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

B. Compositions and Methods

Inflammatory arthritis is a prominent clinical manifestation in diverse autoimmune disorders including rheumatoid arthritis (RA), psoriatic arthritis (PsA), systemic lupus erythematosus (SLE), Sjogren's Syndrome and polymyositis. Most of these patients develop joint deformities on physical examination but typically only RA and PsA patients manifest bone erosions on imaging studies.

Chronic inflammatory bone diseases, such as rheumatoid arthritis (RA), are accompanied by bone loss around affected joints due to increased osteoclastic resorption. This process is mediated largely by increased local production of pro-inflammatory cytokines (Teitelbaum S L. *Science* 2000; 289(5484): 1504-1508; Goldring S R and Gravallese E M. *Arthritis Res* 2000; 2(1):33-7). These cytokines can act directly on cells in the osteoclast lineage or indirectly by affecting the production of the essential osteoclast differentiation factor, receptor activator of NFκB ligand (RANKL), and/or its soluble decoy receptor, osteoprotegerin (OPG), by osteoblast/stromal cells (Hofbauer L C, et al. *J Bone Miner Res* 2000; 15(1):2-12). TNFα is a major mediator of inflammation, whose importance in the pathogenesis of various forms of bone loss is supported by several lines of experimental and clinical evidence (Feldmann M, et al. *Cell* 1996; 85(3):307-10). However, TNFα is not essential for osteoclastogenesis (Douni E, et al. *J Inflam.* 1996; 47:27-38), erosive arthritis (Campbell I K, et al. *J Clin Invest* 2001; 107(12):1519-27), or osteolysis (Childs L M, et al. *J Bon. Min. Res.* 2001; 16:338-347), as these can occur in the absence of TNFα. The critical question of how TNFα increases osteoclastogenesis in vivo remains to be answered.

Disclosed herein, Psoriatic arthritis (PsA) is an inflammatory joint disease characterized by extensive bone resorption. Also disclosed herein, blood samples from PsA patients, particularly those with bone erosions on plain radiographs, exhibit a marked increase in osteoclast precursors (OCP) compared to healthy controls. Additionally disclosed, PsA PBMC readily formed osteoclasts in vitro without exogenous RANKL or M-CSF, and both osteoprotegerin (OPG) and anti-tumor necrosis factor (TNF) antibodies inhibited osteoclast formation. Additionally, cultured PsA PBMC spontaneously secreted higher levels of TNF-α than healthy controls. In vivo, OCP frequency declined substantially in PsA patients following treatment with anti-TNF agents. Immunohistochemical analysis of subchondral bone and synovium revealed RANK positive perivascular mononuclear cells and osteoclasts in PsA specimens. RANKL expression was dramatically upregulated in the synovial lining layer while OPG immunostaining was restricted to the endothelium. These results indicate a model for understanding the pathogenesis of aggressive bone erosions in PsA. OCP arise from TNF-α activated peripheral blood mononuclear cells that migrate to the inflamed synovium and subchondral bone where they are exposed to unopposed RANKL and TNF-α. This leads to osteoclastogenesis at the erosion front and in subchondral bone resulting in a bi-directional assault on psoriatic bone.

In general, the efficacy of anti-TNF biological therapies (Enbrel® (etanercept), infliximab and adalimumab) in rheumatoid and psoriatic arthritis, psoriasis and ankylosing spondylitis is assessed three months after beginning treatment. Response is traditionally defined in terms of clinical improvement (decrease in the number of tender and swollen joints, decline in the Psoriasis Assessment Severity Index and improved patient and global assessment) and a decline in the level of the erythrocyte sedimentation rate and/or the C-reactive protein level. Due to the high cost of anti-TNF therapies, patients who fail to reach the endpoints outlined above are frequently deemed non-responders and treatment is terminated.

Based on data from the clinical trial and experience in the clinic, it was found that these endpoints are inadequate, since a significant number of "non-responders" ultimately achieve these endpoints following longer courses of therapy. Thus, the biomarker used herein, the frequency of circulating osteoclast precursors (OCP), can be an invaluable tool for rapidly screening potential responders from non-responders. An extremely high correlation in psoriatic arthritis patients between improved clinical response, lessening bone marrow edema on MRI (a known predictor of subsequent bone damage) and the decline in OCP frequency after treatment with Enbrel® etanercept has been observed. Hence, OCP frequency can be a useful biomarker for predicting which patients with Crohn's disease, psoriasis, rheumatoid arthritis and ankylosing spondylitis will respond to anti-TNF therapy.

Disclosed herein are methods and compositions for diagnosing, monitoring, and treating inflammatory joint diseases, as well as compositions for the same. Many inflammatory joint diseases are discussed herein including arthritis, as discussed herein, including rheumatoid arthritis (RA) and psoriatic arthritis (PsA), and systemic lupus erythematosus (SLE), Sjogren's Syndrome, and polymyositis as discussed herein. In certain embodiments the disclosed methods revolve around osteoclast precursor cells (OCPs) and markers related to these cells because the presence of the cells, as discussed herein, is associated with the presence and severity of inflammatory joint diseases. Furthermore, in certain embodiments the methods revolve around peripheral blood -mononuclear cells (PBMCs) and assaying samples of PBMCs for the presence of OCPs. As discussed herein there are many markers for OCPs and PBMCs which can be used in the methods, as well as many different diseases correlated with the presence of OCPs. Furthermore, any method for monitoring the disclosed cells can be used including those specifically disclosed herein. Additionally, there are many different signaling molecules, as disclosed herein, related to the activation, presence, and persistence of inflammatory joint diseases. For example, TNF, such as TNF-α, and its cognate receptors, such as TNF-R1 and TNF-R2, RANKL, and its cognate receptor RANK, as well as OPG and IFN and their cognate receptors can be involved in the disclosed methods and diseases. It is understood that the disclosed methods can incorporated the characteristics of these and other molecules. For example, molecules that bind to these molecules and inihibit their function can be used in the disclosed methods. Furthermore, it is understood that the discussion of arthritis, osteoclasts and osteoclast precursors, as well as other cells, the role of certain cells in diseases of joint inflammation, such as PSA and RA, as well as the disclosed molecules and various cellular and animal, such as mouse, models of the diseases discussed herein, as well as general characteristics, such as sequence similarities nucleotides and proteins and peptides and expression systems for the same, and antibodies and pharmaceutical compositions and delivery techniques, as well as any other concepts discussed herein, can be incorporated in the disclosed methods and compositions.

1. Arthritis

Inflammatory arthritis is one of the most common clinical features in autoimmune disorders manifesting as pain, stiffness and inflammation. Psoriatic Arthritis is characterized by chronic, autoimmune inflammatory arthritis, and can be associated with psoriasis. Often PsA patients are seronegative for rheumatoid factor. Clinical Features of PsA include progressive and destructive, joints are less painful and tender, joints are less swollen and erosions and fusion can occur early and rapidly. There are cytokines in PsA synovium. For example, IL-2, IFN-γ, and IL-10 present at levels significantly higher than in RA (Ritchlin, C., et al. 1998. *J Rheumatol* 25:1544-1552), and IL-1β and TNF are also present at high levels (Ritchlin, C., et al. 1998. *J Rheumatol* 25:1544-1552; Danning, C. L., et al. 2000. *Arthritis Rheum.* 43:1244-1256).

PsA can be distinguished from RA on the basis of unique clinical features, the absence of rheumatoid factor and characteristic radiographic findings (Winchester, R. 1993. Psoriatic Arthritis. In Dermatology in General Medicine. T. B. Fitzpatrick, et al., editors. 515-527). Patients frequently develop focal inflammation at multiple sites involving skin, joints and tendon insertion sites or entheses (Helliwell, P., et al. 1991. *Brit J of Rheuma* 30:339-345). Radiologic evidence of joint damage (erosions and joint space narrowing) is observed in almost all patients with rheumatoid arthritis (RA), followed for more than five years (Kaarela, K., et al. 1993. J Rheumatol 20:1670; Kaarela, K., and S. Sarna. 1993. Clin Exp Rheumatol 11:643). Joint damage is also very common in psoriatic arthritis (PsA), an inflammatory joint disease that occurs in 10-15% of psoriasis patients (Mease, P. J. 2002. Ann Rheum Dis 61:298). Gladman and colleagues noted that two-thirds of PsA patients had bone erosions on initial presentation to a rheumatologist (Gladman, D. D., et al. 1995. J Rheumatol 22:675). Radiographs often show extensive bone loss manifesting as eccentric erosions, frank tuft resorption and pencil-in cup deformities and acrolysis (Gladman, D. D. 1998. Psoriatic arthritis. Rheumatic Diseases Clinics of North America 24:829-844; Resnick, D. and Niwayama, G. 1981. Psoriatic Arthritis. In Diagnosis of Bone and Joint Disorders. D. Resnick and Niwayama, G., editors. 1103; Resnick, D., and G. Niwayama. 1989. In Resnick (Ed) Bone and Joint Imaging Philadelphia: W B Saunders:320.). Histopathologically, many PsA patients have aggressive synovitis with marked synovial hyperplasia, extensive vascular proliferation with a tortuous morphology and pannus tissue penetrating deep into cartilage and bone (Fearon, U., K. et al. 2003. J Rheumatol 30:260). In PsA, periarticular bone mineralization is maintained and there is often concomitant new bone formation in the form of periostitis and frank ankylosis, findings not seen in RA (Resnick, D. and Niwayama, G. 1977. *American J of Roentgenology.* 129:275-278; Bywaters, E. G. and Dixon, A. S. 1965. *Annals of the Rheum. Dis.* 24:313-331). The presence of marked bone resorption coupled with adjacent new bone formation (often in the same digit) suggests a disordered pattern of bone remodeling in the psoriatic joint. In addition, osteoclasts are prominently situated at the bone-pannus junction and in bone marrow-derived cutting cones traversing the bone matrix, which is consistent with the bi-directional attack originally described by Wooley in severely affected RA joints (Bromley, M., et al. 1985. Ann Rheum Dis 44:676).

Despite the presence of joint deformities on physical examination, not all forms of inflammatory arthritis degrade cartilage and resorb bone. For example, SLE is a systemic autoimmune disorder with diverse clinical manifestations, but musculoskeletal symptoms are usually the chief complaint with 50% of patients reporting articular pain on presentation (Kaposi, M. 1972. *Arch Dermat u Syph* 4:36; Stevens, M. 1983. In: Shur P H, ed New York: *Grune & Stratton*:63). Lupus patients often develop rheumatoid-like deformities (ulnar deviation, tendonopathies and subluxation) but only 4-6% of patients display erosive changes on plain radiographs (Esdaile, J. M., et al. 1981. *Ann Rheum Dis* 40:124; Grigor, R., et al. 1978. *Ann Rheum Dis* 37:121). Histopathologic analysis of SLE synovium shows mild to moderate synovial hyperplasia, microvascular changes and perivascular inflammation with mononuclear cells (Goldenberg, D. L., and A. S. Cohen. 1978. *Medicine (Baltimore)* 57:239; Labowitz, R., and H. R. Schumacher, Jr. 1971. *Ann Intern Med* 74:911; Natour, J., et al. 1991. *Clin Exp Rheumatol* 9:221). Notably, aggressive synovial tissue invading cartilage or bone is not described in these studies. Indeed, Bywaters noted the similarity of the SLE joint pattern to that reported by Jaccoud in rheumatic fever. In Jaccoud's arthropathy, joint deformities are manually reducible and radiographs do not depict bone or joint damage. In one large study of 939 SLE patients, Jaccoud's arthropathy was identified in 43% of the patients and was associated with a benign prognosis (Molina, J. F., et al. 1995. *J Rheumatol* 22:347). Hand radiographs from a patient with SLE and PsA show that both patients demonstrated deformities of digits on physical exam. However, only the PsA patient displayed marked erosive changes in the proximal and distal joints in both hands. Radiographs from the SLE patient showed no bone erosions or joint space narrowing.

Periprosthetic osteolysis as it relates to aseptic loosening of total hip replacements also involves inflammatory erosions at the joint space (Schwarz, E. M., et al. 2000. *Arthritis Res.* 2:165). Towards a solution to this problem, a volumetric CT method to quantify osteolysis in patients with aseptic loosening was developed, and used it to publish the first study demonstrating the direct relationship between polyethylene wear and osteolysis (Looney, R. J., et al. 2002. *Arthritis Res* 4:59). This study demonstrated that some people are resistant to wear debris-induced osteolysis (FIG. 20). Subsequently, a wear analysis was performed on an SLE patient who underwent a polyethylene liner replacement surgery due to excessive wear, as evidenced by the migration of the femoral component. Remarkably, while this patient had a wear rate that was well above average (885 mm$^3$ of polyethylene wear), there was no evidence of any periprosthetic bone loss. Considering the lack of surgical and material variables between this patient and a previous cohort, an innate resistance to osteolysis must be considered to best explain this observation.

2. Osteoclasts and Osteoclast Precursors (OCPs)

Osteoclasts, the principal cells responsible for bone resorption (Teitelbaum, S. L. 2000. *Science* 289:1504-1508), are multinucleated cells derived from mononuclear cell precursors of the monocyte/macrophage lineage (Massey, H. M. and Flanagan, A. M. 1999. *British Journal of Haematology* 106: 167-170). Cell culture techniques (Suda T, et al. J Bone Miner Res 1997; 12(6):869-79) and transgenic and knockout mice (Karsenty G. Genes Dev 1999; 13(23):3037-51) have advanced the understanding of osteoclastogenesis and established that macrophage-colony stimulating factor (M-CSF) and RANKL are required for osteoclastogenesis (Lacey D L, et al. Cell 1998; 93(2):165-76; Yasuda H, et al. Proc Natl Acad Sci USA 1998; 95(7):3597-602; Yoshida H, et al. Nature 1990; 345(6274):442-4; Kodama H, et al. J Exp Med 1991; 173(1):269-72; Kong Y Y, et al. Nature 1999; 397(6717):315-23; Dougall W C, et al. Genes Dev 1999; 13(18):2412-24; Dougall W C, et al. Genes Dev 1999; 13(18):2412-24). Osteoclastogenesis is also dependent on intracellular signaling molecules, including the adapter protein TRAF6 (Lomaga M A, et al. Genes Dev 1999; 13(8):1015-24; Kobayashi N, et al. Embo J 2001; 20(6):1271-1280), the transcription factors AP-1 (Wang Z Q, et al. Nature 1992; 360(6406):741-5; Johnson R S, et al. Cell 1992; 71(4):577-86) and NF-□B (Franzoso G, et al. Genes Dev 1997; 11(24):3482-96; Iotsova V, et al. Nature Medicine 1997; 3(11):1285-9), which are involved in mediating the M-CSF and RANKL signals (Anderson D M, et al. Nature 1997; 390(6656):175-9; Wong B R, et al. J Biol Chem 1997; 272(40):25190-4; Hsu H, et al. Proc Natl Acad Sci USA 1999; 96(7):3540-5).

It has been proposed from experimental models that pathological resorption is at least, in part due to an increase in the number of these precursors (Li, P., et al. 2002. *Journal of Bone & Mineral Research* 17:s130). Indeed, elevated numbers of circulating osteoclast precursors (OCP) have been identified in the peripheral blood of patients with aggressive multiple myeloma and the bone marrow of patients with Paget's disease. (Gregoretti, M. G., et al. 1995. *Leukemia* 9:1392-1397; Demulder, A., et al. 1993. *Endocrinology* 133: 1978-1982). Thus, investigation of the factors that promote osteoclast development can lead to control of events responsible for pathologic bone loss in PsA.

Homeostatic differentiation of osteoclasts or osteoclastogenesis is a contact dependent process directed by osteoblasts and stromal cells in the bone microenvironment (Lam, J., et al. 2000. *J of Clin. Inv.* 106:1481-1488; Suda, T., et al. 1999. *End Rev* 20:345-357). The osteoblasts/stromal cells release 2 different signals that are necessary and sufficient for differentiation of OCP into osteoclasts. The first, macrophage-colony stimulating factor (M-CSF) binds the receptor c-fms and the second, receptor activator of NFκB ligand (RANKL), binds to RANK on the surface of OCP (Lacey, D. L., et al. 1998. *Cell* 93:165-176). Since permissive quantities of M-CSF are constitutively expressed in the bone microenvironment, it has been proposed that the relative expression of RANKL and its natural antagonist OPG ultimately control osteoclastogenesis (Teitelbaum, S. L. 2000. *Science* 289: 1504-1508; Hofbauer, L. C. and Heufelder, A. E. 2001. *Arthritis Rheum.* 44:253-259; Nakagawa, N., et al. 1998. *Bioch & Biophys Res Comm* 253:395-400; Simonet, W. S., et al. 1997. *Cell* 89:309-319). Furthermore, it has been demonstrated that miniscule quantities of RANKL are sufficient to synergize with TNF-α and potentiate osteoclastogenesis (Lam, J., et al. 2000. *J of Clin. Inv.* 106:1481-1488)

It has been found that TNF-α directly increases the number of OCP in mice genetically modified to over-express TNF-α (hTNF-transgenic) and in normal mice injected with TNF-α (Li, P., et al. 2002. *Journal of Bone & Mineral Research* 17:s130). Additionally, treatment of hTNF mice with anti-TNF agents reduces the number of OCP to baseline. In humans, TNF-α levels are elevated in the psoriatic synovium and joint fluid (Ritchlin, C., et al. 1998. *J Rheum* 25:1544-1552; Partsch, G., et al. 1998. *Ann. of Rheum. Dis.* 57:691-693; Danning, C. L., et al. 2000. Arthritis Rheum. 43:1244-1256). Disclosed herein osteoclast precursor frequency in PsA patients is increased, but it is not increased in healthy controls. The role of TNF-α and RANKL in promoting osteoclast formation is also disclosed herein. Immunohistochemistry was performed on synovial tissues and bone obtained from patients with PsA and osteoarthritis (OA) to determine expression patterns of RANKL, RANK and OPG protein. The synovial expression of RANK, RANKL and OPG mRNA was also examined by RT-PCR. Lastly, the ability of TNF-α to modulate OCP frequency in vivo was examined by determining the number of circulating OCP in PsA patients before and after anti-TNF therapy.

CD11b, CD14, CD51/61 and RANK are established markers of mononuclear OCP (Suda, T., et al. 1999. *End Rev* 20:345-357). It has been shown that approximately 2% of PBMC can be stimulated to give rise to osteoclasts in vitro (Fujikawa, Y., et al. 1996. *Ann. of Rheum. Dis.* 55:816-822; Quinn, J. M., et al. 1998. *Endocrinology* 139:4424-4427). Interestingly, CD14$^+$ monocytes can also differentiate into dendritic cells and macrophages (Massey, H. M. and Flanagan, A. M. 1999. *British Journal of Haematology* 106:167-170), (Kotake, S., et al. 2001. *Arthritis Rheum.* 44:1003-1012). Presumably events in the bone marrow, circulation and possibly the synovium determine the fate of a particular monocyte. Indeed, following exposure to RANKL and M-CSF, a sub-population of monocytes rapidly loses the CD14 marker and acquires an osteoclast phenotype (Nicholson, G. C., et al. 2000. *Clin Science* 99:133-140) underscoring the critical importance of the RANK signaling pathway in osteoclastogenesis.

3. PsA and Osteoclasts

In psoriatic arthritis (PsA), bone erosions can be extensive, resulting in joint deformity and disability. These erosions differ markedly from the periarticular osteopenia and pericapsular bone loss commonly observed in rheumatoid joints, but OCPs are increased in RA as well. (Martel, W., et al. 1965. *Radiology* 84:204). While these radiographic features suggest a different mechanism of bone loss in PsA, understanding the basis for this difference was impeded because the events that lead to psoriatic bone resorption have not been well defined. To elucidate this process, disclosed herein is how osteoclast precursors and the regulatory molecules RANK, RANKL and OPG can orchestrate osteolysis in PsA.

The results disclosed herein demonstrate that osteoclasts are prominently situated at the bone-pannus junction and in cutting cones traversing the subchondral bone in the psoriatic joint. In addition, osteoclast precursors are markedly increased in the circulation of PsA patients, most strikingly in those with bone erosions on plain radiographs. These cells express the surface markers CD11b, CD14, CD51/61 and RANK. A pivotal role for TNF-α in promoting OCP formation is supported by the observations that blocking TNF-α in vivo markedly suppressed the number of circulating OCP and that cultured PsA PBMC spontaneously release high quantities of biologically active TNF-α. Immunohistochemical studies delineated the presence of RANK positive cells in synovium and adjacent to blood vessels in subchondral bone. Furthermore, synovial lining cells stained strongly for RANKL while OPG expression was confined to the endothelium. These data indicate that OCP enter a synovial microenvironment characterized by a high ratio of RANKL to OPG expression, facilitating osteoclastogenesis and bone resorption.

Examination of bone marrow cultures from Paget's patients revealed an increase in the number of committed OCP compared to healthy controls (Demulder, A., et al. 1993. *Endocrinology* 133:1978-1982). Similarly, PBMC cultured from patients with multiple myeloma and bone lesions, but not those without bony involvement or healthy controls, gave rise to osteoclasts that resorbed bone in vitro when cultured in the presence of a murine stromal line (Gregoretti, M. G., et al. 1995. *Leukemia* 9:1392-1397). Faust et al. extended these observations by showing that osteoclasts can develop from unstimulated PBMC derived from healthy controls when grown at high density, however, the number of osteoclasts was not quantified and they demonstrated weak bone resorption properties (Faust, J., et al. 1999. *J Cell Biochem.* 72:67-80). In pilot studies, it was noted that numerous osteoclasts were present in unstimulated wells of PBMC cultured from PsA patients even when cultured at low density. Thus, the experimental protocol was modified, analyzing OCP frequency at low density in the absence of exogenous factors such as RANKL and M-CSF. Using this approach, osteoclasts were identified by positive TRAP staining and multinuclearity. These cells were shown to be functional by their ability to form pits on bone wafers. Compared to healthy controls, PsA patients had markedly more OCP and these cells resorbed significantly greater quantities of bone. The difference in resorption area between control and PsA patients was less than the difference in OCP frequency between the two groups. The additional finding that the increase in OCP frequency correlated with clinical erosions indicates that the size of the precursor pool can be a dependent factor that contributes directly to bone resorption in PsA.

Studies in mice demonstrated that systemic TNF-α directly increases OCP frequency and that this elevation is reversible by anti-TNF therapy (Li, P., et al. 2002. *Journal of Bone & Mineral Research* 17:s130). Here it is shown that this is also true in PsA as increased OCP frequency declined significantly in 5 of 5 patients treated with anti-TNF therapy, which paralleled clinical improvement. Moreover, PsA PBMC spontaneously released high levels of TNF-α in vitro. TNF-α secreted by these cells promoted osteoclastogenesis that was blocked with anti-TNF-α antibodies. Blocking RANKL with OPG also substantially decreased the number of OCP that arose from PsA PBMC. Thus, the results imply that TNF-α triggers a systemic increase in the number of circulating OCP and this is consistent with it being a critical event in the modulation of psoriatic bone resorption. While these data strongly support the concept that TNF-α released by PsA PBMC could promote an increased OCP frequency, they do not establish these cells as the principal source of the TNF-α. Further studies designed to specifically address this question are required.

Osteoclasts have been detected in rheumatoid synovium (Gravallese, E. M., et al. 1998. *Am J Path* 152:943-951; Bromley, M. and Woolley, D. E. 1984. *Arthritis Rheum.* 27:968-975). Furthermore, while osteoclast numbers in PsA tissues were considerably greater than in OA samples, they were not significantly different from RA. First, circulating OCP can be higher in PsA than RA resulting in a more sustained assault on bone. Second, the ratio of RANKL to OPG can be significantly greater in patients with destructive PsA or, alternatively, levels of anti-osteoclastogenic factors such as; interferon-γ, IL-12 or GM-CSF could be higher in the rheumatoid joint. Third, the striking increased vascularity and vessel tortuosity characteristic of PsA but not RA (Reece, R. J., et al. 1999. *Arthritis Rheum.* 42:1481-1484) can facilitate enhanced recruitment and entry of OCP into the joint. Finally, other pro-osteoclastogenic factors such as IL-1 can be present in greater quantities in PsA joints providing an additional osteoclast activation signal. In support of this latter mechanism is the observation that IL-1 was markedly elevated in psoriatic but not rheumatoid synovial explants obtained from patients with erosive joint disease (Ritchlin, C., et al. 1998. *J Rheum* 25:1544-1552).

Disclosed herein in pre-clinical studies utilizing the TNF-transgenic (TNF-Tg) mouse model of erosive arthritis, and clinical studies with PsA patients, a dominant role for monocytes effector cells in the perpetuation of these chronic autoimmune diseases was identified. Specifically, it was found that monocyte effector cells activated by the receptor activator of NFκB ligand (RANKL)-RANK signaling pathway, differentiate into osteoclasts that mediate erosive arthritis in mice and humans. In contrast, mononuclear cells similarly isolated from SLE patients differentiate along a dendritic cell pathway. The mechanisms responsible for these divergent events arise in response to the dominance of tumor necrosis factor-α (TNF) in PsA; and interferon-α (IFN) in SLE. Interestingly, there is a subset of patients that suffer from both inflammatory arthritis and SLE. While the vast majority of these patients do not have erosive disease, a minority develops erosions and joint space narrowing.

4. The Role of Innate Immunity in Autoimmune Rheumatic Diseases

Innate immune mechanisms play a central role in the establishment and maintenance of autoimmune diseases like inflammatory arthritis and SLE. Although the underling etiologic agents responsible for these diseases have yet to be defined, a general paradigm to explain how these conditions become chronic via an auto-regulatory cytokine cascade has emerged. This model posits that effector cells are stimulated to produce cytokines involved in innate immune responses that systemically activate downstream target cells, which respond directly or indirectly by producing the same cytokines in a vicious cycle. Over the last decade, genetically manipulated animal models and both pre-clinical and clinical biological therapies have generated formal proof of this model. What remains to be elucidated is how cytokines mediate organ specific pathology and if there is a fundamental relationship between the cytokine-induced genes in circulating cells and the phenotype of the end-organ pathology. These issues are addressed herein. Shown herein are two cytokines, tumor necrosis factor-alpha (TNF) and interferon-alpha (IFN), which are known to play a prominent role in innate immunity and autoimmune inflammatory arthritis. The relationship between TNF and IFN in erosive arthritis towards the development of safer and more effective therapeutic agents is disclosed herein as well as methods of monitoring treatment protocols.

5. TNF-α

TNF-α is a pivotal cytokine in PsA. TNFα stimulates RANKL production by stromal cells (Hofbauer L C, et al. Bone 1999; 25(3):255-9), T lymphocytes (Cenci S, et al. J Clin Invest 2000; 106(10):1229-37), B lymphocyte (Kanematsu M, et al. J Bone Miner Res 2000; 15(7):1321-9), and endothelial cell (Collin-Osdoby P, et al. J Biol Chem 2001; 276(23):20659-72), and M-CSF production by murine or human stromal cells (Srivastava S, et al. J Biol Chem 2001; 276(12):8836-40). In addition to this indirect mechanism for osteoclastogenesis, TNFα also can stimulate osteoclastogenesis directly (Abu-Amer Y, et al. J Biol Chem 2000; 275(35): 27307-10) and strongly synergizes with IL-1 and RANKL to promote osteoclast differentiation and activation (Kobayashi K, et al. J Exp Med 2000; 191(2):275-86; Azuma Y, et al. J Biol Chem 2000; 275(7):4858-64; Lam J, et al. J Clin Invest 2000; 106(12):1481-8). TNFα has been isolated from psoriatic synovial fluid and psoriatic synovial explants release elevated levels of TNF-α, which were highest in patients with erosive arthritis (Ritchlin, C., et al. 1998. *J Rheum* 25:1544-1552; Partsch, G., et al. 1998. *Ann. of Rheum. Dis.* 57:691-693). Also, psoriatic synovial lining cells express TNF-α protein (Danning, C. L., et al. 2000. *Arthritis Rheum.* 43:1244-1256). Perhaps the most convincing evidence stems from clinical trials showing that TNF alpha blockade dramatically ameliorates psoriatic joint pain and swelling, resulting in FDA approval of Enbrel® (etanercept) for PsA, the first drug to receive this indication (Mease, P. J., et al. 2000. *Lancet* 356:385-390; Mease, P. J., et al. 1999. *Arthritis Rheum.* 42:377 (Abstr.)). Lastly, in a recent report, TNF inhibition improved clinical parameters of arthritis and reversed abnormal MRI bone and soft tissue signals in spondyloarthropathy patients with active joint and entheseal inflammation (Marzo-Ortega, H., et al. 2001. *Arthritis Rheum.* 44:2112-2117). When looking at Tumor Necrosis Factor (TNF) alpha (TNF-α) in Psoriatic Arthritis/Psoriasis, its levels are elevated in the synovium (Terajima. Arch Dermatol Res.1998;290:246-252. 2. Ettehadi. Clin Exp Immunol. 1994;96:146-151.) and serum (Shiohara. J Am Acad Dermatol. 1992;27:568-574.) in affected patients. The serum levels fluctuate with disease activity. TNF can also be found in active plaques (Partsch. J Rheumatol. 1997;24:518-523 and Ritchlin. J Rheumatol. 1998;25:1544-1552.). There is also higher TNF bioactivity in involved vs uninvolved skin.

6. Monocyte Differentiation Pathways

Monocytes, pivotal effector cells of innate immunity, differentiate into dendritic cells (DC), macrophages or osteoclasts (OC) in response to environmental signals. Monocyte precursors stimulated with granulocyte-macrophage colony-stimulating factor (GM-CSF) plus interleukin (IL)-4 yield dendritic cells, but form osteoclasts if exposed to receptor activator of NFκB ligand (RANKL) and monocyte colony stimulating factor (M-CSF). Treatment of monocytes with M-CSF alone produces tissue macrophages and IFN-γ or IL-6 treatment shifts monocyte precursor differentiation to macrophages rather than DC and OC (Delneste, Y., et al. 2003. *Blood.* 101:143). In vivo, these differentiation pathways can be altered by trauma, infection and inflammation. In trauma patients, differentiation is dramatically switched from DC to macrophages. Likewise, infection of human monocytes with live *Mycobacterium tuberculosis* interferes with differentiation to competent DC. DC yield was also diminished in pre-diabetic autoantibody-positive type 1 diabetes mellitus relatives compared to healthy controls following treatment with GM-CSF and IL-4 (Takahashi, K., et al. 1998. *J Immunol* 161:2629). IFN therapy is also know to bias monocyte differentiation in a manner that reduces osteoclast numbers in vivo (Thiele, J., et al. 1998. *Journal of Pathology.* 186:331). These data indicate that cytokines and possibly other signals released by cells and inflamed tissues can alter monocyte differentiation and effector cell function and have global effects on disease.

7. TNF in Erosive Arthritis

Experimental and clinical data demonstrating that TNF induces upregulation of other pro-inflammatory cytokines, adhesion molecules, matrix metalloproteinases, and oxygenases and potentiates osteoclastogenesis; places this cytokine at the apex of pro inflammatory cascade that leads to synovial inflammation and joint destruction (Feldmann, M., et al. 2003. *Blood* 101:143, Maini, R. N., et al. 1995. *Immunol Rev* 144:195). Of particular importance, however, there are two critical findings that for the material disclosed herein. First, TNF is necessary and sufficient to induce erosive arthritis in transgenic mice (TNF-Tg) (Keffer, J., et al. 1991. *Embo J* 10:4025), which is discussed in detail below. Second, multiple placebo controlled, double-blinded, muticenter phase III clinical trails with three different FDA approved anti-TNF biologics: the soluble p75 TNF receptor-Fc fusion protein Enbrel® (etanercept) (Moreland, L. W., et al. 1997. *N Engl J Med* 337:141; Bathon, J. M., et al. 2000. *N Engl J Med* 343:1586), the chimeric anti-TNF monoclonal antibody infliximab (Lipsky, P. E., et al. 2000. *N Engl J Med* 343:1594, Braun, J., et al. 2002. *Lancet* 359:1187), and the humanized anti-TNF monoclonal antibody adalimumab (den Broeder, A., et al. 2002. *J Rheumatol* 29:2288, Weinblatt, M. E., et al. 2003. *Arthritis Rheum* 48:35), showed that ~70% of RA patients, who were refractory to standard DMARDs, improved physically, functionally and radiographically (Weinblatt, M. E., et al. 2003. *Arthritis Rheum* 48:35). Similarly, Enbrel® (etanercept) and infliximab have been remarkably effective in psoriatic arthritis. In phase II trials, both Enbrel® (etanercept) and infliximab treatment resulted in marked improvement in clinical outcome measures and Enbrel® (etanercept) inhibited joint destruction as early as six months after starting therapy (Mease, P. J. 2002. *Ann Rheum Dis* 61:298). Thus, studies in preclinical models and in patients with RA and PsA underscore the pivotal role of TNF-α in sustaining ongoing joint inflammation and destruction.

8. The TNFα Transgenic Mouse (hTNF-Tg) Model of Chronic Erosive Arthritis

Over the last two decades, several different animal models of arthritis have been developed, including adjuvant arthritis, streptococcal cell-wall arthritis, and antigen induced arthritis (Feldmann, M., et al. 2003. *Blood* 101:143). These models have provided valuable insights; however, each have limitations because the pathobiology of the arthritis differs from the synovitis and joint destruction observed in RA or PsA. More importantly, a major drawback of these models is that they represent acute synovitis facilitating evaluation of prophylactic but not long-term anti-inflammatory or immunosuppressive therapies. For these purposes, the hTNFα-transgenic mouse is an ideal model because the etiologic mechanism is evident and the chronic course of the synovitis and joint damage mirrors RA more closely. George Kollias' laboratory developed this animal model of arthritis by generating mice with a human TNFα transgene in which the AU rich 3' UT region (which shortens mRNA half life) was replaced by the stable β globin 3' UT, resulting in over-expression of TNFα (Keffer, J., et al. 1991. *Embo J* 10:4025). The transgene engenders multiple lines of mice which develop polyarthritis. Anti-TNFα therapy alone completely prevents development of this disease. Macroscopic pathology includes swelling of the ankle joints at 6 to 8 weeks of age and impairment of movement. Beginning at 6 weeks of age and continuing throughout their life (>1 year), hyperplasia of the synovial membrane, as well as cellular inflammatory infiltrates of the synovial space can be seen in nearly all joints examined. Pannus formation, articular cartilage destruction, and massive destruction of fibrous tissue are observed in the advanced stages of disease. These symptoms all closely mimic those of human disease. Interestingly, the inflammatory-erosive disease in hTNF-Tg mice is immune cell independent. These animals do not develop rheumatoid factor (Keffer, J., et al. 1991. *Embo J* 10:4025), and hTNF-Tg mice crossed with RAG-2 knockout mice (hTNF-Tg×RAG−/−), which have no T-cells or B-cells, suffer from arthritis that is almost indistinguishable from that of the parental strain (Douni, E., K. et al. 1996. *J Inflam.* 47:27). Thus, consistent with the mission of this RFA, this model relies exclusively on innate immune mechanisms.

9. RANK, RANKL, TNF-α TNF-R1, TNF-R2, and OPG

The discovery of RANK, RANKL and OPG as the final effector molecules ultimately regulating osteoclastogenesis and bone resorption has provided a fundamental insight into the mechanisms of osteolysis in metabolic bone diseases (Gori, F., et al. 2000. *Endocrinology* 141:4768-4776; Teitelbaum, S. L. 2000. *Science* 289:1504-1508; Gravallese, E. M. and Goldring, S. R. 2000. *Arthritis Res.* 2:33-37). Definitive proof in support of this paradigm has also been provided in animal models of inflammatory arthritis (Li, P., et al. 2002. *Journal of Bone & Mineral Research* 17:s130), (Fujikawa, Y., et al. 1996. *Ann. of Rheum. Dis.* 55:816-822; Quinn, J. M., et al. 1998. *Endocrinology* 139:4424-4427; Kotake, S., et al. 2001. *Arthritis Rheum.* 44:1003-1012). In RA, investigators found that RANKL mRNA is expressed by T lymphocytes and synoviocytes isolated from lining membranes Gravallese, E. M., et al. 2000. *Arthritis Rheum.* 43:250-258; Shigeyama, Y., et al. 2000. *Arthritis Rheum.* 43:2523-2530; Takayanagi, H., et al. 2000. *Nature* 408:600-605). It has also been demonstrated that fibroblast-like synoviocytes can induce osteoclastogenesis when co-cultured with PBMC (Takayanagi, H., et al. 1997. *Biochem. & Biophys. Res. Comm.* 240:279-286). In the immunohistochemistry experiments, it was found that PsA synovial lining cells stained intensely for RANKL, a finding not observed in OA synovial tissues. The RANKL appeared to be relatively unopposed by OPG, since staining for this molecule was restricted to the endothelium. The likely targets for this synovial cell RANKL are the perivascular RANK positive mononuclear cells in the synovium and subchondral bone. The finding of RANK positive mononuclear cells in the synovium, confirmed by elevated RANK mRNA expression in at least some of the PsA patients, was in line with previous studies that detected TRAP positive cells in RA synovium and reported that osteoclasts can be generated from RA synovium and bone (Azuma, Y., et al. 2000. *J Bio Chem* 275:4858-4864; Gravallese, E. M., et al. 1998. *Am J Path* 152:943-951; Toritsuka, Y., et al. 1997. *J Rheumat* 24:1690-1696). A gradient of RANK staining was observed in mononuclear cells, increasing in intensity from the perivascular region in the subsynovium to the erosion front where synoviocytes and osteoclasts exhibited the strongest RANK expression. This gradient is directed by the elevated RANKL and TNF-α expressed by PsA synoviocytes. Ultimately, RANKL stimulation of these precursor cells could result in the genesis of RANK positive multinucleated osteoclasts that directly erode the bone matrix. Support for the critical role of RANKL is provided by the disclosed experiments indicating that OPG significantly blocked osteoclast formation in PsA PBMC.

10. RANK, RANKL and OPG are the Final Effector Molecules that Control Osteoclastogenesis and Bone Resorption.

Osteoclasts are multinucleated cells formed by fusion of mononuclear progenitors derived from the monocyte/macrophage lineage (Teitelbaum, S. L. 2000. Bone Resorption by Osteoclasts. *Science* 289:1504). Two distinct signals are necessary and sufficient for the differentiation of monocytes/macrophages into osteoclasts. The first is delivered by macrophage-colony stimulating factor (M-CSF), which signals through its receptor c-Fms. Receptor activator of nuclear factor kappa B ligand (RANKL) mediates the second through its receptor RANK. Cell culture conditions have been established in which M-CSF and RANKL are the only requirements for osteoclastogenesis (Lacey, D. L., et al. 1998. *Cell* 93:165; Yasuda, H., et al. 1998. *Proc Natl Acad Sci USA* 95:3597); and mice genetically deficient in M-CSF (Yoshida, H., et al. 1990. *Nature* 345:442; Kodama, H., et al. 1991. *J Exp Med* 173:269) or RANKL (Kong, Y. Y., et al. 1999. *Nature* 397:315; Dougall, W. C., et al. 1999. *Genes Dev* 13:2412) signaling are incapable of osteoclastogenesis and suffer from osteopetrosis. Since M-CSF is constitutively expressed at permissive levels within the bone microenvironment it is believed that delivery of the RANK signal stimulates osteoclastogenesis in vivo. This event is negatively regulated by osteoprotegerin (OPG) (Simonet, W. S., et al. 1997. *Cell* 89:309), which is a natural decoy receptor that binds to RANKL blocking its interaction with RANK, and thereby inhibiting osteoclast development and activation (Teitelbaum, S. L. 2000. Bone Resorption by Osteoclasts. *Science* 289:1504). Disclosed herein, the ratio of RANKL to OPG is the major factor determining the extent of bone resorption in bone. In the revised paradigm of metabolic bone disease, RANKL and OPG are the final effector molecules that ultimately control osteoclastogenesis and bone resorption. Other factors modulate osteolysis (i.e. TNF) by altering the expression of RANKL and/or OPG (Hofbauer, L. C., et al. 2000. *J Bone Miner Res* 15:2).

In RA, RANKL mRNA is up-regulated in T cells freshly isolated from the peripheral blood and synovium (Shigeyama, Y., et al. 2000. *Arthritis Rheum* 43:2523; Goldring, S. R., and E. M. Gravallese. 2000. *Arthritis Res* 2:33). Additionally, synoviocytes isolated from rheumatoid synovium express RANKL mRNA and induce osteoclastogenesis when co-cultured with peripheral blood mononuclear cells (Gravallese, E. M., et al. 2000. *Arthritis Rheum* 43:250; Takayanagi, H., et al. 2000. *Arthritis Rheum* 43:259). Similarly, it was found that RANKL, is highly expressed in the synovial membrane adjacent to periarticular erosions and in stromal cells lining cutting cones in subchondral bone pointing to the pivotal importance of this molecule in the bi-directional attack on psoriatic bone. Although TNF is a potent stimulator of osteoclastogenesis (Abu-Amer, Y., et al. 2000. *J Biol Chem* 275:27307) and osteoclast activity (Bertolini, D. R., et al. 1986. *Nature* 319:516) it is not essential, since osteoclastogenesis (Douni, E., K. et al. 1996. *J Inflam.* 47:27), erosive arthritis (Campbell, I. K., et al. 2001. *J Clin Invest* 107:1519) and osteolysis (Childs, L. M., et al. 2001. *J. Bon. Min. Res.* 16:338), occur in its absence. Indeed, the specific role of TNF in osteoclastogenesis has been the subject of intense investigation. It has been shown that TNF is able to stimulate osteoclastogenesis indirectly through RANKL production by stromal cells (Hofbauer, L. C., et al. 1999. *Bone* 25:255), T cells (Cenci, S., et al. 2000. *J Clin Invest* 106:1229), B cells (Kanematsu, M., et al. 2000. *J Bone Miner Res* 15:1321) and endothelial cells (Collin-Osdoby, P., et al. 2001. *J Biol Chem* 276:20659). However, whether or not TNFα promotes osteoclast formation independently of RANK signaling is controversial. Two independent groups reported that TNFα promotes osteoclast formation in vitro under conditions of RANK blockade (Kobayashi, K., et al. 2000. *J Exp Med* 191:275; Azuma, Y., et al. 2000. *J Biol Chem* 275:4858) suggesting that TNFα can compensate for RANKL to induce osteoclastogenesis. This conclusion has been refuted by others who demonstrated that "permissive" levels of RANKL are required for TNFα-induced osteoclastogenesis (Lam, J., et al. 2000. *J Clin Invest* 106:1481). Furthermore, RANK independent osteoclastogenesis under physiological conditions in vivo has never been demonstrated. These latest observations are consistent with the murine studies of wear debris-induced osteolysis (Childs, L. M., et al. 2002. *J Bone Miner Res* 17:192), fracture healing, and erosive arthritis, where RANK blockade with 10 mg/kg of RANK:Fc or genetic ablation of RANK completely eliminates all osteoclasts.

11. Negative Regulation of Osteoclastogenesis and Bone Resorption by IFN.

Bone is an active tissue that is continually remodeled by osteoclasts and osteoblasts resulting in complete skeleton turnover every 10 years. Under normal homeostasis, this metabolic cycle is initiated by a decrease in blood calcium, which triggers parathyroid hormone (PTH) synthesis. PTH induces RANKL expression on stromal cells, which stimulates osteoclastic bone resorption and release of calcium. Once blood calcium levels normalize, PTH expression is extinguished and resorption is replaced by osteoblastic bone formation. Recently, Taniguchi and colleagues identified a novel autoregulatory loop. They found that the induction of type-I IFN (IFN-β) by RANKL delivers a critical signal to inhibit osteoclastogenesis (Takayanagi, H., et al. 2002. *Nature* 416:744). This was formally demonstrated with the IFN type-I receptor knockout mice (identical to the Ifnr1−/− mice disclosed herein) and IFNβ−/− mice, who demonstrate an increase in circulating OCP and enhanced osteoclastogenesis. These mice also have increased osteoclast numbers in vivo and develop severe osteopenia. They also demonstrated that direct administration of IFNβ together with LPS onto the calvaria of mice significantly inhibited bone loss, osteoclast formation and activation. The mechanism responsible for this autoregulatory loop was RANKL-induced cFos expression in bone marrow monocytes, which leads to increased production of IFNβ that directly inhibits osteoclastogenesis in a paracrine fashion.

Type-II interferon (IFNγ) is also known to have potent anti-osteoclastic effects in vivo and in vitro. In similar studies, Takayanagi et al, utilized IFNγ deficient mice to demonstrate that T-cell production of IFNγ strongly suppresses osteoclastogenesis in bone marrow cultures by interfering with the RANKL-RANK signaling pathway. Furthermore, IFNγ induced rapid degradation of the RANK adapter protein, TRAF6 (TNF receptor-associated factor 6) via ubiquitination, which resulted in strong inhibition of the RANKL-induced activation of the transcription factor NFκB and JNK. This inhibition of osteoclastogenesis was rescued by overexpressing TRAF6 in precursor cells, confirming that TRAF6 is the target critical for the IFNγ action (Takayanagi, H., et al. 2000. *Nature* 408:600). These data were confirmed using a murine monocyte/macrophage cell line (RAW264.7) and primary murine splenocyte cultures (Huang, W., et al. 2003. *Arthritis Res Ther* 5:R49). However, in the models no evidence was found of IFNγ-induced TRAF6 degradation or perturbations of NFκB, AP-1 or STAT signaling. Thus, it was concluded that these effects are more consistent with the cellular transformation that occurs during macrophage activation, which irreversibly differentiates monocytes out of the osteoclast lineage.

12. Interferon in SLE

Tissue damage resulting from antibody and complement-fixing immune complex deposition is one of the hallmarks of SLE. High titers of autoantibodies predominantly specific for DNA and nucleosomes, are among the immunologic features of SLE, leading to the hypothesis that inappropriate handling of dying (apoptotic) cells can represent a key pathogenic event (Mills, J. A. 1994. N Engl J Med 330:1871; Hahn, B. H. 1998. N Engl J Med 338:1359). Altered T-B cell interactions are thought to be a central mechanism leading to the loss of tolerance that characterizes SLE (Shlomchik, M. J., et al. 2001. Nat Rev Immunol 1:147), however, the recognition of DCs are key controllers of immunity (Steinman, R. M. 1991. Annu Rev Immunol 9:271) and tolerance (Steinman, R. M., et al. 2000. *J Exp Med* 191:411; Steinman, R. M., and M. C. Nussenzweig. 2002. *Proc Natl Acad Sci USA* 99:351) led to the hypothesis that SLE can be driven by unabated DC activation. Over the last few years a new paradigm has emerged to explain the mechanism of unabated DC activation, which is primarily regulated by systemic IFNγ (IFN). This model is based on three fundamental observations: 1) CD14+ monocytes isolated from the blood of patients with systemic lupus erythematosus, but not those from healthy individuals, act as DCs. 2) These DCs appear to be activated by circulating IFN that is released by plasmacytoid DCs infiltrating lupus skin lesions. And most convincingly, 3) although only a fraction of patients with active SLE have detectable IFN levels in their serum, PBMC isolated from these patients express a unique IFN transcriptome, which reverts to a more normal pattern following effective steroid therapy (Baechler, E. C., et al. 2003. *Proc Natl Acad Sci USA* 100:2610).

FIGS. 21 and 30, which are compilations of the microarray data disclosed herein (Baechler, E. C., et al. 2003. *Proc Natl Acad Sci USA* 100:2610), demonstrate several important points. First, a single cytokine can exert systemic effects that dominantly alter monocyte activation. Second, the IFN-induced transcriptome in SLE PBMC is completely different from that observed in juvenile RA patients. This is consistent with the understanding that PsA patients with erosive disease can have a unique TNF-induced transcriptome in isolated PBMC that is consistent with differentiation towards the osteoclast rather than the dendritic cell lineage, as was observed in SLE.

13. Mouse Models of SLE also Demonstrate a Systemic IFN Disease

To understand the etiology of SLE and evaluate potential therapeutics, many labs have analyzed the hybrids of New Zealand black (NZB) and New Zealand white (NZW) mice. These mice develop severe immune complex-mediated glomerulonephritis associated with high serum levels of IgG antinuclear autoantibodies. As such, these mice are recognized as a model of human SLE. Based on the strong evidence indicating that the development of lupus in humans and in this murine model has a strong but complex genetic basis (Harley, J. B., et al. 1998. *Curr Opin Immunol* 10:690; Vyse, T. J., and B. L. Kotzin. 1998. *Annu Rev Immunol* 16:261; Theofilopoulos, A. N., and D. H. Kono. 1999. *Proc Assoc Am Physicians* 111:228; Wakeland, E. K., et al. 1999. *Curr Opin Immunol* 11:701), the identification of susceptibility genes has been a major focus of research. Specifically, much focus has been on the loci on distal chromosome 1, for which contributing genes from both the NZB and NZW have been localized (Vyse, T. J., and B. L. Kotzin. 1998. *Annu Rev Immunol* 16:261; Wakeland, E. K., et al. 1999. *Curr Opin Immunol* 11:701; Morel, L., et al. 1994. *Immunity* 1:219; Kono, D. H., et al. 1994. *Proc Natl Acad Sci USA* 91:10168; Drake, C. G., et al. 1995. *J Immunol* 154:2441; Rozzo, S. J., et al. 1996. *Proc Natl Acad Sci USA* 93:15164; Rozzo, S. J., et al. 2000. *J Immunol* 164:5515; Vyse, T. J., et al. 1997. *J Immunol* 158:5566; Vyse, T. J., et al. 1998. *J Immunol* 160:2757). In the laboratory, a NZB lupus-susceptibility locus on distal chromosome 1 (named Nba2 for New Zealand black autoimmunity 2) has been apparent in multiple different backcrosses (Drake, C. G., et al. 1995. *J Immunol* 154:2441; Rozzo, S. J., et al. 1996. *Proc Natl Acad Sci USA* 93:15164; Rozzo, S. J., et al. 2000. *J Immunol* 164:5515; Vyse, T. J., et al. 1997. *J Immunol* 158: 5566; Vyse, T. J., et al. 1998. *J Immunol* 160:2757; Kotzin, B. L. 1996. *Cell* 85:303). In one cross, it was found that Nba2, in combination with the NZW MHC haplotype, accounted for >90% of the genetic contribution to IgG autoantibody production and disease (Rozzo, S. J., et al. 1996. *Proc Natl Acad Sci USA* 93:15164). In different crosses, Nba2 also showed evidence for linkage as a quantitative trait locus with nearly all of the lupus autoantibodies studied, including IgG autoantibodies to chromatin, DNA, histones, and the retroviral envelope glycoprotein, gp70 (Vyse, T. J., et al. 1997. *J Immunol* 158:5566; Vyse, T. J., et al. 1998. *J Immunol* 160:2757). On the basis of these findings and enhancing effects on total IgG levels, it was understood that Nba2 can act as an immune response gene that influences antigen-driven B cell responses to self and possibly to exogenous antigens. More recently, mice congenic for the Nba2 locus were generated and showed the contribution of this chromosomal region to autoantibody production and lupus nephritis (Rozzo, S. J., et al. 2001. *Immunity* 15:435). Expression profiling with oligonucleotide microarrays demonstrated differential expression of two IFN-inducible genes, which both localized to the Nba2 interval (Rozzo, S. J., et al. 2001. *Immunity* 15:435). The finding that these candidates are known IFN-inducible genes has led others to formally investigate the role of IFN-α in this model. Santiago-Raber et al examined the contribution of IFN by generating congenic NZB mice lacking the alpha-chain of IFN-alpha/betaR, the common receptor for the multiple IFN-alpha/beta species. Compared with littermate controls, Ifnar1−/−xNZB mice had significantly reduced autoimmune symptoms, kidney disease, and mortality. These reductions were intermediate in the heterozygous-deleted mice. Most notably, the disease-ameliorating effects were accompanied by reductions in dendritic cell maturation and T cell stimulatory activity, as disclosed herein. Based on these finding and the ability to use these mouse models in a pure C57B/6 background, TNF-Tg and Nba2 congenic mice can be used to test the action of Nba2 as an immune response gene.

Collectively, the studies disclosed herein form a solid framework for understanding the cellular and molecular events responsible for the erosive phenotype in inflammatory arthritis. The observation that type I IFN inhibits osteoclastogenesis coupled with skewing of lupus monocyte differentiation down the dendritic cell pathway in SLE favors an IFN-based disease mechanism. In contrast, PsA is associated with a strong TNF signal that directs monocytes along an osteoclast pathway. Thus, the dominance of IFN in SLE patients provides a mechanism to explain the relative resistance of lupus patients to bone erosion.

14. Methods of Diagnosing

Disclosed are methods of diagnosing a subject with an inflammatory joint disease comprising measuring the number of osteoclast precursor cells (OCP) in the blood of the subject. Also disclosed are methods of determining the presence of an inflammatory joint disease in a subject comprising, obtaining a PBMC sample from the subject, and measuring the number of OCP in the PBMC of the subject, wherein a number of OCP in the PBMC of the subject greater than the number of OCP in a control subject indicates the presence of disease in the subject. Also disclosed are methods of diagnosing an inflammatory joint disease in a subject comprising, obtaining a sample from the subject and assaying the number of OCP in the sample, wherein an increase in OCP compared to a healthy control indicates an inflammatory joint disease in the subject.

An inflammatory joint disease refers to any condition in which cytokine release in an area of bone-bone or bone cartilage interaction results in the modification of healthy tissue, the development of synovitis i.e. transformation of the normal delicate synovial membrane into a hyperplastic inflamed tissue from its normal state. This modification can be destruction of healthy bone or cartilage tissue (e.g., bone resorption) or development. The result of this cytokine mediated modification is the inflammation of the joint which manifests as pain, welling, itching, and heat. Examples of inflammatory joint disease are psoriatic arthritis, rheumatoid arthritis, systemic lupus erythematosus (SLE), Sjogren's Syndrome and polymyositis. The disclosed methods and compositions could also be used for example to treat aseptic joint loosening of orthopedic implants, non-nion of a fracture, spondyloarthropathies, psoriasis, and Crohns disease.

Typically osteoclast precursor cell refers to a circulating monocyte/macrophage lineage cell capable of osteoblast directed differentiation into osteoclasts. Two signals are necessary and sufficient for the differentiation process to occure 1) MCSF binds c-fms and 2) RANKL binds RANK on the osteoclast precursor cell surface.

A control subject refers to any individual that has not been diagnosed as having the disorder or condition being assayed. The terms "normal control" and healthy control" likewise mean a sample (e.g., cells, serum, tissue) taken from a source (e.g., subject, control subject, cell line) that does not have the condition or disorder being assayed and therefore may be used to determine the baseline for the condition or disorder being measured. Normal control and healthy control may also refer to samples taken from a source but not subject to a modification or stimulus that would result in the activation of differentiation of the sample. It is also understood that the control subject, normal control, and healthy control, include data obtained and used as a standard, i.e. it can be used over and over again for multiple different subjects. In other words, for example, when comparing a subject sample to a control sample, the data from the control sample could have been obtained in a different set of experiments, for example, it could be an average obtained from a number of healthy subjects and not actually obtained at the time the data for the subject was obtained.

Also disclosed are methods further comprising collecting the subject's PBMCs and methods wherein the step of measuring comprises counting the number of cells comprising at least one, two, three, four, five, six, seven, or eight markers selected from the group consisting of CD14, CD11a, CD11b, CD51/CD61, RANK, CCR1, CCR4, VCAM (CD106), VLA-4 (CD49d), and CD16, MHC Class II, B7.1, B7.2, CD40, c-fms. A marker has a well understood meaning in the art and can include for example, a molecule that is associated with a particular type of cells or set of types of cells, such as surface protein or expressed protein or lipid or carbohydrate. It is also understood that markers can be assayed for their presence or absence, each of which can give information.

For example, disclosed are methods, wherein the step of measuring comprises counting the number of cells that are CD16– (negative).

Disclosed are methods, wherein the number of cells in the subject is compared to the number of cells obtained in a healthy control.

Disclosed are methods, wherein the amount of OCP is determined by staining the PBMC sample with fluorescently labeled antibodies for at least one marker selected from the group consisting of CD14, CD11b, CD51/CD61, RANK, CCR1, CCR4, VCAM (CD106), VLA-4 (CD49d), and CD16, CD11a, MHC Class II, B7.1, B7.2, CD40, c-fms and visualizing the cells with labeled antibody bound to at least one of CD14+, CD11b+, CD51/CD61+, RANK+, CCR1+, CCR4+, VCAM+(CD106), VLA-4+(CD49d), CD11a, MHC Class II, B7.1, B7.2, CD40, c-fms or CD16– using Fluorescence Activated Cell Sorting (FACS).

Herein, the terms "labeling" and "labeled" are used in reference to states of molecules that allow the molecules to be assayed. For example, molecules can be modified, labeled, such that the molecule can be visualized using detection methods well known in the art for radioactivity or fluorescence, for example. Examples of well known labels include but are not limited to fluorescent tags (e.g., Fuorescein isothiocyanate (FITC), Cascade Yellow, Cascade Blue®, Phycoerythrin (PE), PE-Texas Red®, Allophycocyanin (APC), Cy-5-PE, Cy-7-APC, and Peridinin Chlorophyll Protein (PerCP)), Biotin, Alkoline phosphatase, Horseradaish peroxidase, and directly conjugated dies.

Fluorescence activated cells sorting (FACS)" and "flow cytometry" are well understood methods in the art and include the ability to identify and mechanically sort cells based on whether the cell is labeled with a fluorescent label either directly or indirectly, i.e. a labeled molecule internalized by the cell or labeled molecule bound to the cell through binding to a marker on the cell.

Disclosed are methods wherein the number of OCP is determined by removing a tissue sample from the subject and visualizing the sample using immunohistochemistry for at least one marker selected from the group consisting of CD14, CD11b, CD51/CD61, RANK, CCR1, CCR4, VCAM (CD106), VLA-4 (CD49d), CD11a, MHC Class II, B7.1, B7.2, CD40, c-fms and CD16.

Tissue sample means any portion of an organism, organ, tissue, or cell that can be used for any diagnostic, screening, or testing purpose. Immunohistochemistry is well understood in the art and includes refers the use of labeled antibodies to directly visualize via microscopy (e.g., fluorescence microcopy, transmission electron microscopy, and light microscopy) the presence of features (ie., any cell structure, protein, glycoprotein, or marker to which an antibody may be directed) on or inside a given sample (e.g., tissue section or cells).

Disclosed are methods, wherein the amount of OCP is measured by removing a tissue sample from the subject and staining a tissue section with TRAP, counting the number of multinucleated cells, and comparing the number of multinucleated cells in the sample from the subject to the number of multinucleated cells in a sample from a healthy control, wherein more multinucleated cells in the sample from the subject than in the sample from the healthy control indicates an inflammatory joint disease in the subject.

Disclosed are methods, wherein the sample is a blood sample, wherein the sample is from the synovium of the subject, wherein the sample comprises bone marrow, and wherein the sample comprises perivascular mononuclear cells. Synovium is the delicate tissue that lines the joint space and is the primary site of inflammation in inflammatory arthritis and perivascular cells (cells that line the vasculature as it traverses in the synovium.

Disclosed are methods, wherein the amount of OCP in the subject's blood is measured using a colorimetric assay, and comparing the amount of OCP in the subject's blood to a standard curve. A standard curve has a well understood meaning and can refer to a set of samples used in an assay as a method of calibration among samples and separate assays. Also disclosed are methods, wherein the amount of OCP in the subject's blood is measured using a calorimetric assay, and comparing the amount of OCP in the subject's blood to the amount of OCP in a healthy control's blood. A calorimetric assay refers to any nonfluorescence assay where the results are quantified by measuring the amount of absorbance at a given wavelength of light. Such assays can include but are not limited to Enzyme-linked immunosorbance assays (ELISA).

Disclosed are methods, wherein the amount of OCP in the subject's blood is measured using FACS methods, Immunohistochemistry methods, Western methods, Southern methods, hybridization methods, RT-PCR methods, ELISA methods, ELISPOT methods, labeling methods, microarrays, bone wafer resorption, or Immunoprecipitation methods. These methods, as well as other detection methods, are well understood in the art. All of these methods, as well as others, are capable of, for example, identifying OCP cells, by for example, binding markers on OCP cells. For example, an Enzyme-linked immunospot (ELISpot) can refer to any assay in which the labeled antibodies are used to identify cells with a given characteristic, activity, or surface marker and the results are quantified by the visual enumeration of spots formed by the presence of antibody bound to a filter Disclosed are methods, wherein the disease is psoriatic arthritis (PsA) or Rheumatoid arthritis (RA). Also disclosed methods designed to address, for example, aseptic joint loosening of orthopedic implants, non-nion of a fracture, spondyloarthropathies, psoriasis and Crohns disease.

Disclosed are methods, wherein measuring the number of OCP comprises identifying RANK, CD11b and CD14 positive cells in the blood sample. There are numerous markers disclosed herein that are associated with OCP cells. For example, the presence of one or more CD14, CD11b, CD51/CD61, RANK, CCR1, CCR4, VCAM (CD106), VLA-4 (CD49d), CD11a, MHC Class II, B7.1, B7.2, CD40, c-fms and the absence of CD16 are associated with OCPs. These markers can be identified using disclosed means, for example, through binding with labeled antibodies. Antibodies can be purchased, obtained, or made for these markers and others using standard means.

Disclosed are methods, wherein the subject shows bone erosion on a radiograph.

Also disclosed are methods of diagnosing an inflammatory joint disease comprising culturing peripheral blood mononuclear cells from a subject (PBMC) and assaying the number of osteoclasts formed.

Disclosed are methods, wherein assaying the number of osteoclasts formed comprises monitoring the amount of TRAP positive cells.

Disclosed are methods, wherein assaying the number of osteoclasts formed comprises monitoring the number of multinucleated cells, methods wherein an increased number of osteoclasts in the culture from the subject relative to the number of osteoclasts in a culture of PBMC from a control subject without joint inflammation disease indicates the subject has an inflammatory joint disease.

Disclosed are methods, wherein the culture has no exogenous RANKL or M-CSF added.

Disclosed are methods, wherein addition of RANKL or M-CSF increases the number of osteoclasts in the culture from the subject relative to the number of osteoclasts in a culture of PBMA from a control subject without an inflammatory joint disease, and wherein this increase indicates the subject has an inflammatory joint disease.

Disclosed are methods of diagnosing an inflammatory joint disease comprising culturing peripheral blood mononuclear cells (PBMC) from a subject and measuring the amount of TNF-α secreted.

Disclosed are methods of determining whether a subject has an inflammatory joint disease comprising, collecting PBMCs from the subject, allowing the PBMC to settle, fixing the cells, staining with anti-TRAP or TRAP activity, and examining the stained cells under a microscope, wherein the presence of TRAP indicates the subject has an inflammatory joint disease.

Also disclosed are methods of determining whether a subject has an inflammatory joint disease comprising isolating PBMC from the subject, and probing for a surface marker of mononuclear OCP. Probing is well understood in the art and can refer to using any method needed to identify the presence or absence of a marker. Disclosed are methods, wherein the surface marker comprises a marker selected from the group consisting of CD14, CD11b, CD51/CD61, RANK, CCR1, CCR4, VCAM (CD106), VLA-4 (CD49d), CD1a, MHC Class II, B7.1, B7.2, CD40, C-fins and or CD16.

Disclosed are methods, wherein the surface markers are analyzed by FACS, methods wherein probing for a surface marker comprises assaying for at least one, two, three, four, five, six, seven, eight, or more surface markers.

Also disclosed are methods, wherein the subject is diagnosed with an inflammatory joint disease if the PBMC of the subject has more OCP than the PBMC of a control subject without an inflammatory joint disease.

Disclosed are methods of determining whether a subject has an inflammatory joint disease, comprising obtaining PBMC from the subject, culturing the PBMC on cortical bone wafers, and assaying the amount of eroded bone material in the cortical bone wafer. Cortical bone wafers can refer to thin slices of bovine bone that can be purchased commercially. Bone or other tissue is eroded when it is its density and composition is lessened.

Disclosed are methods, wherein the culturing occurs for any number of days including, for example, at least or greater than or equal to or less than or equal to 1, 2, 3, 4, 5, 6, 7, 8, 9, 10, 11, 12, 13, 14, 15, 16, 17, 18, 19. 20, 21, 22, 23, 24, 25, 30, 35, 40, 45, or 50 days.

Disclosed are methods, wherein the subject is diagnosed with an inflammatory joint disease if the PBMC from the subject erodes more bone than the PBMC of a control subject.

Disclosed are methods of determining whether a subject has an inflammatory joint disease comprising assaying whether the osteoclasts of the subject express RANK.

15. Method of Following Treatment Claims

Disclosed are methods of monitoring the treatment of subjects with an inflammatory joint disease using any of the disclosed methods herein. For example, disclosed are methods of monitoring the treatment for an inflammatory joint disease in a subject comprising, administering an anti-inflammatory disease agent to the subject, and measuring the number of osteoclast precursor cells (OCP) in the blood of the subject. Treatment refers to a method designed to reduce or alleviate the conditions associated with a disease or to diminish the disease or condition. It is specifically contemplated that treatment can include but is not limited to any change in the subject's disease state toward a non-diseased state. Treatment does not require the complete ablation of a disease or condition, but can include it. For example, a treatment can result in a 1, 2, 3, 4, 5, 6, 7, 8, 9, 10, 15, 20, 25, 30, 35, 40, 45, 50, 60, 70, 80, or 90 percent reduction in the amount of a symptom of a disease of inflammation of the joint in a subject.

An anti-inflammatory disease agent means any agent that results in the reduction of the symptoms or underlying disease that results in inflammation. For example, biologics, such as infliximab, Enbrel® (etanercept), adludimab, kinaret, raptiva, osteoprotegerin (OPG), RANKFc, anti-RANKL, Bisphosphonates such as pamidronate, alendronate, actonel, zolendronate, clodronate and traditional DMARDS, such as methotrexate, azulfidine, hydroxychloroquine Corticosteroids-prednisone, methylprednisilone are anti-inflammatory disease agents, as well as salicylic acid, and ibuprofen.

Disclosed are methods of monitoring the treatment for an inflammatory joint disease in a subject comprising, administering an anti-inflammatory disease agent to the subject, obtaining a PBMC sample from the subject, and measuring the number of OCP in the PBMC of the subject, wherein a decrease in the number of OCP in the PBMC of the subject after treatment indicates the anti-inflammatory disease agent is having an effect on the disease.

16. Method of Treating Claims

Disclosed are methods of treating inflammatory disease, which involve assaying the subject to be treated using methods disclosed herein to diagnose the presence of the inflammatory disease. For example, disclosed are methods of treating a subject with an inflammatory joint disease comprising measuring the number of OCP in the PMBC of the subject, and administering an anti-inflammatory disease agent if the number of OCP in the PMBC of the subject is greater than the number of OCP in the PBMC of a control subject.

Disclosed are methods, wherein the number of OCP are assayed a second time after the administration of the anti-inflammatory disease agent.

Also disclosed are methods, wherein the anti-inflammatory disease agent comprises OPG. The disclosed methods of treatment can use any any anti-inflammatory disease agent including Biologics such as infliximab, Enbrel® (etanercept), adludimab, kinaret, raptiva, osteoprotegerin (OPG), RANKFc, anti-RANKL, Bisphosphonates, such as pamidronate, alendronate, actonel, zolendronate, clodronate and traditional DMARDS, such as methotrexate, azulfidine, hydroxychloroquine Corticosteroids-prednisone, methyl-prednisilone. These therapies can be administered in any combination along with any other therapy, including for example physical therapy, or anti-inflammatory molecules such as acetiminophen or ibuprofren.

Disclosed are methods, where the anti-inflammatory disease agent comprises a composition that binds RANK, wherein the composition inhibits RANKL from binding RANK, wherein the anti-inflammatory disease agent comprises a composition that binds RANKL, wherein the composition inhibits RANK from binding RANKL, and wherein the composition is an antibody.

Also disclosed are methods wherein the anti-inflammatory disease agent comprises a composition that binds TNF-R1, wherein the antibody inhibits TNF-α from binding to TNF-R1, wherein the anti-inflammatory disease agent comprises a composition that binds TNF-α, wherein the antibody inhibits TNF-R1 from binding to TNF-α, and wherein the composition is an antibody. Also disclosed are methods wherein the anti-inflammatory disease agent comprises a composition that binds TNF-R2, wherein the antibody inhibits TNF-α from binding to TNF-R2, wherein the anti-inflammatory disease agent comprises a composition that binds TNF-α, wherein the antibody inhibits TNF-R2 from binding to TNF-α, and wherein the composition is an antibody.

Binds or binding refers to the interaction between two or more molecules beyond background or non-specific interaction. Inhibits or inhibiting refer to any reduction in a state, such as a disease, a binding interaction, or a condition. It is specifically contemplated that this action or result can include, but is not limited to the complete ablation of the state.

Disclosed are methods, wherein the anti-inflammatory disease agent comprises an anti-TNF-α agent, and methods wherein the anti-TNF-α agent comprises, for example, Enbrel® (etanercept) or infliximab.

Disclosed are methods of treating a subject with an inflammatory joint disease comprising administering an anti-inflammatory disease agent to the subject, and after administering the anti-inflammatory disease agent measuring the number of OCP in the PMBC of the subject, and adjusting the administration of the anti-inflammatory disease agent based on the number of OCP in the PBMC.

17. Methods of Selecting New Anti-arthritic Compounds

As disclosed herein, the knowledge that the various molecules, such as RANK, RANKL, and TNF, and how they are related to the production of osteoclasts involved in inflammatory joint diseases, such as psoriatic arthritis, through the regulation of osteoclast precursors can be used to identify new therapeutics for the treatment of inflammatory joint diseases. For example, disclosed are methods of screening the efficacy of a pharmaceutical agent for the ability to treat an inflammatory joint disease comprising measuring the number of OCP in the PBMC of a subject, wherein the subject was administered the pharmaceutical agent, wherein a decrease in the number of OCP in the subject after treatment indicates efficacy of the pharmaceutical agent. Also disclosed are methods of identifying pharmaceutical agents having the ability to treat an inflammatory joint disease comprising measuring the number of OCP in a sample, assaying the number of OCP in sample from a non-treated control, and comparing the number of OCP in the subject and the non-treated control. Disclosed are methods, wherein the step of measuring comprises treating a PBMC sample with the agent, culturing the cells, and screening for cells comprising at least one marker selected from the group consisting of CD14, CD11b, CD51/CD61, RANK, CCR1, CCR4, VCAM (CD106), VLA-4 (CD49d), and CD11a, MHC Class II, B7.1, B7.2, CD40, c-fms and CD16

18. Kits for Diagnosing Joint Disease

57. Disclosed are kits for diagnosing an inflammatory joint disease comprising any of the reagents discussed herein to perform, for example, the methods discussed herein. For example, disclosed are kits for diagnosing an inflammatory joint disease comprising reagents for identifying a marker selected from the group consisting of CD14, CD11b, CD51/CD61, RANK, CCR1, CCR4, VCAM (CD106), VLA-4 (CD49d), CD11a, MHC Class II, B7.1, B7.2, CD40, c-fms and and CD16, and a standard sample of a control subject without an inflammatory joint disease.

Disclosed are kits for diagnosing an inflammatory joint disease comprising reagents for identifying an OCP, and a standard sample of a control subject without an inflammatory joint disease. Also disclosed are for example, kits, wherein the reagent comprises a primer capable of hybridizing to the transcript of the marker, kits wherein the reagent comprises a composition capable of binding to the marker, or wherein the composition comprises an antibody.

C. Methods and Reagents Generally Applicable to the Disclosed Methods and Compositions There are a variety of methods and compositions disclosed herein, which might rely on, in a certain embodiment, an antibody, the hybridization of nucleic acids, a protein variant, a pharmaceutical composition, or methods of making recombinant cells, for example, to be screened for a therapeutic or produce a reagent. Disclosed is general and specific guidance for these and other methods, reagents, techniques, related to the disclosed compositions and methods.

1. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

2. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA: DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

3. Nucleic Acids

There are a variety of molecules disclosed herein that are nucleic acid based, including for example the nucleic acids that encode, for example, RANK, RANKL, TNF-α TNF-R1, and TNF-R2 as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantagous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate., An non-limiting example of a nucleotide would be 3'-AMP (3'-adenosine monophosphate) or 5'-γMP (5'-γuanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989,86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to, for example, RANK, RANKL, TNF-α TNF-R1, and TNF-R2 as well as any other protein disclosed herein that are disclosed on Genbank, and these sequences and others are herein incorporated by reference in their entireties as well as for individual subsequences contained therein.

A variety of sequences are provided herein and these and others can be found in Genbank, at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

c) Primers and Probes

Disclosed are compositions including primers and probes, which are capable of interacting with the genes disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the nucleic acid or region of the nucleic acid or they hybridize with the complement of the nucleic acid or complement of a region of the nucleic acid.

d) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of RANK, RANKL, TNF-α TNF-R1, and TNF-R2 or the genomic DNA of RANK, RANKL, TNF-α TNF-R1, and TNF-R2 or they can interact with the polypeptide RANK, RANKL, TNF-α TNF-R1, and TNF-R2. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide. For example, when determining the specificity of RANK, RANKL, TNF-α TNF-R1, and TNF-R2 aptamers, the background protein could be RANK, RANKL, TNF-α TNF-R1, and TNF-R2. Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616, 466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in the following non-limiting list of U.S. Pat. Nos. 5,176,996, 5,645,985, 5,650, 316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukarotic cells. (Yuan et al., *Proc. Natl. Acad. Sci. USA* 89:8006-8010 (1992); WO 93/22434 by Yale; WO 95/24489 by Yale; Yuan and Altman, *EMBO J* 14:159-168 (1995), and Carrara et al., *Proc. Natl. Acad. Sci.* (USA) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162.

4. Nucleic Acid Delivery

In the methods described above which include the administration and uptake of exogenous DNA into the cells of a subject (i.e., gene transduction or transfection), the disclosed nucleic acids can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). This disclosed compositions and methods can be used in conjunction with any of these or other commonly used gene transfer methods.

As one example, if the antibody-encoding nucleic acid is delivered to the cells of a subject in an adenovirus vector, the dosage for administration of adenovirus to humans can range from about 107 to $10^9$ plaque forming units (pfu) per injection but can be as high as 1012 pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

a) In Vivo/Ex Vivo

As described above, the compositions can be administered in a pharmaceutically acceptable carrier and can be delivered to the subjects cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

5. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature*, 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-γalactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR– cells and mouse LTK– cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

6. Peptides a) Protein Variants

As discussed herein there are numerous variants of, for example, the RANK, RANKL, TNF-α TNF-R1, and TNF-R2 proteins. In addition, to the known functional strain variants there are derivatives of the, for example, RANK, RANKL, TNF-α TNF-R1, and TNF-R2 proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 2

Amino Acid Abbreviations

| Amino Acid | Abbreviations |
| --- | --- |
| Alanine | Ala, A |
| Allosoleucine | AIle |
| Arginine | Arg, R |
| Asparagines | Asn, N |
| aspartic acid | Asp, D |
| Cysteine | Cys, C |
| glutamic acid | Glu, E |
| Glutamine | Gln, K |
| Glycine | Gly, G |
| Histidine | His, H |
| Isolelucine | Ile, I |
| Leucine | Leu, L |
| Lysine | Lys, K |
| Phenylalanine | Phe, F |
| Proline | Pro, P |
| pyroglutamic acidp | Glup |
| Serine | Ser, S |
| Threonine | Thr, T |
| Tyrosine | Tyr, Y |
| Tryptophan | Trp, W |
| Valine | Val, V |

TABLE 3

Amino Acid Substitutions
Original Residue Exemplary
Conservative Substitutions, others
are known in the art.

| | |
| --- | --- |
| Ala | ser |
| Arg | lys, gln |
| Asn | gln; his |
| Asp | glu |
| Cys | ser |
| Gln | asn, lys |
| Glu | asp |
| Gly | pro |
| His | asn; gln |
| Ile | leu; val |
| Leu | ile; val |
| Lys | arg; gln; |
| Met | Leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 3, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein in the particular organism from which that protein arises is also known and herein disclosed and described.

It is understood that there are numerous amino acid and peptide analogs, which can be incorporated into the disclosed compositions. For example, there are numerous D amino acids or amino acids, which have a different functional substituient then the amino acids shown in Table 2 and Table 3. The opposite stereo-isomers of naturally occurring peptides are disclosed, as well as the stereo-isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Enginerring Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —$CH$=$CH$—(cis and trans), —$COCH_2$—, —$CH(OH)CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—S); Hann J. Chem. Soc Perkin Trans. 1307-314 (1982) (—$CH$—$CH$—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—$CH(OH)CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

7. Antibody

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as F(ab')$_2$, Fab', Fab and the like, including hybrid fragments. Thus, fragments of the antibodies that retain the ability to bind their specific antigens are provided. For example, fragments of antibodies which maintain, for example, RANK, RANKL, TNF-α TNF-R1, or TNF-R2 binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., J. Immunol., 151:2296 (1993) and Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published 3 Mar. 1994).

Transgenic animals (e.g., mice) that are capable, upon immunization, of producing a fill repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al: are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991)).

Disclosed are hybidoma cells that produces the monoclonal antibody. The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816,567 and Morrison et al., *Proc. Natl. Acad. Sci. USA,* 81:6851-6855 (1984)).

Monoclonal antibodies may be prepared using hybridoma methods, such as those described by Kohler and Milstein, Nature, 256:495 (1975) or Harlow and Lane. Antibodies, A Laboratory Manual. Cold Spring Harbor Publications, New York, (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. Preferably, the immunizing agent comprises, for example, RANK, RANKL, TNF-α TNF-R1, or TNF-R2. Traditionally, the generation of monoclonal antibodies has depended on the availability of purified protein or peptides for use as the immunogen. More recently DNA based immunizations have shown promise as a way to elicit strong immune responses and generate monoclonal antibodies. In this approach, DNA-based immunization can be used, wherein DNA encoding a portion of the, for example, RANK, RANKL, TNF-α TNF-R1, or TNF-R2 expressed as a fusion protein with human IgG1 is injected into the host animal according to methods known in the art (e.g., Kilpatrick K E, et al. Gene gun delivered DNA-based immunizations mediate rapid production of murine monoclonal antibodies to the Flt-3 receptor. Hybridoma. 1998 December;17(6):569-76; Kilpatrick K E et al. High-affinity monoclonal antibodies to PED/PEA-15 generated using 5 microg of DNA. Hybridoma. 2000 August;19(4):297-302, which are incorporated herein by referenced in full for the the methods of antibody production) and as described in the examples.

An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing domains of the, for example, RANK, RANKL, TNF-® TNF-R1, or TNF-R2 antibody as fusion proteins. The antigen is produced by inserting a gene fragment in-frame between the signal sequence and the mature protein domain of the, for example, RANK, RANKL, TNF-α TNF-R1, or TNF-R2 antibody nucleotide sequence. This results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, J. Immunol., 133:3001 (1984); Brodeur et al., "Monoclonal Antibody Production Techniques and Applications" Marcel Dekker, Inc., New York, (1987) pp. 51-63). The culture medium in which the hybridoma cells are cultured can then be assayed for the presence of monoclonal antibodies directed against, for example, RANK, RANKL, TNF-α TNF-R1, or TNF-R2. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane "Antibodies, A Laboratory Manual" Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Optionally, such a non-immunoglobulin polypeptide is substituted for the constant domains of an antibody or substituted for the variable domains of one antigen-combining site of an antibody to create a chimeric bivalent antibody comprising one antigen-combining site having specificity for, for example, RANK, RANKL, TNF-α TNF-R1, or TNF-R2 and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')$_2$ fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')$_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Also disclosed are fragments of antibodies which have bioactivity. The polypeptide fragments can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with, for example, RANK, RANKL, TNF-α TNF-R1, or TNF-R2. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. Nucl. Acids Res. 10:6487-500 (1982).

A variety of immunoassay formats may be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

Also provided is an antibody reagent kit comprising containers of the monoclonal antibody or fragment thereof and one or more reagents for detecting binding of the antibody or fragment thereof to, for example, RANK, RANKL, TNF-α TNF-R1, or TNF-R2. The reagents can include, for example, fluorescent tags, enzymatic tags, or other tags. The reagents can also include secondary or tertiary antibodies or reagents for enzymatic reactions, wherein the enzymatic reactions produce a product that can be visualized.

8. Pharmaceutical Carriers/Delivery of Pharamceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews,* 129: 57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

Following administration of a disclosed composition, such as an antibody, for treating, inhibiting, or preventing a joint inflammation disease the efficacy of the therapeutic antibody can be assessed in various ways well known to the skilled practitioner. For instance, one of ordinary skill in the art will understand that a composition, such as an antibody, disclosed herein is efficacious in treating or inhibiting a joint inflammation disease in a subject by observing that the composition reduces viral load or prevents a further increase in the symptoms related to the joint inflammation disease.

There are a variety of ways for determining level of PsA. For example, there is a Psoriatic Arthritis Response Criteria (PsARC). This looks at improvement of a number of factors at will typically look for improvement of at least 2 of 4 criteria, including, a physician global assessment, a patient global assessment, a tender joint score, and a swollen joint score. A reduction in disease can also be characterized by improvement in at least 1 of 2 joint scores, including no worsening in any criteria and the ACR Response Criteria. (Clegg D O. Arthritis Rheum 1996;39:2013-20). The level of disease can also be assessed by the psoriasis area and severity index (Fredricksson. Dermatologica. 1978) by using the composite index of disease severity which includes evaluation of scale, erythema, induration which can be weighted by severity and by body surface area. The psoriasis area and severity index (PASI; Fredriksson 1978) was used to assess the severity of psoriasis at baseline and any change in severity or lesion surface area from baseline to the end-of study assessment. In both protocols, only patients with plaque psoriasis involvement ∞ 3% body surface area at baseline were evaluated for the PASI. Evaluations also included the percentage of patients achieving a 50%, 75%, and 90% improvement from baseline in PASI score.

9. Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

10. Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Disclosed are computer readable mediums comprising the sequences and information regarding the sequences set forth herein.

11. Compositions Identified by Screening with Disclosed Compositions/Combinatorial Chemistry a) Combinatorial Chemistry The disclosed compositions can be used as targets for any combinatorial technique to identify molecules or macromolecular molecules that interact with the disclosed compositions in a desired way. The nucleic acids, peptides, and related molecules disclosed herein can be used as targets for the combinatorial approaches. Also disclosed are the compositions that are identified through combinatorial techniques or screening techniques in which the compositions disclosed in herein, such as the, for example, RANK, RANKL, TNF-α TNF-R1, or TNF-R2, or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, for example, RANK, —RANKL, TNF-α TNF-R1, or TNF-R2, are also disclosed. Thus, the products produced using the combinatorial or screening approaches that involve the disclosed compositions, such as, for example, RANK, RANKL, TNF-α TNF-R1, or TNF-R2, are also considered herein disclosed.

It is understood that the disclosed methods for identifying molecules that inhibit the interactions between, for example, RANK, RANKL, TNF-α TNF-R1, or TNF-R2 can be performed using high through put means. For example, putative inhibitors can be identified using Fluorescence Resonance Energy Transfer (FRET) to quickly identify interactions. The underlying theory of the techniques is that when two molecules are close in space, ie, interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptdyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23) 12997-302 (1997)).

Another preferred method for combinatorial methods designed to isolate peptides is described in Cohen et al. (Cohen B. A., et al., Proc. Natl. Acad. Sci. USA 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain. A peptide of choice, for example, RANK, RANKL, TNF-α TNF-R1, or TNF-R2 is attached to a DNA binding domain of a transcriptional activation protein, such as Gal 4. By performing the Two-hybrid technique on this type of system, molecules that bind the extracellular portion of, for example, RANK, RANKL, TNF-α TNF-R1, or TNF-R2 can be identified.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449, 754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. No. 6,017,768 and 5,821,130), amide alcohols (U.S. Pat. No. 5,976,894), hydroxy-amino acid amides (U.S. Pat. No. 5,972, 719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916, 899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. No. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in iterative processes.

b) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as, RANK, RANKL, TNF-α TNF-R1, or TNF-R2 are also disclosed. Thus, the products produced using the molecular modeling approaches that involve the disclosed compositions, such as, RANK, RANKL, TNF-α TNF-R1, or TNF-R2 are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

12. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended.

D. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

2. Peptide Synthesis

One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. *Science*, 256:221 (1992)). This technique has been used to synthesize analogs of protein domains as well as large amounts of relatively pure proteins with full biological activity (deLisle Milton R C et al., *Techniques in Protein Chemistry IV*. Academic Press, New York, pp. 257-267 (1992)).

E. Methods of Using the Compositions

1. Methods of Using the Compositions as Research Tools

The disclosed compositions can be used in a variety of ways as research tools.

The compositions can be used for example as targets in combinatorial chemistry protocols or other screening protocols to isolate molecules that possess desired functional properties related to joint inflammation diseases.

The disclosed compositions can also be used diagnostic tools related to joint inflammation diseases.

The disclosed compositions can be used as discussed herein as either reagents in micro arrays or as reagents to probe or analyze existing microarrays. The disclosed compositions can be used in any known method for isolating or identifying single nucleotide polymorphisms. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1 a) Materials and Methods (1) Study Population and Treatment Protocol

All clinical studies were carried out with approval of the University of Rochester Medical Center Research Subjects Review Board and informed consent. Synovium, cartilage and bone specimens were obtained at the time of joint replacement surgery from 5 PsA, 4 RA and 4 OA patients. PsA was diagnosed according to the Moll and Wright criteria (Moll, J. M. and Wright, V. 1973. Psoriatic arthritis. Seminars in Arthritis & Rheumatism 3:55-78), RA by the American College of Rheumatology criteria (Arnett, F. C., et al. 1988. *Arthritis Rheum.* 31:315-324) and OA by physical examination and characteristic findings on plain x-ray. A blinded radiologist evaluated radiographs from PsA patients. Healthy controls had no acute or chronic joint pain and were in good health. None of the patients or controls was taking corticosteroids or second line agents (methotrexate, gold, hydroxychloroquine, leflunomide, Enbrel® (etanercept) or infliximab). Nine patients with erosive PsA were treated with anti-TNF agents: 8 patients with Enbrel® (etanercept) 25 mg twice per week and 1 patient with infliximab 5 mg/kg at weeks 0, 2, 6 and 14).

(2) Osteoclast Precursors From Peripheral Blood Mononuclear Cells (PBMCs)

PBMCs were isolated from whole blood obtained from 24 PsA patients and 12 healthy controls. The PBMC were separated on Ficoll gradients. Unfractionated PBMC ($1 \times 10^6$ cells/ml) were placed in 8 well chamber slides containing 0.5 ml 10% FCS—RPMI. Cultures were incubated in 6% $CO_2$ at 37° C. for 14 days. Media was replenished every 2-3 days. After 14 days in culture, slides were stained for tartrate resistant acid phosphatase (TRAP) (Sigma Diagnostics St. Louis Mo.). Slides were viewed by light microscopy and TRAP positive cells with 3 or more nuclei were counted as osteoclasts. The scoring system that was used presents the data as the number of OCP per $10^6$ PBMC in the initial cell culture even though the final readout is the number of TRAP positive multinuclear cells. This is based on the fact that osteoclasts are derived exclusively from OCP and there is currently no recognized surface marker for OCP per se. (Massey, H. M. and Flanagan, A. M. 1999. *British Journal of Haematology* 106:167-170; Shalhoub, V., et al. 2000. *Br J of Haematol* 111:501-512)

Cultures stimulated with M-CSF (25 ng/ml) and RANKL (10 ng/ml) served as positive controls. The ability of these cells to resorb bone was demonstrated by culturing PBMC in 0.5 ml 10% FBS-RPMI on bovine bone wafers for 21 days. The cultured bone wafers, together with uncultured wafers, were stained with toludine blue and photographed. The resorption area was quantified by density scan using Scion imaging software, after subtracting the background in the uncultured wafers. These data are expressed as the % resorption area, calculated by dividing the total pitted area by the total surface area of the bone wafer.

(3) Flow Cytometry

PBMC were prepared as described above and the cells were centrifuged and re-suspended in PBS containing 4% of fetal bovine serum (FBS). Aliquots of $1\times10^6$ cells were incubated with anti-human CD11b (ICRF44), CD14 (M5E2), $\alpha v\beta 3$ (CD51/61), and related isotype controls (Pharmingen, San Diego, Calif.), or with fluorescein-conjugated RANKL (a gift from Dr. M. Tondravi, American Red Cross, Rockville, Md.). The cells were then washed with 4% FBS-PBS. Data were acquired using a FACScalibur instrument (Beckton Dickenson, Bedford, Mass.) and analyzed by Cellquest software (ver.3.1).

(4) Immunohistochemistry on Synovial Tissues, Bone and Cartilage

All tissue samples were formalin fixed and bone specimens were decalcified in Immunocal (Decal Corporation Congers, N.Y.), dehydrated in a graded series of alcohols and embedded in paraffin. Samples were cut in 3 µm sections and mounted on glass slides. Sections were de-paraffinized in xylene and rehydrated through a graded series of alcohols to distilled water. Endogenous peroxidase activity was quenched by 3% hydrogen peroxide. Antigen retrieval was performed in a pressure cooker (de-cloaking chamber, Biocare Medical Walnut Creek, Calif.) using 0.01M Citrate Buffer. For OPG staining, citrate/glycerol buffer was used. Slides were blocked in 1:20 normal goat serum (Vector Labs Burlingame, Calif.). For OPG staining, normal horse serum was used as a blocking agent. Antibodies were diluted as noted below and incubated overnight at 4° C. Following the incubation, slides were rinsed in PBS and the biotin-conjugated secondary antibodies applied for 30 minutes at room temperature. Slides were washed and HRP Streptavidin (Zymed Labs, Burlingame, Calif.) was added at a 1:250 dilution in PBS for 30 minutes at room temperature. Sections were washed once in PBS followed by deionized water, then incubated in AEC Chromagen (Romulin, AEC Biocare Medical, Walnut Creek, Calif.). Slides were counter stained with hematoxylin. Primary antibodies to RANK (rabbit anti-human ab1861) and RANKL (rabbit anti-human ab1862) were purchased from Chemicon (Temecula, Calif.). RANK and RANKL antibodies were diluted in 2% normal goat serum in 1:20 BSA/PBS and applied at a 1:800 dilution. The secondary antibody, biotinylated goat anti-rabbit (Vector Labs, Burlingame Calif.), was added at 1:200 dilution. OPG antibody (mouse anti-human MAB805), purchased from R&D Systems (Minneapolis, Minn.) was used at a dilution of 1:30. The secondary antibody, biotinylated horse anti-mouse (Vector Labs, Burlingame, Calif.) was applied at a 1:200 dilution. Sections stained with only the secondary antibody served as a negative control. Slides were reviewed and scored by an independent pathologist blinded to the diagnosis. The osteoclast score was based on an assessment of the number of osteoclasts in Howship's resorption lacunae per 20×, intermediate power fields in areas of active bone remodeling. 1+: 1-2° C. per 10 fields (20×), 2+: 2-5 OC per 10 fields (20×), 3+: >5 OC per 10 fields (20×).

(5) Analysis of RANKL, RANK and OPG Gene Expression by RT-PCR

Synovium was obtained from patients (6 PsA and 2 OA) undergoing total joint replacement or at the time of hand or foot surgery. RNA was isolated as previously described (Ritchlin, C. and Haas-Smith, S. A. 2001. *J of Rheumatol* 28:698-705), reverse transcribed and PCR carried out under conditions described by Gravallese Gravallese, E. M., et al. 2000. *Arthritis Rheum.* 43:250-258) with custom primers from Gibco Life Technologies (Rockville, Md.). Primer sequences: RANKL sense 5' CTATTTCAGAGCGCA-GATGGAT 3' (SEQ ID NO:1); RANKL anti-sense 5' TAT-GAGAACTTGGGATTTTGATGC 3' (SEQ ID NO:2) (Gravallese, E. M., et al. 2000. *Arthritis Rheum.* 43:250-258); RANK sense 5' TTAAGCCAGTGCTTCACGGG 3' (SEQ ID NO:3); RANK anti-sense 5' ACGTAGACCACGATGAT-GTCGC 3' (SEQ ID NO:4)(Myers, D. E., et al. 1999. *FEBS Letters* 463:295-300); OPG sense 5' GCTAACCTCACCT-TCGAG 3' (SEQ ID NO:5); OPG anti-sense 5' TGATTG-GACCTGGTTACC 3' (SEQ ID NO:6)(Huang, L., et al. 2000. *Am J Path* 156:761-767); GAPDH sense 5' GCTCTCCA-GAACATCATCCCTGCC 3' (SEQ ID NO:7); GAPDH anti-sense 5'CGTTGTCATACCAGGAAATGAGCTT. (SEQ ID NO:8)(Gravallese, E. M., et al. 2000. *Arthritis Rheum.* 43:250-258)

(6) TNF-α ELISA

PBMC cultures were established in 24 well tissue culture plates with cells from 5 PsA patients and 5 healthy controls. Unfractionated PBMCs were plated at $1\times10^6$ cells/ml in 10% FBS-RPMI in 1 ml total volume. The cells were incubated at 37° C. and 6% $CO_2$ for 14 days. Culture supernatants were harvested and passed through a syringe filter to remove debris. Samples were stored at −20° C. until assayed. The assay was performed using matched antibody pairs against human TNF-α (Pierce Endogen Rockford, Ill.) following the manufactures technical application procedure. Standards were serially diluted recombinant human TNF-α in culture media (Pierce Endogen Rockford, Ill.). Optical density was recorded on a Bio-Rad (Life Technologies Grand Island, N.Y.) microtiter plate reader. TNF-α is expressed as pg/ml.

(7) Co-Cultures

PBMC from PsA patients were cultured in 24 well tissue culture plates at a density of $10\times10^6$ cells/ml in 1.0 ml of 10% FBS RPMI. Supernatants were harvested at day 14, filtered and stored at −20° C. Healthy donor PBMC isolated from 3 individuals were seeded in 96 well flat bottomed culture plates at $2\times10^5$ cells per well with 50% PsA culture supernatant and 50% normal media in 200 µl total volume. In the initial experiments, supernatants from 3 different PsA PBMC cultures were added to PBMC isolated from the 3 healthy controls. In subsequent experiments, supernatant from a PsA PBMC culture was added to PBMC isolated from 2 different healthy controls. TNF-α activity was blocked by the addition of anti-TNF-α antibody (Pierce-Endogen Rockford, Ill.) at a final concentration of 2.51 µg/ml. The media was replenished 2 times weekly after 14 days in culture; cells were stained for TRAP and osteoclasts were counted as described above.

(8) Osteoclastogenesis Inhibition by OPG

PBMC cultures were established from PsA donors as described above. OPG-Fc (R&D Systems, Minneapolis, Minn.) was added at a final concentration of 1.0 ug/ml). Enbrel® (etanercept) (Amgen, Thousand Oaks, Calif.) was also added to cultures as indicated at a final concentration of 1 ug/ml. Cultures were maintained as described in Methods for 14 days prior to TRAP staining and osteoclast scoring.

(9) Statistics

OCP data are expressed as the number of OCP per $10^6$ PBMC. Students t test of non-paired data was used to analyze differences in OCP frequency, resorption area on bone wafers, expression of CD14, CD11b and supernatant TNF-α levels in PsA patients versus healthy controls. The number of PBMC expressing CD14 in PsA patients before and after anti-TNF therapy, OCP numbers before and after supernatant stimulation and blocking experiments with TNF and RANKL were analyzed by paired t tests. The difference in the median number of OCP in PsA patients with and without erosions was analyzed by the Mann-Whitney test.

b) Results (1) Osteoclasts Were Present in Bone Obtained from PsA Patients

Although it is generally accepted that osteoclasts are the only cell type capable of bone resorption, these cells have not been characterized in the psoriatic joint. To formally document their role in this disease, initial studies were performed to ascertain if osteoclasts were present at sites of focal erosion in PsA bone. Histology specimens from PsA, RA and OA bone were examined and scored for osteoclast number as described in Methods. Histology shows that osteoclasts are prominent in the psoriatic joint. Table 1 shows moderate to large numbers of osteoclasts were detected in bone samples from PsA patients.

TABLE 1

Semiquantitative analysis of osteoclast numbers in PsA, RA, and OA

|  | Tissue | Osteoclasts |
|---|---|---|
| PsA | Hip | 3+ |
|  | Knee | 2+ |
|  | Hip | 1+ |
|  | Foot | 1+ |
|  | Knee | 3+ |
| RA | Hip | 2+ to 3+ |
|  | Knee | 3+ |
|  | Foot | 2+ |
|  | Knee | 1+ |
| OA | Knee | 0 to 1+ |
|  | Hip | 0 to 1+ |
|  | Knee | 0 to 1+ |
|  | Knee | 0 to 1+ |

Tissue sampls, obtained at surgery, from five patients with PsA, four patients with RA, and four patients with OA were fixed, embedded, sectioned, and stained with H&E. A pathologist blinded to the diagnosis semiquantitatively assessed the number of osteoclasts using the system described in Methods.

The majority of osteoclasts were found in resorption pits at the bone-pannus junction, or in cutting cones crossing the subchondral bone. Morphologically mature osteoclasts were not observed in the vascular lumen. Similarly, osteoclasts were increased in RA bone while comparatively few were observed in the OA samples. In some PsA specimens large osteoclasts with high nuclearity (>20 nuclei per cell) were observed in Howship's lacuna.

(2) Osteoclasts Arise in Unstimulated Cultures of PBMCs from Patients with PsA

Numerous multinucleated TRAP positive cells were identified in low density PBMC cultures from PsA patients without exogenous RANKL (10 ng/ml) or M-CSF (25 ng/ml), while such cells were rare in PBMC cultures from healthy controls. Addition of RANKL and M-CSF to the cultures increased the size and number of osteoclasts in cultures from PsA patients and to a lesser degree in cultures from healthy controls. To quantify this effect, PBMC were isolated from 24 PsA patients and 12 healthy controls (FIG. 1). The average number of circulating pre-osteoclasts in unstimulated cultures was significantly higher in PsA patients compared to healthy controls (mean 168±39.9 vs. 3.7+1.1 OCP per $10^6$ PBMC; p<0.006). These results indicate that OCP circulate in the peripheral blood of PsA patients in greater numbers than in healthy controls. Furthermore, these precursors progress to mature osteoclasts without exogenous RANKL and M-CSF stimulation.

To determine if the increased number of TRAP$^+$ multinucleated cells are derived from an increase in mononuclear OCP or from multinucleated inflammatory cells, the following experiments were performed. First, PBMCs isolated from 7 PsA patients with erosive arthritis were allowed to settle overnight in 8-well chamber slides. The cells were fixed, TRAP-stained and examined under a light microscope. Multinucleated or TRAP positive cells in any of the patients were not identified. Second, using probes for surface markers of mononuclear OCP, freshly isolated PBMC from 7 erosive PsA patients and 7 healthy donors were stained for CD11b, CD14, CD51/CD61 and RANK and analyzed by FACS. The percentage of PsA PBMC expressing CD11b and CD14 was significantly greater than in healthy control PBMC (23.9%±3.15% vs. 13.8%±1.3%, p<0.006). Furthermore, CD11b+ and CD14+ PBMC from PsA patients and controls also expressed CD51/CD61 and RANK, matching a phenotypic profile previously described for OCP (Shalhoub, V., et al. 2000. *Br J of Haematol* 111:501-512). In addition, large or multinucleated cells in the forward and side scatter analysis were not identified.

To assess the bone resorbing capacity of these cells, unstimulated PBMC derived from PsA patients and healthy controls were cultured for 21 days on cortical bone wafers. The mean unstimulated values for all patients is shown in FIG. 2. Cells from PsA patients (n=6) eroded approximately seven times the surface area as healthy controls (n=6) (mean 0.49%±0.31% vs. 0.08%±0.12% p<0.009). These data demonstrate a functional osteoclast phenotype in cultured PsA PBMC capable of enhanced bone-resorbing activity. This finding is consistent with the increased pre-osteoclast number detected in the PsA population.

(3) Circulating Pre-Osteoclasts are Highest in Patients with Erosive Arthritis.

If OCP frequency contributes to inflammatory bone loss in PsA, one would predict that patients with erosions on plain radiographs would have higher numbers of circulating OPC than PsA patients without erosions. Therefore, OCP frequency was analyzed in unstimulated PBMC cultures from 10 PsA patients with and 10 without bone erosions (FIG. 3). PsA patients with one or more erosions on plain radiographs had a significantly greater number of OCP compared to PsA patients without erosions. (median: 224 vs. 85 OCP/10 PBMC, p<0.002) These results indicate that OCP contribute to osteolysis in PsA patients.

(4) RANK RANKL and OPG Expression in the PsA Joint and Bone

Based on knowledge of the role of osteoclasts in mediating bone erosions in RA and the importance of RANK-RANKL signaling in the process, the expression pattern of RANK, RANKL and OPG in PsA synovium and bone was investigated. Tissues from PsA patients containing synovium and bone were obtained following surgery and processed for immunohistochemistry as described in Methods. Immunohistochemical analysis revealed that osteoclasts in resorption lacunae strongly express RANK. These RANK positive OC were located at the synovial border of the pannus-bone interface and in cutting cones in the subchondral bone that were void of other cell types. Additionally, RANK positive mononuclear cells increase in number moving from the endothelial cells the erosion front. Furthermore, RANK positive mononuclear cells were detected adjacent to blood vessels traversing the synovium and around vessels located in the subchondral bone. The staining patterns of RANKL and OPG in the synovium was observed. Specifically, retrieval tissues from PsA patients containing synovium were processed for immunohistochemistry with antibodies specific for RANKL and OPG as described in Methods. A representative synovial membrane from a PsA patient stained with anti-RANKL antibody, and anti-OPG antibody, secondary antibody only, and H & E. Intense RANKL immunoreactivity was present throughout the synovial lining layer while OPG staining was restricted to endothelial cells beneath the synovial lining, away from sites of active erosion. Tissue architecture can be determined in H and E stained sections while specific staining is not seen in the negative control. RANK and RANKL staining was weak to absent in all OA tissues examined.

To confirm the immunohistochemical studies, RT-PCR was performed on synovial membranes to analyze the pattern of RANK, RANKL and OPG expression in tissues isolated from 6 patients with PsA and 2 with OA. Briefly, total RNA was isolated from PsA and OA synovium and used as the template to determine RANK, RANKL and OPG mRNA expression by RT-PCR as described in Methods. Five patients with erosive PsA expressed RANKL mRNA in synovial tissues, however, the sixth PsA patient, without bone erosions, did not express RANKL message. The finding of RANK expression in 3 of the 6 PsA synovial samples further supports the immunohistochemical data. Five of 6 PsA and 1 of 2 OA tissues expressed OPG.

(5) Anti-TNF Therapy Reduces OCP Frequency in PsA

It has been previously demonstrated that TNF-α is elevated in psoriatic synovium and synovial fluid (Simonet, W. S., et al. 1997. *Cell* 89:309-319; Ritchlin, C., et al. 1998. *J Rheumatol* 25:1544-1552; Partsch, G., et al. 1998. *Ann. of Rheum. Dis.* 57:691-693). Furthermore, TNF-α can enhance osteoclastogenesis in the presence of miniscule amounts of RANKL (Lam, J., et al. 2000. *J of Clin. Inv.* 106:1481-1488). To delineate the effects of TNF-α on OCP frequency in vivo, five patients with erosive PsA treated with anti-TNF agents (4 with Enbrel® (etanercept) and one with infliximab) were studied. The number of osteoclast precursors was measured before and 12 weeks after initiation of therapy (FIG. 4A). Each of the patients experienced a decrease in the number of tender and swollen joints and improved physician and patient global assessment. There was also a significant reduction (79%-96%, $p<.001$) in the number of OCP following anti-TNF therapy in all patients. In addition, a consistent decrease in the percentage of $CD11b^+/CD14^+$ PBMCs (9B-D) was observed. These results strongly indicate that TNF-α directly contributes to the increased OCP frequency observed in PsA patients.

(6) Release of Biologically Active TNF-α by PsA PBMCs

To determine if the increase in OCP is the result of elevated TNF-α in PsA patients, the amount of TNF-α released by unfractionated PBMCs cultured without M-CSF and RANKL from 5 PsA patients and 5 healthy controls was analyzed, (198.6 pg/ml±86.07 vs. 25.8 pg/ml±13.40, respectively ($p<0.04$)). In parallel experiments, PsA culture supernatants harvested from 3 PsA patients with high TNF-α levels stimulated increased osteoclast formation when added in vitro to PBMCs from healthy donors (n=3). As shown in FIG. 5a unstimulated PBMC from healthy controls yield few OCP. The number of osteoclasts increased following addition of each of the 3 PsA supernatants. Two of three supernatants significantly increased OCP numbers in the healthy control PBMC cultures. In subsequent experiments, the addition of anti-TNF-α antibody blocked supernatant-induced osteoclastogenesis (FIG. 5b). Two healthy controls, different from those in FIG. 5a, showed an increase in OCP following addition of PsA supernatant 2 from 5a. This OCP increase was inhibited by addition of anti-TNF antibodies. These experiments indicate that PBMC from PsA patients secrete significantly greater quantities of biologically active TNF-α than PBMC from healthy controls.

(7) OPG Inhibits Osteoclastogenesis in Unstimulated PsA PBMC

Previous studies have convincingly established that RANKL is an essential factor promoting osteoclast development in the inflamed joint (Kong, Y. Y., et al. 1999. *Neurosurgery* 402:304-309; Pettit, A. R., et al. 2001. *Am. J. Pathol.* 159:1689-1699; Redlich, K., et al. 2002. *Arthritis Rheum.* 46:785-792). To examine the impact of RANKL on osteoclast formation in PsA, unstimulated PsA PBMC were cultured in the presence of OPG (FIG. 6). The mean number of TRAP positive multinuclear cells in 16 unstimulated cultures was 45+5 per 10 PBMCs. This number significantly declined to 14±4 in the presence of of 1.0 ug/ml of OPG. Since it is known that TNF-α strongly synergizes with trace amounts of RANKL (Lam, J., et al. 2000. *J of Clin. Inv.* 106:1481-1488; Kobayashi K, et al. J Exp Med 2000; 191(2):275-86; Azuma Y, et al. J Biol Chem 2000; 275(7):4858-64) the combination of OPG and Enbrel® (etanercept) was tested, which further suppressed osteoclast formation to 8±2 OCP per $10^6$ PBMC. The marked reduction in osteoclast formation in cultures incubated with OPG supports the concept that RANKL expression is a critical event promoting osteoclastogenesis in the psoriatic joint.

Taken together with the established literature, the results of this study indicate a mechanism for the destructive pathology observed in many psoriatic joints (FIG. 7). In this model, TNF-α increases the number of circulating OCP in PsA patients. In the case of "outside-in" erosion, OCP enter a highly vascular psoriatic synovial membrane containing tortuous blood vessels and adhere to activated endothelial cells that have been stimulated by pro-inflammatory cytokines (Collin-Osdoby, P., et al. 2001. *J Biol Chem* 276:20659). Exposure to TNF-α can induce the expression of fibronectin and vitronectin receptors on endothelial cells as described by McGowan et al facilitating OCP binding and tissue migration (McGowan, N. W., et al. 2001. *Endocrinology* 142:1678-1681). Simultaneously, the high level of OPG expressed by the endothelial cells would suppress osteoclastogenesis permitting smaller undifferentiated OCP to migrate through the dense pannus and target bone at a significant distance from the vessel. Upon arrival to the bone-pannus junction, OCP bind RANKL on the surface of synoviocytes and in the presence of TNF-α and M-CSF, undergo osteoclastogenesis and erode bone. In the case of "outside-in" resorption, OCP enter the subchondral environment in vessels that are in immediate proximity to bone. Following translocation through the endothelium, it is consistent that OCP are exposed to TNF-α induced RANKL on the surface of osteoblasts and stromal cells (Collin-Osdoby, P., et al. 2001. *J Biol Chem* 276:20659; Hofbauer, L. C., and Heufelder, A. E. 2000. *J Clin Endocrin & Metabolism* 85:2355-2363) resulting in the generation of osteoclasts lining cutting cones devoid of synovial tissue. In this scenario, mature osteoclasts mount a bi-directional assault, resorbing bone matrix in the subchondral bone and at the pannus-bone interface. Thus, there are two critical steps in the osteolytic pathway mediated by TNF-α increase in the frequency of circulating OCP and upregulation of RANKL expression in the joint. In this model, patients with generalized inflammatory disease (Crohn's disease, psoriasis) can have an expansion of $CD14^+/CD11b^+$ cells that differentiate into dendritic cells or macrophages, but not osteoclasts. In view of the reported findings, antagonism of TNF-α can be an effective strategy for inhibiting bone destruction in PsA.

2. Example 2

Systemic TNFα Mediates an Increase in Peripheral CD11bhi Osteoclast Precursors in TNFα Transgenic Mice a) Material and Methods (1) Reagents.

Human RANKL and Enbrel® (etanercept) were provided by Dr. W. Dougall (Amgen Inc., Seattle, Wash.); murine TNFα by Dr. C. R. Dustan (Amgen Inc., Thousand Oaks, Calif.) and fluorescein-conjugated RANKL by Dr. M. Tondravi (American Red Cross, Rockville, Md.). Recombinant human M-CSF was purchased from R&D Systems Inc. (Minneapolis, Minn.); anti-murine CD11b (M1/70), c-Fms (AFS98), CD3 (145-2C11), B220 (RA3-6B2), and isotype controls from eBioscience Inc. (San Diego, Calif.); anti-murine CD16/32 (FcγIII/II), c-Kit (2B8), Gr-1 (1A8), and isotype controls from Pharmingen (San Diego, Calif.); anti-murine F4/80 (A3-1) and isotype control from Serotec Ltd. (Oxford, UK).

(2) Animals.

TNF-Tg mice in a CBA×C57B1/6 background (3647 TNF-Tg line) were obtained from Dr. G. Kollias 5. The Institutional Animal Care and Use Committee approved all animal studies.

(3) Generation of Osteoclasts.

Splenocytes, peripheral blood mononuclear cells (PBMC), and bone marrow cells from TNF-Tg mice and their wild type littermates were used to generate osteoclasts in the absence of osteoblast/stromal cells as described previously (Kobayashi K, et al. *J Exp Med* 2000; 191(2):275-86). These cells were cultured in α-modified essential medium (GIBCO BRL, Grand Island, N.Y.) with 10% fetal calf serum (FCS, Hyclone Laboratories, Logan, Utah), RANKL (100 ng/ml) and M-CSF (10 ng/ml) for 5 days. Cells were fixed and stained for tartrate-resistant acid phosphatase (TRAP) using the Diagnostics Acid Phosphatase Kit (Sigma, St. Louis, Mo.) to identify osteoclasts. TRAP-positive cells containing $\geq 3$ nuclei were counted as mature osteoclasts. For the functional study, splenocytes were cultured on bone slices for 10 days under the same conditions as described above. Osteoclasts were then removed and the pits were visualized by 0.1% toluidine blue. The area of pits was quantified, and the data were expressed as the average area of pits ($mm^2$)/osteoclast±SEM as described previously (Schwarz E M, et al. *Arthritis Res.* 2000; 2:165-168).

(4) CFU-M Colony Assay.

The in vitro colony-forming assay was performed, as described previously (Xing L, et al. *J Bone Miner Res* 2002; 17(7):1200-10). Freshly isolated spleen cells from wt or TNF-Tg mice were plated at a density of $10^5$ cells/ml in a 35 mm dish. Cells were cultured in the methyl cellulose-based medium (StemCell Technologies Inc, Vancouver, Canada) supplemented with 30 ng/ml of M-CSF for 10 days. Colonies composed of more than 40 cells were counted under an inverted microscope.

(5) FACS Analysis and Cell Sorting.

Surface protein staining was performed on freshly isolated splenocytes, blood cells, and bone marrow cells. After red blood cell lysis, a single cell suspension was incubated with anti-murine CD16/32 to block Fc receptor-mediated antibody binding. Cells were then labeled with fluorescent probes, as described previously (Li P, et al. *J Immunol* 2000; 164(11): 5990-5997). Data were acquired using a FACScalibur instrument (Beckton Dickenson, Bedford, Mass.) and analyzed by Cellquest software (ver.3.1). Pooled splenocytes from TNF-Tg or wt mice were labeled with anti-murine CD11b or double-stained with anti-murine CD11b and c-Fms antibodies and sorted on a FACScalibur instrument. $CD11b^{hi}$, $CD11b^{lo}$, and $CD11b^-$ or $CD11b^{hi}/c$-$Fms^+$ and $CD11b^{hi}/c$-$Fms^-$ cells were collected separately, reanalyzed to assure their purity ($\geq 98\%$), and used for osteoclastogenesis assays, as described above.

(6) ELISA for Human TNFa in Mouse Serum

Blood was drawn from TNF-Tg mice by cardio-puncture, and the serum was collected by centrifugation. The levels of human TNFα were detected according to the manufacturer's instruction (R & D Systems, Minneapolis, Minn.). The whole procedure was carried at room temperature. Briefly, 96-well plates were coated with 4 µg/ml of capture antibody (MAB610) for overnight and blocked with PBS containing 1% BSA, 5% sucrose, and 0.05% NaN3 for 2 hr. Serum samples and standards were added and incubated for 2 hr. The plates were incubated with 200 ng/ml of biotinylated detection antibody (BAF210) for 1 hr, and then streptavidin HRP (DY 998) for 20 min. The color reaction was developed by adding substrate solutions to the plates, and the OD was read at 450 nm.

(7) In Vivo BrdU (5-bromo-2-deoxyuridine) Labeling.

TNF-Tg mice and their wt littermates were given intraperitoneal injections of 1 mg BrdU (Sigma, St. Louis, Mo.) three times over the course of one day at 8 hr intervals. Spleens were collected 8 hr after the last injection. BrdU staining was performed using the standard immunohistochemistry (Penit C and Vasseur F. Cytometry 1993; 14(7): 757-63). Briefly, Spleen cell suspensions were surface labeled with anti-CD11b antibody as described above, then fixed and permeabilized in PBS containing 1% paraformaldehyde plus 0.05% Tween 20 for 48-72 hr at 4° C. The cells were treated with 250 U/ml DNase I (Sigma, St. Louis, Mo.) for 60 min at 37° C., and BrdU incorporation was revealed with anti-BrdU antibody (Pharmingen, San Diego, Calif.).

(8) Quantitative Real-Time PCR.

RNA from TNFα treated and non-treated whole spleen cells, sorted CD11b–, and CD11blo cells was extracted using the RNeasy kit and the QiaShredder from Qiagen (Valencia, Calif.). cDNA synthesis was performed, as described previously (Xing L, et al. J Bone Miner Res 2002; 17(7):1200-10). Quantitative PCR amplification was performed with gene-specific primers using a Rotor-γene 2000 real time amplification operator (Corbett Research, Mortlake, Australia). The primer sequences included: 1) CD11b primers: 5'-ACAGA-CAAACAGCCCAAACC-3' (SEQ ID NO. 24) and 5'-GCCT-CACCCATCAGTTGTTT-3', and 2) (SEQ ID NO. 25) actin primers: 5'-AGATGTGGATCAGCAAGCAG-3' (SEQ ID NO. 26) and 5'-GCGCAAGTTAGGTTTTGTCA-3' (SEQ ID NO. 27). The quantity of CD11b mRNA in each sample was normalized using the CT (threshold cycle) value obtained for the actin RNA amplifications run in the same plate.

(9) In Vivo Blockade with Etanercept

TNF-Tg mice (5-month-old, 3 mice per group) were given intraperitoneal injections of Enbrel® (etanercept) (10 mg/kg) or PBS twice a week for 2 weeks. The mice were sacrificed 3 days after the last injection, and spleen cells were subjected to FACS analysis, osteoclastogenesis, and CFU-M colony assays.

(10) In Vivo Administration of TNFα

Two protocols were used in this study. (1). CBA×C57B/6 mice of 8-week old were first given intraperitoneal injections of BrdU (1 mg/mouse), three times daily for three days to obtain a maximal labeling of bone marrow CD11b+ cells (>96%). The mice were then challenged with a single intraperitoneal injection of murine TNFα (1 µg/mouse). After 4 hr, bone marrow, spleen, and blood cells were collected for FACS analysis with antibodies to CD11b and BrdU. (2). TNFα (1 µg/mouse) was injected into wt mice four times daily for 3 days, as described previously (Boyce B F, et al. *J Clin Invest* 1992; 90(4): 1622-7). Two hours after the last injection, spleens were taken for FACS analysis, osteoclastogenesis, and CFU-M colony assays. Blood were collected for FACS analysis.

(11) Statistics.

All results are given as means±SEM. Comparisons were made by analysis of variance and Student's t-test for unpaired data. P values <0.05 were considered statistically significant.

b) Results (1) Systemic TNFα Increases the Osteoclastogenic Potential of Splenocytes and Peripheral Blood Mononuclear Cells (PBMC).

The TNF-Tg mice (3647 line) used in this study were generated in Dr. Kollias's laboratory (Douni E, et al. *J Inflam.* 1996; 47:27-38). These mice contain one copy of a modified human TNFα transgene in which the ARE-containing 3'UTR was replaced with the 3'UTR from the β-globin gene. This mutation increases the stability and translational efficiency of TNFα mRNA and results in chronic TNFα over-expression.

To determine if exposure to chronic low levels of TNFα increases osteoclast formation, in vitro osteoclastogenesis assays were performed using splenocytes, PBMC, and bone marrow cells from TNF-Tg mice and their wt littermates. Splenocytes and blood cells from TNF-Tg mice cultured with 100 ng/ml of RANKL and 10 ng/ml of M-CSF for 5 days formed more mature osteoclasts than those from wt cells (FIG. 8A). However, no significant differences were observed in the bone marrow cultures. In vitro TNFα blockade with a $10^5$-fold excess of the TNFα antagonist, Enbrel® (etanercept), over the media concentration of TNFα (<10 pg/ml) had no effect on the enhanced osteoclast formation in TNF-Tg cultures (FIG. 8B). Furthermore, splenocytes from TNF-Tg mice formed 2 to 3-fold more CFU-M colonies than those from wt mice (FIG. 8C). Taken together, these findings indicate that TNFα can stimulate osteoclastogenesis by increasing OCP numbers, but it does not directly affect this process beyond the precursor stage.

To examine if TNFα over-expression affects mature osteoclast function ex vivo, splenocytes from TNF-Tg and wt mice were cultured on bone slices under the osteoclastogenic condition for 10 days, and measured the area of the resorption pits excavated by the mature osteoclasts. No difference was observed in the resorptive activity of osteoclasts from the two types of mice (pit area/osteoclast: 0.0044±0.0005 mm² in wt vs. 0.00525±0.0007 mm² in TNF-Tg mice).

(2) TNF-Tg mice have increased late stage osteoclast precursors in spleens.

Figure 10A:
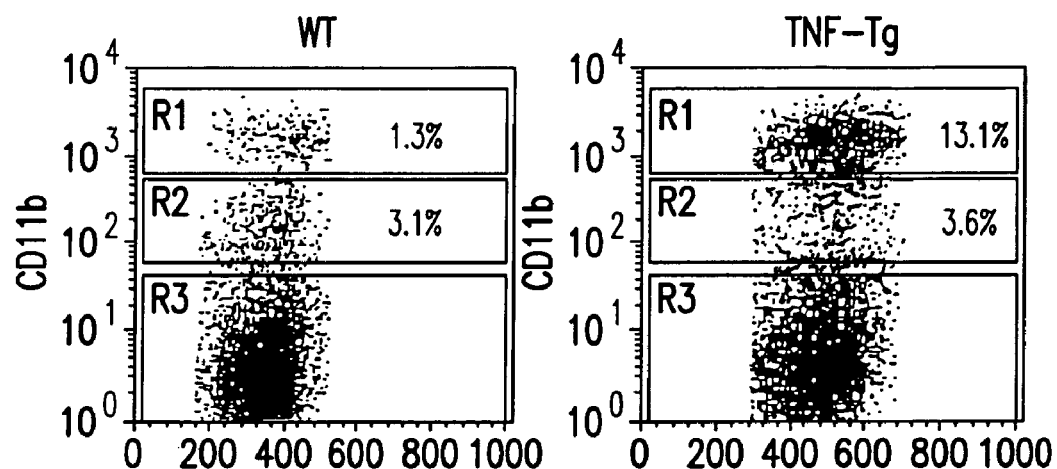
Figure 10B:
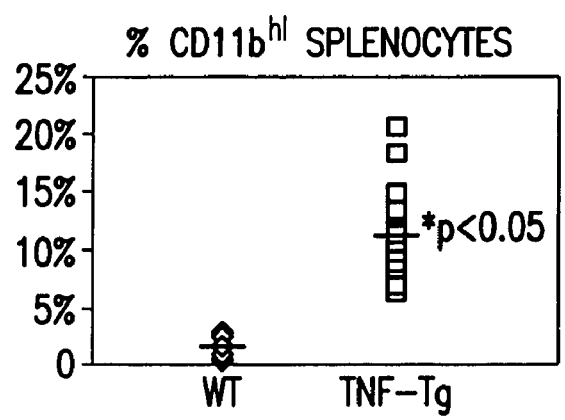

Cell surface markers have been used to characterize OCP at various differentiation stages (Arai F, et al. *J Exp Med* 1999; 190(12):1741-54). The earliest OCP, which differentiates from the pluripotent hematopoietic stem cell, is c-Kit+/c-Fms−/CD11b−/RANK−. This cell differentiates into the c-Kit+/c-Fms+/CD11b−/RANK− early stage precursor and following M-CSF stimulation, proceeds to the c-Kit−/c-Fms+/CD11b+/RANK+ late stage precursor, which differentiates fully in response to RANKL (Lacey D L, et al. *Cell* 1998; 93(2):165-76; Yasuda H, et al. *Proc Natl Acad Sci USA* 1998; 95(7):3597-602; Hsu H, et al. *Proc Natl Acad Sci USA* 1999; 96(7):3540-5; Arai F, et al. *J Exp Med* 1999; 190(12): 1741-54). FACS characterization of splenocytes from TNF-Tg mice showed a 4-7 fold increase in the CD11b+ population compared to wt cells (FIG. 9) and a consistent increase in the c-Fms+ population. According to their expression levels of CD11b, the CD11b+ splenocytes can be further divided into $CD11b^{high}$ ($CD11b^{hi}$) and $CD11b^{low}$ ($CD11b^{lo}$) cells. Only the $CD11b^{hi}$ population was significantly increased in TNF-Tg mice compared to that in wt mice (FIG. 10A). To functionally characterize this $CD11b^{hi}$ population, $CD11b^{hi}$, $CD11b^{lo}$, and CD11b− splenocytes were sorted and cultured them with M-CSF and RANKL. TRAP+ osteoclasts formed only from the $CD11b^{hi}$ population (FIG. 10B, C). Thus, all of OCP capable of forming mature osteoclasts in the culture are in the $CD11b^{hi}$ population.

To further characterize the increased $CD11b^{hi}$ cell population, the cells were double stained with antibodies to CD11b and markers for other cell lineages including CD3 (T cells), B220 (B cells), F4/80 (mature macrophages), and Gr-1 (granulocytes). Markers for OCP including c-Kit, c-Fms, and RANK were also investigated. Representative histograms from experiments in which the $CD11b^{hi}$ splenocytes were gated on, are shown in FIG. 11. Since this population contains both c-Fms+ and c-Fms− cells, the $CD11b^{hi}$/c-Fms+ and $CD11b^{hi}$/c-Fms− sub-populations were sorted and the osteoclastogenesis assay was performed. Both sub-populations had osteoclastogenic potential, and the $CD11b^{hi}$/c-Fms+ cells formed more osteoclasts than $CD11b^{hi}$/c-Fms− cells (FIG. 12). Thus, $CD11b^{hi}$ alone can be used as a representative marker for OCP in the spleen.

To determine if there is a correlation between the increased $CD11b^{hi}$ OCP frequency and the blood concentration of human TNFα in the transgenic mice, splenocytes were collected and blood from wt and TNF-Tg mice at different ages, corresponding to various stages the development and progression of inflammatory arthritis: prior to onset (1 month), onset (2-3 months), and advanced stage (4 months). The frequency of $CD11b^{hi}$ OCP in the spleen was determined by FACS (FIG. 13A), and the concentration of human TNFα in the serum was measured by ELISA (FIG. 13B). Increased $CD11b^{hi}$ OCP numbers were first observed in TNF-Tg mice at 2 months of age, corresponding to the time of initial detection of human TNFα in serum and the development of swollen ankles, the first macroscopic sign of inflammatory arthritis. After the onset of arthritis, the frequency of CD11b$^{hi}$ OCP and human TNFα serum concentrations remained elevated and did not increase further with progression of erosive arthritis.

(3) Increased CD11b$^{hi}$ Osteoclast Precursor Frequency And Enhanced Osteoclastogenesis in TNF-Tg Mice are Reversible by Etanercept Treatment In Vivo.

To investigate if TNFα blockade in vivo prevents the increases in CD11b$^{hi}$ OCP and osteoclast formation, Enbrel® (etanercept) (10 mg/kg) or placebo intraperitoneally was administered into TNF-Tg mice with establish joint disease, twice a week for 2 weeks. Enbrel® (etanercept) reduced the numbers of CD11b$^{hi}$ splenocytes (FIG. 14A) and the osteoclastogenic and CFU-M colony-forming potential (FIG. 14B, C) of these cells to wt levels. Thus, the TNFα-mediated increase in OCP is reversible with anti-TNF therapy, which is consistent with the findings of Example 1.

(4) Systemic TNFα does not Affect the Proliferation Rate, Differentiation, or Apoptosis of CD11b$^{hi}$ Osteoclast Precursors in the Periphery, but can Mobilize Them from the Bone Marrow into the Circulation.

There are four fundamental mechanisms by which TNFα can increase the number of CD11b$^{hi}$ OCP in the periphery: proliferation, survival, differentiation, and redistribution from the bone marrow. In proliferation assays, TNF-Tg and wt mice were labeled with BrdU for 24 hr, and spleen cells were stained with antibodies against CD11b and BrdU. TNF-Tg mice had the expected increase in CD11b$^{hi}$ cells (FIG. 15A), but no increase in the percentage of BrdU$^+$ CD11b$^{hi}$ cells (FIG. 15B, C). In survival assays, freshly isolated spleen cells from TNF-Tg and wt mice were analyzed by FACS using antibodies against CD11b, fluorescently labeled annexin V, and 7-AAD. In the CD11b$^{hi}$ population, the percentage of annexin V$^+$/7-AAD$^-$ cells (apoptotic cells) was similar in TNF-Tg (9.5%) and wt (9.6%) mice. In differentiation assays, wt splenocytes were cultured with TNFα (10 ng/ml), and the percentage of CD11b$^{hi}$ OCP after 24 hr was similar in control and TNF-treated cultures (FIG. 16A), as was the levels of CD11b mRNA analyzed by quantitative real-time PCR after 1, 4 and 24 hr TNF treatment (FIG. 16B). Furthermore, CD11b mRNA expression assessed by real-time PCR in CD11b$^-$ and CD11b$^{lo}$ splenocytes sorted by FACS, as described in FIG. 10, and cultured in the presence of TNFα (10 ng/ml) for 12 hr, was not detectable above background levels (FIG. 16C).

To examine if accumulation of CD11b$^{hi}$ cells in the periphery is due to TNFα-induced mobilization of precursors from bone marrow, wt mice were labeled with BrdU for 3 days, then challenged with one injection of TNFα (1 μg i.p.) or PBS. After 4 hr, bone marrow, spleen, and blood cells were collected and analyzed by FACS with antibodies to CD11b and BrdU. No change in the percentage of CD11b$^+$ cells was observed in bone marrow (FIG. 17A) or spleen, but a 4-fold increase in the percentage of CD11b$^+$/BrdU$^+$ cells in blood (FIG. 17B), indicating that TNFα rapidly mobilizes a small fraction of OCP from the bone marrow to produce a marked increase in the blood. However, further distribution of these cells into peripheral tissues like spleen can require more time.

To test this possibility, wt mice were given TNFα injections for 3 days (1 μg/injection, i.p. 4× per day) and sacrificed 2 hr after the last injection. The percentage of CD11b$^{hi}$ splenocytes (FIG. 17C) and PBMC was increased significantly in the TNFα-treated mice compared with controls, which is similar to that observed in untreated TNF-Tg mice. Correspondingly, this treatment caused an increase in the osteoclastogenic and CFU-M colony-forming potential of the splenocytes from these mice (FIG. 17D).

c) Discussion

A relationship between TNFα and osteoclastic resorption was firmly established in diseases associated with erosive bone loss, such as RA. (Feldmann M, et al. *Cell* 1996; 85(3): 307-10; Maini R N, et al. *Immunol Rev* 1995; 144:195-223) TNFα increases osteoclast formation in vitro (Abu-Amer Y, et al. *J Biol Chem* 2000; 275(35):27307-10; Kobayashi K, et al. *J Exp Med* 2000; 191(2):275-86; Azuma Y, et al. *J Biol Chem* 2000; 275(7):4858-64), and directly affects OCP in vivo in normal mice (Lam J, et al. *J Clin Invest* 2000; 106 (12):1481-8). However, in these studies very large amounts of TNFα were used either in vitro or in vivo, which may not mimic the disease states. Thus, it was important to determine if chronic exposure to a relevant concentration of TNFα affects osteoclast formation, considering the number of RA patients receiving anti-TNF therapy (Moreland L W, et al. *J Rheumatol* 2001; 28(6):1238-44; Keystone E C. *Rheum Dis Clin North Am* 2001; 27(2):427-43) and the potential new indications for other inflammatory bone diseases (Schwarz E M, et al. *Arthritis Res.* 2000; 2:165-168). While it is clear that anti-TNF therapy is efficacious for RA, clinical studies to evaluate its effects on bone resorption have commenced only recently (Lipsky P E, et al. *N Engl J Med* 2000; 343(22): 1594-602; Bathon J M, et al. *N Engl J Med* 2000; 343(22): 1586-93), and a unifying hypothesis as to how anti-TNF therapy inhibits bone erosion in patients is warranted.

In TNF-Tg mice (3647 line), there was a chronic low-level expression of TNFα. As a result, these mice develope an erosive arthritis with features similar to those seen in human RA (Keffer J, et al. *Embo J* 1991; 10(13):4025-31), including focal erosions affecting the immediate subchondral bone and bone at the joint margins. Therefore, this model was appropriate to study the mechanisms of TNFαα-mediated osteoclast formation in inflammatory arthritis. As expected, splenocytes from TNF-Tg mice had enhanced osteoclastogenic and CFU-M colony forming potential compared to wt mice (FIG. 8). This enhanced osteoclastogenesis was not inhibited by TNFα blockade in vitro (FIG. 8B), but could be recapitulated in cultures of splenocytes from wt mice injected with TNFα (FIG. 17). From these data, it is understood that TNFα had a priming effect on OCP in vivo thereby increasing the number of pre-osteoclasts in the periphery outside the bone environment. However, these TNFα-induced pre-osteoclasts did not have increased bone-resorbing capacity, indicating that the systemic TNFα effect was restricted to increasing the number of these cells and not their function.

Systemic TNFα increased the number of pre-osteoclasts in peripheral tissues like spleen and blood. Thus, these cells were identifiable by phenotypic surface markers. Indeed, splenocytes from TNF-Tg mice had 4-7 fold more CD11b$^{hi}$ cells compared to wt mice. It is important to note that the characterization of the majority of these cells as RANK$^-$ by FACS (81% by double staining) did not preclude them as the RANKL responsive pre-osteoclasts that ultimately fuse to form the bone-resorbing cell. These cells could express low levels of functional RANK or up-regulate surface RANK expression shortly after stimulation with M-CSF (Arai F, et al. *J Exp Med* 1999; 190(12):1741-54). The CD11b$^{hi}$ cells did not express common markers for T or B lymphocytes or mature macrophages, but they did express osteoclast precursor markers such as c-Fms (FIG. 11). Furthermore, all of the OCP in spleen are CD11b$^{hi}$ because CD11b$^{lo}$ and CD11b$^-$ cells do not form osteoclasts. Both CD11b$^{hi}$/c-Fms$^+$ and CD11b$^{hi}$/c-Fms$^-$ populations have the potential to form osteoclasts. Thus, in subsequent studies, CD11b was used as a single surface marker to identify the TNFα-induced pre-osteoclasts.

The increase in the number of OPC in the blood was observed between 2 and 3 months of age in the transgenic mice at the same time when blood concentrations of TNFα increased. At one month of age, TNF-Tg mice had undetectable blood concentrations of human TNF and normal OPC numbers (FIG. 13). This increase in the number of CD11b$^{hi}$ splenocytes and their osteoclastogenic and CFU-M colony forming potential to wt levels was reversible by in vivo TNF blockade with Enbrel® (etanercept) (FIG. 14). Based on these two findings, it was concluded that the increase in peripheral OCP numbers is due directly to chronic TNF exposure. Consistent with the finding in the TNF-Tg mice, it was demonstrated in Example 1 that patients with psoriatic arthritis (PsA) have a marked increase in the number of pre-osteoclasts in their PBMC population compared to normal and osteoarthritic controls. This increase also appears to be reversible with anti-TNF therapy and can be a dominant mechanism by which this treatment inhibits erosions.

Last, the cellular mechanisms of TNFα-mediated increase in CD11b$^{hi}$ OCP frequency in the periphery was examined. It was observed that accumulation of these cells was not due to alteration in differentiation, proliferation, or survival of the cells (FIGS. 15 and 16), and another mechanism must be involved. In adult life, hematopoietic precursors that give rise to pre-osteoclasts are derived mainly from the differentiation of stem cells in the bone marrow compartment. The finding that injection of TNFα into wt mice induced a remarkable change in the tissue distribution of CD11b$^{hi}$ cells, similar to that observed in the blood and spleen of TNF-Tg mice, indicates that redistribution can be a mechanism responsible for the TNFα-mediated increase in peripheral OCP frequency (FIG. 17).

Taken together, the findings disclosed herein support a new mechanism for TNFα-induced erosive arthritis in which a significant component of its effect could be due to the mobilization of CD11b$^{hi}$ OCP from the bone marrow, thereby increasing their numbers in the circulation. The results of these studies show that the frequency of CD11b$^{hi}$ PBMC could be used as a diagnostic to identify patients with active disease or "flares" that can lead to further bone erosion. Furthermore, patients that are responsive or refractory to anti-TNF therapy can be identified by changes in this population following therapy.

3. Example 3 a) Materials and Methods

The independent variable was patients with erosive arthritis on Enbrel® (etanercept). The two primary response variables were the change in the number of circulating OCP and change in level of enhancing bone marrow edema (EBME) on MRI in one inflamed joint after 6 months of Enbrel® (etanercept) treatment.

(1) Patient Enrollment and Assessment

Twenty PsA patients (Moll & Wright criteria) over the age of 18 with >1 erosions on plain radiographs were given Enbrel® (etanercept) 25 mg twice per week in an open label trial for 6 months. Patients were excluded if they were taking a DMARD, an anti-TNF agent or had previously taken an anti-TNF agent. The total joint count, total number of swollen joints, physician and patient global assessment and Health Assessment Questionnaire (HAQ) scores were recorded at baseline, 2 week, 3 month and 6 month intervals.

(2) Conventional and 3 Dimensional MRIs

Gadolinium (Gd) enhanced and 3 dimensional (3D) MRIs were performed at baseline and at 6 months in all 20 patients. 6 wrists, 3 thumbs, 3 knees and 1 toe were imaged. T2W fat suppressed Fast Spin Echo (2-3 mm slices) were acquired in sagittal plane. The fat suppressed T1W pre and post Gadolinium SE images were acquired in axial plane. Two radiologists independently scored enhancing bone marrow edema (EBME) lesions using a 9 point scale measuring intensity of EBME on T2-weighted imaging (0-3), contrast enhancement post-yd (0-3) and size of lesion (0-3).

(3) Level of Circulating OCP

The frequency of OCP was measured at baseline, 2, 12 and 14 weeks. OCP levels were obtained by counting the number of tartrate resistant acid phosphatase (TRAP) positive cells with >3 nuclei present in unstimulated peripheral blood mononuclear cells (PBMC) after 2 weeks in culture.

b) Results

All patients completed the trial and no adverse events were reported. MRI data on 13 patients have been analyzed to date (Table 4). Patients experienced decreased tender (24 to 9, p<0.001) and swollen (27 to 10, p<0.001) joints and improved physician and patient global assessments (3.5 to 0.68, p<0.001, 3.5 to 1.3, p<0.001) after 6 months of therapy (Table 5). A significant decline in the HAQ and SF36 was also noted. OCP were elevated in 18 of 20 patients at baseline ranging from 4 to 226OC/106 PBMC. Overall, OCP decreased from a mean of 55.45±73.4 to 11.4±13.8OC/10 6 PBMC, (p<0.01) at 6 months. A significant drop in OCP was noted as early as 2 weeks in 14 of 20 patients after starting Enbrel® (etanercept) therapy (p<0.04). Mean EBME decreased from 5.9 to 3.9, (p<0.004). Interestingly, in 10 of the 13 patients who had MRIs, a decrease in OCP was associated with lessening EBME. In one patient with no change in OCP at 6 months, EBME increased (FIGS. 18 and 19).

TABLE 4

| Demographics: | |
| --- | --- |
| number of subjects | 20 |
| male/female | 13/7 |
| mean age | 47.5 years |
| mean duration of Ps | 21.2 years |
| mean duration of PsA | 11.8 years |
| previous DMARDs | 13/20 |

TABLE 5

| Outcome measures | Screening | 6 Months | p value |
|---|---|---|---|
| Number of Tender joints | 24 | 9 | 0.001 |
| Number of Swollen Joints | 27 | 10 | 0.001 |
| MD global assessment | 3.5 | 0.68 | 0.001 |
| Patient assessment | 3.5 | 1.3 | 0.001 |
| HAQ score | 1.21 | 0.36 | 0.0001 |
| SF-36: physical component | 31.17 | 46.30 | 0.0001 |
| SF-36: mental component | 46.07 | 53.94 | 0.017 | c) Conclusion

PsA patients taking Enbrel® (etanercept) demonstrated significant improvement in all clinical parameters as early as 2 weeks after beginning therapy with continued improvement noted over the next 22 weeks.

Increased OCP were noted at baseline in almost all patients and the frequency of OCP declined significantly after Enbrel® (etanercept) therapy. The decline in OCP frequency was associated with a significant decline in EBME on conventional and 3D MRI. Persistent EBME was present after 6 months of Enbrel® (etanercept) therapy in many patients despite significant improvement in clinical symptoms and decline in OCP frequency PsA patients on Enbrel® (etanercept) demonstrated significant improvement in all clinical parameters at 6 months. Increased OCP were observed in the majority of PsA pts. Moreover, the decline in OCP frequency was associated with lessening EBME in individual pts. These findings coupled with the rapid decline in OCP following treatment suggest a potential mechanism to explain the protective effects of Enbrel® (etanercept) on inflammatory bone loss in PsA.

4. Example 4 a) CD11b+ Osteoclast Precursors (OCP) Frequency as a Marker of Erosive Disease.

In an effort to understand the mechanism of TNFα-induced osteoclastogenesis in the hTNF-Tg mice, and to develop a quantitative hematological outcome measure of erosive disease, the OCP frequency in the spleen and blood (FIG. 22) was determined. It was found that the OCP frequency in the spleen and PBMC of hTNF-Tg mice can be markedly increased compared to non-transgenic controls as determined by osteoclastogenesis and the number of colonies that form on methylcellulose media supplemented with M-CSF (CFU-M colonies) (FIG. 22A). However, osteoclasts from TNF-Tg mice did not demonstrate a significant increase in activity as determined by in vitro bone wafer resorption assays. In order to better characterize the TNF-induced OCP, an extensive FACS analysis with various antibodies against hematopoietic surface markers was performed. Of these, CD11b proved to be the most useful, as cell sorting experiments showed that all of the OCP are in the CD11b$^{hi}$ population and that TNF-Tg mice have a significant increase in this population.

In the next series of experiments, it was established that anti-TNF therapy completely reverses this phenotype in TNF-Tg mice (FIGS. 23A-C). This was done by treating the TNF-Tg mice with Enbrel® (etanercept) for 2-weeks and assaying for CD11b, TRAP osteoclastogenesis and CFU-M colony forming units. Furthermore, it was demonstrated that TNF-induced OCP frequency could be recapitulated in wild-type mice injected with TNF (FIGS. 23D-F). These results indicate that systemic TNF can induce and increase OCP frequency in peripheral tissues. The OCP response can be transient and can require continuous TNF stimulation to be maintained.

An analysis of serum TNF levels vs. OCP frequency vs. inflammatory-erosive arthritis was also performed. These studies demonstrated a direct correlation between these variables. In the 3647 TNF-Tg mice, synovitis, focal erosions, increased serum TNF levels and increased OCP frequency all commence at two-months of age.

b) TNF Induces CD11b+ OCP Frequency Independent of RANK Signaling.

As stated above, it has become clear that RANK signaling can be required for osteoclastic bone resorption in vivo. In order to better characterize the TNF-induced OCP and determine if RANK signaling is required for their formation, hTNF-Tg mice were crossed with RANK knockout mice (hTNF-Tg×RANK−/−) (FIG. 24). To assess the effects of the cross, bone density and tooth eruption were assessed by x-ray radiography. It was found that the phenotype of the double transgenics was essentially identical to that of their RANK−/− littermates, in that the animals had no osteoclasts, failed tooth eruption and suffer from severe osteopetrosis. Additionally, tibia from WT, TNF-Tg, RANK−/−, and TNF-Tg×RANK−/− mice were prepared for histology, stained for TRAP activity, and counter-stained with hematoxylin/fast-green. The only difference was the presence of some inflammation in some joints, which was markedly reduced from that observed in the hTNF-Tg littermates. Moreover, the extramedullary hematopoiesis combined with the systemic TNF in these animals generated a very large population of CD11b+ cells in spleen, demonstrating that RANK signaling is not required for this event.

In a second model, the effects of RANK:Fc (10 mg/kg/48 hr) were evaluated in 4-month-old hTNF-Tg mice with established arthritis and found that RANK blockade rapidly eliminates osteoclasts at the leading edge of the erosion front and at sites of normal bone remodeling, but has no effect on OCP frequency (FIG. 25). This information was obtained by staining for TRAP activity and counter staining with hematoxylin/fast-green and then comparing photomicrographs of sections from PBS and RANK:Fc treated hTNF-Tg mice. Osteoclast numbers in the tibia (remodeling) and at the pannus-bone junction (erosion) of the hTNF-Tg mice were quantified by histomorphometry. A similar analysis was performed with H&E and TRAP stained sections to evaluate bone erosion, which was done by dividing the eroded surface in mm by the total surface of the proximal tibia and distal femur. These results confirm that RANK signaling is not required for the generation of TNF-induced OCP, but can be required for the differentiation of these cells into active osteoclasts in vivo.

c) TNF-Induced CD11b+ OCP in PsA Correlates with Erosive Disease.

Based on studies of TNF-induced OCP in mice described above, clinical studies were commenced to see if these observations would hold true in humans. A study to evaluate OCP was performed in a subset of these patients with and without erosive arthritis before and after anti-TNF therapy. These studies revealed several remarkable findings including: 1) expression of RANK, RANKL and OPG in the PsA joint, 2) OCP frequency in PBMC of PsA patients is significantly higher than healthy controls 3) the OCP frequency in PBMC of PsA patients with erosions can be significantly greater than that in PsA patients without erosions (FIG. 26A), and that 12-weeks of anti-TNF therapy significantly reduced the OCP frequency in 5 of 5 patients tested (FIGS. 26B-D). In addition to the standard clinical outcome measures (Mease, P. J. 2002. Ann Rheum Dis 61:298), OCP frequency in PBMC was also evaluated. These data confirmed that PsA patients have a significant increase in OCP frequency that can be reversible with anti-TNF therapy. To the end of quantifying the effects of this treatment on erosive disease in these patients, bone marrow edema was evaluated, which has been validated as a predictive marker by Gd-enhanced fat suppressed MRI. This technique was modified with VirtualScopics technology to generate precision volumetric measurements as was done for periacetabular osteolysis. FIG. 18 shows the quantitative radiology results from the first 13 patients and reconstructed 3D-MRI images from a representative patient. These preliminary data formally demonstrate the feasibility of the approach and provide the first evidence in humans that there is a direct correlation between TNF-induced OCP frequency and bone marrow edema in erosive disease; and that anti-TNF therapy corrects both abnormalities.

d) Biased Monocyte Differentiation Towards Osteoclastogenesis has an Inverse Effect on Macrophage and Dendritic Cell Potential.

Disclosed herein, aberrant myelopoesis and monocyte effector function induces an increase in OCP and erosive disease. In an attempt to validate the working hypothesis it was demonstrated the reciprocal inhibitory effects of IFN-γ on osteoclastogenesis and RANKL suppression of macrophage activation (Huang, W., et al. 2003. Arthritis Res Ther 5:R49). In these studies it was shown that IFN-γ stimulation of OCP leads to the immediate and complete loss of their osteoclastic potential. Furthermore, a mutiparameter assays was utilized to demonstrate that co-stimulation with a vast array of osteoclastic factors cannot reverse this inhibition. However, if these OCP were treated with RANKL 48 hr before IFN-γ stimulation, the inhibitory effects were not observed. By assaying these same cultures for NO production and expression of IFN-γ inducible surface markers, it was also discovered that RANKL pretreatment (osteoclastogenesis) leads to the loss of macrophage activation potential (FIG. 27).

Very recently, the first evidence that the increase in PBMC OCP frequency in PsA occurs with a concomitant decrease in DCP frequency was obtained. FIG. 28 shows the results of an experiment in which purified CD11c+ monocytes from a naive PsA patient and an age/sex matched healthy control were analyzed for their ability to differentiate in response to GM-CSF and IL-4. These individuals had an equivalent distribution of CD11c+ monocytes in their blood that displayed a similar induction of the IL-4 inducible marker CD209 after 6 days of culture. However, the PsA cells demonstrated a remarkable defect in the induction of the mature dendritic cell marker CD1a+ compared to the control (57.6% vs 100.1% conversion).

Delneste et al demonstrated that addition of IFNγ to IL-4 plus GM-CSF-stimulated monocytes switches their differentiation from CD1a+ DCs to CD14(−)CD64(+) macrophages (Delneste, Y., et al. 2003. Blood. 101:143). Results from neutralizing experiments showed that both M-CSF and IL-6 are involved in the ability of IFNγ to skew monocyte differentiation from DCs to macrophages. Similar to the findings with OCP, these investigators found that the IFNγ effect can be limited to early stages of differentiation. When added to immature DCs, IFNγ does not convert them to macrophages, even in the presence of exogenous M-CSF and IL-6. This interplay between IL-6 and M-CSF that switches monocyte differentiation to macrophages rather than DCs was also demonstrated by Chomarat et al (Chomarat, P., et al. 2000. Nat Immunol 1:510), suggesting that STAT signaling can be the central pathway through with both OCP and DCP are removed from their respective lineages during monocyte differentiation towards an activated macrophage.

Disclosed herein a unifying model is proposed to explain the mechanism through which chronic innate autoimmunity dictates the erosive vs nonerosive phenotype in inflammatory arthritis (FIG. 29). This model posits: 1) osteoclasts are responsible for bone erosions; 2) osteoclasts are derived from CD11b+/CD14+ myeloid precursors that are released from bone marrow into the blood. Macrophages and myeloid dendritic cells are also derived from this CD11b+/CD14+ myeloid precursors; 3) TNF directly and/or indirectly stimulates the RANKL+M-CSF mediated differentiation of these cells into a mononuclear OCP that looses its potential to transdifferentiate into activated macrophages or dendritic cells; 4) a mutually exclusive monocyte differentiation cascade also exists for macrophage activation and DC differentiation, which can be mediated by distinct signals, resulting in a loss of osteoclastic potential; and 5) the systemic IFN signal in SLE stimulates DC differentiation at the expense of osteoclastogenesis resulting in a nonerosive phenotype.

e) Determine if a Divergent Pathway of Monocyte Differentiation is the Central Mechanism Underlying the Erosive Phenotype in Inflammatory Arthritis.

Disregulated innate immunity in inflammatory arthritis leads to systemic TNF that directly and indirectly through M-CSF and RANKL biases monocyte differentiation towards osteoclastogenesis and away from the macrophage and dendritic cell lineages. This results in an increase in PBMC OCP frequency and a decrease in DCP and macrophage activation potential. These phenomena are reversible via anti-TNF therapy and are absent in patients with SLE because systemic IFNα biases monocyte differentiation toward dendritic cells and away from osteoclasts. Thus, the TNF/IFN axis in inflammatory arthritis dictates erosive disease via these mechanisms.

In clinical trials it was demonstrated that PsA patients have a significant increase in CD11b+ OCP in their PBMC that correlates with erosive disease and can be reversible with anti-TNF therapy. It was also demonstrated that a large component of SLE can be IFNα-induced monocyte differentiation to the dendritic cell lineage (Blanco, P., et al. 2001. Science 294:1540). Since it is known that inflammatory arthritis in SLE is rarely erosive and that osteoclasts and dendritic cells are derived from the same myeloid precursor, it is shown that these processes are mutually exclusive.

(1) Experimental Design and Methods:

The OCP frequency, DCP and macrophage activation potential are determined in peripheral blood mononuclear cells (PBMC) from 20 normal healthy controls, 20 erosive PsA patients, 20 SLE patients with non-erosive arthritis and 20 SLE patients erosive arthritis. Sharp Scores can be determined from x-rays performed in SLE and PsA patients. Serum TNFα, IFNα, M-CSF, RANKL, GM-CSF and IL-4 levels can be determined as well, and total RNA samples from the PBMC can be banked.

The impact of TNF-blockade therapy on OCP and DC and macrophage activation in PBMC can be determined in the 20 erosive PsA patients 6 months after treatment with Enbrel® (etanercept), infliximab or adalimumab. Sharp Scores can be determined from x-rays. Serum TNFα, IFNα, M-CSF, RANKL, GM-CSF and IL-4 levels can be determined as well, and total RNA samples from the PBMC can be banked. Additionally, the erosive phenotype in each patient by MRI before and 6 months after therapy can be determined. Clinical assessment, plain radiographs and cellular and serologic studies can be repeated after 6 months of therapy with Enbrel® (etanercept), adalimumab or infliximab.

(a) SLE Patients.

Twenty SLE patients with nonerosive arthritis, and twenty SLE patients with erosive arthritis are recruited SLE patients with inflammatory arthritis, defined as joint swelling and pain with morning stiffness in the absence of clinical features of osteoarthritis, are evaluated. Plain radiographs of hands and feet are performed, and patients can be split into 2 groups based on the presence or absence of erosive arthritis.

(b) Healthy Normal Controls.

Healthy controls are recruited from the general population and receive a standard honorarium for their blood donation.

(c) Evaluation of the erosive phenotype.

Plain x-ray films are obtained from the PsA patients at baseline and 6-months after anti-TNF therapy. Plain x-rays films are also obtained from the SLE patients with inflammatory arthritis.

(d) Purification of monocytes from PBMC.

30 ml of EDTA anticoagulated blood from each individual can be processed with Rosettsept and a Ficol Paque Plus separation according to the manufacture's instructions (StemCell Technologies Inc). The cells are then resuspended in PBS and counted. This process typically yields ~10-12 million monocytes that contains >2% lymphocytes. $10^6$ of these cells can be used immediately for OCP and DCP analysis by FACS. $2\times10^6$ of these cells can be used for TRAP osteoclastogenesis. $10^6$ of these cells can be used for CFU-M colony formation. $10^6$ of these cells can be used for NO assays. $2\times10^6$ of these cells can be used to assay macrophage activation by FACS. $2\times10^6$ of these cells can be used to assay for dendritic cell differentiation by FACS.

(e) OCP Frequency and Osteoclastogenesis.

OCP and DCP frequency can be determined simultaneously, immediately after monocyte purification by four-color FACS. $10^6$ monocytes are separated into two tubes. The cells in the first tube are stained with CD11b-PE (clone ICRF44), CD11c-APC (clone B-ly6), CD64-FITC (clone 10.1) and CD33-PerCP-Cy5.5 (clone P67.6) antibodies (BD Pharmingen). The cells in the other tube are stained with isotype controls (BD Pharmingen). These samples are then run through a FACScalibur instrument (Beckton Dickenson) and analyzed with Cellquest software (ver.3.1) as done previously. The OCP frequency can be determined by the % of CD11b stained cells that have a MFI greater than 99% of the PE-conjugated isotype control stained cells. TRAP osteoclastogenesis can be performed as described previously. Briefly, $2\times10^6$ monocytes are divided into 4 wells on a glass culture slide (Costar) and cultured in α-MEM (GIBCO BRL) supplemented with 10% FCS (Hyclone Laboratories), M-CSF (25 ng/ml) and RANKL (100 ng/ml) (R&D Systems) and incubated in 6% $CO_2$ at 37° C. for 14 days. Media can be replenished every 3 days. After 14 days in culture, the slides are stained for TRAP (Sigma Diagnostics) and the number of TRAP positive cells with 3 or more nuclei (osteoclasts) per $10^6$ monocytes plated can be determined by light microscopy.

(f) CFU-M Colony Formation and Macrophage Activation.

The in vitro colony-forming assay can be performed as described herein. Briefly, $2.5\times10^5$ freshly isolated monocytes are plated in 2.5 ml of methyl cellulose-based medium (StemCell Technologies Inc) supplemented with 30 ng/ml of M-CSF in 35 mm culture dishes for 10 days (N=4). Colonies composed of more than 40 cells are counted under an inverted microscope and the data are presented as CFU-M colonies per $10^6$ monocytes plated. Macrophage activation can be determined by NO respiratory burst assays and FACS analysis as described previously (Huang, W., et al. 2003. *Arthritis Res Ther* 5:R49). NO production can be measured by the Greiss reaction (Promega), which spectrophotometrically detects nitrite, a stable breakdown product of nitric oxide whose accumulation reflects NO production. Briefly, $10^4$ freshly isolated monocytes are suspended in 20011 of α-MEM (GIBCO BRL) supplemented with 10% FCS (Hyclone Laboratories), plated in 96-well plates (N=4) and left untreated (control) or activated with 11 g/ml LPS (Sigma), and/or 10 ng/ml IFN-γ (R&D Systems). Cell supernatants are harvested at 24 hr and reacted with 1% sulfanilamide and 0.1% naphthyl-ethylenediamine. A standard curve can be constructed using dilutions of sodium nitrite, and absorbance can be measured at 550 nm. Total protein concentration in each well can be used to normalize the data to control for variation in cell number or proliferation and the NO can be calculated as a percentage of the untreated control. Macrophage activation can also be assessed by expression of surface markers. Briefly, $2\times10^6$ freshly isolated monocytes are divided in half and plated in a 12-well plate. One well can be activated with LPS and IFN-γ as described above. After 24 hr the cells in each well are harvested and divided into two tubes. One tube can be stained with CD11b/Mac1-PE (clone ICRF44), CD54/ICAM1-APC (clone HA58), CD80/B7.1-FITC (clone L307.4) (BD Pharmingen) and panMHCII-PerCP-Cy5.5 (Ancell, clone:TDR31.1) antibodies. The cells in the other tube are stained with isotype controls for compensation. These samples are then run through a FACScalibur instrument (Beckton Dickenson) and analyzed with Cellquest software (ver.3.1) as done previously. Activation can be determined as the difference in MFI between the LPS+IFN-γ treated sample and the unstimulated control.

(g) DCP Frequency and Dendritic Cell Differentiation.

The DCP frequency assays are performed together with the OCP frequency assays immediately after monocyte purification by four-color FACS as described above. The DCP frequency can be presented as the % of CD11c stained cells that have a MFI greater than 99% of the APC-conjugated isotype control stained cells. Dendritic cell differentiation assays are performed as described in FIG. 28. Briefly, $2\times10^6$ monocytes are incubated in 2 ml of RPMI-10% FCS medium supplemented with 100 ng/ml GM-CSF and 100 ng/ml IL-4 (R&D Systems) for 6 days. On days 2 and 4, half of the supernatant can be replaced with fresh media containing GM-CSF and IL-4. Afterwards the cells are harvested and divided into two tubes. The cells in the first tube are stained with CD209-PE (E Bioscience clone h209), CD1a-APC (clone H1149), CD64-FITC (clone 10.1) and CD14-percp Cy5.5 (clone MφP9) (BD Pharmingen). The cells in the other tube are stained with isotype controls. These samples are then analyzed by FACS as described above. Dendritic cell differentiation can be quantified by determining the % of CD1a stained cells that have a MFI greater than 99% of the APC-conjugated isotype control stained cells. It can also be quantified as the % conversion of CD11b DCP to CD1a mature dendritic cells. Results with CD209 are used as a positive control for the IL-4 treatment and CD14 and CD64 are used to identify the macrophage population.

(h) Serum ELISA.

ELISA to determine the serum TNFα, IFNα, M-CSF, RANKL, GM-CSF and IL-4 levels can be performed as described previously. Briefly, 10 ml of blood from each individual can be collected in a serum separation tube (Beckton Dickenson), and centrifuged for 10 min at 2,500 RPM. The serum can be decanted and aliquoted into 1 ml cryovials (Falcon) and stored at −80° C. Once all of the serum samples from all of the groups have been collected the concentration of TNFα, IFNα, M-CSF, RANKL, GM-CSF and IL-4 in the samples can be determined using specific sandwich ELISA (Amgen, R&D Systems or Endogen) according to the manufactures instructions. The data are presented as ng/ml of serum.

(i) Data Analysis and Interpretation

Statistical analyses for each outcome measure can be performed by calculating the mean±SEM of the group (normal, PsA, nonerosive SLE, erosive SLE) and performing a multi-parameter analysis of variance test (ANOVA). The results of the patient groups compared to the normal healthy controls as outlined in the table below.

|  | PsA | PsA + anti-TNF | nonerosive SLE | erosive SLE |
|---|---|---|---|---|
| OCP frequency | higher | normal | lower |  |
| DCP frequency | lower | normal | higher |  |
| CFU-M | higher | normal | lower | lower |
| MΦ activation | lower | normal | lower | lower |
| TNF, M-CSF, RANKL | higher | normal | normal |  |
| IFN, GM-CSF, IL-4 | normal | normal | higher | higher | f) Demonstrate the Direct Role of Systemic TNF, IFN, and the Combination of These Cytokines on Monocyte Differentiation and Erosive Arthritis in Mice.

Introduction of a systemic TNF signal biases monocyte differentiation towards osteoclastogenesis and away from the macrophage and dendritic cell lineages resulting in erosive inflammatory arthritis in mice. Introduction of a systemic IFN signal biases monocyte differentiation towards dendritic cell differentiation and away from the macrophage and osteoclast lineages resulting in a nonerosive phenotype. In the presence of both signals, IFN dominates over TNF such that monocyte differentiation can be biased towards dendritic cell differentiation and away from the macrophage and osteoclast lineages resulting in a nonerosive phenotype. Thus, the TNF/IFN axis in inflammatory arthritis dictates erosive disease via these mechanisms.

Findings show that systemic TNF induces the release of large numbers of osteoclast precursors from the bone marrow into the blood, which must home to sites of inflammation in the bone microenvironment and receive a RANKL signal to differentiate into active osteoclasts, in order to mediate peri-articular erosions. Simultaneously, work in the NZB×NZW mouse model of lupus has demonstrated the presence and critical role of systemic IFN in disease pathogenesis. The dominant role of IFN signaling in OCP resulting in the inhibition of inflammatory bone loss and maintenance of bone homeostasis has also been demonstrated in Ifnr1−/− mice (Takayanagi, H., et al. 2002. *Nature* 416:744). Having generated the TNF-Tg, Nba2 and Ifnr1$^{-/-}$ mice in a pure C57B/6 background, it can be shown that the TNF/IFN axis in monocyte differentiation dictates the erosive phenotype in inflammatory arthritis using gain and loss of function studies.

(1) Experimental Design and Methods:

The gain-of-function effects of introducing systemic TNF, IFN and their combination on OCP and DC and macrophage activation in PBMC and splenocytes of C57B/6 mice can be determined and examine the impact this has on erosive arthritis can be shown by quantitative histomorphometry. In these experiments it is understood that one can use control C57B/6, C57B/6 injected with TNF, C57B/6 injected with poly I:C, TNF-Tg, TNF-Tg injected with poly I:C, (Nba2×NZW)F1, (Nba2×NZW)F1 injected with TNF, and (TNF-Tg×Nba2×NZW)F1. Furthermore, serum TNFα, IFNα, M-CSF, RANKL, GM-CSF and IL-4 levels can be determined by ELISA.

Additionally, the loss-of-function effects of removing systemic TNF, IFN and their combination on OCP and DC and macrophage activation in PBMC and splenocytes of C57B/6 mice can be determined and the impact this has on erosive arthritis by quantitative histomorphometry examined. These experiments can utilize control C57B/6, TNF-Tg treated with anti-TNF, and (TNF-Tg×Nba2×NZW×IFNAR1$^{-/-}$). Furthermore, serum TNFα, IFNα, M-CSF, RANKL, GM-CSF and IL-4 levels by ELISA can be determined.

(a) Genotyping and Generation of Congenic Mice.

C57B/6 and TNF-Tg mice in a pure C57B/6 background are propagated by mating C57B/6 females to TNF-Tg heterozygous males, to produce both WT controls and TNF-Tg mice with normal Mendelian distribution. 21 days after birth, the mice are ear punched and a tail biopsy can be taken to determine the genotype by PCR as described. Similarly, Nba2 locus has been identified in the NZB mice and crossed into a pure C57B/6 background (Rozzo, S. J., et al. 2001. *Immunity* 15:435). These mice (Nba2) can be mated with NZW/LacJ mice from Jackson Laboratories (NZW) to generate the F1 hybrids that develop lupus. To evaluate lupus in these mice in a type I IFN null background, the Nba2 mice and the NZW mice were crossed with the Ifnr1$^{-/-}$ mice. Matings with the TNF-Tg mice generates the TNF-Tg×Nba2 line and the TNF-Tg×Nba2×Ifnr1−/− line. The genotyping for the human TNF transgene and the Ifnr1 null mutation are done by PCR as done previously (Schwarz, E. M., et al. 1998. *J. Virol.* 72:5654). Genotyping can be done for the Nba2 locus by assaying for the polymorphic (between NZB and B6) microsatellite markers D1Mit36, D1Mit113, Crp, D1Mit541, and D1Mit166, as described previously (Rozzo, S. J., et al. 2001. *Immunity* 15:435). This ensures that the full interval is inherited. These mice can be crossed to the NZW and NZW×Ifnr1−/− mice to generate the TNF-Tg×(Nba2×NZW)F1 and TNF-Tg×Nba2×NZW×Ifnr1−/− mice. In all cases, age matched, female mice can be used for the experiments.

(b) TNF, Anti-TNF and Poly I:C Administrations.

Acute administration of 10 μg murine TNFα (Amgen) can be injected i.p. daily as described previously. The murine anti-TNF-α mAb (Centocor) used in this study binds with high affinity to hTNFα (Knight, D. M., et al. 1993. *Mol Immunol* 30:1443) and effectively cures arthritis in the hTNF-Tg mouse (Keffer, J., et al. 1991. *Embo J* 10:4025). For acute administration, 200%1 g anti-TNF-α mAb can be administered once i.p. For chronic administration 200 μg anti-TNF-α mAb can be administered weekly i.p. as described previously (Shealy, D. J., et al. 2002. *Arthritis Res* 4). For acute poly (I:C) (Sigma) administration, 100 μg can be injected daily i.p. as described previously.

(c) Experimental Groups.

The most efficient and rigorous approach is to independently evaluate the effects of the TNF/IFN axis on monocyte differentiation acutely and chronically. The acute experiments are designed to provide information on direct effects, but are too short to evaluate effects on the erosive phenotype. The chronic experiments are design to provide information on the long-term effects of disregulated TNF/IFN signaling on monocyte differentiation and the pathogenesis of erosions in inflammatory arthritis. An outline of the experimental groups and the outcome is listed below.

Acute Gain of TNF and IFN on Osteoclastogenesis, Macrophage Activation and Dendritic Cell Differentiation.

Seven Groups (N=10) of 3 Month-Old Mice are Treated as Follows and Sacrificed on Day 3: Phenotype
  Group 1 wild-type C57B/6 placebo (100 μl PBS i.p.) every day for 3 days normal
  Group 2 wild-type C57B/6 TNF (10 μg of TNF in 100 μl i.p.) every day for 3 days OCP high
  Group 3 wild-type C57B/6 IFN (100 μg of poly I:C in 100 μl i.p.) every day for 3 days DCP high
  Group 4 TNF-Tg placebo (100 μl PBS i.p.) every day for 3 days OCP high
  Group 5 TNF-Tg IFN (100 μg of poly I:C in 100 μl i.p.) every day for 3 days DCP high
  Group 6 (Nba2×NZW)F1 placebo (100 μl PBS i.p.) every day for 3 days DCP high
  Group 7 (Nba2×NZW)F1 TNF (10 μg of TNF in 100 μl i.p.) every day for 3 days DCP high Acute Loss of TNF and IFN on Osteoclastogenesis, Macrophage Activation and Dendritic Cell Differentiation.

Seven Groups (N=10) of 3 Month-Old Mice are Treated as Follows and Sacrificed on Day 3: Phenotype
  Group 1 wild-type C57B/6 placebo (100 μl PBS i.p.) once normal
  Group 2 wild-type C57B/6 anti-TNF (200 μg of anti-TNF in 100 μl i.p.) once normal
  Group 3 TNF-Tg placebo (100 μl PBS i.p.) once OCP high
  Group 4 TNF-Tg anti-TNF (200 μg anti-TNF in 100 μl i.p.) once normal
  Group 5 (Nba2×NZW)F1 placebo (100 μl PBS i.p.) once DCP high Chronic Gain of TNF and IFN on Osteoclastogenesis, Macrophage Activation, Dendritic Cell Differentiation and Erosive Arthritis.

Four Strains of Mice are Analyzed at 3, 6, 9 and 12 Months of Age (N=10): PBMC & Bone Phenotype

| | |
|---|---|
| Group 1 wild-type C57B/6 | normal-normal |
| Group 2 TNF-Tg | OCP high-erosive |
| Group 3 (Nba2 × NZW)F1 | DCP high-normal |
| Group 4 TNF-Tg × (Nba2 × NZW)F1 | DCP high-nonerosive |

Chronic Loss of TNF and IFN on Osteoclastogenesis, Macrophage Activation, Dendritic Cell Differentiation and Erosive Arthritis.

Four Strains of Mice are Analyzed at 3, 6, 9 and 12 Months of Age (N=10): PBMC & Bone Phenotype
  Group 1 wild-type C57B/6 placebo (100 μl PBS i.p.) weekly normal-normal
  Group 2 wild-type C57B/6 anti-TNF (200 μg in 10011 i.p.) weekly normal-normal
  Group 3 Ifnr1−/− OCP high-osteoporotic
  Group 4 TNF-Tg placebo (100 μl PBS i.p.) weekly OCP high-erosive
  Group 5 TNF-Tg anti-TNF (200 μg in 10011 i.p.) weekly normal-normal
  Group 6 (Nba2×NZW)F1 DCP high-normal
  Group 7 (Nba2×NZW)F1×Ifnr1−/− normal-osteoporotic
  Group 8 TNF-Tg×(Nba2×NZW)F1 placebo (100 μl PBS i.p.) weekly DCP high-nonerosive
  Group 9 TNF-Tg×(Nba2×NZW)F1 anti-TNF (200 μg in 11001 i.p.) weekly DCP high-normal
  Group 10 TNF-Tg×(Nba2×NZW)F1×Ifnr1−/− placebo (100 μl PBS i.p.) weekly OCP high-erosive/osteoporotic
  Group 11 TNF-Tg×(Nba2×NZW)F1×Ifnr1−/− anti-TNF (200 μg in 100 μl i.p.) weekly OCP-osteoporotic (d) Collection of Serum, PBMC and Splenocytes.

At the time of sacrifice, the mice are euthanized by cervical dislocation and the chest cavity can be opened to collect blood via ventricular nicking. This method produces 1.5-2.0 ml of blood per mouse. The first 200 ml of blood are used to obtain serum after clotting and stored at −80° C. for ELISA and future studies as described previously. The rest of the blood can be washed in PBS and resuspended in red cell lysis buffer and monocytes are isolated from a ficol gradient as described previously. This method produces >1 million cells which can be sufficient to determine OCP frequency by FACS and TRAP assay as described in FIG. 22. Splenocytes are prepared from a tissue squash followed by red cell lysis and ficol gradient purification as described previously. This method produces >10 million cells which can be sufficient to determine OCP frequency, DC activation, CFU-M colonies, and macrophage activation.

(e) OCP Frequency and Osteoclastogenesis.

OCP and DCP frequency can be determined simultaneously, immediately after monocyte purification of PBMC and splenocytes, by four-color FACS exactly as described in the human study above. The murine specific antibodies to be used are CD11b-PE (clone M1/70), CD11c-APC (clone HL3), CD80-FITC (16-10A1) and CD8-PerCP-Cy5.5 (clone 53-6.7) (BD Pharmingen). The OCP frequency can be determined by the % of CD11b$^{hi}$ cells as described previously. TRAP osteoclastogenesis can be performed as described previously.

(f) CFU-M Colony Formation and Macrophage Activation.

The in vitro colony-forming assay can be performed as above, with splenocytes as described previously. Macrophage activation can be determined by NO respiratory burst assays and FACS analysis of splenocytes as described above. The murine specific antibodies used are CD11b/Mac1-PE (clone M1/70), CD54/ICAM1-APC (clone 3E2), CD80/B7.1-FITC (clone 16-10A1) (BD Pharmingen) and I-A$^b$-PerCP-Cy5.5 (clone AF6-120.1) antibodies. Activation can be determined as the difference in MFI between the LPS+IFN-γ treated sample and the unstimulated control.

(g) DCP Frequency and Dendritic Cell Activation.

The DCP frequency assays are performed together with the OCP frequency assays immediately after monocyte purification of PBMC and splenocytes by four-color FACS as described above. The splenocyte-derived DC activation in response to IFN-α are performed as previously described. Briefly, 2×10$^6$ cells are incubated in 5 ml RPMI-10% FCS medium supplemented with 3 ng/ml GM-CSF and 5 ng/ml IL-4 (BD Biosciences) for 6 days. On days 3 and 6, half of the supernatant can be replaced with fresh media containing GM-CSF and IL-4. To induce final maturation, 1,000 U/ml IFN-α (Calbiochem) can be added for another 24 h. Control cells receive media alone. The cells are then analyzed with murine specific antibodies against CD11c, CD80, I-A$^b$, and H-2 K$^b$ by FACS as described above. Activation can be determined as the difference in MFI between the IFN-α treated sample and the unstimulated control.

(h) Serum ELISA.

ELISA to determine the serum TNFα, IFNα, M-CSF, RANKL, GM-CSF and IL-4 levels can be performed as described previously, using specific sandwich ELISA (Amgen, R&D Systems or Endogen) according to the manufactures instructions. The data are presented as ng/ml of serum.

The development of lupus in the mice can be monitored by serum Igs and autoantibodies (anti-dsDNA and anti-ssDNA) by ELISA, as described previously. Microtiter plates are coated with either 5 μg/ml Fc-specific F(ab')$_2$ goat anti-mouse IgG (Jackson ImmunoResearch Laboratories), 5 μg/ml anti-mouse IgM (Southern Biotechnology Associates, Inc.), 25 μg/ml calf thymus dsDNA, or 25 μg/ml ssDNA. Total bound IgM or IgG, and IgG subclasses are measured by alkaline phosphatase-labeled goat anti-mouse Abs (Caltag Laboratories) and compared with a standard serum (Bethyl Laboratories).

(i) Histomorphometry.

The primary outcome measure to determine the erosive phenotype can be histomorphometry of the knee joints as described in FIG. 25, specifically, the percent eroded surface (eroded surface/total joint surface in mm). Osteoclast numbers and bone volume are quantified to assess osteoporosis. This can be done by harvesting the left knees at the time of sacrifice followed by formalin fixation. The tissues are then decalcified in EDTA, paraffin embedded and serial 3 μm sections are stained with H&E and for TRAP as described previously. The mean of 3 TRAP stained sections 100 μm apart represents the value per animal and used to derive the mean±SEM of the group (N=10). Statistically significant differences between groups can be determined by analysis of variance for multiple group comparisons (ANOVA), where $p<0.05$ can be considered to be significant.

As a secondary outcome measure to evaluate the arthritis, the H&E sections can be evaluated in a blinded manner by two independent observers (ES&CR) for histologic signs of arthritis and scored as described previously (Yin, G., et al. 2002. *Mol Ther* 5:547), where: 1, synovial cell proliferation, synovial hypertrophy with villus formation and/or fibrin deposition; 2, inflammation, synovitis and/or generalized inflammation; 3, cartilage disruption, chondrocyte degeneration and/or ruffling of cartilage surface and/or dystrophic cartilage; and 4, joint destruction, cartilage erosion with abundant inflammation and pannus formation with bone erosion. Non-parametric statistical analyses can be performed to determine statistical significance between groups in which $p<0.05$.

The kidneys of the mice are also harvested at the time of sacrifice. They can be fixed in paraformaldehyde, rehydrated in sucrose and frozen in OTC block for storage at −80° C. as done previously (Schwarz, E. M., et al. 1997. *Genes Dev* 11:187). These tissues can be used to assess for evidence of lupus nephritis as described previously (Rozzo, S. J., et al. 2001. *Immunity* 15:435).

(j) Radiographic Evaluation.

As an additional secondary outcome measure, erosions are evaluated radiographicly with x-rays obtained in an anteroposterior position as described previously (Zhang, X., et al. 2002. *J Clin Invest* 109:1405). The radiographs are evaluated in a blinded manner by two independent observers (ES&CR) according to the Larsen method and statistical analyses can be performed accordingly (Larsen, A., and J. Thoen. 1987. *Scand J Rheumatol* 16:395).

G. REFERENCES

Aaronson, D. S., and C. M. Horvath. 2002. A road map for those who don't know JAK-STAT. *Science* 296:1653.

Abu-Amer, Y., J. Erdmann, L. Alexopoulou, G. Kollias, F. P. Ross, and S. L. Teitelbaum. 2000. Tumor necrosis factor receptors types 1 and 2 differentially regulate osteoclastogenesis [In Process Citation]. *J Biol Chem* 275(35):27307-10.

Anderson D M, Maraskovsky E, Billingsley W L, et al. A homologue of the TNF receptor and its ligand enhance T-cell growth and dendritic-cell function. *Nature* 1997; 390(6656):175-9.

Anolik, J. H., D. Campbell, R. E. Felgar, F. Young, I. Sanz, J. Rosenblatt, and R. J. Looney. 2002. B lymphocyte depletion in the treatment of systemic lupus: phase I/II trial of rituximab in SLE. *Arthritis Rheum* 47:S289.

Anolik, J. H., D. Campbell, R. E. Felgar, F. Young, I. Sanz, J. Rosenblatt, and R. J. Looney. 2003. The relationship of FcgammaRIIIa genotype to degree of B cell depletion by rituximab in the treatment of systemic lupus erythematosus. *Arthritis Rheum* 48:455.

Antoni, C. e. a. 2003. The one year results of the infliximab multinational psoriatic arthritis controlled trial (IMPACT). *Arthritis & Rheumatism.* 48: (9S):S265.

Arai F, Miyamoto T, Ohneda 0, et al. Commitment and differentiation of osteoclast precursor cells by the sequential expression of c-Fms and receptor activator of nuclear factor kappaB (RANK) receptors. J Exp Med 1999; 190(12): 1741-54.

Arend, W. P. 2001. The innate immune system in rheumatoid arthritis. *Arthritis Rheum* 44:2224.

Arend, W. P., and J. M. Dayer. 1990. Cytokines and cytokine inhibitors or antagonists in rheumatoid arthritis. *Arthritis Rheum* 33:305.

Arnett, F. C., Edworthy, S. M., Bloch, D. A., McShane, D. J., Fries, J. F., Cooper, N. S., Healey, L. A., Kaplan, S. R., Liang, M. H., and Luthra, H. S. 1988. The American Rheumatism Association 1987 revised criteria for the classification of rheumatoid arthritis. Arthritis Rheum. 31:315-324.

Azuma, Y., K. Kaji, R. Katogi, S. Takeshita, and A. Kudo. 2000. Tumor necrosis factor-alpha induces differentiation of and bone resorption by osteoclasts. *J Biol Chem* 275: 4858-64.

Baechler, E. C., F. M. Batliwalla, G. Karypis, P. M. Gaffney, W. A. Ortmann, K. J. Espe, K. B. Shark, W. J. Grande, K. M. Hughes, V. Kapur, P. K. Gregersen, and T. W. Behrens. 2003. Interferon-inducible gene expression signature in peripheral blood cells of patients with severe lupus. *Proc Natl Acad Sci USA* 100:2610.

Bathon, J. M., R. W. Martin, R. M. Fleischmann, J. R. Tesser, M. H. Schiff, E. C. Keystone, M. C. Genovese, M. C. Wasko, L. W. Moreland, A. L. Weaver, J. Markenson, and B. K. Finck. 2000. A comparison of etanercept and methotrexate in patients with early rheumatoid arthritis. *N Engl J Med* 343(22): 1586-93.

Behar, S. M., and S. A. Porcelli. 1995. Mechanisms of autoimmune disease induction. The role of the immune response to microbial pathogens. *Arthritis Rheum* 38:458.

Bennett, L., A. K. Palucka, E. Arce, V. Cantrell, J. Borvak, J. Banchereau, and V. Pascual. 2003. Interferon and granulopoiesis signatures in systemic lupus erythematosus blood. *J Exp Med* 197:711.

Bertolini, D. R., G. E. Nedwin, T. S. Bringman, D. D. Smith, and G. R. Mundy. 1986. Stimulation of bone resorption and inhibition of bone formation in vitro by human tumour necrosis factors. *Nature* 319:516.

Blanco, P., A. K. Palucka, M. Gill, V. Pascual, and J. Banchereau. 2001. Induction of dendritic cell differentiation by IFN-alpha in systemic lupus erythematosus. *Science* 294:1540.

Boyce B F, Yoneda T, Lowe C, et al. Requirement of pp60c-src expression for osteoclasts to form ruffled borders and resorb bone in mice. J Clin Invest 1992; 90(4): 1622-7.

Boyle, W. J., W. S. Simonet, and D. L. Lacey. 2003. Osteoclast differentiation and activation. *Nature* 423:337.

Braun, J., J. Brandt, J. Listing, A. Zink, R. Alten, W. Golder, E. Gromnica-Ihle, H. Kellner, A. Krause, M. Schneider, H. Sorensen, H. Zeidler, W. Thriene, and J. Sieper. 2002. Treatment of active ankylosing spondylitis with infliximab: a randomised controlled multicentre trial. *Lancet* 359:1187.

Bromley, M., H. Bertfield, J. M. Evanson, and D. E. Woolley. 1985. Bidirectional erosion of cartilage in the rheumatoid knee joint. *Ann Rheum Dis* 44:676.

Bromley, M. and Woolley, D. E. 1984. Chondroclasts and osteoclasts at subchondral sites of erosion in the rheumatoid joint. *Arthritis Rheum.* 27:968-975.

Bywaters, E. G. and Dixon, A. S. 1965. Paravertebral ossification in psoriatic arthritis. Annals of the Rheum. Dis. 24:313-331.

Campbell, I. K., K. O'Donnell, K. E. Lawlor, and I. P. Wicks. 2001. Severe inflammatory arthritis and lymphadenopathy in the absence of TNF. *J Clin Invest* 107(12):1519.

Cenci, S., M. N. Weitzmann, C. Roggia, N. Namba, D. Novack, J. Woodring, and R. Pacifici. 2000. Estrogen deficiency induces bone loss by enhancing T-cell production of TNF-alpha. *J Clin Invest* 106(10):1229-37.

Chen, G., and D. V. Goeddel. 2002. TNF-R1 signaling: a beautiful pathway. *Science* 296:1634.

Childs, L. M., E. P. Paschalis, L. Xing, W. C. Dougall, D. Anderson, A. L. Boskey, J. E. Puzas, R. N. Rosier, R. J. O'Keefe, B. F. Boyce, and E. M. Schwarz. 2002. In vivo RANK signaling blockade using the receptor activator of NF-kappaB:Fc effectively prevents and ameliorates wear debris-induced osteolysis via osteoclast depletion without inhibiting osteogenesis. *J Bone Miner Res* 17:192.

Childs, L. M., J. J. Goater, O'Keefe, and E. M. Schwarz. 2001. Efficacy of Etanercept for Wear Debris-Induced Osteolysis. *J. Bon. Min. Res.* 16:338-47.

Chomarat, P., J. Banchereau, J. Davoust, and A. K. Palucka. 2000. IL-6 switches the differentiation of monocytes from dendritic cells to macrophages. *Nat Immunol* 1:510.

Collin-Osdoby, P., L. Rothe, F. Anderson, M. Nelson, W. Maloney, and P. Osdoby. 2001. Receptor activator of NF-kappa B and osteoprotegerin expression by human microvascular endothelial cells, regulation by inflammatory cytokines, and role in human osteoclastogenesis. *J Biol Chem* 276(23):20659-72.

Danning, C. L., Illei, G. G., Hitchon, C., Greer, M. R., Boumpas, D. T., and McInnes, I. B. 2000. Macrophage-derived cytokine and nuclear factor kappa B p65 expression in synovial membrane and skin of patients with psoriatic arthritis. Arthritis Rheum. 43:1244-1256.

Daro E, Pulendran B, Brasel K, et al. Polyethylene glycol-modified GM-CSF expands CD11b(high)CD11c(high) but notCD11b(low)CD11c(high) murine dendritic cells in vivo: a comparative analysis with Flt3 ligand. J Immunol 2000; 165(1):49-58.

De, A. K., K. Laudanski, and C. L. Miller-γraziano. 2003. Failure of monocytes of trauma patients to convert to immature dendritic cells is related to preferential macrophage-colony-stimulating factor-driven macrophage differentiation. *J Immunol* 170:6355.

Delneste, Y., P. Charbonnier, N. Herbault, G. Magistrelli, G. Caron, J. Y. Bonnefoy, and P. Jeannin. 2003. Interferon-γamma switches monocyte differentiation from dendritic cells to macrophages. *Blood* 101:143.

Demulder, A., Takahashi, S., Singer, F. R., Hosking, D. J., Roodman, and GD. 1993. Abnormalities in osteoclast precursors and marrow accessory cells in Paget's disease. Endocrinology 133:1978-1982.

den Broeder, A., L. van de Putte, R. Rau, M. Schattenkirchner, P. Van Riel, O. Sander, C. Binder, H. Fenner, Y. Bankmann, R. Velagapudi, J. Kempeni, and H. Kupper. 2002. A single dose, placebo controlled study of the fully human anti-tumor necrosis factor-alpha antibody adalimumab (D2E7) in patients with rheumatoid arthritis. *J Rheumatol* 29:2288.

Dougall, W. C., M. Glaccum, K. Charrier, K. Rohrbach, K. Brasel, T. De Smedt, E. Daro, J. Smith, M. E. Tometsko, C. R. Maliszewski, A. Armstrong, V. Shen, S. Bain, D. Cosman, D. Anderson, P. J. Morrissey, J. J. Peschon, and J. Schuh. 1999. RANK is essential for osteoclast and lymph node development. *Genes Dev* 13(18):2412-24.

Douni, E., K. Akassoglou, L. Alexopoulou, S. Georgopoulos, S. Haralambous, S. Hill, G. Kassiotis, D. Konotoyiannis, M. Pasparakis, D. Plows, L. Probert, and G. Kollias. 1996.

Transgenic and knockout analyses of the role of TNF in immune regulation and disease pathogenesis. *J. Inflam.* 47:27.

Drake, C. G., S. J. Rozzo, H. F. Hirschfeld, N. P. Smarnworawong, E. Palmer, and B. L. Kotzin. 1995. Analysis of the New Zealand Black contribution to lupus-like renal disease. Multiple genes that operate in a threshold manner. *J Immunol* 154:2441.

Esdaile, J. M., D. Danoff, L. Rosenthall, and A. Gutkowski. 1981. Deforming arthritis in systemic lupus erythematosus. *Ann Rheum Dis* 40:124.

Faust, J., Lacey, D. L., Hunt, P., Burgess, T. L., Scully, S., Van, G., Eli, A., Qian, Y., and Shalhoub, V. 1999. Osteoclast markers accumulate on cells developing from human peripheral blood mononuclear precursors. Journal of Cellular Biochemistry 72:67-80.

Fearon, U., K. Griosios, A. Fraser, R. Reece, P. Emery, P. F. Jones, and D. J. Veale. 2003. Angiopoietins, growth factors, and vascular morphology in early arthritis. *J Rheumatol* 30:260.

Feldmann, M., F. M. Brennan, and R. N. Maini. 1996. Rheumatoid arthritis. *Cell* 85:307.

Flick, L. M., J. M. Weaver, M. Ulrich-Vinther, F. Abuzzahab, X. Zhang, W. C. Dougall, D. Anderson, R. J. O'Keefe, and E. M. Schwarz. 2003. Effects of receptor activator of NFkappaB (RANK) signaling blockade on fracture healing. *J Orthop Res* 21:676.

Franzoso G, Carlson L, Poljak L, et al. 1998. Mice deficient in nuclear factor (NF)-kappa B/p52 present with defects in humoral responses, germinal center reactions, and splenic microarchitecture. *J of Exp. Med.* 187(2):147-59.

Franzoso G, Carlson L, Xing L, et al. 1997. Requirement for NF-kappaB in osteoclast and B-cell development. *Genes & Dev.* 11 (24):3482-96.

Fujikawa, Y., Sabokbar, A., Neale, S., and Athanasou, N. A. 1996. Human osteoclast formation and bone resorption by monocytes and synovial macrophages in rheumatoid arthritis. *Ann. of Rheum. Dis.* 55:816-822.

Gladman, D. D., V. T. Farewell, and C. Nadeau. 1995. Clinical indicators of progression in psoriatic arthritis: multivariate relative risk model. *J Rheumatol* 22:675.

Gladman, D. D. 1998. Psoriatic arthritis. Rheumatic Diseases Clinics of North America 24:829-844.

Goldenberg, D. L., and A. S. Cohen. 1978. Synovial membrane histopathology in the differential diagnosis of rheumatoid arthritis, gout, pseudogout, systemic lupus erythematosus, infectious arthritis and degenerative joint disease. *Medicine (Baltimore)* 57:239.

Goldring, S. R., and E. M. Gravallese. 2000. Mechanisms of bone loss in inflammatory arthritis: diagnosis and therapeutic implications. *Arthritis Res* 2(1):33-7.

Gori, F., Hofbauer, L. C., Dunstan, C. R., Spelsberg, T. C., Khosla, S., and Riggs, B. L. 2000. The expression of osteoprotegerin and RANK ligand and the support of osteoclast formation by stromal-osteoblast lineage cells is developmentally regulated. Endocrinology 141:4768-4776.

Gravallese, E. M. and Goldring, S. R. 2000. Mechanisms of bone loss in inflammatory arthritis: diagnosis and therapeutic implications. *Arthritis Res.* 2:33-37.

Gravallese, E. M., Harada, Y., Wang, J. T., Gorn, A. H., Thornhill, T. S., and Goldring, S. R. 1998. Identification of cell types responsible for bone resorption in rheumatoid arthritis and juvenile rheumatoid arthritis. *Am J Path* 152:943-951.

Gravallese, E. M., Manning, C., Tsay, A., Naito, A., Pan, C., Amento, E., and Goldring, S. R. 2000. Synovial tissue in rheumatoid arthritis is a source of osteoclast differentiation factor. *Arthritis Rheum.* 43:250-258.

Gregoretti, M. G., Bergui, L., Aragno, M., Cremona, O., Marchisio, PC, and Caligaris-Cappio, F. 1995. Osteoclast precursors circulate in the peripheral blood of patients with aggressive multiple myeloma. *Leukemia* 9:1392-1397.

Grigor, R., J. Edmonds, R. Lewkonia, B. Bresnihan, and G. R. Hughes. 1978. Systemic lupus erythematosus. A prospective analysis. *Ann Rheum Dis* 37:121.

Hahn, B. H. 1998. Antibodies to DNA. *N Engl J Med* 338:1359.

Hanekom, W. A., M. Mendillo, C. Manca, P. A. Haslett, M. R. Siddiqui, C. Barry, 3rd, and G. Kaplan. 2003. *Mycobacterium tuberculosis* inhibits maturation of human monocyte-derived dendritic cells in vitro. *J Infect Dis* 188:257.

Harley, J. B., K. L. Moser, P. M. Gaffney, and T. W. Behrens. 1998. The genetics of human systemic lupus erythematosus. *Curr Opin Immunol* 10:690.

Helliwell, P., Marchesoni, A., Peters, M., Barker, M., and Wright, V. 1991. A re-evaluation of the osteoarticular manifestations of psoriasis British Journal of Rheumatology 30:339-345.

Hofbauer, L. C., D. L. Lacey, C. R. Dunstan, T. C. Spelsberg, B. L. Riggs, and S. Khosla. 1999. Interleukin-1beta and tumor necrosis factor-alpha, but not interleukin-6, stimulate osteoprotegerin ligand gene expression in human osteoblastic cells. *Bone* 25:255-9.

Hofbauer, L. C., S. Khosla, C. R. Dunstan, D. L. Lacey, W. J. Boyle, and B. L. Riggs. The roles of osteoprotegerin and osteoprotegerin ligand in the paracrine regulation of bone resorption. *J Bone Miner Res* 15:2-12.

Hofbauer, L. C. and Heufelder, A. E. 2001. The role of osteoprotegerin and receptor activator of nuclear factor kappaB ligand in the pathogenesis and treatment of rheumatoid arthritis. *Arthritis Rheum.* 44:253-259.

Hofbauer, L. C., Heufelder, A. E. 2000. The role of receptor activator of nuclear factor-kappa B ligand and osteoprotegerin in the pathogenesis and treatment of metabolic bone diseases. *J Clin Endocrin & Metabolism* 85:2355-2363.

Hsu H, Lacey D L, Dunstan C R, et al. Tumor necrosis factor receptor family member RANK mediates osteoclast differentiation and activation induced by osteoprotegerin ligand. Proc Natl Acad Sci USA 1999; 96(7):3540-5.

Huang, W., M. H. Drissi, R. J. O'Keefe, and E. M. Schwarz. 2003. A Rapid Multiparameter Approach to Study Factors that Regulate Osteoclastogenesis: Demonstration of the Combinatorial Dominant Effects of TNF-alpha and TGF-ss in RANKL-Mediated Osteoclastogenesis. *Calcif Tissue Int.*

Huang, W., R. J. O'Keefe, and E. M. Schwarz. 2003. Exposure to receptor-activator of NFkappaB ligand renders pre-osteoclasts resistant to IFN-γamma by inducing terminal differentiation. *Arthritis Res Ther* 5:R49.

Huang, L., Xu, J., Wood, D. J., and Zheng, M. H. 2000. Gene expression of osteoprotegerin ligand, osteoprotegerin, and receptor activator of NF-kappaB in giant cell tumor of bone: possible involvement in tumor cell-induced osteoclast-like cell formation. *Am J Path* 156:761-767.

Iotsova V, Caamano J, Loy J, et al. Osteopetrosis in mice lacking NF-kappaB1 and NF-kappaB2 [see comments]. Nature Medicine 1997; 3(11):1285-9.

Johnson R S, Spiegelman B M, Papaioannou V. Pleiotropic effects of a null mutation in the c-fos proto-oncogene. Cell 1992; 71(4):577-86.

Kaarela, K., and S. Sarna. 1993. Correlations between clinical facets of outcome in rheumatoid arthritis. *Clin Exp Rheumatol* 11:643.

Kaarela, K., R. Luukkainen, and S. Koskimies. 1993. How often is seropositive rheumatoid arthritis an erosive disease? A 17-year followup study. *J Rheumatol* 20:1670.

Kanematsu, M., T. Sato, H. Takai, K. Watanabe, K. Ikeda, and Y. Yamada. 2000. Prostaglandin E2 induces expression of receptor activator of nuclear factor-kappa B ligand/osteoprotegrin ligand on pre-B cells: implications for accelerated osteoclastogenesis in estrogen deficiency. *J Bone Miner Res* 15:1321-9.

Kaposi, M. 1972. New reports on know;edge of systemic lupus erythematosus. *Arch Dermat u Syph* 4:36.

Karsenty G. The genetic transformation of bone biology. Genes Dev 1999; 13(23):3037-51.

Keffer, J., L. Probert, H. Cazlaris, S. Georgopoulos, E. Kaslaris, D. Kioussis, and G. Kollias. 1991. Transgenic mice expressing human tumour necrosis factor: a predictive genetic model of arthritis. *Embo J* 10:4025-31.

Keystone E C. Tumor necrosis factor-alpha blockade in the treatment of rheumatoid arthritis. Rheum Dis Clin North Am 2001; 27(2):427-43.

Knight, D. M., H. Trinh, J. Le, S. Siegel, D. Shealy, M. McDonough, B. Scallon, M. A. Moore, J. Vilcek, P. Daddona, and et al. 1993. Construction and initial characterization of a mouse-human chimeric anti-TNF antibody. *Mol Immunol* 30:1443.

Kobayashi N, Kadono Y, Naito A, et al. *Segregation of TRAF6-mediated signaling pathways clarifies its role in osteoclastogenesis. Embo J* 2001; 20(6):1271-1280.

Kobayashi, K., N. Takahashi, E. Jimi, N. Udagawa, M. Takami, S. Kotake, N. Nakagawa, M. Kinosaki, K. Yamaguchi, N. Shima, H. Yasuda, T. Morinaga, K. Higashio, T. J. Martin, and T. Suda. 2000. Tumor necrosis factor alpha stimulates osteoclast differentiation by a mechanism independent of the ODF/RANKL-RANK interaction. *J Exp Med* 191:275-86.

Kodama, H., A. Yamasaki, M. Nose, S. Niida, Y. Ohgame, M. Abe, M. Kumegawa, and T. Suda. 1991. Congenital osteoclast deficiency in osteopetrotic (op/op) mice is cured by injections of macrophage colony-stimulating factor. *J Exp Med* 173:269-72.

Koller M, Willheim M, Krugluger W, et al. Immunophenotyping of human bone marrow-derived macrophages. Scand J Immunol 1996; 43(6):626-32.

Kong, Y. Y., H. Yoshida, I. Sarosi, H. L. Tan, E. Timms, C. Capparelli, S. Morony, A. J. Oliveira-dos-Santos, G. Van, A. Itie, W. Khoo, A. Wakeham, C. R. Dunstan, D. L. Lacey, T. W. Mak, W. J. Boyle, and J. M. Penninger. 1999. OPGL is a key regulator of osteoclastogenesis, lymphocyte development and lymph-node organogenesis. *Nature* 397:315-323.

Kong, Y. Y., Feige, U., Sarosi, I., Bolon, B., Tafuri, A., Morony, Capparelli, C., Li, J., Elliott, R., McCabe, S. et al. 1999. Activated T cells regulate bone loss and joint destruction in adjuvant arthritis through osteoprotegerin ligand. *Neurosurgery* 402:304-309.

Kono, D. H., R. W. Burlingame, D. G. Owens, A. Kuramochi, R. S. Balderas, D. Balomenos, and A. N. Theofilopoulos. 1994. Lupus susceptibility loci in New Zealand mice. *Proc Natl Acad Sci USA* 91:10168.

Kotake, S., Udagawa, N., Hakoda, M., Mogi, M., Yano, K., Tsuda, E., Takahashi, K., Furuya, T., Ishiyama, S., Kim, K. J. et al. 2001. Activated human T cells directly induce osteoclastogenesis from human monocytes: possible role of T cells in bone destruction in rheumatoid arthritis patients. Arthritis Rheum. 44:1003-1012.

Kotzin, B. L. 1996. Systemic lupus erythematosus. *Cell* 85:303.

Labowitz, R., and H. R. Schumacher, Jr. 1971. Articular manifestations of systemic lupus erythematosus. *Ann Intern Med* 74:911.

Lacey, D. L., Timms, E., Tan, H. L., Kelley, M. J., Dunstan, C. R., Burgess, T., Elliott, R., Colombero, A., Elliott, G., Scully, S. et al. 1998. Osteoprotegerin ligand is a cytokine that regulates osteoclast differentiation and activation. *Cell* 93:165-176.

Lam, J., Takeshita, S., Barker, J. E., Kanagawa, O., Ross, F. P., and Teitelbaum, S. L. 2000. TNF-alpha induces osteoclastogenesis by direct stimulation of macrophages exposed to permissive levels of RANK ligand. *J of Clin. Inv.* 106: 1481-1488.

Landewé, R. B. M., P. Geusens, M. Boers, P. Gamero, D. van der Heijde, and S. van der Linden. 2003. Serum RANK-ligand Modifies the effect of Disease Activity on Radiographic Progression. *Arthritis & Rheumatism* 48:S268.

Larsen, A., and J. Thoen. 1987. Hand radiography of 200 patients with rheumatoid arthritis repeated after an interval of one year. *Scand J Rheumatol* 16:395.

Li P, Sanz I, O'Keefe R J, Schwarz E M. 2000. NF-kappaB Regulates VCAM-1 Expression on Fibroblast-Like Synoviocytes. *J Immunol.* 164(11):5990-5997.

Li, P., and E. M. Schwarz. 2003. The TNF-alpha transgenic mouse model of inflammatory arthritis. *Springer Semin Immunopathol* 25:19.

Li, P., E. M. Schwarz, M. L., R. J. Looney, C. T. Ritchlin, R. J. O'Keefe, B. F. Boyce, and L. Xing. 2003. Systemic TNFα mediates an increase in peripheral CD11bhi osteoclast precursors in TNFα transgenic mice. *Arthritis Rheum In Press.*

Li, P., E. M. Schwarz, R. J. O'Keefe, B. F. Boyce, and L. Xing. 2003. RANK signaling independent and dependent stages of osteoclastogenesis in TNF-induced erosive arthritis. *J Bon. Min. Res. In Press.*

Li, P., Schwarz, E. M., O'Keefe, R. J., Boyce, B. F., and Xing, L. 2002. Systemic TNFα promotes erosive bone resorption by increasing the number of CD11b+ osteoclast progenitors in the periphery which are dependent on RANK signaling for osteoclastogenesis. *J Bone & Mineral Res.* 17:s130.

Lipsky, P. E., D. M. van der Heijde, E. W. St Clair, D. E. Furst, F. C. Breedveld, J. R. Kalden, J. S. Smolen, M. Weisman, P. Emery, M. Feldmann, G. R. Harriman, and R. N. Maini. 2000. Infliximab and methotrexate in the treatment of rheumatoid arthritis. Anti-Tumor Necrosis Factor Trial in Rheumatoid Arthritis with Concomitant Therapy Study Group. *N Engl J Med* 343: 1594.

Locksley, R. M., N. Killeen, and M. J. Lenardo. 2001. The TNF and TNF receptor superfamilies: integrating mammalian biology. *Cell* 104:487.

Logan T F, Gooding W, Kirkwood J M, Shadduck R K. Tumor necrosis factor administration is associated with increased endogenous production of M-CSF and G-CSF but not GM-CSF in human cancer patients. Exp Hematol 1996; 24(1): 49-53.

Lomaga M A, Yeh W C, Sarosi I, et al. *TRAF6 deficiency results in osteopetrosis and defective interleukin-1, CD40, and LPS signaling.* Genes Dev 1999; 13(8):1015-24.

Looney, R. J., A. Boyd, S. Totterman, G. S. Seo, J. Tamez-Pena, D. Campbell, L. Novotny, C. Olcott, J. Martell, F. A. Hayes, R. J. O'Keefe, and E. M. Schwarz. Volumetric computerized tomography as a measurement of periprosthetic acetabular osteolysis and its correlation with wear. *Arthritis Res* 4:59.

Maini R N, Elliott M J, Brennan F M, et al. Monoclonal anti-TNF alpha antibody as a probe of pathogenesis and therapy of rheumatoid disease. *Immunol Rev* 1995; 144: 195-223.

Maini, R. N., M. J. Elliott, F. M. Brennan, R. O. Williams, C. Q. Chu, E. Paleolog, P. J. Charles, P. C. Taylor, and M. Feldmann. 1995. Monoclonal anti-TNF alpha antibody as a probe of pathogenesis and therapy of rheumatoid disease. *Immunol Rev* 144:195.

Martel, W., Hayes, J. T., and Duff, I. F. 1965. The pattern of bone erosion in the hand and wrist in rheumatoid arthrits. *Radiology* 84:204.

Marzo-Ortega, H., McGonagle, D., O'Connor, P., and Emery, P. 2001. Efficacy of etanercept in the treatment of the entheseal pathology in resistant spondylarthropathy: a clinical and magnetic resonance imaging study. *Arthritis Rheum.* 44:2112-2117.

Massey, H. M. and Flanagan, A. M. 1999. Human osteoclasts derive from CD14-positive monocytes. British Journal of Haematology 106:167-170.

McGowan, N. W., Walker, E. J., Macpherson, H., Ralston, S. H., and Helfrich, M. H. 2001. Cytokine-activated endothelium recruits osteoclast precursors. *Endocrinology* 142:1678-1681.

McQueen, F. M., N. Benton, D. Perry, J. Crabbe, E. Robinson, S. Yeoman, L. McLean, and N. Stewart. 2003. Bone edema scored on magnetic resonance imaging scans of the dominant carpus at presentation predicts radiographic joint damage of the hands and feet six years later in patients with rheumatoid arthritis. *Arthritis Rheum* 48:1814.

Mease, P. J. 2002. Tumour necrosis factor (TNF) in psoriatic arthritis: pathophysiology and treatment with TNF inhibitors. *Ann Rheum Dis* 61:298.

Mease, P. J., Goffe, B., Metz, J., and Vanderstoep, A. 1999. Embrel (Etanercept) in patients with Psoriatic Arthritis and Psoriasis. *Arthritis Rheum.* 42:377 (Abstr.) Mease, P. J., Goffe, B. S., Metz, J., Vanderstoep, A., Finck, B., and Burge, D. J. 2000. Etanercept in the treatment of psoriatic arthritis and psoriasis: a randomised trial. *Lancet* 356:385-390.

Mills, J. A. 1994. Systemic lupus erythematosus. *N Engl J Med* 330:1871.

Molina, J. F., G. Citera, D. Rosler, M. L. Cuellar, J. Molina, O. Felipe, and L. R. Espinoza. 1995. Coexistence of human immunodeficiency virus infection and systemic lupus erythematosus. *J Rheumatol* 22:347.

Moll, J. M., and V. Wright. 1973. Familial occurrence of psoriatic arthritis. *Ann Rheum Dis* 32:181.

Moll, J. M. and Wright, V. 1973. Psoriatic arthritis. Seminars in Arthritis & Rheumatism 3:55-78.

Morel, L., U. H. Rudofsky, J. A. Longmate, J. Schiffenbauer, and E. K. Wakeland. 1994. Polygenic control of susceptibility to murine systemic lupus erythematosus. *Immunity* 1:219.

Moreland L W, Cohen S B, Baumgartner S W, et al. 2001. Long-term safety and efficacy of etanercept in patients with rheumatoid arthritis. *J Rheumatol* 28(6):1238-44.

Moreland, L. W., S. W. Baumgartner, M. H. Schiff, E. A. Tindall, R. M. Fleischmann, A. L. Weaver, R. E. Ettlinger, S. Cohen, W. J. Koopman, K. Mohler, M. B. Widmer, and C. M. Blosch. 1997. Treatment of rheumatoid arthritis with a recombinant human tumor necrosis factor receptor (p75)-Fc fusion protein. *N Engl J Med* 337:141.

Myers, D. E., Collier, F. M., Minkin, C., Wang, H., Holloway, W. R., Malakellis, M., and Nicholson, G. C. 1999. Expression of functional RANK on mature rat and human osteoclasts. *FEBS Letters* 463:295-300.

Nakagawa, N., Kinosaki, M., Yamaguchi, K., Shima, N., Yasuda, H., Yano, K., Morinaga, T., and Higashio, K. 1998. RANK is the essential signaling receptor for osteoclast differentiation factor in osteoclastogenesis. Biochemical & Biophysical Research Communications 253:395-400.

Natour, J., L. C. Montezzo, L. A. Moura, and E. Atra. 1991. A study of synovial membrane of patients with systemic lupus erythematosus (SLE). *Clin Exp Rheumatol* 9:221.

Nicholson, G. C., Malakellis, M., Collier, F. M., Cameron, P. U., Holloway, W. R., Gough, T J, Gregorio-King, C., Kirkland, M. A., and Myers, D. E. 2000. Induction of osteoclasts from CD14-positive human peripheral blood mononuclear cells by receptor activator of nuclear factor kappab ligand (RANKL). Clinical Science 99:133-140.

Partsch, G., Wagner, E., Leeb, B. F., Broll, H., Dunky, A., and Smolen, J. S. 1998. T cell derived cytokines in psoriatic arthritis synovial fluids. Ann. of Rheum. Dis. 57:691-693.

Pascual, V., J. Banchereau, and A. K. Palucka. 2003. The central role of dendritic cells and interferon-alpha in SLE. *Curr Opin Rheumatol* 15:548.

Penit C, Vasseur F. Phenotype analysis of cycling and post-cycling thymocytes: evaluation of detection methods for BrdUrd and surface proteins. Cytometry 1993; 14(7):757-63.

Pettit, A. R., Ji, H., von Stechow, D., Muller, R., Goldring, S. R., Choi, Y., Benoist, C., and Gravallese, E. M. 2001. TRANCE/RANKL knockout mice are protected from bone erosion in a serum transfer model of arthritis. *Am. J. Pathol.* 159:1689-1699.

Quinn, J. M., Elliott, J., Gillespie, M. T., and Martin, T. J. 1998. A combination of osteoclast differentiation factor and macrophage-colony stimulating factor is sufficient for both human and mouse osteoclast formation in vitro. Endocrinology 139:4424-4427.

Redlich, K., Hayer, S., Maier, A., Dunstan, C. R., Tohidast-Akrad, M., Lang, S., Turk, B., Pietschmann, P., Woloszczuk, W., Haralambous, S. et al. 2002. Tumor necrosis factor alpha-mediated joint destruction is inhibited by targeting osteoclasts with osteoprotegerin. Arthritis Rheum. 46:785-792.

Reece, R. J., Canete, J. D., Parsons, W. J., Emery, P., and Veale, D. J. 1999. Distinct vascular patterns of early synovitis in psoriatic, reactive, and rheumatoid arthritis. Arthritis Rheum. 42:1481-1484.

Resnick, D., and G. Niwayama. 1989. Psoriatic arthritis. *In Resnick (Ed) Bone and Joint Imaging* Philadelphia: W B Saunders:320.

Resnick, D. and Niwayama, G. 1977. On the nature and significance of bony proliferation in "rheumatoid variant" disorders. AJR *Am J Roentgen.* 129:275-278.

Resnick, D. and Niwayama, G. 1981. Psoriatic Arthritis. In Diagnosis of Bone and Joint Disorders. D. Resnick and Niwayama, G., editors. W. B. Saunders, Philadelphia. 1103.

Resnick, D. and Niwayama, G. 1989. Psoriatic Arthritis. In Bone and Joint Imaging. D. Resnick, editor. W. B. Saunders, Philadelphia, Pa. 320-328.

Ritchlin C T, Haas-Smith S A, Li P, et al. Mechanisms of TNF-alpha- and RANKL-mediated osteoclastogenesis and bone resorption in psoriatic arthritis. *J Clin Invest* 2003; 111(6):821-31.

Ritchlin, C. T., S. A. Haas-Smith, T. Shao, R. Durham, J. Monu, G. S. Seo, S. Totterman, A. P. Anandarajah, and E. M. Schwarz. 2003. Etanercept Lowers the Frequency of Circulating Osteoclast Precursors (OCP) and Improves Bone Marrow Edema in Patients with Erosive Psoriatic Arthritis. *Late-Breaking Abstract ACR.*

Ritchlin, C. and Haas-Smith, S. A. 2001. Expression of interleukin 10 mRNA and protein by synovial fibroblastoid cells. Journal of Rheumatology 28:698-705.

Ritchlin, C., Haas-Smith, S., Hicks, D., Cappuccio, J., Osterland, C. K., and Looney, R. J. Patterns of Cytokine Production in Psoriatic Synovium. Journal of Rheumatology 25:1544-1552.

Rozzo, S. J., J. D. Allard, D. Choubey, T. J. Vyse, S. Izui, G. Peltz, and B. L. Kotzin. Evidence for an interferon-inducible gene, Ifi202, in the susceptibility to systemic lupus. *Immunity* 15:435.

Rozzo, S. J., T. J. Vyse, C. G. Drake, and B. L. Kotzin. 1996. Effect of genetic background on the contribution of New Zealand black loci to autoimmune lupus nephritis. *Proc Natl Acad Sci USA* 93:15164.

Rozzo, S. J., T. J. Vyse, K. Menze, S. Izui, and B. L. Kotzin. 2000. Enhanced susceptibility to lupus contributed from the nonautoimmune C57BL/10, but not C57BL/6, genome. *J Immunol* 164:5515.

Santiago-Raber, M. L., R. Baccala, K. M. Haraldsson, D. Choubey, T. A. Stewart, D. H. Kono, and A. N. Theofilopoulos. 2003. Type-I interferon receptor deficiency reduces lupus-like disease in NZB mice. *J Exp Med* 197: 777.

Santiago-Schwarz F, Sullivan C, Rappa D, Carsons S E. Distinct alterations in lineage committed progenitor cells exist in the peripheral blood of patients with rheumatoid arthritis and primary Sjogren's syndrome. J Rheumatol 1996; 23(3):439-46.

Schwarz E M, Looney R J, O'Keefe R J. 2000. Anti-TNFalpha therapy as a clinical intervention for periprosthetic osteolysis. Arthritis Res. 2:165-168.

Schwarz, E. M., C. Badorff, T. S. Hiura, R. Wessely, A. Badorff, I. M. Verma, and K. U. Knowlton. 1998. NFkB mediated inhibition of apoptosis is required for encephalomyocarditis virus virulence: A mechanism of resistance in p50 knockout mice. *J. Virol.* 72:5654.

Schwarz, E. M., D. Campbell, S. Totterman, A. Boyd, R. J. O'Keefe, and R. J. Looney. Use of volumetric computerized tomography as a primary outcome measure to evaluate drug efficacy in the prevention of peri-prosthetic osteolysis: a 1-year clinical pilot of etanercept vs. placebo. *J Orthop Res* 21:1049.

Schwarz, E. M., P. Krimpenfort, A. Berns, and I. M. Verma. 1997. Immunological defects in mice with a targeted disruption in Bcl-3. *Genes Dev* 11:187.

Shalhoub, V., Elliott, G., Chiu, L., Manoukian, R., Kelley, M., Hawkins, N., Davy, Shimamoto, G., Beck, J., Kaufman, S. A. et al. 2000. Characterization of osteoclast precursors in human blood. British Journal of Haematology 111:501-512.

Sharp, J. T., D. Y. Young, G. B. Bluhm, A. Brook, A. C. Brower, M. Corbett, J. L. Decker, H. K. Genant, J. P. Gofton, N. Goodman, and et al. 1985. How many joints in the hands and wrists should be included in a score of radiologic abnormalities used to assess rheumatoid arthritis? Arthritis Rheum 28:1326.

Sharp, J. T., M. D. Lidsky, L. C. Collins, and J. Moreland. 1971. Methods of scoring the progression of radiologic changes in rheumatoid arthritis. Correlation of radiologic, clinical and laboratory abnormalities. *Arthritis Rheum* 14:706.

Shealy, D. J., P. H. Wooley, E. Emmell, A. Volk, A. Rosenberg, G. Treacy, C. L. Wagner, L. Mayton, D. E. Griswold, and X. Y. Song. 2002. Anti-TNF-alpha antibody allows healing of joint damage in polyarthritic transgenic mice. *Arthritis Res* 4.

Shigeyama, Y., T. Pap, P. Kunzler, B. R. Simmen, R. E. Gay, and S. Gay. 2000. Expression of osteoclast differentiation factor in rheumatoid arthritis. *Arthritis Rheum* 43:2523-2530.

Shlomchik, M. J., J. E. Craft, and M. J. Mamula. 2001. From T to B and back again: positive feedback in systemic autoimmune disease. *Nat Rev Immunol* 1:147.

Simonet, W. S., D. L. Lacey, C. R. Dunstan, M. Kelley, M. S. Chang, R. Luthy, H. Q. Nguyen, S. Wooden, L. Bennett, T. Boone, G. Shimamoto, M. DeRose, R. Elliott, A. Colombero, H. L. Tan, G. Trail, J. Sullivan, E. Davy, N. Bucay, L. Renshaw-yegg, T. M. Hughes, D. Hill, W. Pattison, P. Campbell, W. J. Boyle, and et al. 1997. Osteoprotegerin: a novel secreted protein involved in the regulation of bone density [see comments]. *Cell* 89:309-319.

Srivastava S, Toraldo G, Weitzmann M N, et al. Estrogen decreases osteoclast formation by down-regulating receptor activator of NF-kappa B ligand (RANKL)-induced JNK activation. J Biol Chem 2001; 276(12):8836-40.

Steinman, R. M. 1991. The dendritic cell system and its role in immunogenicity. *Annu Rev Immunol* 9:271.

Steinman, R. M., and M. C. Nussenzweig. 2002. Avoiding horror autotoxicus: the importance of dendritic cells in peripheral T cell tolerance. *Proc Natl Acad Sci USA* 99:351.

Steinman, R. M., S. Turley, I. Mellman, and K. Inaba. 2000. The induction of tolerance by dendritic cells that have captured apoptotic cells. *J Exp Med* 191:411.

Stevens, M. 1983. The clinical management of systemic lupus erythematosus. *In: Shur P H, ed New York: Grune & Stratton:* 63.

Suda T, Nakamura I, Jimi E, Takahashi N. Regulation of osteoclast function. *J Bone Miner Res* 1997; 12(6):869-79.

Suda, T., Takahashi, N., Udagawa, N., Jimi, E., Gillespie, M. T., and Martin, T. J. 1999. Modulation of osteoclast differentiation and function by the new members of the tumor necrosis factor receptor and ligand families. Endocrine Reviews 20:345-357.

Takahashi, K., M. C. Honeyman, and L. C. Harrison. 1998. Impaired yield, phenotype, and function of monocyte-derived dendritic cells in humans at risk for insulin-dependent diabetes. *J Immunol* 161:2629.

Takayanagi, H., H. Iizuka, T. Juji, T. Nakagawa, A. Yamamoto, T. Miyazaki, Y. Koshihara, H. Oda, K. Nakamura, and S. Tanaka. 2000. Involvement of receptor activator of nuclear factor kappaB ligand/osteoclast differentiation factor in osteoclastogenesis from synoviocytes in rheumatoid arthritis. *Arthritis Rheum* 43:259.

Takayanagi, H., K. Ogasawara, S. Hida, T. Chiba, S. Murata, K. Sato, A. Takaoka, T. Yokochi, H. Oda, K. Tanaka, K. Nakamura, and T. Taniguchi. 2000. T-cell-mediated regulation of osteoclastogenesis by signalling cross-talk between RANKL and IFN-γamma. *Nature* 408:600.

Takayanagi, H., Oda, H., Yamamoto, S., Kawaguchi, H., Tanaka, S., Nishikawa, T., and Koshihara, Y. 1997. A new mechanism of bone destruction in rheumatoid arthritis: synovial fibroblasts induce osteoclastogenesis. *Biochem. Biophys. Res. Comm.* 240:279-286.

Takayanagi, H., S. Kim, K. Matsuo, H. Suzuki, T. Suzuki, K. Sato, T. Yokochi, H. Oda, K. Nakamura, N. Ida, E. F. Wagner, and T. Taniguchi. 2002. RANKL maintains bone homeostasis through c-Fos-dependent induction of interferon-beta. *Nature* 416:744.

Tan, E. M., A. S. Cohen, J. F. Fries, A. T. Masi, D. J. McShane, N. F. Rothfield, J. G. Schaller, N. Talal, and R. J. Winchester. 1982. The 1982 revised criteria for the classification of systemic lupus erythematosus. *Arthritis Rheum* 25:1271.

Teitelbaum, S. L. 2000. Bone Resorption by Osteoclasts. *Science* 289:1504.

Theofilopoulos, A. N., and D. H. Kono. 1999. The genes of systemic autoimmunity. *Proc Assoc Am Physicians* 111: 228.

Thiele, J., B. Schmitz, R. Fuchs, H. M. Kvasnicka, J. Lorenzen, and R. Fischer. 1998. Detection of the bcr/abl gene in bone marrow macrophages in CML and alterations during interferon therapy—a fluorescence in situ hybridization study on trephine biopsies. *Journal of Pathology.* 186:331.

Toritsuka, Y., Nakamura, N., Lee, S. B., Hashimoto, J., Yasui, N., Shino, K., and Ochi, T. Osteoclastogenesis in iliac bone marrow of patients with rheumatoid arthritis. Journal of Rheumatology 24:1690-1696.

van der Heijde, D. M. 1996. Plain X-rays in rheumatoid arthritis: overview of scoring methods, their reliability and applicability. *Baillieres Clin Rheumatol* 10:435.

Vyse, T. J., and B. L. Kotzin. 1998. Genetic susceptibility to systemic lupus erythematosus. *Annu Rev Immunol* 16:261.

Vyse, T. J., S. J. Rozzo, C. G. Drake, S. Izui, and B. L. Kotzin. 1997. Control of multiple autoantibodies linked with a lupus nephritis susceptibility locus in New Zealand black mice. *J Immunol* 158:5566.

Vyse, T. J., S. J. Rozzo, C. G. Drake, V. B. Appel, M. Lemeur, S. Izui, E. Palmer, and B. L. Kotzin. 1998. Contributions of Ea(z) and Eb(z) MHC genes to lupus susceptibility in New Zealand mice. *J Immunol* 160:2757.

Wakeland, E. K., A. E. Wandstrat, K. Liu, and L. Morel. 1999. Genetic dissection of systemic lupus erythematosus. *Curr Opin Immunol* 11:701.

Wang Z Q, Ovitt C, Grigoriadis A E, et al. Bone and haematopoietic defects in mice lacking c-fos. Nature 1992; 360 (6406):741-5.

Weinblatt, M. E., E. C. Keystone, D. E. Furst, L. W. Moreland, M. H. Weisman, C. A. Birbara, L. A. Teoh, S. A. Fischkoff, and E. K. Chartash. 2003. Adalimumab, a fully human anti-tumor necrosis factor alpha monoclonal antibody, for the treatment of rheumatoid arthritis in patients taking concomitant methotrexate: the ARMADA trial. *Arthritis Rheum* 48:35.

Winchester, R. 1993. Psoriatic Arthritis. In Dermatology in General Medicine. T. B. Fitzpatrick, Eisen, A. Z., Wolff, K., Freeberg, F. M., and Austin, K. F., editors. McGraw-Hill, New York. 515-527.

Wong B R, Rho J, Arron J, et al. TRANCE is a novel ligand of the tumor necrosis factor receptor family that activates c-Jun N-terminal kinase in T cells. J Biol Chem 1997; 272(40):25190-4.

Xing L, Bushnell T P, Carlson L, et al. NF-kappaB p50 and p52 expression is not required for RANK-expressing osteoclast progenitor formation but is essential for RANK- and cytokine-mediated osteoclastogenesis. J Bone Miner Res 2002; 17(7):1200-10.

Yasuda, H., N. Shima, N. Nakagawa, K. Yamaguchi, M. Kinosaki, S. Mochizuki, A. Tomoyasu, K. Yano, M. Goto, A. Murakami, E. Tsuda, T. Morinaga, K. Higashio, N. Udagawa, N. Takahashi, and T. Suda. 1998. Osteoclast differentiation factor is a ligand for osteoprotegerin/osteoclastogenesis-inhibitory factor and is identical to TRANCE/RANKL. *Proc Natl Acad Sci USA* 95:3597.

Yin, G., W. Liu, P. An, P. Li, I. Ding, V. Planelles, E. M. Schwarz, and W. Min. 2002. Endostatin gene transfer inhibits joint angiogenesis and pannus formation in inflammatory arthritis. *Mol Ther* 5:547.

Yoshida, H., S. Hayashi, T. Kunisada, M. Ogawa, S. Nishikawa, H. Okamura, T. Sudo, and L. D. Shultz. 1990. The murine mutation osteopetrosis is in the coding region of the macrophage colony stimulating factor gene. *Nature* 345: 442.

Zhang, X., E. M. Schwarz, D. A. Young, J. E. Puzas, R. N. Rosier, and R. J. O'Keefe. Cyclooxygenase-2 regulates mesenchymal cell differentiation into the osteoblast lineage and is critically involved in bone repair. *J Clin Invest* 109:1405.

H. Sequences

1. SEQ ID NO:1 RANKL anti-sense 5'
2. SEQ ID NO:2 RANK sense 5'
3. SEQ ID NO:3 RANK anti-sense 5'
4. SEQ ID NO:4 OPG sense 5'
5. SEQ ID NO:5 OPG anti-sense 5'
6. SEQ ID NO:6 GAPDH sense 5'
7. SEQ ID NO:7 GAPDH anti-sense 5'
8. SEQ ID NO:8
9. SEQ ID NO:9 RANKL AF019048 *Mus musculus* mRNA, complete cds
10. SEQ ID NO:10 RANKL AF019048 *Mus musculus* Protein
11. SEQ ID NO:11 RANKL AF019047 *Mus musculus* mRNA, complete cds
12. SEQ ID NO:12 RNKL AF019047 *Homo Sapiens* Protein
13. SEQ ID NO:13 RANK AF018253 *Homo sapiens* receptor activator of nuclear factor-kappa B (RANK) mRNA
14. SEQ ID NO:14 RANK AF018253 *Homo sapiens* receptor activator of nuclear factor-kappa B (RANK) Protein
15. SEQ ID NO:15 RANK AF019046 *Mus musculus* receptor activator of nuclear factor-kappa B (RANK) mRNA
16. SEQ ID NO:16 RANK AF019046 *Mus musculus* receptor activator of nuclear factor-kappa B (RANK) Protein
17. SEQ ID NO:17 TNF alpha *homo sapiens* mRNA
18. SEQ ID NO:18 TNF alpha *homo sapiens* protein
19. SEQ ID NO:19 TNF alpha NM_013693 *Mus musculus* mRNA
20. SEQ ID NO:20 TNF alpha NM_013693 *Mus musculus* mRNA
21. SEQ ID NO:21 TNFR1 M75866 Human tumor necrosis factor receptor 1 (TNFR1) complete cds
22. SEQ ID NO:22 TNFR1 M75866 Human tumor necrosis factor receptor 1 (TNFR1) Protein
23. SEQ ID NO:23 TNFR1 L26349 *Mus Musculus* tumor necrosis factor receptor 1 (TNFR1) complete cds
24. SEQ ID NO:24 TNFR1 L26349 *Mus Musculus* tumor necrosis factor receptor 1 (TNFR1) Protein
25. SEQ ID NO. 25 CD11b primers
26. SEQ ID NO. 26 CD11b primers
27. SEQ ID NO. 27 actin primers
28. SEQ ID NO. 28 actin primers

What is claimed is:

1. A method of diagnosing a subject with erosive arthritis comprising measuring how many osteoclast precursor cells (OCP) are in the blood of the subject and correlating the number of OCP in the blood of the subject with the presence of erosive arthritis, wherein a significant increase in the number of OCP in the subject relative to a healthy control subject having no erosive arthritis indicates the presence of erosive arthritis.

2. The method of claim 1, wherein the OCP in the blood are obtained by collecting the subject's Peripheral Blood Mononuclear Cells (PBMCs).

3. The method of claim 2, wherein the step of measuring comprises counting the number of cells comprising at least one marker selected from the group consisting of CD14, CD11a, CD11b, CD51/CD61, RANK, CCR1, CCR4, VCAM (CD106), VLA-4 (CD49d), CD16, MHC Class II, B7.1, B7.2, CD40, and c-fms.

4. The method of claim 2, wherein the step of measuring comprises counting the number of cells comprising at least two markers selected from the group consisting of CD14, CD11a, CD11b, CD51/CD61, RANK, CCR1, CCR4, VCAM (CD106), VLA-4 (CD49d), CD16, MHC Class II, B7.1, B7.2, CD40, and c-fms.

5. The method of claim 2, wherein the step of measuring comprises counting the number of cells comprising at least three markers selected from the group consisting of CD14, CD11a, CD11b, CD51/CD61, RANK, CCR1, CCR4, VCAM (CD106), VLA-4 (CD49d), CD16, MHC Class II, B7.1, B7.2, CD40, and c-fms.

6. The method of claim 2, wherein the step of measuring comprises counting the number of cells comprising at least four markers selected from the group consisting of CD14, CD11a, CD11b, CD51/CD61, RANK, CCR1, CCR4, VCAM (CD106), VLA-4 (CD49d), CD16, MHC Class II, B7.1, B7.2, CD40, and c-fms.

7. The method of claim 1, wherein the amount of OCP is determined by staining the PBMC sample with fluorescently labeled antibodies for at least one marker selected from the group consisting of CD14, CD11b, CD51/CD61, RANK, CCR1, CCR4, VCAM (CD106), VLA-4 (CD49d), CD16, CD11a, MHC Class II, B7.1, B7.2, CD40, and c-fms and visualizing the cells with labeled antibody bound to at least one of CD14+, CD11b+, CD51/CD61+, RANK+, CCR1+, CCR4+, VCAM+(CD106), VLA-4+(CD49d), CD11a, MHC Class II, B7.1, B7.2, CD40, c-fms or CD16- (negative) using Fluorescence Activated Cell Sorting (FACS).

8. The method of claim 1, wherein the number of OCP is further determined by removing a tissue sample from the subject and visualizing the sample using immunohistochemistry for at least one marker selected from the group consisting of CD14, CD11b, CD51/CD61, RANK, CCR1, CCR4, VCAM (CD106), VLA-4(CD49d), CD11a, MHC Class II, B7.1, B7.2, CD40, c-fms and CD16.

9. The method of claim 1, wherein the amount of OCP is measured by obtaining a blood sample from the subject and staining the blood sample with Tartrate Resistant Acid Phosphatase (TRAP), counting how many multinucleated cells there are in the sample, and comparing the number of multinucleated cells in the blood sample from the subject to a number of multinucleated cells in a blood sample from a healthy control subject having no erosive arthritis, wherein a significant increase in the number of multinucleated cells in the sample from the subject than in the sample from the healthy control indicates erosive arthritis in the subject.

10. The method of claim 1, wherein the amount of OCP in the subject's blood is measured using FACS methods, Immunohistochemistry methods, Western methods, Southern methods, hybridization methods, reverse transcription polymerase chain reaction (RT-PCR) methods, enzyme-linked immunosorbent assay (ELISA) methods, enzyme-linked immunosorbent spot (ELISPOT) methods, microarray methods, bone wafer resorption methods or Immunoprecipitation methods.

11. The method of claim 1, wherein measuring the number of OCP comprises identifying RANK, CD11b and CD14 positive cells in the blood sample.

12. The method of claim 1, wherein the subject shows bone erosion on a radiograph.

13. The method of claim 1, wherein the amount of OCP is measured by obtaining a blood sample from the subject and staining the blood sample with Tartrate Resistant Acid Phosphatase (TRAP), counting how many multinucleated cells there are in the sample from the subject, and comparing the number of multinucleated cells in the blood sample from the subject to a number of multinucleated cells in a blood sample from a healthy control subject having no erosive arthritis, wherein greater than 2.5 times more multinucleated cells in the sample from the subject than in the sample from the healthy control indicates erosive arthritis in the subject.

14. A method of diagnosing erosive arthritis comprising culturing peripheral blood mononuclear cells (PBMC) from a subject and assaying the number of osteoclasts formed and correlating the number of OCP in the PBMC of the subject with the presence of erosive arthritis, wherein a significant increase in the number of osteoclasts in the culture from the subject relative to the number of osteoclasts in a culture of PBMC from a healthy control subject without erosive arthritis indicates the subject has erosive arthritis.

15. The method of claim 14, wherein assaying the number of osteoclasts formed comprises monitoring the amount of TRAP positive cells.

16. The method of claim 14, wherein assaying the number of osteoclasts formed comprises monitoring the number of multinucleated cells.

17. The method of claim 14, wherein the culture has no exogenous RANKL or M-CSF added.

18. The method of claim 14, wherein addition of RANKL or M-CSF increases the number of osteoclasts in the culture from the subject relative to the number of osteoclasts in a culture of PBMC from a control subject without erosive arthritis, and wherein this increase indicates the subject has erosive arthritis.

19. A method of determining the presence of an erosive arthritis in a subject comprising, obtaining a PBMC sample from the blood of a subject, and measuring how many OCP are in the PBMC of the subject, wherein greater than 2.5 times more OCP in the PBMC of the subject than in a sample of PBMC from a control subject without erosive arthritis indicates the presence of erosive arthritis in the subject.

20. A method of determining whether a subject has erosive arthritis comprising isolating PBMC from the subject, and probing for the presence of three or more surface markers of mononuclear OCP, wherein the surface markers are selected from the group consisting of CD14, CD11b, CD51/CD61, RANK, CCR1, CCR4, VCAM (CD106), VLA-4 (CD49d), CD11a, MHC Class II, B7.1, B7.2, CD40, c-fms and CD16, and wherein a significant increase in the number of mononuclear OCP in the PBMC of the subject as determined by the presence of the three or more surface markers relative to a healthy control without erosive arthritis indicates that the subject has erosive arthritis.

21. The method of claim 20, wherein the surface markers are analyzed by FACS.

22. The method of claim 20, wherein probing for a surface marker comprises assaying for at least four surface markers.

* * * * *

SEQUENCE LISTING

<160> NUMBER OF SEQ ID NOS: 28

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 1
ctatttcaga gcgcagatgg at                                              22

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 2
tatgagaact tgggattttg atgc                                            24

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 3
ttaagccagt gcttcacggg                                                 20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 4
acgtagacca cgatgatgtc gc                                              22

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 5
gctaacctca ccttcgag                                                   18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 6

```
tgattggacc tggttacc                                                   18

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 7
gctctccaga acatcatccc tgcc                                            24

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 8
cgttgtcata ccaggaaatg agctt                                           25

<210> SEQ ID NO 9
<211> LENGTH: 2225
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 9
cggggagcca ctgccaggac tctctgtgaac cggtcggggc ggggggccgcc tggccgggag    60 tctgctcggc ggtgggtggc cgaggaaggg agagaacgat cgcggagcag ggcgcccgaa    120
ctccgggcgc cgcgccatgc gccgggccag ccagagactac ggcaagtacc tgcgcagctc   180
ggaggagatg ggcagcggcc ccggcgtccc acacgagggt ccgctgcacc ccgcgccttc    240
tgcaccggct ccggcgccgc caccgccgc ctcccgctcc atgttcctgg ccctcctggg    300
gctgggactg ggccaggtgg tctgcagcat cgctctgttc ctgtactttc gagcgcagat    360
ggatcctaac agaatatcag aagacagcac tcactgcttt tatagaatcc tgagactcca    420
tgaaaacgca gatttgcagg actcgactct ggagagtgaa gacacactac ctgactcctg    480
caggaggatg aaacaagcct ttcaggggge cgtgcagaag gaactgcaac acattgtggg    540
gccacagcgc ttctcaggag ctccagctat gatggaaggc tcatggttgg atgtggccca    600
gcgaggcaag cctgaggccc agccatttgc acacctcacc atcaatgctg ccagcatccc    660
atcgggttcc cataaagtca ctctgtcctc ttggtaccac gatcgaggct gggccaagat    720
ctctaacatg acgttaagca acggaaaact aagggttaac caagatggct tctattacct    780
gtacgccaac atttgctttc ggcatcatga acatcgggga agcgtaccta cagactatct    840
tcagctgatg gtgtatgtcg ttaaaaccag catcaaaatc ccaagttctc ataacctgat    900
gaaaggaggg agcacgaaaa actggtcggg caattctgaa ttccactttt attccataaa    960
tgttggggga ttttcaagc tccgagctgg tgaagaaatt agcattcagg tgtccaaccc    1020
ttccctgctg gatccggatc aagatgcgac gtactttggg gctttcaaag ttcaggacat   1080
agactgagac tcatttcgtg gaacattagc atggatgtcc tagatgtttg gaaacttctt   1140
aaaaaatgga tgatgtctat acatgtgtaa gactactaag agacatggcc cacggtgtat   1200
```

-continued

```
gaaactcaca gccctctctc ttgagcctgt acaggttgtg tatatgtaaa gtccataggt     1260
gatgttagat tcatggtgat tacacaacgg ttttacaatt ttgtaatgat ttcctagaat     1320
tgaaccagat tgggagaggt attccgatgc ttatgaaaaa cttacacgtg agctatggaa     1380
gggggtcaca gtctctgggt ctaaccctg  gacatgtgcc actgagaacc ttgaaattaa     1440
gaggatgcca tgtcattgca aagaaatgat agtgtgaagg gttaagttct tttgaattgt     1500
tacattgcgc tgggacctgc aaataagttc ttttttctca atgaggagag aaaaatatat     1560
gtatttttat ataatgtcta aagttatatt tcaggtgtaa tgttttctgt gcaaagtttt     1620
gtaaattata tttgtgctat agtatttgat tcaaaatatt taaaaatgtc tcactgttga     1680
catatttaat gttttaaatg tacagatgta tttaactggt gcactttgta attcccctga     1740
aggtactcgt agctaagggg gcagaatact gtttctggtg accacatgta gtttatttct     1800
ttattctttt taacttaata gagtcttcag acttgtcaaa actatgcaag caaaataaat     1860
aaataaaaat aaaatgaata ccttgaataa taagtaggat gttggtcacc aggtgccttt     1920
caaatttaga agctaattga ctttaggagc tgacatagcc aaaaaggata cataataggc     1980
tactgaaatc tgtcaggagt atttatgcaa ttattgaaca ggtgtctttt tttacaagag     2040
ctacaaattg taaattttgt ttctttttt tcccatagaa aatgtactat agtttatcag      2100
ccaaaaaaca atccactttt taattagtg aaagttattt tattatactg tacaataaaa      2160
gcattgtctc tgaatgttaa ttttttggta caaaaaataa atttgtacga aaacctgaaa     2220
aaaaa                                                                 2225
```

<210> SEQ ID NO 10
<211> LENGTH: 316
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 10

```
Met Arg Arg Ala Ser Arg Asp Tyr Gly Lys Tyr Leu Arg Ser Ser Glu
 1               5                  10                  15

Glu Met Gly Ser Gly Pro Val Pro His Glu Gly Pro Leu His Pro
            20                  25                  30

Ala Pro Ser Ala Pro Ala Pro Pro Ala Ala Ser Arg Ser
        35                  40                  45

Met Phe Leu Ala Leu Leu Gly Leu Gly Leu Gly Gln Val Val Cys Ser
    50                  55                  60

Ile Ala Leu Phe Leu Tyr Phe Arg Ala Gln Met Asp Pro Asn Arg Ile
 65                  70                  75                  80

Ser Glu Asp Ser Thr His Cys Phe Tyr Arg Ile Leu Arg Leu His Glu
                85                  90                  95

Asn Ala Asp Leu Gln Asp Ser Thr Leu Glu Ser Glu Asp Thr Leu Pro
            100                 105                 110

Asp Ser Cys Arg Arg Met Lys Gln Ala Phe Gln Gly Ala Val Gln Lys
        115                 120                 125

Glu Leu Gln His Ile Val Gly Pro Gln Arg Phe Ser Gly Ala Pro Ala
    130                 135                 140

Met Met Glu Gly Ser Trp Leu Asp Val Ala Gln Arg Gly Lys Pro Glu
145                 150                 155                 160

Ala Gln Pro Phe Ala His Leu Thr Ile Asn Ala Ala Ser Ile Pro Ser
```

```
                165                 170                 175
Gly Ser His Lys Val Thr Leu Ser Ser Trp Tyr His Asp Arg Gly Trp
            180                 185                 190
Ala Lys Ile Ser Asn Met Thr Leu Ser Asn Gly Lys Leu Arg Val Asn
        195                 200                 205
Gln Asp Gly Phe Tyr Tyr Leu Tyr Ala Asn Ile Cys Phe Arg His His
    210                 215                 220
Glu Thr Ser Gly Ser Val Pro Thr Asp Tyr Leu Gln Leu Met Val Tyr
225                 230                 235                 240
Val Val Lys Thr Ser Ile Lys Ile Pro Ser Ser His Asn Leu Met Lys
                245                 250                 255
Gly Gly Ser Thr Lys Asn Trp Ser Gly Asn Ser Glu Phe His Phe Tyr
            260                 265                 270
Ser Ile Asn Val Gly Gly Phe Phe Lys Leu Arg Ala Gly Glu Glu Ile
        275                 280                 285
Ser Ile Gln Val Ser Asn Pro Ser Leu Leu Asp Pro Asp Gln Asp Ala
    290                 295                 300
Thr Tyr Phe Gly Ala Phe Lys Val Gln Asp Ile Asp
305                 310                 315

<210> SEQ ID NO 11
<211> LENGTH: 2201
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 11
ggccaaagcc gggctccaag tcggcgcccc acgtcgaggc tccgccgcag cctccggagt     60
tggccgcaga caagaagggg agggagcggg agagggagga gagctccgaa gcgagagggc    120
cgagcgccat gcgccgcgcc agcagagact acaccaagta cctgcgtggc tcggaggaga    180
tgggcggcgg ccccggagcc ccgcacgagg gccccctgca cgccccgccg ccgcctgcgc    240
cgcaccagcc cccgccgcc tcccgctcca tgttcgtggc cctcctgggg ctggggctgg    300
gccaggttgt ctgcagcgtc gccctgttct tctatttcag agcgcagatg gatcctaata    360
gaatatcaga agatggcact cactgcattt atagaatttt gagactccat gaaaatgcag    420
attttcaaga cacaactctg agagtcaag atacaaaatt aatacctgat tcatgtagga    480
gaattaaaca ggcctttcaa ggagctgtgc aaaaggaatt acaacatatc gttggatcac    540
agcacatcag agcagagaaa gcgatggtgg atggctcatg gttagatctg gccaagagga    600
gcaagcttga agctcagcct tttgctcatc tcactattaa tgccaccgac atcccatctg    660
gttcccataa agtgagtctg tcctcttggt accatgatcg gggttgggcc aagatctcca    720
acatgacttt tagcaatgga aaactaatag ttaatcagga tggcttttat tacctgtatg    780
ccaacatttg ctttcgacat catgaaactt caggagacct agctacagag tatcttcaac    840
taatggtgta cgtcactaaa accagcatca aaatcccaag ttctcatacc ctgatgaaag    900
gaggaagcac caagtattgg tcagggaatt ctgaattcca tttttattcc ataaacgttg    960
gtggattttt taagttacgg tctggagagg aaatcagcat cgaggtctcc aacccctcct   1020
tactggatcc ggatcaggat gcaacatact tggggctttt aaagttcga gatatagatt   1080 gagccccagt ttttggagtg ttatgtattt cctggatgtt tggaaacatt ttttaaaaca   1140
agccaagaaa gatgtatata ggtgtgtgag actactaaga ggcatggccc caacggtaca   1200
```

-continued

```
cgactcagta tccatgctct tgaccttgta gagaacacgc gtatttacct gccagtggga   1260
gatgttagac tcatggtgtg ttacacaatg ttttttaaat tttgtaatga attcctagaa   1320
ttaaaccaga ttggagcaat tacgggttga ccttatgaga aactgcatgt gggctatggg   1380
aggggttggt ccctggtcat gtgcccccttc gcagctgaag tggagagggt gtcatctagc   1440
gcaattgaag gatcatctga aggggcaaat tcttttgaat tgttacatca tgctggaacc   1500
tgcaaaaaat acttttctca atgaggagag aaaatatatg tatttttata taatatctaa   1560
agttatattt cagatgtaat gttttctttg caaagtattg taaattatat ttgtgctata   1620
gtatttgatt caaaatattt aaaaatgtct tgctgttgac atatttaatg ttttaaatgt   1680
acagacatat ttaactggtg cactttgtaa attccctggg gaaaacttgc agctaaggag   1740
gggaaaaaaa tgttgtttcc taatatcaaa tgcagtatat ttcttcgttc tttttaagtt   1800
aatagatttt ttcagacttg tcaagcctgt gcaaaaaaat taaaatggat gccttgaata   1860
ataagcagga tgttggccac caggtgcctt tcaaatttag aaactaattg actttagaaa   1920
gctgacattg ccaaaaagga tacataatgg gccactgaaa tttgtcaaga gtagttatat   1980
aattgttgaa caggtgtttt tccacaagtg ccgcaaattg taccttttt ttttttttcaa   2040 aatagaaaag ttattagtgg tttatcagca aaaaagtcca attttaattt agtaaatgtt   2100
attttatact gtacaataaa aacattgcct ttgaatgtta attttttggt acaaaaataa   2160
atttatatga aaaaaaaaa aaaaaaaaaa aaaaaaaaaa a                        2201
```

<210> SEQ ID NO 12
<211> LENGTH: 317
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 12

```
Met Arg Arg Ala Ser Arg Asp Tyr Thr Lys Tyr Leu Arg Gly Ser Glu
 1               5                  10                  15

Glu Met Gly Gly Gly Pro Gly Ala Pro His Glu Gly Pro Leu His Ala
            20                  25                  30

Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
    130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175
```

```
Ser Gly Ser His Lys Val Ser Leu Ser Trp Tyr His Asp Arg Gly
        180                 185                 190

Trp Ala Lys Ile Ser Asn Met Thr Phe Ser Asn Gly Lys Leu Ile Val
            195                 200                 205

Asn Gln Asp Gly Phe Tyr Tyr Leu Tyr Ala Asn Ile Cys Phe Arg His
        210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
        290                 295                 300

Ala Thr Tyr Phe Gly Ala Phe Lys Val Arg Asp Ile Asp
305                 310                 315

<210> SEQ ID NO 13
<211> LENGTH: 3136
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 13
ccgctgaggc cgcggcgccc gccagcctgt cccgcgccat ggccccgcgc gccggcggc      60 gccgcccgct gttcgcgctg ctgctgctct gcgcgctgct cgcccggctg caggtggctt     120
tgcagatcgc tcctccatgt accagtgaga agcattatga gcatctggga cggtgctgta    180
acaaatgtga accaggaaag tacatgtctt ctaaatgcac tactacctct gacagtgtat    240
gtctgccctg tggcccggat gaatacttgg atagctggaa tgaagaagat aaatgcttgc    300
tgcataaagt ttgtgataca ggcaaggccc tggtggccgt ggtcgccggc aacagcacga    360
ccccccggcg ctgcgcgtgc acggctgggt accactggag ccaggactgc gagtgctgcc    420
gccgcaacac cgagtgcgcg ccgggcctgg gcgcccagca cccgttgcag ctcaacaagg    480
acacagtgtg caaaccttgc cttgcaggct acttctctga tgccttttcc tccacggaca    540
aatgcagacc ctggaccaac tgtaccttcc ttggaaagag agtagaacat catgggacag    600
agaaatccga tgcggtttgc agttcttctc tgccagctag aaaaccacca aatgaacccc    660
atgtttactt gccccggttta ataattctgc ttctcttcgc gtctgtggcc ctggtggctg    720
ccatcatctt tggcgtttgc tataggaaaa aagggaaagc actcacagct aatttgtggc    780
actggatcaa tgaggcttgt ggccgcctaa gtggagataa ggagtcctca ggtgacagtt    840
gtgtcagtac acacacggca aactttggtc agcagggagc atgtgaaggt gtcttactgc    900
tgactctgga ggagaagaca tttccagaag atatgtgcta cccagatcaa ggtggtgtct    960
gtcagggcac gtgtgtagga ggtggtccct acgcacaagg cgaagatgcc aggatgctct    1020
cattggtcag caagaccgag atagaggaag acagcttcag acagatgccc acagaagatg    1080
aatacatgga caggccctcc cagcccacag accagttact gttcctcact gagcctggaa    1140
gcaaatccac acctcctttc tctgaacccc tggaggtggg ggagaatgac agtttaagcc    1200
agtgcttcac ggggacacag agcacagtgg gttcagaaag ctgcaactgc actgagcccc    1260
```

```
tgtgcaggac tgattggact cccatgtcct ctgaaaacta cttgcaaaaa gaggtggaca    1320
gtggccattg cccgcactgg gcagccagcc ccagccccaa ctgggcagat gtctgcacag    1380
gctgccggaa ccctcctggg gaggactgtg aaccccctcgt gggttcccca aaacgtggac   1440
ccttgcccca gtgcgcctat ggcatgggcc ttcccctga agaagaagcc agcaggacgg     1500
aggccagaga ccagcccgag gatggggctg atgggaggct cccaagctca gcagggcag    1560 gtgccgggtc tggaagctcc cctggtggcc agtccctgc atctggaaat gtgactggaa     1620
acagtaactc cacgttcatc tccagcgggc aggtgatgaa cttcaagggc gacatcatcg    1680
tggtctacgt cagccagacc tcgcaggagg gcgcggcggc ggctgcggag cccatgggcc   1740
gcccggtgca ggaggagacc ctggcgcgcc gagactcctt cgcggggaac ggcccgcgct    1800
tcccggaccc gtgcggcggc cccgagggc tgcgggagcg ggagaaggcc tcgaggccgg    1860
tgcaggagca aggcggggcc aaggcttgag cgccccccat ggctgggagc cgaagctcg     1920 gagccagggc tcgcgagggc agcaccgcag cctctgcccc agccccggcc acccagggat    1980
cgatcggtac agtcgaggaa gaccaccccgg cattctctgc ccactttgcc ttccaggaaa   2040
tgggcttttc aggaagtgaa ttgatgagga ctgtccccat gcccacggat gctcagcagc    2100
ccgccgcact ggggcagatg tctcccctgc cactcctcaa actcgcagca gtaatttgtg    2160
gcactatgac agctattttt atgactatcc tgttctgtgg ggggggggtc tatgttttcc    2220
ccccatattt gtattccttt tcataacttt tcttgatatc tttcctcct cttttttaat     2280 gtaaaggttt tctcaaaaat tctcctaaag gtgagggtct cttctttc tcttttcctt     2340 tttttttct tttttggca acctggctct ggcccaggct agagtgcagt ggtgcgatta      2400
tagcccggtg cagcctctaa ctcctgggct caagcaatcc aagtgatcct cccacctcaa    2460
ccttcggagt agctgggatc acagctgcag gccacgccca gcttcctccc ccgactccc     2520 ccccccaga gacacggtcc caccatgtta cccagcctgg tctcaaactc cccagctaaa    2580
gcagtcctcc agcctcggcc tcccaaagta ctgggattac aggcgtgagc ccccacgctg    2640
gcctgcttta cgtatttct tttgtgcccc tgctcacagt gttttagaga tggctttccc     2700
agtgtgtgtt cattgtaaac acttttggga aagggctaaa catgtgaggc ctggagatag    2760
ttgctaagtt gctaggaaca tgtggtggga ctttcatatt ctgaaaaatg ttctatattc    2820
tcatttttct aaaagaaaga aaaaggaaa cccgatttat ttctcctgaa tcttttaag     2880 tttgtgtcgt tccttaagca gaactaagct cagtatgtga ccttacccgc taggtggtta    2940
atttatccat gctggcagag gcactcaggt acttggtaag caaatttcta aaactccaag    3000
ttgctgcagc ttggcattct tcttattcta gaggtctctc tggaaaagat ggagaaaatg    3060
aacaggacat ggggctcctg gaaagaaagg gcccgggaag ttcaaggaag aataaagttg    3120
aaattttaaa aaaaaa                                                     3136
```

<210> SEQ ID NO 14
<211> LENGTH: 616
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 14

Met Ala Pro Arg Ala Arg Arg Arg Pro Leu Phe Ala Leu Leu Leu Leu
1               5                   10                  15

-continued

```
Leu Cys Ala Leu Leu Ala Arg Leu Gln Val Ala Leu Gln Ile Ala Pro
            20                  25                  30

Pro Cys Thr Ser Glu Lys His Tyr Glu His Leu Gly Arg Cys Cys Asn
            35                  40                  45

Lys Cys Glu Pro Gly Lys Tyr Met Ser Ser Lys Cys Thr Thr Thr Ser
 50                  55                  60

Asp Ser Val Cys Leu Pro Cys Gly Pro Asp Glu Tyr Leu Asp Ser Trp
 65                  70                  75                  80

Asn Glu Glu Asp Lys Cys Leu Leu His Lys Val Cys Asp Thr Gly Lys
                85                  90                  95

Ala Leu Val Ala Val Ala Gly Asn Ser Thr Thr Pro Arg Arg Cys
                100                 105                 110

Ala Cys Thr Ala Gly Tyr His Trp Ser Gln Asp Cys Glu Cys Cys Arg
            115                 120                 125

Arg Asn Thr Glu Cys Ala Pro Gly Leu Gly Ala Gln His Pro Leu Gln
130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                165                 170                 175

Phe Leu Gly Lys Arg Val Glu His His Gly Thr Glu Lys Ser Asp Ala
                180                 185                 190

Val Cys Ser Ser Ser Leu Pro Ala Arg Lys Pro Pro Asn Glu Pro His
            195                 200                 205

Val Tyr Leu Pro Gly Leu Ile Ile Leu Leu Leu Phe Ala Ser Val Ala
            210                 215                 220

Leu Val Ala Ala Ile Ile Phe Gly Val Cys Tyr Arg Lys Lys Gly Lys
225                 230                 235                 240

Ala Leu Thr Ala Asn Leu Trp His Trp Ile Asn Glu Ala Cys Gly Arg
                245                 250                 255

Leu Ser Gly Asp Lys Glu Ser Ser Gly Asp Ser Cys Val Ser Thr His
                260                 265                 270

Thr Ala Asn Phe Gly Gln Gln Gly Ala Cys Glu Gly Val Leu Leu Leu
            275                 280                 285

Thr Leu Glu Glu Lys Thr Phe Pro Glu Asp Met Cys Tyr Pro Asp Gln
290                 295                 300

Gly Gly Val Cys Gln Gly Thr Cys Val Gly Gly Pro Tyr Ala Gln
305                 310                 315                 320

Gly Glu Asp Ala Arg Met Leu Ser Leu Val Ser Lys Thr Glu Ile Glu
                325                 330                 335

Glu Asp Ser Phe Arg Gln Met Pro Thr Glu Asp Glu Tyr Met Asp Arg
            340                 345                 350

Pro Ser Gln Pro Thr Asp Gln Leu Leu Phe Leu Thr Glu Pro Gly Ser
            355                 360                 365

Lys Ser Thr Pro Pro Phe Ser Glu Pro Leu Glu Val Gly Glu Asn Asp
            370                 375                 380

Ser Leu Ser Gln Cys Phe Thr Gly Thr Gln Ser Thr Val Gly Ser Glu
385                 390                 395                 400

Ser Cys Asn Cys Thr Glu Pro Leu Cys Arg Thr Asp Trp Thr Pro Met
                405                 410                 415

Ser Ser Glu Asn Tyr Leu Gln Lys Glu Val Asp Ser Gly His Cys Pro
            420                 425                 430

His Trp Ala Ala Ser Pro Ser Pro Asn Trp Ala Asp Val Cys Thr Gly
```

-continued

```
                435                 440                 445
Cys Arg Asn Pro Pro Gly Glu Asp Cys Glu Pro Leu Val Gly Ser Pro
    450                 455                 460

Lys Arg Gly Pro Leu Pro Gln Cys Ala Tyr Gly Met Gly Leu Pro Pro
465                 470                 475                 480

Glu Glu Glu Ala Ser Arg Thr Glu Ala Arg Asp Gln Pro Glu Asp Gly
                485                 490                 495

Ala Asp Gly Arg Leu Pro Ser Ser Ala Arg Ala Gly Ala Gly Ser Gly
            500                 505                 510

Ser Ser Pro Gly Gly Gln Ser Pro Ala Ser Gly Asn Val Thr Gly Asn
    515                 520                 525

Ser Asn Ser Thr Phe Ile Ser Ser Gly Gln Val Met Asn Phe Lys Gly
    530                 535                 540

Asp Ile Ile Val Val Tyr Val Ser Gln Thr Ser Gln Glu Gly Ala Ala
545                 550                 555                 560

Ala Ala Ala Glu Pro Met Gly Arg Pro Val Gln Glu Glu Thr Leu Ala
                565                 570                 575

Arg Arg Asp Ser Phe Ala Gly Asn Gly Pro Arg Phe Pro Asp Pro Cys
            580                 585                 590

Gly Gly Pro Glu Gly Leu Arg Glu Pro Glu Lys Ala Ser Arg Pro Val
    595                 600                 605

Gln Glu Gln Gly Gly Ala Lys Ala
    610                 615

<210> SEQ ID NO 15
<211> LENGTH: 2116
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 15
cgcccagccc gcccgcaccg cgccatggcc ccgcgcgccc ggcggcgccg ccagctgccc      60
gcgccgctgc tggcgctctg cgtgctgctc gttccactgc aggtgactct ccaggtcact     120
cctccatgca cccaggagag gcattatgag catctcggac ggtgttgcag cagatgcgaa     180
ccaggaaagt acctgtcctc taagtgcact cctacctccg acagtgtgtg tctgccctgt     240
ggccccgatg agtacttgga cacctggaat gaagaagata atgcttgct gcataaagtc     300 tgtgatgcag gcaaggccct ggtggcgtg atcctggca ccacacggc ccgcgtcgc     360 tgtgcttgca cggctggcta ccactggaac tcagactgcg agtgctgccg caggaacacg     420
gagtgtgcac ctggcttcgg agctcagcat cccttgcagc tcaacaagga tacggtgtgc     480
acaccctgcc tcctgggctt cttctcagat gtcttttcgt ccacagacaa atgcaaacct     540
tggaccaact gcaccctcct tggaaagcta aagcacacc agggacaac ggaatcagat     600 gtggtctgca gctcttccat gacactgagg agaccacca aggaggccca ggcttacctg     660
cccagtctca tcgttctgct cctcttcatc tctgtggtag tagtggctgc catcatcttc     720
ggcgtttact acaggaaggg agggaaagcg ctgacagcta atttgtggaa ttgggtcaat     780
gatgcttgca gtagtctaag tggaaataag gagtcctcag ggaccgttg tgctggttcc     840 cactcggcaa cctccagtca gcaagaagtg tgtgaaggta tcttactaat gactcgggag     900
gagaagatgg ttccagaaga cggtgctgga gtctgtgggc ctgtgtgtgc ggcaggtggg     960
ccctgggcag aagtcagaga ttctaggacg ttcacactgg tcagcgaggt tgagacgcaa    1020
```

```
ggagacctct cgaggaagat tcccacagag gatgagtaca cggaccggcc ctcgcagcct    1080
tcgactggtt cactgctcct aatccagcag ggaagcaaat ctatacccccc attccaggag   1140 cccctggaag tgggggagaa cgacagttta agccagtgtt tcaccgggac tgaaagcacg    1200
gtggattctg agggctgtga cttcactgag cctccgagca gaactgactc tatgcccgtg    1260
tcccctgaaa agcacctgac aaaagaaata gaaggtgaca gttgcctccc ctgggtggtc    1320
agctccaact caacagatgg ctacacaggc agtgggaaca ctcctgggga ggaccatgaa    1380
ccctttccag ggtccctgaa atgtggacca ttgccccagt gtgcctacag catgggcttt    1440
cccagtgaag cagcagccag catggcagag gcgggagtac ggccccagga cagggctgat    1500
gagaggggag cctcagggtc cgggagctcc cccagtgacc agccacctgc ctctgggaac    1560
gtgactggaa acagtaactc cacgttcatc tctagcgggc aggtgatgaa cttcaagggt    1620
gacatcatcg tggtgtatgt cagccagacc tcgcaggagg gcccgggttc cgcagagccc    1680
gagtcggagc ccgtgggccg ccctgtgcag gaggagacgc tggcacacag agactccttt    1740
gcgggcaccg cgccgcgctt ccccgacgtc tgtgccaccg gggctgggct gcaggagcag    1800
ggggcacccc ggcagaagga cgggacatcg cggccggtgc aggagcaggg tggggcgcag    1860
acttcactcc atacccaggg gtccggacaa tgtgcagaat gacctcacct tctctgtctg    1920
ccctgggtgc agggcaccag tgcctttcca aaaacatggt gtagctagcc actgtgcacc    1980
tcctcactgg tgcaggctgc tggcatggtg atggagccca cctctcactt cctccagtgc    2040
ccctctcctc tgcctcctac cacctggcat cattcagttt ggcctttttt tgcaacgttg    2100
gtgtcctgca ttattg                                                    2116
```

<210> SEQ ID NO 16
<211> LENGTH: 625
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 16

```
Met Ala Pro Arg Ala Arg Arg Arg Gln Leu Pro Ala Pro Leu Leu
 1               5                  10                  15

Ala Leu Cys Val Leu Leu Val Pro Leu Gln Val Thr Leu Gln Val Thr
                20                  25                  30

Pro Pro Cys Thr Gln Glu Arg His Tyr Glu His Leu Gly Arg Cys Cys
            35                  40                  45

Ser Arg Cys Glu Pro Gly Lys Tyr Leu Ser Ser Lys Cys Thr Pro Thr
50                  55                  60

Ser Asp Ser Val Cys Leu Pro Cys Gly Pro Asp Glu Tyr Leu Asp Thr
65                  70                  75                  80

Trp Asn Glu Glu Asp Lys Cys Leu Leu His Lys Val Cys Asp Ala Gly
                85                  90                  95

Lys Ala Leu Val Ala Val Asp Pro Gly Asn His Thr Ala Pro Arg Arg
            100                 105                 110

Cys Ala Cys Thr Ala Gly Tyr His Trp Asn Ser Asp Cys Glu Cys Cys
        115                 120                 125

Arg Arg Asn Thr Glu Cys Ala Pro Gly Phe Gly Ala Gln His Pro Leu
    130                 135                 140

Gln Leu Asn Lys Asp Thr Val Cys Thr Pro Cys Leu Leu Gly Phe Phe
145                 150                 155                 160
```

-continued

```
Ser Asp Val Phe Ser Ser Thr Asp Lys Cys Lys Pro Trp Thr Asn Cys
            165                 170                 175

Thr Leu Leu Gly Lys Leu Glu Ala His Gln Gly Thr Thr Glu Ser Asp
            180                 185                 190

Val Val Cys Ser Ser Ser Met Thr Leu Arg Arg Pro Pro Lys Glu Ala
            195                 200                 205

Gln Ala Tyr Leu Pro Ser Leu Ile Val Leu Leu Phe Ile Ser Val
    210                 215                 220

Val Val Val Ala Ala Ile Ile Phe Gly Val Tyr Tyr Arg Lys Gly Gly
225                 230                 235                 240

Lys Ala Leu Thr Ala Asn Leu Trp Asn Trp Val Asn Asp Ala Cys Ser
            245                 250                 255

Ser Leu Ser Gly Asn Lys Glu Ser Ser Gly Asp Arg Cys Ala Gly Ser
            260                 265                 270

His Ser Ala Thr Ser Ser Gln Gln Glu Val Cys Glu Gly Ile Leu Leu
            275                 280                 285

Met Thr Arg Glu Glu Lys Met Val Pro Glu Asp Gly Ala Gly Val Cys
            290                 295                 300

Gly Pro Val Cys Ala Ala Gly Gly Pro Trp Ala Glu Val Arg Asp Ser
305                 310                 315                 320

Arg Thr Phe Thr Leu Val Ser Glu Val Glu Thr Gln Gly Asp Leu Ser
            325                 330                 335

Arg Lys Ile Pro Thr Glu Asp Glu Tyr Thr Asp Arg Pro Ser Gln Pro
            340                 345                 350

Ser Thr Gly Ser Leu Leu Leu Ile Gln Gln Gly Ser Lys Ser Ile Pro
            355                 360                 365

Pro Phe Gln Glu Pro Leu Glu Val Gly Glu Asn Asp Ser Leu Ser Gln
            370                 375                 380

Cys Phe Thr Gly Thr Glu Ser Thr Val Asp Ser Glu Gly Cys Asp Phe
385                 390                 395                 400

Thr Glu Pro Pro Ser Arg Thr Asp Ser Met Pro Val Ser Pro Glu Lys
            405                 410                 415

His Leu Thr Lys Glu Ile Glu Gly Asp Ser Cys Leu Pro Trp Val Val
            420                 425                 430

Ser Ser Asn Ser Thr Asp Gly Tyr Thr Gly Ser Gly Asn Thr Pro Gly
            435                 440                 445

Glu Asp His Glu Pro Phe Pro Gly Ser Leu Lys Cys Gly Pro Leu Pro
            450                 455                 460

Gln Cys Ala Tyr Ser Met Gly Phe Pro Ser Glu Ala Ala Ser Met
465                 470                 475                 480

Ala Glu Ala Gly Val Arg Pro Gln Asp Arg Ala Asp Glu Arg Gly Ala
            485                 490                 495

Ser Gly Ser Gly Ser Ser Pro Ser Asp Gln Pro Pro Ala Ser Gly Asn
            500                 505                 510

Val Thr Gly Asn Ser Asn Ser Thr Phe Ile Ser Ser Gly Gln Val Met
            515                 520                 525

Asn Phe Lys Gly Asp Ile Ile Val Val Tyr Val Ser Gln Thr Ser Gln
            530                 535                 540

Glu Gly Pro Gly Ser Ala Glu Pro Glu Ser Pro Val Gly Arg Pro
545                 550                 555                 560

Val Gln Glu Glu Thr Leu Ala His Arg Asp Ser Phe Ala Gly Thr Ala
            565                 570                 575
```

```
Pro Arg Phe Pro Asp Val Cys Ala Thr Gly Ala Gly Leu Gln Glu Gln
            580                 585                 590
Gly Ala Pro Arg Gln Lys Asp Gly Thr Ser Arg Pro Val Gln Glu Gln
        595                 600                 605
Gly Gly Ala Gln Thr Ser Leu His Thr Gln Gly Ser Gly Gln Cys Ala
    610                 615                 620
Glu
625

<210> SEQ ID NO 17
<211> LENGTH: 1669
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 17
```

| | | | | | |
|---|---|---|---|---|---|
| ctccctcagc | aaggacagca | gaggaccagc | taagagggag | agaagcaact | acagacccccc | 60 |
| cctgaaaaca | accctcagac | gccacatccc | ctgacaagct | gccaggcagg | ttctcttcct | 120 |
| ctcacatact | gacccacggc | tccaccctct | ctcccctgga | aaggacacca | tgagcactga | 180 |
| aagcatgatc | cgggacgtgg | agctggccga | ggaggcgctc | cccaagaaga | cagggggggcc | 240 |
| ccagggctcc | aggcggtgct | tgttcctcag | cctcttctcc | ttcctgatcg | tggcaggcgc | 300 |
| caccacgctc | ttctgcctgc | tgcactttgg | agtgatcggc | ccccagaggg | aagagttccc | 360 |
| cagggacctc | tctctaatca | gccctctggc | ccaggcagtc | agatcatctt | ctcgaacccc | 420 |
| gagtgacaag | cctgtagccc | atgttgtagc | aaaccctcaa | gctgaggggc | agctccagtg | 480 |
| gctgaaccgc | cgggccaatg | ccctcctggc | caatggcgtg | gagctgagag | ataaccagct | 540 |
| ggtggtgcca | tcagagggcc | tgtacctcat | ctactccag | gtcctcttca | agggccaagg | 600 |
| ctgcccctcc | acccatgtgc | tcctcaccca | caccatcagc | cgcatcgccg | tctcctacca | 660 |
| gaccaaggtc | aacctcctct | ctgccatcaa | gagcccctgc | cagagggaga | ccccagaggg | 720 |
| ggctgaggcc | aagccctggt | atgagcccat | ctatctggga | ggggtcttcc | agctggagaa | 780 |
| gggtgaccga | ctcagcgctg | agatcaatcg | gcccgactat | ctcgactttg | ccgagtctgg | 840 |
| gcaggtctac | tttgggatca | ttgccctgtg | aggaggacga | acatccaacc | ttcccaaacg | 900 |
| cctccccctgc | cccaatccct | ttattacccc | ctccttcaga | caccctcaac | ctcttctggc | 960 |
| tcaaaaagag | aattggggggc | ttagggtcgg | aacccaagct | tagaacttta | agcaacaaga | 1020 |
| ccaccacttc | gaaacctggg | attcaggaat | gtgtggcctg | cacagtgaag | tgctggcaac | 1080 |
| cactaagaat | tcaaactggg | gcctccagaa | ctcactgggg | cctacagctt | tgatccctga | 1140 |
| catctggaat | ctggagacca | gggagccttt | ggttctggcc | agaatgctgc | aggacttgag | 1200 |
| aagacctcac | ctagaaattg | acacaagtgg | accttaggcc | ttcctctctc | cagatgtttc | 1260 |
| cagacttcct | tgagacacgg | agcccagccc | tccccatgga | gccagctccc | tctatttatg | 1320 |
| tttgcacttg | tgattattta | ttatttattt | attatttatt | tatttacaga | tgaatgtatt | 1380 |
| tatttgggag | accggggtat | cctgggggac | ccaatgtagg | agctgccttg | gctcagacat | 1440 |
| gttttccgtg | aaaacggagc | tgaacaatag | gctgttccca | tgtagccccc | tggcctctgt | 1500 |
| gccttctttt | gattatgttt | tttaaaatat | ttatctgatt | aagttgtcta | aacaatgctg | 1560 |
| atttggtgac | caactgtcac | tcattgctga | gcctctgctc | ccagggggag | ttgtgtctgt | 1620 |
| aatcgcccta | ctattcagtg | gcgagaaata | aagtttgctt | agaaaagaa | | 1669 |

<210> SEQ ID NO 18
<211> LENGTH: 233
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 18

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 19
<211> LENGTH: 1619
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 19
cctcagcgag acagcaagg gactagccag gagggagaac agaaactcca gaacatcttg      60
gaaatagctc ccagaaaagc aagcagccaa ccaggcaggt tctgtccctt tcactcactg    120
gcccaaggcg ccacatctcc ctccagaaaa gacaccatga gcacagaaag catgatccgc    180
gacgtggaac tggcagaaga ggcactcccc caaagatgg ggggcttcca gaactccagg      240
cggtgcctat gtctcagcct cttctcattc ctgcttgtgg caggggccac cacgctcttc    300
tgtctactga acttcggggt gatcggtccc caaagggatg agaagttccc aaatggcctc    360

```
cctctcatca gttctatggc ccagaccctc acactcagat catcttctca aaattcgagt    420
gacaagcctg tagcccacgt cgtagcaaac caccaagtgg aggagcagct ggagtggctg    480
agccagcgcg ccaacgccct cctggccaac ggcatggatc tcaaagacaa ccaactagtg    540
gtgccagccg atgggttgta ccttgtctac tcccaggttc tcttcaaggg acaaggctgc    600
cccgactacg tgctcctcac ccacaccgtc agccgatttg ctatctcata ccaggagaaa    660
gtcaacctcc tctctgccgt caagagcccc tgccccaagg acacccctga ggggctgag     720 ctcaaaccct ggtatgagcc catatacctg ggaggagtct tccagctgga aggggggac     780 caactcagcg ctgaggtcaa tctgcccaag tacttagact ttgcggagtc cgggcaggtc    840
tactttggag tcattgctct gtgaagggaa tgggtgttca tccattctct acccagcccc    900
cactctgacc cctttactct gaccccttta ttgtctactc ctcagagccc ccagtctgtg    960
tccttctaac ttagaaaggg gattatggct cagagtccaa ctctgtgctc agagctttca   1020
acaactactc agaaacacaa gatgctggga cagtgacctg gactgtgggc ctctcatgca   1080
ccaccatcaa ggactcaaat gggctttccg aattcactgg agcctcgaat gtccattcct   1140
gagttctgca agggagagt ggtcaggttg cctctgtctc agaatgaggc tggataagat    1200
ctcaggcctt cctaccttca gacctttcca gactcttccc tgaggtgcaa tgcacagcct   1260
tcctcacaga gccagccccc ctctatttat atttgcactt attatttatt atttatttat   1320
tatttattta tttgcttatg aatgtattta tttggaaggc cggggtgtcc tggaggaccc   1380
agtgtgggaa gctgtcttca gacagacatg ttttctgtga aaacggagct gagctgtccc   1440
cacctggcct ctctaccttg ttgcctcctc ttttgcttat gtttaaaaca aaatatttat   1500
ctaacccaat tgtcttaata acgctgattt ggtgaccagg ctgtcgctac atcactgaac   1560
ctctgctccc cacgggagcc gtgactgtaa ttgccctaca gtcaattgag agaaataaa    1619
```

<210> SEQ ID NO 20
<211> LENGTH: 235
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 20

```
Met Ser Thr Glu Ser Met Ile Arg Asp Val Glu Leu Ala Glu Glu Ala
 1               5                  10                  15

Leu Pro Gln Lys Met Gly Gly Phe Gln Asn Ser Arg Arg Cys Leu Cys
                20                  25                  30

Leu Ser Leu Phe Ser Phe Leu Leu Val Ala Gly Ala Thr Thr Leu Phe
            35                  40                  45

Cys Leu Leu Asn Phe Gly Val Ile Gly Pro Gln Arg Asp Glu Lys Phe
        50                  55                  60

Pro Asn Gly Leu Pro Leu Ile Ser Ser Met Ala Gln Thr Leu Thr Leu
 65                  70                  75                  80

Arg Ser Ser Ser Gln Asn Ser Ser Asp Lys Pro Val Ala His Val Val
                85                  90                  95

Ala Asn His Gln Val Glu Glu Gln Leu Glu Trp Leu Ser Gln Arg Ala
            100                 105                 110

Asn Ala Leu Leu Ala Asn Gly Met Asp Leu Lys Asp Asn Gln Leu Val
        115                 120                 125

Val Pro Ala Asp Gly Leu Tyr Leu Val Tyr Ser Gln Val Leu Phe Lys
    130                 135                 140
```

```
Gly Gln Gly Cys Pro Asp Tyr Val Leu Leu Thr His Thr Val Ser Arg
145                 150                 155                 160

Phe Ala Ile Ser Tyr Gln Glu Lys Val Asn Leu Leu Ser Ala Val Lys
                165                 170                 175

Ser Pro Cys Pro Lys Asp Thr Pro Glu Gly Ala Glu Leu Lys Pro Trp
            180                 185                 190

Tyr Glu Pro Ile Tyr Leu Gly Gly Val Phe Gln Leu Glu Lys Gly Asp
        195                 200                 205

Gln Leu Ser Ala Glu Val Asn Leu Pro Lys Tyr Leu Asp Phe Ala Glu
    210                 215                 220

Ser Gly Gln Val Tyr Phe Gly Val Ile Ala Leu
225                 230                 235

<210> SEQ ID NO 21
<211> LENGTH: 2254
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 21
ccaacaatct gtgtggttgt ttttctgtgt tcctccaatg gtagggcctc tgttcaccag      60
tgccgtctct tcttttagct gtaagaaaag cctggagtgc acgaagttgt gcctacccca     120
gattgagaat gttaagggca ctgaggactc aggtgaggag aggtgacctg gtgcccatgc     180
tcacctgccc tctccctctt cttgccccca cccgtccatc catcccaccc atccatctat     240
ccctgcggcc cccctctgcc cgctcctctg accaacacct gctttgtctg caggcaccac     300
agtgctgttg cccctggtca ttttctttgg tctttgcctt ttatccctcc tcttcattgg     360
tttaatgtat cgctaccaac ggtggaagtc caagctctac tccattggtg agtgggggct     420 tgggaggga gagggagctg gtggggggtga gggaggacat gggtgggtgc gatggacatg     480
tgtggaggga ggtgaggagt gtcccctcag ttcataccgc tggggactct gggcagaagg     540
tggccctgga tggctgggga gatgtcgagc tgcatcagta gctctctcgt ccctggggcc     600
acataggccc tgaggcatgt caccacaagt ccccactgcc agctgagtcc agggtgccag     660
ggctgagaga ggaagtgaaa tttatgatgc tttctttctt tttcctcagt tgtgggaaa     720 tcgacacctg aaaagaggt gagatgaaat gagagagtta ctcccaaatg tccctgacca     780
ttccttataa ttgcctaatg ctcagatccc ctggaatcat ccttcacttt ccggggctc     840 gcctcattcc ctctaagtcc caaccccac gtagaataaa gagggccggg gctggttttc     900
gctgccgcac taatctgcgc caccttctct ctttcagggg gagcttgaag gaactactac     960 taagccccctg gccccaaacc caagcttcag tcccactcca ggcttcaccc ccaccctggg    1020
cttcagtccc gtgcccagtt ccaccttcac ctccagctcc acctatacc ccggtgactg    1080 tcccaacttt gcggctcccc gcagagaggt ggcaccaccc tatcagggg ctgaccccat    1140 ccttgcgaca gccctcgcct ccgacccccat ccccaacccc cttcagaagt gggaggacag    1200
cgcccacaag ccacagagcc tagacagtgc gtttctcccg cggctggaga cgaggaggct    1260 ggggggagggc cggggagcg cgggaggcgt cagaggggac cacgagaggc ggagggcgcg    1320
ggatgcgggg cggggcctgg ggttgccgcc cgaggctcac cggcccgcgt cccgcagct    1380 gatgaccccg cgacgctgta cgccgtggtg gagaacgtgc cccgttgcg ctggaaggaa    1440 ttcgtgcggc gcctagggct gagcgaccac gagatcgatc ggctggagct gcagaacggg    1500
```

```
cgctgcctgc gcgaggcgca atacagcatg ctggcgacct ggaggcggcg cacgccgcgg   1560
cgcgaggcca cgctggagct gctgggacgc gtgctccgcg acatggacct gctgggctgc   1620
ctggaggaca tcgaggaggc gctttgcggc cccgccgccc tcccgcccgc gcccagtctt   1680
ctcagatgag gctgcgcccc tgcgggcagc tctaaggacc gtcctgcgag atcgccttcc   1740
aaccccactt ttttctggaa aggaggggtc ctgcaggggc aagcaggagc tagcagccgc   1800
ctacttggtg ctaaccccct gatgtacata gcttttctca gctgcctgcg cgccgccgac   1860
agtcagcgct gtgcgcgcgg agagaggtgc gccgtgggct caagagcctg agtgggtggt   1920
ttgcgaggat gagggacgct atgcctcatg cccgttttgg gtgtcctcac cagcaaggct   1980
gctcgggggc ccctggttcg tccctgagcc ttttcacag tgcataagca gttttttttg    2040
tttttgtttt gttttgtttt gttttttaaat caatcatgtt acactaatag aaacttggca   2100
ctcctgtgcc ctctgcctgg acaagcacat agcaagctga actgtcctaa ggcaggggcg   2160
agcacggaac aatgggcct tcagctggag ctgtggactt ttgtacatac actaaaattc     2220
tgaagttaaa gctctgctct tggagacagt ggct                                2254
```

<210> SEQ ID NO 22
<211> LENGTH: 455
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 22

```
Met Gly Leu Ser Thr Val Pro Asp Leu Leu Pro Leu Val Leu Leu
 1               5                  10                  15

Glu Leu Leu Val Gly Ile Tyr Pro Ser Gly Val Ile Gly Leu Val Pro
                 20                  25                  30

His Leu Gly Asp Arg Glu Lys Arg Asp Ser Val Cys Pro Gln Gly Lys
             35                  40                  45

Tyr Ile His Pro Gln Asn Asn Ser Ile Cys Cys Thr Lys Cys His Lys
         50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                 85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220
```

```
Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
            245                 250                 255

Gly Glu Leu Glu Gly Thr Thr Thr Lys Pro Leu Ala Pro Asn Pro Ser
        260                 265                 270

Phe Ser Pro Thr Pro Gly Phe Thr Pro Thr Leu Gly Phe Ser Pro Val
    275                 280                 285

Pro Ser Ser Thr Phe Thr Ser Ser Thr Tyr Thr Pro Gly Asp Cys
290                 295                 300

Pro Asn Phe Ala Ala Pro Arg Arg Glu Val Ala Pro Pro Tyr Gln Gly
305             310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
        420                 425                 430

Cys Leu Glu Asp Ile Glu Glu Ala Leu Cys Gly Pro Ala Ala Leu Pro
            435                 440                 445

Pro Ala Pro Ser Leu Leu Arg
    450                 455

<210> SEQ ID NO 23
<211> LENGTH: 2154
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 23
ttcccctcct accttctctc tccccctcagc ttaaattttc tccgagtttt ccgaactctg      60
gctcatgatc gggcctactg ggtgcgaggt cctggaggac cgtaccctga tctctatctg     120
cctctgactt tcagcttctc gaactcgagg cccaggctgc atcgcccgg gccacctggt     180 ccgatcatct tacttcattc acgagcgttg tcaattgctg ccctgtcccc agccccaatg     240
ggggagtgag aggccactgc cggccggaca tgggtctccc caccgtgcct ggcctgctgc     300
tgtcactggt gctcctggct ctgctgatgg ggatacatcc atcagggggtc actggactag     360 tcccttctct tggtgaccgg gagaagaggg atagcttgtg tccccaagga aagtatgtcc     420
attctaagaa caattccatc tgctgcacca agtgccacaa aggaacctac ttggtgagtg     480
actgtccgag cccagggcgg gatacagtct gcagggagtg tgaaagggc accttacgg     540 cttcccagaa ttacctcagg cagtgtctca gttgcaagac atgtcggaaa gaaatgtccc     600
aggtggagat ctctccttgc caagctgaca aggacacggt gtgtggctgt aaggagaacc     660
```

-continued

```
agttccaacg ctacctgagt gagacacact tccagtgcgt ggactgcagc ccctgcttca    720
acggcaccgt gacaatcccc tgtaaggaga ctcagaacac cgtgtgtaac tgccatgcag    780
ggttctttct gagagaaagt gagtgcgtcc cttgcagcca ctgcaagaaa aatgaggagt    840
gtatgaagtt gtgcctacct cctccgcttg caaatgtcac aaaccccag gactcaggta     900
ctgcggtgct gttgccctg gttatcttgc taggtctttg ccttctatcc tttatcttca     960
tcagtttaat gtgccgatat ccccggtgga ggcccgaagt ctactccatc atttgtaggg   1020
atcccgtgcc tgtcaaagag gagaaggctg gaaagcccct aactccagcc ccctccccag   1080
ccttcagccc cacctccggc ttcaaccccca ctctgggctt cagcaccccca ggctttagtt  1140
ctcctgtctc cagtaccccc atcagcccca tcttcggtcc tagtaactgg cacttcatgc   1200
cacctgtcag tgaggtagtc ccaacccagg gagctgaccc tctgctctac gaatcactct   1260
gctccgtgcc agcccccacc tctgttcaga aatgggaaga ctccgcccac cgcaacgtc    1320
ctgacaatgc agaccttgcg attctgtatg ctgtggtgga tggcgtgcct ccagcgcgct   1380
ggaaggagtt catgcgtttc atggggctga gcgagcacga gatcgagagg ctggagatgc   1440
agaacgggcg ctgcctgcgc gaggctcagt acagcatgct ggaagcctgg cggcgccgca   1500
cgccgcgcca cgaggacacg ctggaagtag tgggcctcgt gctttccaag atgaacctgg   1560
ctgggtgcct ggagaatatc ctcgaggctc tgagaaatcc cgcccctcg tccacgaccc    1620
gcctcccgcg ataaagccac acccacaacc ttaggaagag ggacttgaac ttcaaggacc   1680
attctgctag atgccctact ccctgtgggt gaaaagtggg caaaggtctc taagggaag    1740
gctcgagctg gtagccactt ccttggtgct accaacttgg tgtacatagc ttttctcagc   1800
cgccgaggac tgcctgagcc agccacttgt gagtggcagg gagatgtacc atcagctcct   1860
ggccagctga gggtgccaaa gacaggattg tagaggaaag gcacaatgta tctggtgccc   1920
acttgggatg cacagggccc aagccaagct tctcagggcc tcctcagtgg gtttctgggc   1980
cttttttcact tttgataagc aatctttgta tcaattatat cacactaatg gatgaactgt   2040
gtaaggtaag gacaagcata gaaaggcggg gtctccagct ggagccctcg actcttgtaa   2100
atacactaaa cgtctaaaaa tgaaaaaaaa aaaaaaaaa aaaaaaaaaa aaaa          2154
```

<210> SEQ ID NO 24
<211> LENGTH: 454
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 24

```
Met Gly Leu Pro Thr Val Pro Gly Leu Leu Ser Leu Val Leu Leu
1               5                   10                  15

Ala Leu Leu Met Gly Ile His Pro Ser Gly Val Thr Gly Leu Val Pro
            20                  25                  30

Ser Leu Gly Asp Arg Glu Lys Arg Asp Ser Leu Cys Pro Gln Gly Lys
        35                  40                  45

Tyr Val His Ser Lys Asn Asn Ser Ile Cys Cys Thr Lys Cys His Lys
    50                  55                  60

Gly Thr Tyr Leu Val Ser Asp Cys Pro Ser Pro Gly Arg Asp Thr Val
65                  70                  75                  80

Cys Arg Glu Cys Glu Lys Gly Thr Phe Thr Ala Ser Gln Asn Tyr Leu
                85                  90                  95
```

```
Arg Gln Cys Leu Ser Cys Lys Thr Cys Arg Lys Glu Met Ser Gln Val
                100                 105                 110

Glu Ile Ser Pro Cys Gln Ala Asp Lys Asp Thr Val Cys Gly Cys Lys
            115                 120                 125

Glu Asn Gln Phe Gln Arg Tyr Leu Ser Glu Thr His Phe Gln Cys Val
        130                 135                 140

Asp Cys Ser Pro Cys Phe Asn Gly Thr Val Thr Ile Pro Cys Lys Glu
145                 150                 155                 160

Thr Gln Asn Thr Val Cys Asn Cys His Ala Gly Phe Phe Leu Arg Glu
                165                 170                 175

Ser Glu Cys Val Pro Cys Ser His Cys Lys Lys Asn Glu Glu Cys Met
            180                 185                 190

Lys Leu Cys Leu Pro Pro Leu Ala Asn Val Thr Asn Pro Gln Asp
        195                 200                 205

Ser Gly Thr Ala Val Leu Leu Pro Leu Val Ile Leu Leu Gly Leu Cys
210                 215                 220

Leu Leu Ser Phe Ile Phe Ile Ser Leu Met Cys Arg Tyr Pro Arg Trp
225                 230                 235                 240

Arg Pro Glu Val Tyr Ser Ile Ile Cys Arg Asp Pro Val Pro Val Lys
                245                 250                 255

Glu Glu Lys Ala Gly Lys Pro Leu Thr Pro Ala Pro Ser Pro Ala Phe
            260                 265                 270

Ser Pro Thr Ser Gly Phe Asn Pro Thr Leu Gly Phe Ser Thr Pro Gly
        275                 280                 285

Phe Ser Ser Pro Val Ser Ser Thr Pro Ile Ser Pro Ile Phe Gly Pro
290                 295                 300

Ser Asn Trp His Phe Met Pro Pro Val Ser Glu Val Val Pro Thr Gln
305                 310                 315                 320

Gly Ala Asp Pro Leu Leu Tyr Glu Ser Leu Cys Ser Val Pro Ala Pro
                325                 330                 335

Thr Ser Val Gln Lys Trp Glu Asp Ser Ala His Pro Gln Arg Pro Asp
            340                 345                 350

Asn Ala Asp Leu Ala Ile Leu Tyr Ala Val Val Asp Gly Val Pro Pro
        355                 360                 365

Ala Arg Trp Lys Glu Phe Met Arg Phe Met Gly Leu Ser Glu His Glu
370                 375                 380

Ile Glu Arg Leu Glu Met Gln Asn Gly Arg Cys Leu Arg Glu Ala Gln
385                 390                 395                 400

Tyr Ser Met Leu Glu Ala Trp Arg Arg Arg Thr Pro Arg His Glu Asp
                405                 410                 415

Thr Leu Glu Val Val Gly Leu Val Leu Ser Lys Met Asn Leu Ala Gly
            420                 425                 430

Cys Leu Glu Asn Ile Leu Glu Ala Leu Arg Asn Pro Ala Pro Ser Ser
        435                 440                 445

Thr Thr Arg Leu Pro Arg
    450

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 25
```

```
acagacaaac agcccaaacc                                                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 26
gcctcaccca tcagttgttt                                                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 27
agatgtggat cagcaagcag                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 28
gcgcaagtta ggttttgtca                                                    20
```